Figure 1:
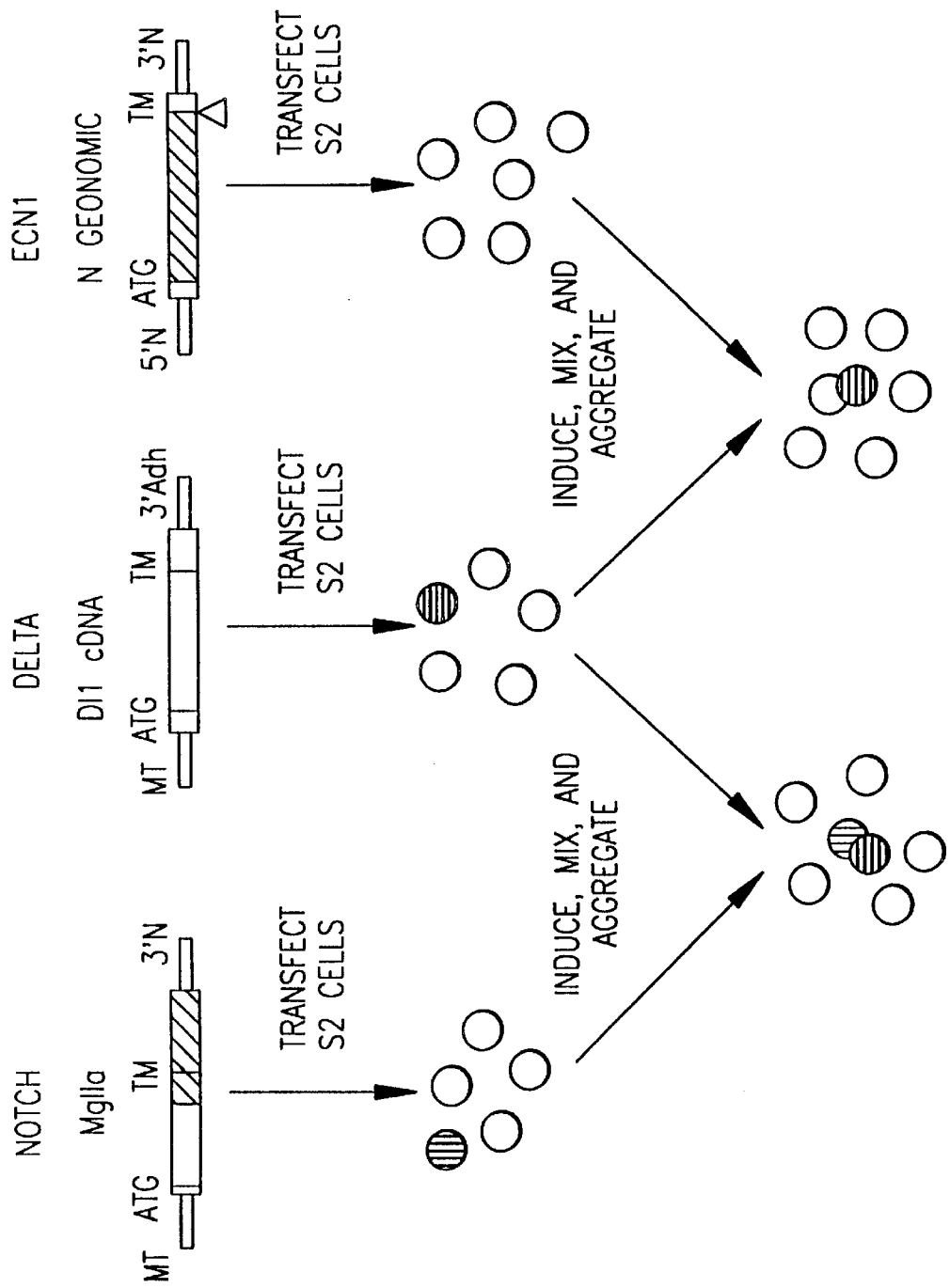

United States Patent [19]
Artavanis-Tsakonas et al.

[11] Patent Number: 5,856,441
[45] Date of Patent: Jan. 5, 1999

[54] SERRATE FRAGMENTS AND DERIVATIVES

[75] Inventors: Spyridon Artavanis-Tsakonas; Richard Grant Fehon, both of Hamden; Ilaria Rebay, New Haven, all of Conn.

[73] Assignee: Yale University, New Haven, Conn.

[21] Appl. No.: 346,128

[22] Filed: Nov. 28, 1994

Related U.S. Application Data

[63] Continuation of Ser. No. 879,038, Apr. 30, 1992, abandoned, which is a continuation-in-part of Ser. No. 791,923, Nov. 14, 1991, abandoned, which is a continuation-in-part of Ser. No. 695,189, May 3, 1991, abandoned.

[51] Int. Cl.$^6$ .................................................. C07K 14/705
[52] U.S. Cl. ......................... 530/350; 530/402; 530/300
[58] Field of Search .................................. 530/350, 402, 530/300

[56] References Cited

U.S. PATENT DOCUMENTS

| 5,098,833 | 3/1992 | Lasky et al. | 435/69.1 |
|---|---|---|---|
| 5,115,096 | 5/1992 | Shoyab et al. | 530/320 |
| 5,580,738 | 12/1996 | Laborda | 435/6 |

OTHER PUBLICATIONS

Bass et al., 1991, Proc. Natl. Acad. Sci. USA 88:4498–4502.
Arthos et al., 1989, Cell 57:469–481.
Ashkenazi et al., 1990, Proc. Natl. Acad. Sci. USA 87:7150–7154.
Kopczynski et al, "Molecular and Genetic Intimations of the Function of Delta . . . ", Mol. Reprod. Devel. 27(1):28–36 (Sep. 1990).
Hjelmeland et al, "Solubilization of Functional Membrane Proteins", Meth. Enzymol. 104 (Part C): 305–318 (1984).
Ahmad et al., 1995, "Involvment of Notch–1 in mammalian retinal neurogenesis: association of Notch–1 activity with both immature and terminally differentiated cells", Mechanisms of Development 53: 73–85.
Artavanis–Tsakonas et al., 1995, "Notch Signaling", Science 268: 225–232.
Bieber et al., 1989, "Drosophila Neuroglian: A Member of the Immunoglobulin Superfamily with extensive Homology to the Vertebrate Neural Adhesion Molecule L1", Cell 59: 447–460.
Chenn and McConnell, 1995, "Cleavage Orientation and the Asymmetric Inheritance of Notch 1 Immunoreactivity in Mammalian Neurogenesis", Cell 82: 631–641.
Kopan et al., 1994, "The intracellular domain of mouse Notch: a constitutively activator of myogenesis directed at the basic helix–loop–helix of MyoD", Development 120: 2385–2396.
Lindsell et al., 1995, "Jagged: A Mammalian Ligand That Activates Notch 1", Cell 80: 909–917.
Milner et al., 1994, "A Human Homologue of the Drosophila Developmental Gene, Notch, Is Expressed in CD34+ Hematopoietic Precursors", Blood 83: 2057–2062.

Nye et al., 1994, "An activated Notch suppresses neurogenesis and myogenesis but not gliogenesis in mammalian cells", Development 120: 2421–2430.
Snow et al., 1989, "Fasciclin III: A Novel Homophilic Adhesion Molecule in Drosophila", Cell 59:313–323.
Speicher et al., 1994, "The Serrate Locus of Drosophila and its role in morphogenesis of the wing imaginal discs: control of cell proliferation", Development 120: 535–544.
Zagouras et al., 1995, "Alterations in Notch signaling in neoplastic lesions of the human cervix", Proc. Natl. Acad. Sci. USA 92: 6414–6418.
Artavanis–Tsakonas et al., 1983, "Molecular cloning of Notch, a locus affecting neurogenesis in Drosophila melanogaster," Proc. Natl. Acad. Sci. USA 80:1977–1981.
Doolittle, 1987, Of URFS and ORFS, A Primer on How to Analyze Derived Amino Acid Sequences, University Science Books, Mill Valley, California, pp. 10–17 and 63–79.
Hopp and Woods, 1981, "Prediction of protein antigenic determinants from amino acid sequences," Proc. Natl. Acad. Sci. USA 78:3824–3828.
Rebay et al., 1991, "Specific EGF repeats of Notch mediate interactions with Delta and Serrate: Implications for Notch as a multifunctional receptor," Cell 67:687–699.
Stifani et al., 1992, "Human homologs of a Drosophila Enhancer of split gene product define a novel family of nuclear proteins," Nature 2:119–127.
Weinmaster et al., 1992, "Notch2: a second mammalian Notch gene," Develop. 116:931–941.
Ohno et al., 1990, "The candidate proto–oncogene bcl–3 is related to genes implicated in cell lineage determination and cell cycle control," Cell 60:991–997.
Dahlback et al., 1990, "Novel type of very high affinity calcium binding sites in β–hydroxy–asparagine–containing epidermal growth factor–like domains in vitamin K–dependent protein S," J. Biol. Chem. 265:18481–18489.
LaMarco et al., 1991, "Identification of Ets– and Notch–related subunits in GA binding protein," Science 253:789–792.
Adams et al., 1991, "Complementary DNA sequencing: expressed sequence tags and human genome project," Science 252:1651–1656.
Thomas et al., 1991, "The Drosophila gene serrate encodes an EGF–like transmembrane protein with a complex expression pattern in embryos and wing discs," Development 111(3):749–761.
Fleming et al., 1990, "The gene Serrate encodes a putative EGF–like transmembrane protein essential for proper ectodermal development in Drosophila melanogaster," Genes Dev. 4:2188–2201.
de la Concha et al., 1988, "Functional interactions of neurogenic genes in Drosophila melanogaster," Genetics 118:499–508.

(List continued on next page.)

Primary Examiner—Stephen Walsh
Assistant Examiner—Kenneth A. Sorensen
Attorney, Agent, or Firm—Pennie & Edmonds LLP

[57] ABSTRACT

The present invention relates to sequences of the serrate amino acid sequence as well as fragments thereof, and fragments which retain binding activity are also provided.

19 Claims, 61 Drawing Sheets

OTHER PUBLICATIONS

Krämer et al., 1991, "Interaction of bride of sevenless membrane–bound ligand and the sevenless tyrosine kinase receptor," Nature 352:207–212.
Welshons, 1965, Science 150:1122–1129.
Portin, 1975, Genetics 81:121–133.
Morita et al., 1984, J. Biol. Chem. 259:5698–5704.
Sugo et al., 1984, J. Biol. Chem. 259:5705–5710.
Lindsley and Zinn, 1985, Drosophila Information Service 62:86.
Südhof et al. 1985, Science 228:815–822.
Doe and Goodman, 1985, Dev. Biol. 111:206–219.
Vässin et al., 1985, J. Neurogenet. 2:291–308.
Wharton et al., 1985, Cell 43:567–581.
Kidd et al., 1986, Mol. Cell. Biol. 6:3094–3108.
Breeden and Nasmyth, 1987, Nature 329:651–654.
Appella et al., 1987, J. Biol. Chem. 262:4437–4440.
Knust et al., 1987, EMBO J. 6(3):761–766.
Suzuki et al., 1987, EMBO J. 6(7):1891–1897.
Hartley et al., 1987, EMBO J. 6(11):3407–3417.
Reynolds et al., 1987, Cell 50:107–117.
Vässin et al., 1987, EMBO J. 6:3431–3440.
Kelley et al., 1987, Cell 51:539–548.
Kopczynski et al., 1988, Genes & Dev. 2:1723–1735.
Kopczynski and Muskavitch, 1989, Development 107:623–636.
Rees et al., 1988, EMBO J. 7(7):2053–2061.
Furie and Furie, 1988, Cell 53:505–518.
Artavanis–Tsakonas, 1988, Trends in Genetics 4:95–100.
Kurosawa et al., 1988, J. Biol. Chem. 263(13):5993–5996.
Yochem et al., 1988, Nature 335:547–550.
Rothberg et al., 1988, Cell 55:1047–1059.
Kidd et al., 1989, Genes & Dev. 3:1113–1129.
Johansen et al., 1989, J. Cell Biol. 109:2427–2440.
Shepard et al., 1989, Genetics 122:429–438.
Alton et al., 1989, Dev. Genet. 10:261–272.
Handford et al., 1990, EMBO J. 9:475–480.
Fehon et al., 1990, Cell 61:523–534.
Coffman et al., 1990, Science 249:1438–1441.
Palka et al., 1990, Develop. 109:167–175.
Xu et al., 1990, Genes & Dev. 4:464–475.
Ellisen et al., 1991, Cell 66:649–661.
Weinmaster et al., 1991, Develop. 113:199–205.
Artavanis–Tsakonas et al., 1991, "The notch locus and the cell biology of neuroblast segregation," Ann. Rev. Cell Biol. 7:427–452.
Digan et al., 1989, "Continuous production of a novel lysozyme via secretion from the yeast, *pichia pastoris*," Bio/technology 7:160–164.
Evan et al., 1985, "Isolation of monoclonal antibodies specific for human c–myc proto–oncogene product," Mol. Cell Biol. 5(12):3610–3616.
Field et al., 1988, "Purification of a RAS–responsive adenylyl cyclase complex from *Saccharomyces cerevisiae* by use of an epitope addition method," Mol. Cell. Biol. 8(5):2159–2165.
Hopp et al., 1988, "A short polypeptide marker sequence useful for recombinant protein identification and purification," Bio/technology 6:1204–1210.
Smith and Johnson, 1988, "Single–step purification of polypeptides expressed in *Escherichia coli* as fusions with glutathione S–transferase," Gene 67:31–40.

S2 N

S2 DI

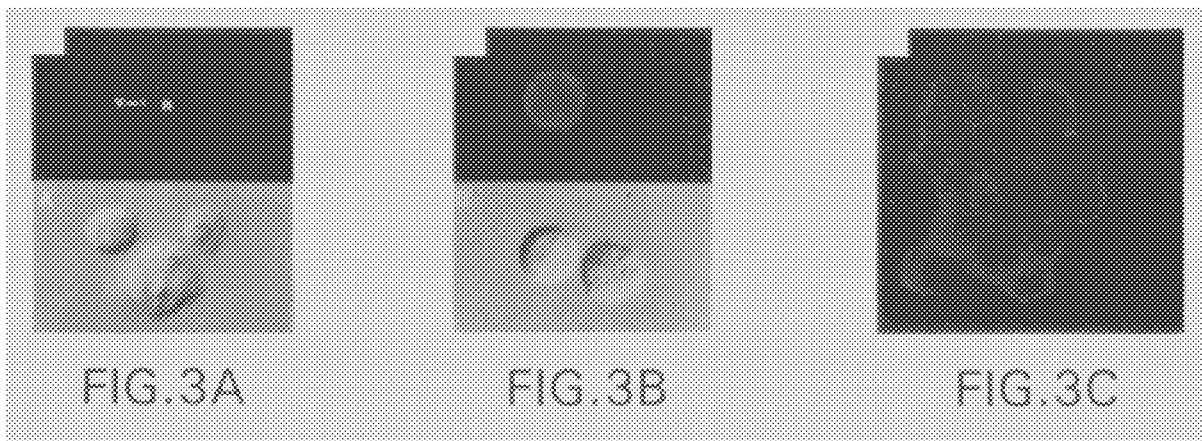

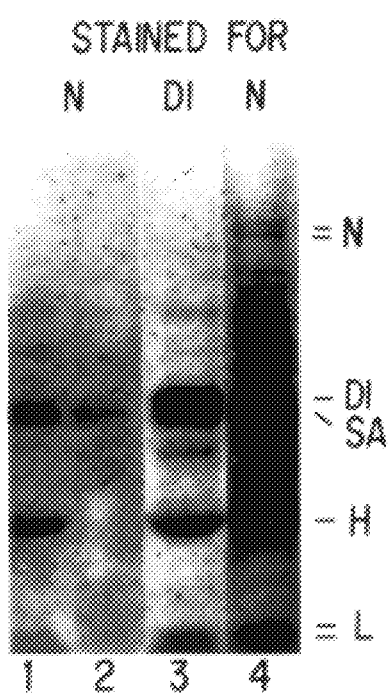
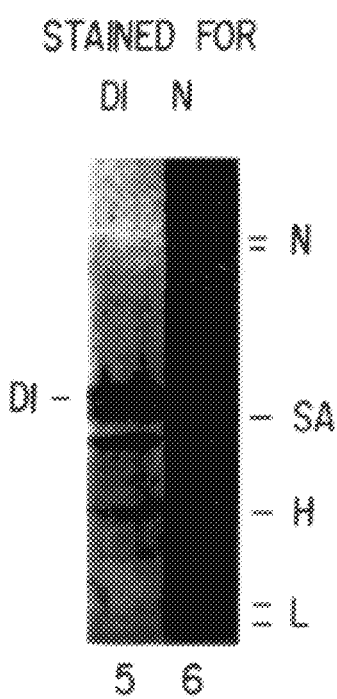

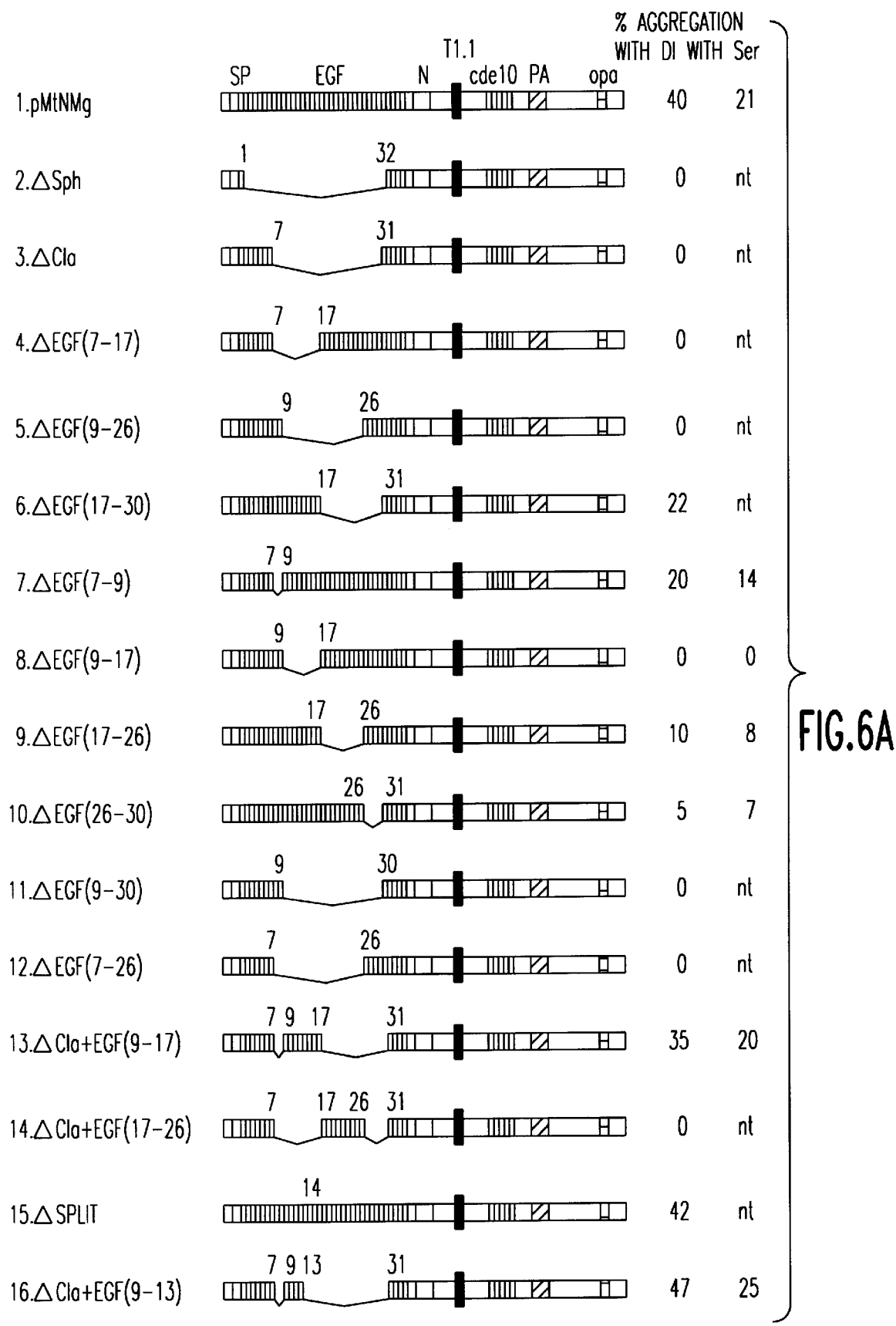

FIG. 8

FIG. 10

```
DI 24
         GSFELRLKYFSNDHGRDNEGRCCSGESDGATGKCL.G.S.CKTRFRVCLKHYQATIDITS...QC
              ||||   |                ||       |     ||||  |           ||
N1       GNFELEILEISNTNSHLLNGYCCGMPAELRATKTIGCSPCTTAFRLCLKEYQTTEQGASISTGC
SER85

STU B
                                              EGKIFPW
         TYGDVITPILGENSVNLTDAQRFQNKGFTNPIQFPFSFSWPGTFSLIVEAW
            |    ||  ||   |         |                |
         SFGNATTKILGGSSFVLSDPG........VGAIVLPFTFRWTKSFTLILQAL

N2       HDTNNSGNARTNKLLIQRLLVQQVLEVSSEWKTNKSESQYTSLEYDFRVT
          |||||||  |||  ||||  |       |       |    |  |||
         DMYNTS..YPDAERLIEETSYSGVILPSPEWKTLDHIGRNARITYRVRVQ

NAE B                                         226
               CRKIFR
         CDLNYYGSGCAKFCRPDDSFGHSTCSETGEIICLTGWQGDYC
         |  |    |   ||||||| |||  |||| |  || || ||
         CAVTYYNTTCTTFCRPDDQFGHYACGSEGQKLCLNGWGGVNC
N3                                                     283
``` trans                cis

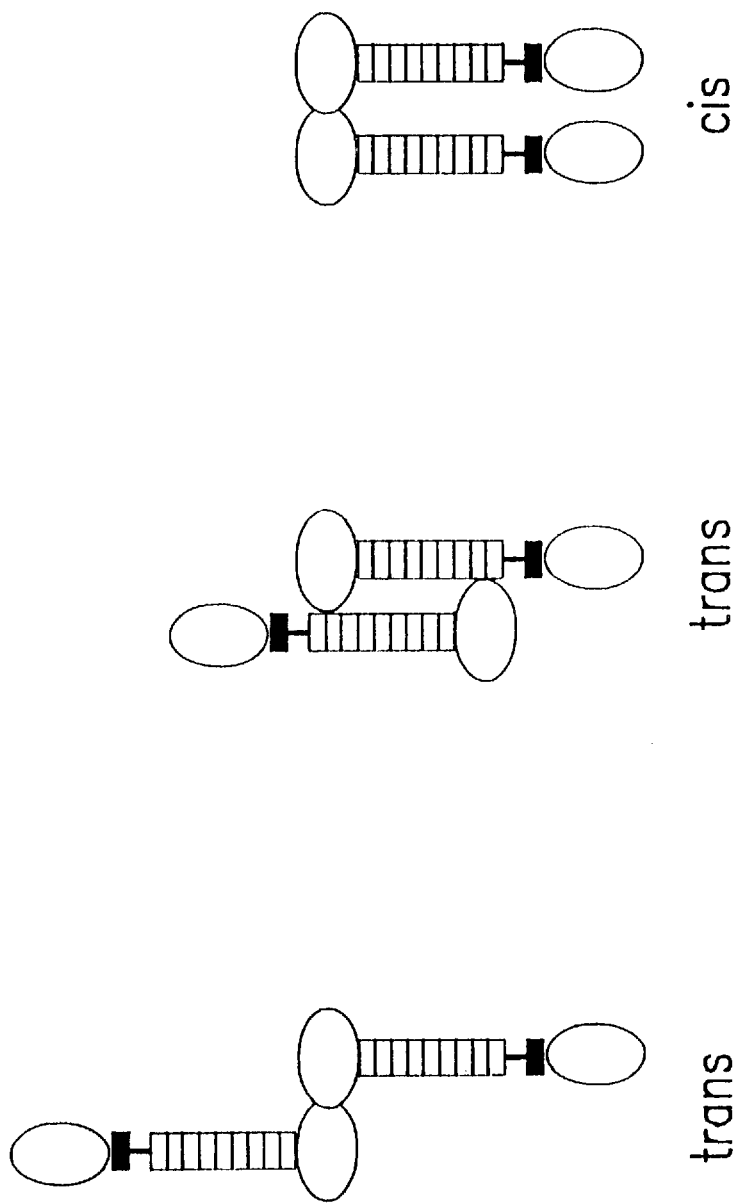

```
GAATTCGGAG GAATTATTCA AAACATAAAC ACAATAAACA ATTTGAGTAG TTGCCGCACA      60

CACACACACA CACAGCCCGT GGATTATTAC ACTAAAAGCG ACACTCAATC CAAAAAATCA     120

GCAACAAAAA CATCAATAAA C ATG CAT TGG ATT AAA TGT TTA TTA ACA GCA      171
                        Met His Trp Ile Lys Cys Leu Leu Thr Ala
                         1           5                       10

TTC ATT TGC TTC ACA GTC ATC GTG CAG GTT CAC AGT TCC GGC AGC TTT      219
Phe Ile Cys Phe Thr Val Ile Val Gln Val His Ser Ser Gly Ser Phe
            15                  20                  25

GAG TTG CGC CTG AAG TAC TTC AGC AAC GAT CAC GGG CGG GAC AAC GAG      267
Glu Leu Arg Leu Lys Tyr Phe Ser Asn Asp His Gly Arg Asp Asn Glu
                30                  35                  40

GGT CGC TGC TGC AGC GGG GAG TCG GAC GGA GCG ACG GGC AAG TGC CTG      315
Gly Arg Cys Cys Ser Gly Glu Ser Asp Gly Ala Thr Gly Lys Cys Leu
            45                  50                  55

GGC AGC TGC AAG ACG CGG TTT CGC GTC TGC CTA AAG CAC TAC CAG GCC      363
Gly Ser Cys Lys Thr Arg Phe Arg Val Cys Leu Lys His Tyr Gln Ala
        60                  65                  70

ACC ATC GAC ACC ACC TCC CAG TGC ACC TAC GGG GAC GTG ATC ACG CCC      411
Thr Ile Asp Thr Thr Ser Gln Cys Thr Tyr Gly Asp Val Ile Thr Pro
75                  80                  85                  90

ATT CTC GGC GAG AAC TCG GTC AAT CTG ACC GAC GCC CAG CGC TTC CAG      459
Ile Leu Gly Glu Asn Ser Val Asn Leu Thr Asp Ala Gln Arg Phe Gln
                95                  100                 105

AAC AAG GGC TTC ACG AAT CCC ATC CAG TTC CCC TTC TCG TTC TCA TGG      507
Asn Lys Gly Phe Thr Asn Pro Ile Gln Phe Pro Phe Ser Phe Ser Trp
            110                 115                 120
```

FIG.13A

```
CCG GGT ACC TTC TCG CTG ATC GTC GAG GCC TGG CAT GAT ACG AAC AAT    555
Pro Gly Thr Phe Ser Leu Ile Val Glu Ala Trp His Asp Thr Asn Asn
            125             130             135

AGC GGC AAT GCG CGA ACC AAC AAG CTC CTC ATC CAG CGA CTC TTG GTG    603
Ser Gly Asn Ala Arg Thr Asn Lys Leu Leu Ile Gln Arg Leu Leu Val
            140             145             150

CAG CAG GTA CTG GAG GTG TCC TCC GAA TGG AAG ACG AAC AAG TCG GAA    651
Gln Gln Val Leu Glu Val Ser Ser Glu Trp Lys Thr Asn Lys Ser Glu
155             160             165             170

TCG CAG TAC ACG TCG CTG GAG TAC GAT TTC CGT GTC ACC TGC GAT CTC    699
Ser Gln Tyr Thr Ser Leu Glu Tyr Asp Phe Arg Val Thr Cys Asp Leu
            175             180             185

AAC TAC TAC GGA TCC GGC TGT GCC AAG TTC TGC CGG CCC CGC GAC GAT    747
Asn Tyr Tyr Gly Ser Gly Cys Ala Lys Phe Cys Arg Pro Arg Asp Asp
            190             195             200

TCA TTT GGA CAC TCG ACT TGC TCG GAG ACG GGC GAA ATT ATC TGT TTG    795
Ser Phe Gly His Ser Thr Cys Ser Glu Thr Gly Glu Ile Ile Cys Leu
            205             210             215

ACC GGA TGG CAG GGC GAT TAC TGT CAC ATA CCC AAA TGC GCC AAA GGC    843
Thr Gly Trp Gln Gly Asp Tyr Cys His Ile Pro Lys Cys Ala Lys Gly
            220             225             230

TGT GAA CAT GGA CAT TGC GAC AAA CCC AAT CAA TGC GTT TGC CAA CTG    891
Cys Glu His Gly His Cys Asp Lys Pro Asn Gln Cys Val Cys Gln Leu
235             240             245             250

GGC TGG AAG GGA GCC TTG TGC AAC GAG TGC GTT CTG GAA CCG AAC TGC    939
Gly Trp Lys Gly Ala Leu Cys Asn Glu Cys Val Leu Glu Pro Asn Cys
            255             260             265
```

FIG.13B

```
ATC CAT GGC ACC TGC AAC AAA CCC TGG ACT TGC ATC TGC AAC GAG GGT      987
Ile His Gly Thr Cys Asn Lys Pro Trp Thr Cys Ile Cys Asn Glu Gly
            270                 275                 280

TGG GGA GGC TTG TAC TGC AAC CAG GAT CTG AAC TAC TGC ACC AAC CAC     1035
Trp Gly Gly Leu Tyr Cys Asn Gln Asp Leu Asn Tyr Cys Thr Asn His
            285                 290                 295

AGA CCC TGC AAG AAT GGC GGA ACC TGC TTC AAC ACC GGC GAG GGA TTG     1083
Arg Pro Cys Lys Asn Gly Gly Thr Cys Phe Asn Thr Gly Glu Gly Leu
            300                 305                 310

TAC ACA TGC AAA TGC GCT CCA GGA TAC AGT GGT GAT GAT TGC GAA AAT     1131
Tyr Thr Cys Lys Cys Ala Pro Gly Tyr Ser Gly Asp Asp Cys Glu Asn
315             320                 325                 330

GAG ATC TAC TCC TGC GAT GCC GAT GTC AAT CCC TGC CAG AAT GGT GGT     1179
Glu Ile Tyr Ser Cys Asp Ala Asp Val Asn Pro Cys Gln Asn Gly Gly
                335                 340                 345

ACC TGC ATC GAT GAG CCG CAC ACA AAA ACC GGC TAC AAG TGT CAT TGC     1227
Thr Cys Ile Asp Glu Pro His Thr Lys Thr Gly Tyr Lys Cys His Cys
            350                 355                 360

GCC AAC GGC TGG AGC GGA AAG ATG TGC GAG GAG AAA GTG CTC ACG TGT     1275
Ala Asn Gly Trp Ser Gly Lys Met Cys Glu Glu Lys Val Leu Thr Cys
            365                 370                 375

TCG GAC AAA CCC TGT CAT CAG GGA ATC TGC CGC AAC GTT CGT CCT GGC     1323
Ser Asp Lys Pro Cys His Gln Gly Ile Cys Arg Asn Val Arg Pro Gly
            380                 385                 390

TTG GGA AGC AAG GGT CAG GGC TAC CAG TGC GAA TGT CCC ATT GGC TAC     1371
Leu Gly Ser Lys Gly Gln Gly Tyr Gln Cys Glu Cys Pro Ile Gly Tyr
395             400                 405                 410
```

FIG.13C

```
AGC GGA CCC AAC TGC GAT CTC CAG CTG GAC AAC TGC AGT CCG AAT CCA    1419
Ser Gly Pro Asn Cys Asp Leu Gln Leu Asp Asn Cys Ser Pro Asn Pro
            415                 420                 425

TGC ATA AAC GGT GGA AGC TGT CAG CCG AGC GGA AAG TGT ATT TGC CCA    1467
Cys Ile Asn Gly Gly Ser Cys Gln Pro Ser Gly Lys Cys Ile Cys Pro
            430                 435                 440

GCG GGA TTT TCG GGA ACG AGA TGC GAG ACC AAC ATT GAC GAT TGT CTT    1515
Ala Gly Phe Ser Gly Thr Arg Cys Glu Thr Asn Ile Asp Asp Cys Leu
            445                 450                 455

GGC CAC CAG TGC GAG AAC GGA GGC ACC TGC ATA GAT ATG GTC AAC CAA    1563
Gly His Gln Cys Glu Asn Gly Gly Thr Cys Ile Asp Met Val Asn Gln
            460                 465                 470

TAT CGC TGC CAA TGC GTT CCC GGT TTC CAT GGC ACC CAC TGT AGT AGC    1611
Tyr Arg Cys Gln Cys Val Pro Gly Phe His Gly Thr His Cys Ser Ser
475                 480                 485                 490

AAA GTT GAC TTG TGC CTC ATC AGA CCG TGT GCC AAT GGA GGA ACC TGC    1659
Lys Val Asp Leu Cys Leu Ile Arg Pro Cys Ala Asn Gly Gly Thr Cys
            495                 500                 505

TTG AAT CTC AAC AAC GAT TAC CAG TGC ACC TGT CGT GCG GGA TTT ACT    1707
Leu Asn Leu Asn Asn Asp Tyr Gln Cys Thr Cys Arg Ala Gly Phe Thr
            510                 515                 520

GGC AAG GAT TGC TCT GTG GAC ATC GAT GAG TGC AGC AGT GGA CCC TGT    1755
Gly Lys Asp Cys Ser Val Asp Ile Asp Glu Cys Ser Ser Gly Pro Cys
            525                 530                 535

CAT AAC GGC GGC ACT TGC ATG AAC CGC GTC AAT TCG TTC GAA TGC GTG    1803
His Asn Gly Gly Thr Cys Met Asn Arg Val Asn Ser Phe Glu Cys Val
            540                 545                 550
```

FIG.13D

```
TGT GCC AAT GGT TTC AGG GGC AAG CAG TGC GAT GAG GAG TCC TAC GAT     1851
Cys Ala Asn Gly Phe Arg Gly Lys Gln Cys Asp Glu Glu Ser Tyr Asp
555                 560                 565                 570

TCG GTG ACC TTC GAT GCC CAC CAA TAT GGA GCG ACC ACA CAA GCG AGA     1899
Ser Val Thr Phe Asp Ala His Gln Tyr Gly Ala Thr Thr Gln Ala Arg
                575                 580                 585

GCC GAT GGT TTG ACC AAT GCC CAG GTA GTC CTA ATT GCT GTT TTC TCC     1947
Ala Asp Gly Leu Thr Asn Ala Gln Val Val Leu Ile Ala Val Phe Ser
                590                 595                 600

GTT GCG ATG CCT TTG GTG GCG GTT ATT GCG GCG TGC GTG GTC TTC TGC     1995
Val Ala Met Pro Leu Val Ala Val Ile Ala Ala Cys Val Val Phe Cys
                605                 610                 615

ATG AAG CGC AAG CGT AAG CGT GCT CAG GAA AAG GAC GAC GCG GAG GCC     2043
Met Lys Arg Lys Arg Lys Arg Ala Gln Glu Lys Asp Asp Ala Glu Ala
620                 625                 630

AGG AAG CAG AAC GAA CAG AAT GCG GTG GCC ACA ATG CAT CAC AAT GGC     2091
Arg Lys Gln Asn Glu Gln Asn Ala Val Ala Thr Met His His Asn Gly
635                 640                 645                 650

AGT GGG GTG GGT GTA GCT TTG GCT TCA GCC TCT CTG GGC GGC AAA ACT     2139
Ser Gly Val Gly Val Ala Leu Ala Ser Ala Ser Leu Gly Gly Lys Thr
                655                 660                 665

GGC AGC AAC AGC GGT CTC ACC TTC GAT GGC GGC AAC CCG AAT ATC ATC     2187
Gly Ser Asn Ser Gly Leu Thr Phe Asp Gly Gly Asn Pro Asn Ile Ile
                670                 675                 680

AAA AAC ACC TGG GAC AAG TCG GTC AAC AAC ATT TGT GCC TCA GCA GCA     2235
Lys Asn Thr Trp Asp Lys Ser Val Asn Asn Ile Cys Ala Ser Ala Ala
                685                 690                 695
```

FIG.13E

```
GCA GCG GCG GCG GCG GCA GCA GCG GCG GAC GAG TGT CTC ATG TAC GGC    2283
Ala Ala Ala Ala Ala Ala Ala Ala Ala Asp Glu Cys Leu Met Tyr Gly
    700             705                 710

GGA TAT GTG GCC TCG GTG GCG GAT AAC AAC AAT GCC AAC TCA GAC TTT    2331
Gly Tyr Val Ala Ser Val Ala Asp Asn Asn Asn Ala Asn Ser Asp Phe
715             720                 725                 730

TGT GTG GCT CCG CTA CAA AGA GCC AAG TCG CAA AAG CAA CTC AAC ACC    2379
Cys Val Ala Pro Leu Gln Arg Ala Lys Ser Gln Lys Gln Leu Asn Thr
                735                 740                 745

GAT CCC ACG CTC ATG CAC CGC GGT TCG CCG GCA GGC AGC TCA GCC AAG    2427
Asp Pro Thr Leu Met His Arg Gly Ser Pro Ala Gly Ser Ser Ala Lys
            750                 755                 760

GGA GCG TCT GGC GGA GGA CCG GGA GCG GCG GAG GGC AAG AGG ATC TCT    2475
Gly Ala Ser Gly Gly Gly Pro Gly Ala Ala Glu Gly Lys Arg Ile Ser
        765                 770                 775

GTT TTA GGC GAG GGT TCC TAC TGT AGC CAG CGT TGG CCC TCG TTG GCG    2523
Val Leu Gly Glu Gly Ser Tyr Cys Ser Gln Arg Trp Pro Ser Leu Ala
    780             785                 790

GCG GCG GGA GTG GCC GGA GCC TGT TCA TCC CAG CTA ATG GCT GCA GCT    2571
Ala Ala Gly Val Ala Gly Ala Cys Ser Ser Gln Leu Met Ala Ala Ala
795             800             805                 810

TCG GCA GCG GGC AGC GGA GCG GGG ACG GCG CAA CAG CAG CGA TCC GTG    2619
Ser Ala Ala Gly Ser Gly Ala Gly Thr Ala Gln Gln Gln Arg Ser Val
            815                 820                 825

GTC TGC GGC ACT CCG CAT ATG TAACTCCAAA AATCCGGAAG GGCTCCTGGT       2670
Val Cys Gly Thr Pro His Met
                830
AAATCCGGAG AAATCCGCAT GGAGGAGCTG ACAGCACATA CACAAAGAAA AGACTGGGTT  2730
GGGTTCAAAA TGTGAGAGAG ACGCCAAAAT GTTGTTGTTG ATTGAAGCAG TTTAGTCGTC  2790
ACGAAAAATG AAAAATCTGT AACAGGCATA ACTCGTAAAC TCCCTAAAAA ATTTGTATAG  2850
TAATTAGCAA AGCTGTGACC CAGCCGTTTC GATCCCGAAT TC                    2892
```

FIG.13F

2889 GATCTACTAC
GAGGAGGTTAAGGAGAGCTATGTGGGCGAGCGACGCGAATACGATCCCCACATCACCGATCCCAGGGTC
ACACGCATGAAGATGGCCGGCCTGAAGCCCAACTCCAAATACCGCATCTCCATCACTGCCACCACGAAA
ATGGGCGAGGGATCTGAACACTATATCGAAAAGACCACGCTCAAGGATGCCGTCAATGTGGCCCCTGCC
ACGCCATCTTTCTCCTGGGAGCAACTGCCATCCGACAATGGACTAGCCAAGTTCCGCATCAACTGGCTG
CCAAGTACCGAGGGTCATCCAGGCACTCACTTCTTTACGATGCACAGGATCAAGGGCGAAACCCAATGG
ATACGCGAGAATGAGGAAAAGAACTCCGATTACCAGGAGGTCGGTGGCTTAGATCCGGAGACCGCCTAC
GAGTTCCGCGTGGTGTCCGTGGATGGCCACTTTAACACGGAGAGTGCCACGCAGGAGATCGACACGAAC
ACCGTTGAGGGACCAATAATGGTGGCCAACGAGACGGTGGCCAATGCCGGATGGTTCATTGGCATGATG
CTGGCCCTGGCCTTCATCATCATCCTCTTCATCATCATCTGCATTATCCGACGCAATCGGGGCGGAAAG
TACGATGTCCACGATCGGGAGCTGGCCAACGGCCGGCGGGATTATCCCGAAGAGGGCGGATTCCACGAG
TACTCGCAACCGTTGGATAACAAGAGCGCTGGTCGCCAATCCGTGAGTTCAGCGAACAAACCGGGCGTG
GAAAGCGATACTGATTCGATGGCCGAATACGGTGATGGCGATACAGGACAATTTACCGAGGATGGCTCC
TTCATTGGCCAATATGTTCCTGGAAAGCTCCAACCGCCGGTTAGCCCACAGCCACTGAACAATTCCGCT
GCGGCGCATCAGGCGGCGCCAACTGCCGGAGGATCGGGAGCAGCCGGATCGGCAGCAGCAGCCGGAGCA
TCGGGTGGAGCATCGTCCGCCGGAGGAGCAGCTGCCAGCAATGGAGGAGCTGCAGCCGGAGCCGTGGCC
ACCTACGTCTAAGCTTGGTACC 3955

FIG. 16A  PRIMER cdc1:  5'  GAT GCI AAT GTI CAA GAT AAT ATG GG  3'
                                C       C   G   C   C FIG. 16B  PRIMER cdc2:  5'  AT IAG ATC TTC IAC CAT ICC TTC AA  3'
                               A G   C           C   G
                                                     T FIG. 16C  PRIMER cdc3:  5'  TC CAT ATG ATC IGT AAT ITC ICG ATT  3'
                               G   G           G       T   G
                                                T

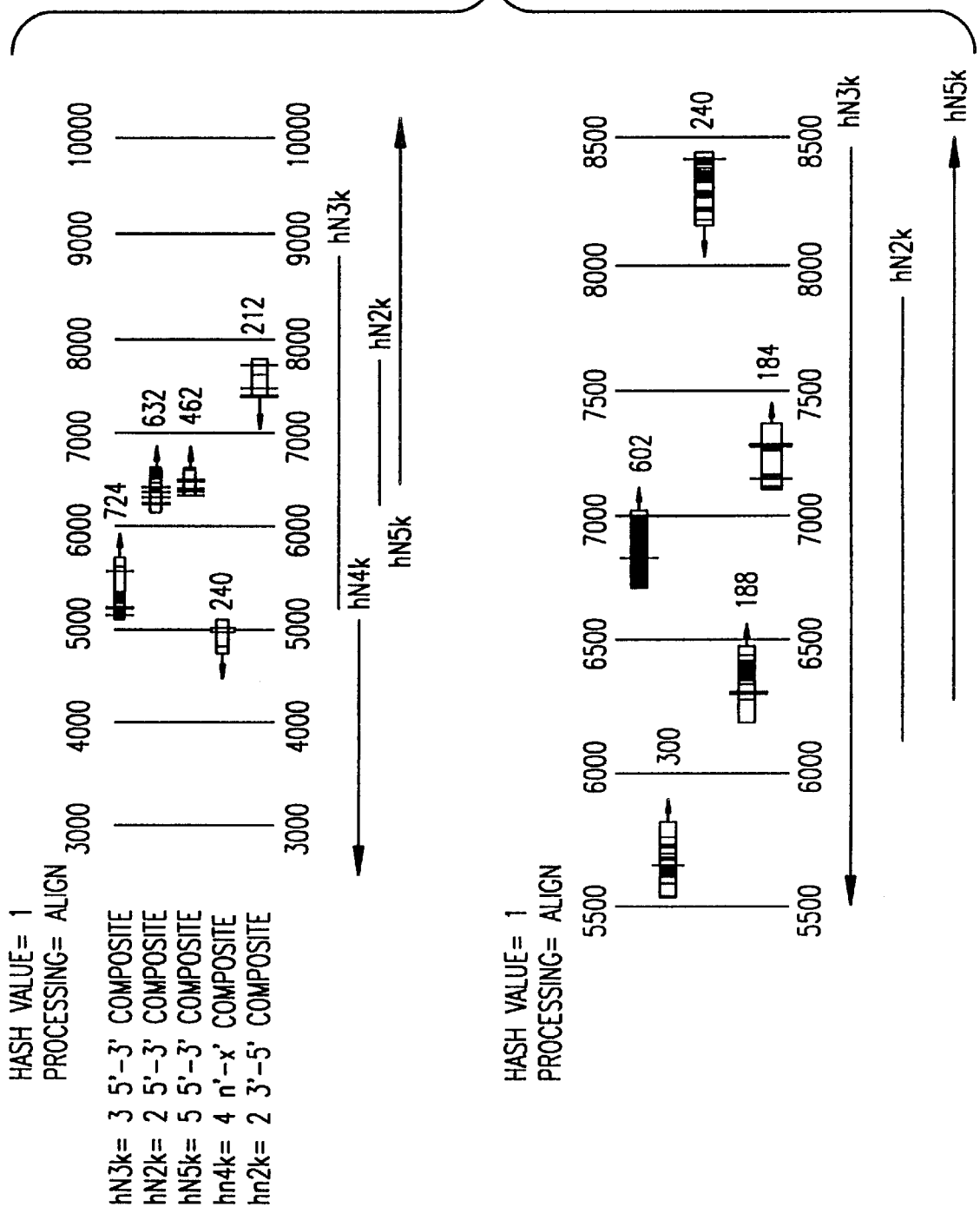

```
  1  GAATTCCGCT GGGAGAATGG TCTGAGCTAC CTGCCCGTCC TGCTGGGGCA TCAATGGCAA
 61  GTGGGGAAAG CCACACTGGG CAAACGGGCC AGGCCATTTC TGGAATGTGG TACATGGTGG
121  GCAGGGGGCC CGCAACAGCT GGAGGGCAGG TGGACTGAGG CTGGGGATCC CCGCTGGTT
181  GGGCAATACT GCCTTTACCC ATGAGCTGGA AAGTCACAAT GGGGGCAAG GGCTCCCGAG
241  GGTGGTTATG TGCTTCCTTC AGGTGGC
```

FIG.19A

```
  1  GAATTCCTTC CATTATACGT GACTTTTCTG AAACTGTAGC CACCCTAGTG TCTCTAACTC
 61  CCTCTGGAGT TTGTCAGCTT TGGTCTTTTC AAAGAGCAGG CTCTCTTCAA GCTCCTTAAT
121  GCGGGCATGC TCCAGTTTGG TCTGCGTCTC AAGATCACCT TTGGTAATTG ATTCTTCTTC
181  AACCCGGAAC TGAAGGCTGG CTCTCACCCT CTAGGCAGAG CAGGAATTCC GAGGTGGATG
241  TGTTAGATGT GAATGTCCGT GGCCCAGATG GCTGCACCCC ATTGATGTTG GCTTCTCTCC
301  GAGGAGGCAG CTCAGATTTG AGTGATGAAG ATGAAGATGC AGAGGACTGT TCTGCTAACA
361  TCATCACAGA CTTGGTCTAC CAGGGTGCCA GCCTCCAGNC CAGACAGACC GGACTGGTGA
421  GATGGCCCTG CACCTTGCAG CCCGCTACTC ACGGGCTGAT GCTGCCAAGC GTCTCCTGGA
481  TGCAGGTGCA GATGCCAATG CCCAGGACAA CATGGGCCGC TGTCCACTCC ATGCTGCAGT
541  GGCACGTGAT GCCAAGGTGT ATTCAGATCT GTTA
```

FIG.19B

```
  1  TCCAGATTCT GATTCGCAAC CGAGTAACTG ATCTAGATGC CAGGATGAAT GATGGTACTA
 61  CACCCCTGAT CCTGGCTGCC CGCCTGGCTG TGGAGGGAAT GGTGGCAGAA CTGATCAACT
121  GCCAAGCGGA TGTGAATGCA GTGGATGACC ATGGAAAATC TGCTCTTCAC TGGGCAGCTG
181  CTGTCAATAA TGTGGAGGCA ACTCTTTTGT TGTTGAAAAA TGGGGCCAAC CGAGACATGC
241  AGGACAACAA GGAAGAGACA CCTCTGTTTC TTGCTGCCCG GGAGGAGCTA TAAGC
```

FIG.19C

```
  1  GAATTCCCAT GAGTCGGGAG CTTCGATCAA AATTGATGAG CCTTTAGAAG GATCCGAAGA
 61  TCGGATCATT ACCATTACAG GAACAGGCAC CTGTAGCTGG TGGCTGGGGG TGTTGTCCAC
121  AGGCGAGGAG TAGCTGTGCT GCGAGGGGGG CGTCAGGAAC TGGGCTGCGG TCACGGGTGG
181  GACCAGCGAG GATGGCAGCG ACGTGGGCAG GGCGGGGCTC TCCTGGGGCA GAATAGTGTG
241  CACCGCCAGG CTGCTGGGGC CCAGTACTGC ACGTCTGCCT GGCTCGGCTC TCCACTCAGG
301  AAGCTCCGGC CCAGGTGGCC GCTGGCTGCT GAG
```

FIG.20A

```
  1  GAATTCCTGC CAGGAGGACG CGGGCAACAA GGTCTGCAGC CTGCAGTGCA ACAACCACGC
 61  GTGCGGCTGG GACGGCGGTG ACTGCTCCCT CAACTTCACA ATGACCCCTG GAAGAACTGC
121  ACGCAGTCTC TGCAGTGCTG GAAGTACTTC AGTGACGGCC ACTGTGACAC CCAGTGCAAC
181  TCAGCCGGCT GCCTCTTCGA CGGCTTTGAC TGCCAGCGGC GGAAGGCCAG TTGCAACCCC
241  CTGTACGACC AGTACTGCAA GGACCACTTG AGCGACGGGC ACTGCGACCA GGGCTGCAAC
301  AGCGCGGAGT NCAGNTGGGA CGGGCTGGAC TGTGCGGCAG TGTACCCGAG AGCTGGCGGC
361  GCACGCTGGT GGTGGTGGTG CTGATGCCGC CGGAGCAGCT GCGCAACAGC TCCTTCCACT
421  TCCTGCGGGA CGTCAGCCGC GTGCTGCACA CCAACGTGTC TTCAAGCGTG ACGCACACGG
481  CCAGCAGATG ATGTTCCCCT ACTACGGCCG CGAGGAGGAG CTGCGCAAGC CCCATCAAGC
541  GTGCCGCCGA GGGCTGGGCC GCACCTGACG CCTGCTGGGC CA
```

FIG.20B

```
  1  TCAGCCGAGT GCTGCACACC AACGTGTCTT CAAGCGTGAC GCACACGGCC AGCAGATGAT
 61  GTTCCCCTAC TACGGCCGCG AGGAGGAGCT GCGCAAGCCC CATCAAGCGT GCCGCCGAGG
121  GCTGGGCCGC ACCTGACGCC TGCTGGGCCA
```

FIG.20C

```
  1  TTACCATTAC AGGAACAGGC ACCTGTAGCT GGTGGCTGGG GGTGTTGTCC ACAGGCGAGG
 61  AGTAGCTGTG CTGCGAGGGG GGCGTCAGGA ACTGGGCTGC GGTCACGGGT GGGACCAGCG
121  AGGATGGCAG CGACGTGGGC AGGGCGGGGC TCTCCTGGGG CAGAATAGTG TGCACCGCCA
181  GCTGCTGGGG CCCAGTGCTG CACGTCTGCC TGGCTCGGCT CTCCACTCAG GAAGCTCCGG
241  CCCAGGT
```

FIG.20D

```
  1 GAATTCCATT CAGGAGGAAA GGGTGGGGAG AGAAGCAGGC ACCCACTTTC CCGTGGCTGG
 61 ACTCGTTCCC AGGTGGCTCC ACCGGCAGCT GTGACCGCCG CAGGTGGGGG CGGAGTGCCA
121 TTCAGAAAAT TCCAGAAAAG CCCTACCCCA ACTCGGACGG CAACGTCACA CCCGTGGGTA
181 GCAACTGGCA CACAAACAGC CAGCGTGTCT GGGGCACGGG GGGATGGCAC CCCCTGCAGG
241 CAGAGCTG
```

FIG.21A

```
  1 CTAAAGGGAA CAAAAGCNGG AGCTCCACCG CGGGCGGCNC NGCTCTAGAA CTAGTGGANN
 61 NCCCGGGCTG CAGGAATTCC GGCGGACTGG GCTCGGGCTC AGAGCGGCGC TGTGGAAGAG
121 ATTCTAGACC GGGAGAACAA GCGAATGGCT GACAGCTGGC CTCCAAAGTC ACCAGGCTCA
181 AATCGCTCGC CCTGGACATC GAGGGATGCA GAGGATCAGA ACCGGTACCT GGATGGCATG
241 ACTCGGATTT ACAAGCATGA CCAGCCTGCT TACAGGGAGC GTGANNTTTT CACATGCAGT
301 CGACAGACAC GAGCTCTATG CAT
```

FIG.21B

```
  1  GAATTCCGAG GTGGATGTGT TAGATGTGAA TGTCCGTGGC CCAGATGGCT GCACCCCATT
 61  GATGTTGGCT TCTCTCCGAG GAGGCAGCTC AGATTTGAGT GATGAAGATG AAGATGCAGA
121  GGACTCTTCT GCTAACATCA TCACAGACTT GGTCTTACCA GGGTGCCAGC CTTCCAGGCC
181  CAAGAACAGA CCGGACTTGG TGAGATGGCC CTGCACCTTG CAGCCCGCTA CTACGGGCTG
241  ATGCTGCCAA GGTTCTGGAT GCAGGTGCAG ATGCCAATGC CCAGGACAAC ATGGGCCGCT
301  GTCCACTCCA TGCTGCAGTG GCACTGATGC
```

FIG.22A

```
  1  CAGAGGATGG TGAGGGTCCA TGCAGATAGG TTCTCCCCAT CCTGTGAATA ATAAATGGGT
 61  GCAAGGGCAG AGAGTCACCA TTTAGAATGA TAAAATGTTT GCACACTATG AAAGAGGCTG
121  ACAGAATGTT GCCACATGGA GAGATAAAGC AGAGAATGAA CAAACTT
```

FIG.22B

```
  1  AGGATGAATG ATGGTACTAC ACCCCTGATC CTGGCTGCCC GCCTGGCTGT GGAGGGAATG
 61  GTGGCAGAAC TGATCAACTG CCAAGCGGAT GTGAATGCAG TGGATGACCA TGGAAAATCT
121  GCTCTTCACT GGGCAGCTGC TGTCAATAAT GTGGAGGCAA CTCTTTTGTT GTTGAAAAAT
181  GGGGCCAACC GAGACATGCA GGACAACAAG GAAGAGACAC CTCTG
```

FIG.22C

```
  1  AATAATAAAT GGGTGCAAGG GCAGAGAGTC ACCATTTAGA ATGATAAAAT GTTTGCACAC
 61  TATGAAAGAG GCTGACAGAA TGTTGCCACA TGGAGAGATA AAGCAGAGAA TGAACAAACT
121  T
```

FIG.22D

```
          10        20        30        40
 *         *         *         *         *
TGC CAG GAG GAC GCG GGC AAC AAG GTC TGC AGC CTG CAG AAC AAC
 C   Q   E   D   A   G   N   K   V   C   S   L   Q   N   N>

50        60        70        80        90
  *         *         *         *         *
CAC GCG TGC GGC TGG GAC TGC GGT GAC TGC TCC CTC AAC TTC AAT GAC
 H   A   C   G   W   D   C   G   D   C   S   L   N   F   N   D>

100       110       120       130       140
  *         *         *         *         *
CCC TGG AAG AAC TGC ACG CAG TCT CTG CAG TCC CTC TGG AAG TAC TTC AGT
 P   W   K   N   C   T   Q   S   L   Q   S   L   W   K   Y   F   S>

150       160       170       180       190
  *         *         *         *         *
GAC GGC CAC TGT GAC AGC CAG TGC AAC TCA GCC GGC TGC CTC TTC GAC
 D   G   H   C   D   S   Q   C   N   S   A   G   C   L   F   D>
```

FIG. 23A

```
      200                 210                 220                 230                 240
       *                   *                   *                   *                   *
GGC  TTT  GAC  TGC  CAG  CGT  GCG  GAA  GGC  CAG  TGC  AAC  CCC  CTG  TAC  GAC
 G    F    D    C    Q    R    A    E    G    Q    C    N    P    L    Y    D 250                 260                 270                 280
       *                   *                   *                   *
CAG  TAC  TGC  AAG  GAC  CAC  TTC  AGC  GAC  GGG  CAC  TGC  GAC  CAG  TGC  GGC
 Q    Y    C    K    D    H    F    S    D    G    H    C    D    Q    C    G 290                 300                 310                 320                 330
   *                   *                   *                   *                   *
AAC  AGC  GCG  GAG  TGG  GAG  TGC  GAG  CTG  GAC  CTG  GTG  GAC  TGT  GAG  CAT  GTA
 N    S    A    E    W    E    C    E    L    D    L    V    D    C    E    H    V 340                 350                 360                 370                 380
   *                   *                   *                   *                   *
CCC  GAG  AGG  CTG  GCG  GCC  ACG  CTG  GTG  GTG  GTG  CTG  ATG  CCG
 P    E    R    L    A    A    T    L    V    V    V    L    M    P
```

FIG.23B

```
      *    390    *    400    *    410    *    420    *    430    *
CCG  GAG  CAG  CTG  CGC  AAC  AGC  TCC  TTC  CAC  TTC  CTG  CGG  GAG  CTC  AGC
 P    E    Q    L    R    N    S    S    F    H    F    L    R    E    L    S

*    440    *    450    *    460    *    470    *    480    *
CGC  GTG  CTG  CAC  ACC  AAC  GTG  GTC  TTC  AAG  CGT  GAC  GCA  CAC  GGC  CAG
 R    V    L    H    T    N    V    V    F    K    R    D    A    H    G    Q

*    490    *    500    *    510    *    520    *
CAG  ATG  ATC  TTC  CCC  TAC  TAC  GGC  CGC  GAG  GAG  CTG  CGC  AAG  CAC
 Q    M    I    F    P    Y    Y    G    R    E    E    L    R    K    H

530    *    540    *    550    *    560    *    570    *
CCC  ATC  AAG  CGT  GCC  GCA  TGG  GCC  GAG  GGC  GCA  CCT  GAC  GCC  CTG  CTG
 P    I    K    R    A    A    W    A    E    G    A    P    D    A    L    L
```

FIG. 23C

```
         580         590         600         610         620
          *           *           *           *           *
GGC CAG GTG AAG GCC TCG CCT GTT GGC AGC GAG GGT GGG CGG
 G   Q   V   K   A   S   P   V   G   S   E   G   G   R>

630         640         650         660         670
          *           *           *           *           *
CGG CGG AGG GAG CTG GAC CCC ATG GAC GTC CGC TCC GGC ATC GTC TAC
 R   R   R   E   L   D   P   M   D   V   R   S   G   I   V   Y>

680         690         700         710         720
          *           *           *           *           *
CTG GAG ATT GAC AAC CGG CAG TGT GTG CAG GCC TCC TCG CAG TGC TTC
 L   E   I   D   N   R   Q   C   V   Q   A   S   S   Q   C   F>

730         740         750         760
          *           *           *           *
CAG AGT GCC ACC GAC GTG GCC GCA TTC CTG GGA GCG CTC GCC TCG CTG
 Q   S   A   T   D   V   A   A   F   L   G   A   L   A   S   L>
```

FIG.23D

```
     770       780       790       800       810
      *         *         *         *         *
GGC AGC CTC AAC ATC CCC TAC AAG ATC GAG GCC GTG CAG AGT GAG ACC
 G   S   L   N   I   P   Y   K   I   E   A   V   Q   S   E   T>

820       830       840       850       860
      *         *         *         *         *
GTG GAG CCG CCC CCG CCG GCG CAG CTG TTC CAC TTC ATG TAC GTG GCG GCG
 V   E   P   P   P   P   A   Q   L   F   H   F   M   Y   V   A   A>

870       880       890       900       910
      *         *         *         *         *
GCC TTT GTG CTT CTG TTC TTC GTG GGC TGC GGG GTG CTG CTG TCC
 A   F   V   L   L   F   F   V   G   C   G   V   L   L   S>

920       930       940       950       960
      *         *         *         *         *
CGC AAG CGC CGG CAG CAT GGC CAG CTC TGG TTC CCT GAG GGC TTC
 R   K   R   R   Q   H   G   Q   L   W   F   P   E   G   F>
```

FIG. 23E

```
        *     970     *     980     *     990     *    1000     *
AAA GTG TCT GAG GCC AGC AAG AAG CGG GAG CCC CTC GGC GAG
 K   V   S   E   A   S   K   K   R   E   P   L   G   E

1010     *    1020     *    1030     *    1040     *    1050     *
GAC TCC GTG GGC CTC AAG CCC CTG AAG AAC GCT TCA GAC GGT GCC CTC
 D   S   V   G   L   K   P   L   K   N   A   S   D   G   A   L

1060     *    1070     *    1080     *    1090     *    1100     *
ATG GAC AAC CAG AAT GAG TGG GGG GAC GAG GAC CTG GAG ACC AAG
 M   D   N   Q   N   E   W   G   D   E   D   L   E   T   K

1110     *    1120     *    1130     *    1140     *    1150     *
AAG TTC CGG TTC GAG GAG CCC GTG GTT CTG CCT GAC CTG GAC GAC CAG
 K   F   R   F   E   E   P   V   V   L   P   D   L   D   D   Q
```

FIG.23F

FIG. 23G

```
      1160          1170          1180          1190          1200
        *             *             *             *             *
ACA GAC CAC CGG CAG TGG ACT CAG CAC CTG GAT GCC GCT GAC CTG
 T   D   H   R   Q   W   T   Q   H   L   D   A   A   D   L 1210          1220          1230          1240
        *             *             *             *
CGC ATG TCT GCC ATG GCC CCC ACA CCG CCC CAG GGT GAG GTT GAC GCC
 R   M   S   A   M   A   P   T   P   P   Q   G   E   V   D   A 1250          1260          1270          1280          1290
  *             *             *             *             *
GAC TGC ATG GAC GTC AAT GTC CGC GGG CCT GAT GGC TTC ACC CCG CTC
 D   C   M   D   V   N   V   R   G   P   D   G   F   T   P   L 1300          1310          1320          1330          1340
  *             *             *             *             *
ATG ATC GCC TCC TGC AGC TGC AGC GGG GGC CTG GAG ACG GGC AAC AGC GAG
 M   I   A   S   C   S   C   S   G   G   L   E   T   G   N   S   E
```

```
      1350         1360         1370         1380         1390
   *    *       *    *       *    *       *    *       *    *
GAA GAG GAC GCG CCG GCC GTC ATC TCC GAC TTC ATC TAC CAG GGC
 E   E   D   A   P   A   V   I   S   D   F   I   Y   Q   G 1400         1410         1420         1430         1440
   *    *       *    *       *    *       *    *       *    *
GCC AGC CTG CAC AAC CAG ACA GAC CGC ACG GGC GAG ACC GCC TTG CAC
 A   S   L   H   N   Q   T   D   R   T   G   E   T   A   L   H 1450         1460         1470         1480         1530
   *    *       *    *       *    *       *    *       *    *
CTG GCC GCC CGC TAC TCA CGC TCT GAT GCC AAG CGC CTG CTG GAG
 L   A   A   R   Y   S   R   S   D   A   K   R   L   L   E 1490        1500         1510         1520         1530
   *    *       *    *       *    *       *    *       *    *
GCC AGC GCA GAT GCC AAC ATC CAG GAC AAC ATG GGC CGC ACC CCG CTG
 A   S   A   D   A   N   I   Q   D   N   M   G   R   T   P   L
```

FIG. 23H

```
1540                1550                1560                1570                1580
  *       *           *       *           *       *           *       *           *       *
CAT GCG GCT GTG TCT GCC GAC GCA CAA GGT GTC TTC CAG ATC CTG ATC
 H   A   A   V   S   A   D   A   Q   G   V   F   Q   I   L   I>

1590                1600                1610                1620                1630
  *       *           *       *           *       *           *       *           *       *
CGG AAC CGA GCC ACA GAC CTG GAT GCC CGC ATG CAT GAT GGC ACG ACG
 R   N   R   A   T   D   L   D   A   R   M   H   D   G   T   T>

1640                1650                1660                1670                1680
  *       *           *       *           *       *           *       *           *       *
CCA CTG ATC CTG GCT GCC CGC CTG GCC GTG GAG GGC ATG CTG GAG GAC
 P   L   I   L   A   A   R   L   A   V   E   G   M   L   E   D>

1690                1700                1710                1720
  *       *           *       *           *       *           *       *
CTC ATC AAC TCA CAC GCC GAC GTC AAC GCC GTA GAT GAC CTG GGC AAG
 L   I   N   S   H   A   D   V   N   A   V   D   D   L   G   K>

1730                1740                1750                1760                1770
  *       *           *       *           *       *           *       *           *
TCC GCC CTG CAC TGG GCC GCC GCC GTG AAC AAT GTG GAT GCC GCA GTT
 S   A   L   H   W   A   A   A   V   N   N   V   D   A   A   V>
```

FIG. 231

```
       1780        1790        1800        1810        1820
        *           *           *           *           *
GTG CTC CTG AAG AAC GGG GCT AAC AAA GAT ATG CAG AAC AAG AGG GAG
 V   L   L   K   N   G   A   N   K   D   M   Q   N   K   R   E >

1830        1840        1850        1860        1870
        *           *           *           *           *
GAG ACA CCC CTG TTT CTG GCC GCC CGG GAG GGC AGC TAC GAG ACC GCC
 E   T   P   L   F   L   A   A   R   E   G   S   Y   E   T   A >

1880        1890        1900        1910        1920
        *           *           *           *           *
AAG GTG CTG CTG CTG GAC CAC TTT GCC AAC CGG GAC ATC ACG GAT CAT ATG
 K   V   L   L   L   D   H   F   A   N   R   D   I   T   D   H   M >

1930        1940        1950        1960
        *           *           *           *
GAC CGC CTG CCG CGC GAC ATC GCA CAG GAG CGC ATG CAT CAC GAC ATC
 D   R   L   P   R   D   I   A   Q   E   R   M   H   H   D   I >
```

FIG.23J

```
1970        1980           1990           2000           2010
 *           *              *              *              *
GTG AGG CTG CTG GAC GAG TAC AAC CTG GTG CGC AGC CCG CAG CTG CAC
 V   R   L   L   D   E   Y   N   L   V   R   S   P   Q   L   H 2020           2030           2040           2050           2060
         *              *              *              *              *
GGA GCC CCG CTG GGG GGC TAC CCG ACG CCC ACC CTG TCG CCC CTC TGC TCG
 G   A   P   L   G   G   Y   P   T   P   T   L   S   P   L   C   S 2070           2080           2090           2100           2110
      *              *              *              *              *
CCC AAC GGC TAC CTG GGC AGC CTC AAG CCC GGC GTG CAG GGC AAG AAG
 P   N   G   Y   L   G   S   L   K   P   G   V   Q   G   K   K 2120           2130           2140           2150           2160
 *              *              *              *              *
CGC AAG CCC AGC AGC AAA GGC CTG GCC TGT GGA AGC AAG GAG GCC
 R   K   P   S   S   K   G   L   A   C   G   S   K   E   A

GTC CGC AAG CCC AGC AGC AAA GGC CTG GCC TGT GGA AGC AAG GAG GCC
 V   R   K   P   S   S   K   G   L   A   C   G   S   K   E   A
```

FIG. 23K

```
                    2170                2180                2190                2200
                     *                   *                   *                   *
              AAG GAC CTC AAG GCA CGG AGG AAG AAG TCC CAG GAT GGC AAG GGC TGC
               K   D   L   K   A   R   R   K   K   S   Q   D   G   K   G   C>

2210                2220                2230                2240                2250
  *                   *                   *                   *                   *
 CTG CTG GAC AGC TCC GGC ATG CTC TCG CCC GTG GAC TCC CTG GAG TCA
  L   L   D   S   S   G   M   L   S   P   V   D   S   L   E   S>

2260                2270                2280                2290                2300
  *                   *                   *                   *                   *
 CCC CAT GGC TAC CTG TCA GAC GTG GCC TCG CCG CCA CTG CTG CCC TCC
  P   H   G   Y   L   S   D   V   A   S   P   P   L   L   P   S>

2310                2320                2330                2340                2350
  *                   *                   *                   *                   *
 CCG TTC CAG CAG TCT CCG TCC GTG CCC CTC AAC CAC CTG CCT GGG ATG
  P   F   Q   Q   S   P   S   V   P   L   N   H   L   P   G   M>
```

FIG. 23L

```
      2360        2370        2380        2390        2400
*    *    *    *    *    *    *    *    *
CCC  GAC  ACC  CAC  CTG  GGC  ATC  GGG  CAC  CTG  AAC  GTG  GCG  GCC  AAG  CCC
 P    D    T    H    L    G    I    G    H    L    N    V    A    A    K    P>

2410        2420        2430        2440
*    *    *    *    *    *    *    *    *
GAG  ATG  GCG  GCG  CTG  CGT  CTC  TCC  CAC  CTG  GGT  GGG  GGC  CGG  CTG  GCC  TTT  GAG  ACT  GGC
 E    M    A    A    L    R    L    S    H    L    G    G    G    R    L    A    F    E    T    G>

2450       2460        2470        2480        2490
*    *    *    *    *    *    *    *    *    *
CCA  CCT  CGT  CTC  TCC  CAC  CTG  CCT  GTG  GCC  CGG  CTG  TCT  GGC  CTG  GCC  ACC  AGC  ACC  GTC
 P    P    R    L    S    H    L    P    V    A    R    L    S    G    L    A    T    S    T    V>

2500       2510        2520        2530        2540
*    *    *    *    *    *    *    *    *    *
CTG  GGC  TCC  AGC  AGC  GGA  GGG  GCC  CTG  AAT  TTC  ACT  GTG  GGC  GGG  TCC
 L    G    S    S    S    G    G    A    L    N    F    T    V    G    G    S>
```

FIG. 23 M

```
      2550                2560                2570                2580                2590
       *                   *                   *                   *                   *
ACC AGT TTG AAT GGT CAA TGC GAG TGG CTG TCC CGG CTG CAG AGC GGC
 T   S   L   N   G   Q   C   E   W   L   S   R   L   Q   S   G>

2600                2610                2620                2630                2640
       *                   *                   *                   *                   *
ATG GTG CCG AAC CAA TAC AAC CCT CTG CGG GGG AGT GTG GCA CCA GGC
 M   V   P   N   Q   Y   N   P   L   R   G   S   V   A   P   G>

2650                2660                2670                2680
       *                   *                   *                   *
CCC CTG AGC ACA CAG GCC CCC TCC CTG CAG CAT GGC ATG GTA GGC CCG
 P   L   S   T   Q   A   P   S   L   Q   H   G   M   V   G   P>

2690                2700                2710                2720                2730
       *                   *                   *                   *                   *
CTG CAC AGT AGC AGC CTT GCT GCC AGC GCC CTG TCC CAG ATG AGC TAC
 L   H   S   S   S   L   A   A   S   A   L   S   Q   M   S   Y>

FIG.23N
```

```
         2740                2750                2760                2770                2780
          *                   *                   *                   *                   *
CAG GGC CTG CCC AGC ACC CGG CTG GCC ACC CAG CCT CAC CTG GTG CAG
 Q   G   L   P   S   T   R   L   A   T   Q   P   H   L   V   Q >

2790                2800                2810                2820                2830
          *                   *                   *                   *                   *
ACC CAG CAG GTG CAG CCA CAA AAC TTA CAG ATG CAG CAG AAC CTG
 T   Q   Q   V   Q   P   Q   N   L   Q   M   Q   Q   N   L >

2840                2850                2860                2870                2880
          *                   *                   *                   *                   *
CAG CCA GCA AAC ATC CAG CAG CAG CAA AGC CTG CAG CCG CCA CCA
 Q   P   A   N   I   Q   Q   Q   Q   S   L   Q   P   P   P >

2890                2900                2910                2920                2930
          *                   *                   *                   *                   *
CCA CCA CAG CCG CAC CTT GGC GTG AGC TCA GCA GCC AGC GGC CAC CTG
 P   P   Q   P   H   L   G   V   S   S   A   A   S   G   H   L >

2930                2940                2950                2960                2970
          *                   *                   *                   *                   *
GGC CGG AGC TTC CTG AGT GGA GAG CCG AGC CAG GCA GAC GTG CAG CCA
 G   R   S   F   L   S   G   E   P   S   Q   A   D   V   Q   P >
```

FIG. 23 O

```
                2990        3000        3010        3020
       *          *           *           *           *
CTG GGC CCC AGC AGC CTG GCG GTG CAC ACT ATT CTG CCC CAG GAG AGC
 L   G   P   S   S   L   A   V   H   T   I   L   P   Q   E   S>

3030        3040        3050        3060        3070
       *          *           *           *           *
CCC GCC CTG CCC ACG TCG CTG CCA TCC TCG CTG GTC CCA CCC GTG ACC
 P   A   L   P   T   S   L   P   S   S   L   V   P   P   V   T>

3080        3090        3100        3110        3120
       *          *           *           *           *
GCA GCC CAG TTC CTG ACG CCC TCG CAG CAC AGC TAC TCC TCG CCT
 A   A   Q   F   L   T   P   S   Q   H   S   Y   S   S   P>
```

FIG.23P

GTG GAC AAC ACC CCC AGC CAC CAG CTA CAG GTG CCT GTT CCT GTA ATG
 V   D   N   T   P   S   H   Q   L   Q   V   P   V   P   V   M>

GTA ATG ATC CGA TCT TCG GAT CCT TCT AAA GGC TCA ATT TTG ATC
 V   M   I   R   S   S   D   P   S   K   G   S   I   L   I>

GAA GCT CCC GAC TCA TGG
 E   A   P   D   S   W>

FIG. 23Q

```
G GAG GTG GAT GTG TTA GAT GTG AAT GTC CGT GGC CCA GAT GGC TGC    46
  Glu Val Asp Val Leu Asp Val Asn Val Arg Gly Pro Asp Gly Cys
   1           5                  10                 15

ACC CCA TTG ATG TTG GCT TCT CTC CGA GGA GGC AGC TCA GAT TTG AGT  94
Thr Pro Leu Met Leu Ala Ser Leu Arg Gly Gly Ser Ser Asp Leu Ser
             20                  25                  30

GAT GAA GAT GAA GAT GCA GAG GAC TCT TCT GCT AAC ATC ATC ACA GAC  142
Asp Glu Asp Glu Asp Ala Glu Asp Ser Ser Ala Asn Ile Ile Thr Asp
             35                  40                  45

TTG GTC TAC CAG GGT GCC AGC CTC CAG GCC CAG ACA GAC CGG ACT GGT  190
Leu Val Tyr Gln Gly Ala Ser Leu Gln Ala Gln Thr Asp Arg Thr Gly
             50                  55                  60

GAG ATG GCC CTG CAC CTT GCA GCC CGC TAC TCA CGG GCT GAT GCT GCC  238
Glu Met Ala Leu His Leu Ala Ala Arg Tyr Ser Arg Ala Asp Ala Ala
             65                  70                  75

AAG CGT CTC CTG GAT GCA GGT GCA GAT GCC AAT GCC CAG GAC AAC ATG  286
Lys Arg Leu Leu Asp Ala Gly Ala Asp Ala Asn Ala Gln Asp Asn Met
 80              85                  90                  95

GGC CGC TGT CCA CTC CAT GCT GCA GTG GCA GCT GAT GCC CAA GGT GTC  334
Gly Arg Cys Pro Leu His Ala Ala Val Ala Ala Asp Ala Gln Gly Val
                100                 105                 110

TTC CAG ATT CTG ATT CGC AAC CGA GTA ACT GAT CTA GAT GCC AGG ATG  382
Phe Gln Ile Leu Ile Arg Asn Arg Val Thr Asp Leu Asp Ala Arg Met
                115                 120                 125

AAT GAT GGT ACT ACA CCC CTG ATC CTG GCT GCC CGC CTG GCT GTG GAG  430
Asn Asp Gly Thr Thr Pro Leu Ile Leu Ala Ala Arg Leu Ala Val Glu
                130                 135                 140
```

FIG.24A

```
GGA ATG GTG GCA GAA CTG ATC AAC TGC CAA GCG GAT GTG AAT GCA GTG    478
Gly Met Val Ala Glu Leu Ile Asn Cys Gln Ala Asp Val Asn Ala Val
    145                 150                 155

GAT GAC CAT GGA AAA TCT GCT CTT CAC TGG GCA GCT GCT GTC AAT AAT    526
Asp Asp His Gly Lys Ser Ala Leu His Trp Ala Ala Ala Val Asn Asn
160                 165                 170                 175

GTG GAG GCA ACT CTT TTG TTG TTG AAA AAT GGG GCC AAC CGA GAC ATG    574
Val Glu Ala Thr Leu Leu Leu Leu Lys Asn Gly Ala Asn Arg Asp Met
                    180                 185                 190

CAG GAC AAC AAG GAA GAG ACA CCT CTG TTT CTT GCT GCC CGG GAG GGG    622
Gln Asp Asn Lys Glu Glu Thr Pro Leu Phe Leu Ala Ala Arg Glu Gly
            195                 200                 205

AGC TAT GAA GCA GCC AAG ATC CTG TTA GAC CAT TTT GCC AAT CGA GAC    670
Ser Tyr Glu Ala Ala Lys Ile Leu Leu Asp His Phe Ala Asn Arg Asp
        210                 215                 220

ATC ACA GAC CAT ATC GAT CGT CTT CCC CGG GAT GTG GCT CGG GAT CGC    718
Ile Thr Asp His Met Asp Arg Leu Pro Arg Asp Val Ala Arg Asp Arg
    225                 230                 235

ATG CAC CAT GAC ATT GTG CGC CTT CTG GAT GAA TAC AAT GTG ACC CCA    766
Met His His Asp Ile Val Arg Leu Leu Asp Glu Tyr Asn Val Thr Pro
240                 245                 250                 255

AGC CCT CCA GGC ACC GTG TTG ACT TCT GCT CTC TCA CCT GTC ATC TGT    814
Ser Pro Pro Gly Thr Val Leu Thr Ser Ala Leu Ser Pro Val Ile Cys
                    260                 265                 270

GGG CCC AAC AGA TCT TTC CTC AGC CTG AAG CAC ACC CCA ATG GGC AAG    862
Gly Pro Asn Arg Ser Phe Leu Ser Leu Lys His Thr Pro Met Gly Lys
            275                 280                 285
```

FIG.24B

```
AAG TCT AGA CGG CCC AGT GCC AAG AGT ACC ATG CCT ACT AGC CTC CCT      910
Lys Ser Arg Arg Pro Ser Ala Lys Ser Thr Met Pro Thr Ser Leu Pro
        290                 295                 300

AAC CTT GCC AAG GAG GCA AAG GAT GCC AAG GGT AGT AGG AGG AAG AAG      958
Asn Leu Ala Lys Glu Ala Lys Asp Ala Lys Gly Ser Arg Arg Lys Lys
        305                 310                 315

TCT CTG AGT GAG AAG GTC CAA CTG TCT GAG AGT TCA GTA ACT TTA TCC     1006
Ser Leu Ser Glu Lys Val Gln Leu Ser Glu Ser Ser Val Thr Leu Ser
320                 325                 330                 335

CCT GTT GAT TCC CTA GAA TCT CCT CAC ACG TAT GTT TCC GAC ACC ACA     1054
Pro Val Asp Ser Leu Glu Ser Pro His Thr Tyr Val Ser Asp Thr Thr
                340                 345                 350

TCC TCT CCA ATG ATT ACA TCC CCT GGG ATC TTA CAG GCC TCA CCC AAC     1102
Ser Ser Pro Met Ile Thr Ser Pro Gly Ile Leu Gln Ala Ser Pro Asn
            355                 360                 365

CCT ATG TTG GCC ACT GCC GCC CCT CCT GCC CCA GTC CAT GCC CAG CAT     1150
Pro Met Leu Ala Thr Ala Ala Pro Pro Ala Pro Val His Ala Gln His
        370                 375                 380

GCA CTA TCT TTT TCT AAC CTT CAT GAA ATG CAG CCT TTG GCA CAT GGG     1198
Ala Leu Ser Phe Ser Asn Leu His Glu Met Gln Pro Leu Ala His Gly
        385                 390                 395

GCC AGC ACT GTG CTT CCC TCA GTG AGC CAG TTG CTA TCC CAC CAC CAC     1246
Ala Ser Thr Val Leu Pro Ser Val Ser Gln Leu Leu Ser His His His
400                 405                 410                 415

ATT GTG TCT CCA GGC AGT GGC AGT GCT GGA AGC TTG AGT AGG CTC CAT     1294
Ile Val Ser Pro Gly Ser Gly Ser Ala Gly Ser Leu Ser Arg Leu His
                420                 425                 430

CCA GTC CCA GTC CCA GCA GAT TGG ATG AAC CGC ATG GAG GTG AAT GAG     1342
Pro Val Pro Val Pro Ala Asp Trp Met Asn Arg Met Glu Val Asn Glu
            435                 440                 445
```

FIG.24C

```
ACC CAG TAC AAT GAG ATG TTT GGT ATG GTC CTG GCT CCA GCT GAG GGC   1390
Thr Gln Tyr Asn Glu Met Phe Gly Met Val Leu Ala Pro Ala Glu Gly
         450             455             460

ACC CAT CCT GGC ATA GCT CCC CAG AGC AGG CCA CCT GAA GGG AAG CAC   1438
Thr His Pro Gly Ile Ala Pro Gln Ser Arg Pro Pro Glu Gly Lys His
         465             470             475

ATA ACC ACC CCT CGG GAG CCC TTG CCC CCC ATT GTG ACT TTC CAG CTC   1486
Ile Thr Thr Pro Arg Glu Pro Leu Pro Pro Ile Val Thr Phe Gln Leu
480             485             490             495

ATC CCT AAA GGC AGT ATT GCC CAA CCA GCG GGG GCT CCC CAG CCT CAG   1534
Ile Pro Lys Gly Ser Ile Ala Gln Pro Ala Gly Ala Pro Gln Pro Gln
                500             505             510

TCC ACC TGC CCT CCA GCT GTT GCG GGC CCC CTG CCC ACC ATG TAC CAG   1582
Ser Thr Cys Pro Pro Ala Val Ala Gly Pro Leu Pro Thr Met Tyr Gln
         515             520             525

ATT CCA GAA ATG GCC CGT TTG CCC AGT GTG GCT TTC CCC ACT GCC ATG   1630
Ile Pro Glu Met Ala Arg Leu Pro Ser Val Ala Phe Pro Thr Ala Met
         530             535             540

ATG CCC CAG CAG GAC GGG CAG GTA GCT CAG ACC ATT CTC CCA GCC TAT   1678
Met Pro Gln Gln Asp Gly Gln Val Ala Gln Thr Ile Leu Pro Ala Tyr
         545             550             555

CAT CCT TTC CCA GCC TCT GTG GGC AAG TAC CCC ACA CCC CCT TCA CAG   1726
His Pro Phe Pro Ala Ser Val Gly Lys Tyr Pro Thr Pro Pro Ser Gln
560             565             570             575

CAC AGT TAT GCT TCC TCA AAT GCT GCT GAG CGA ACA CCC AGT CAC AGT   1774
His Ser Tyr Ala Ser Ser Asn Ala Ala Glu Arg Thr Pro Ser His Ser
                580             585             590

GGT CAC CTC CAG GGT GAG CAT CCC TAC CTG ACA CCA TCC CCA GAG TCT   1822
Gly His Leu Gln Gly Glu His Pro Tyr Leu Thr Pro Ser Pro Glu Ser
         595             600             605
```

FIG.24D

| | |
|---|---|
| CCT GAC CAG TGG TCA AGT TCA TCA CCC CAC TCT GCT TCT GAC TGG TCA<br>Pro Asp Gln Trp Ser Ser Ser Ser Pro His Ser Ala Ser Asp Trp Ser<br>610               615               620 | 1870 |
| GAT GTG ACC ACC AGC CCT ACC CCT GGG GGT GCT GGA GGA GGT CAG CGG<br>Asp Val Thr Thr Ser Pro Thr Pro Gly Gly Ala Gly Gly Gly Gln Arg<br>625               630               635 | 1918 |
| GGA CCT GGG ACA CAC ATG TCT GAG CCA CCA CAC AAC AAC ATG CAG GTT<br>Gly Pro Gly Thr His Met Ser Glu Pro Pro His Asn Asn Met Gln Val<br>640               645               650               655 | 1966 |
| TAT GCG TGAGAGAGTC CACCTCCAGT GTAGAGACAT AACTGACTTT TGTAAATGCT<br>Tyr Ala | 2022 |
| GCTGAGGAAC AAATGAAGGT CATCCGGGAG AGAAATGAAG AAATCTCTGG AGCCAGCTTC | 2082 |
| TAGAGGTAGG AAAGAGAAGA TGTTCTTATT CAGATAATGC AAGAGAAGCA ATTCGTCAGT | 2142 |
| TTCACTGGGT ATCTGCAAGG CTTATTGATT ATTCTAATCT AATAAGACAA GTTTGTGGAA | 2202 |
| ATGCAAGATG AATACAAGCC TTGGGTCCAT GTTTACTCTC TTCTATTTGG AGAATAAGAT | 2262 |
| GGATGCTTAT TGAAGCCCAG ACATTCTTGC AGCTTGGACT GCATTTTAAG CCCTGCAGGC | 2322 |
| TTCTGCCATA TCCATGAGAA GATTCTACAC TAGCGTCCTG TTGGGAATTA TGCCCTGGAA | 2382 |
| TTCTGCCTGA ATTGACCTAC GCATCTCCTC CTCCTTGGAC ATTCTTTTGT CTTCATTTGG | 2442 |
| TGCTTTTGGT TTTGCACCTC TCCGTGATTG TAGCCCTACC AGCATGTTAT AGGGCAAGAC | 2502 |
| CTTTGTGCTT TTGATCATTC TGGCCCATGA AAGCAACTTT GGTCTCCTTT CCCCTCCTGT | 2562 |
| CTTCCCGGTA TCCCTTGGAG TCTCACAAGG TTTACTTTGG TATGGTTCTC AGCACAAACC | 2622 |
| TTTCAAGTAT GTTGTTTCTT TGGAAAATGG ACATACTGTA TTGTGTTCTC CTGCATATAT | 2682 |
| CATTCCTGGA GAGAGAAGGG GAGAAGAATA CTTTTCTTCA ACAAATTTTG GGGCAGGAG | 2742 |
| ATCCCTTCAA GAGGCTGCAC CTTAATTTTT CTTGTCTGTG TGCAGGTCTT CATATAAACT | 2802 |

FIG.24E

```
TTACCAGGAA GAAGGGTGTG AGTTTGTTGT TTTTCTGTGT ATGGGCCTGG TCAGTGTAAA    2862

GTTTTATCCT TGATAGTCTA GTTACTATGA CCCTCCCCAC TTTTTTAAAA CCAGAAAAAG    2922

GTTTGGAATG TTGGAATGAC CAAGAGACAA GTTAACTCGT GCAAGAGCCA GTTACCCACC    2982

CACAGGTCCC CCTACTTCCT GCCAAGCATT CCATTGACTG CCTGTATGGA ACACATTTGT    3042

CCCAGATCTG AGCATTCTAG GCCTGTTTCA CTCACTCACC CAGCATATGA AACTAGTCTT    3102

AACTGTTGAG CCTTTCCTTT CATATCCACA GAAGACACTG TCTCAAATGT TGTACCCTTG    3162

CCATTTAGGA CTGAACTTTC CTTAGCCCAA GGGACCCAGT GACAGTTGTC TTCCGTTTGT    3222

CAGATGATCA GTCTCTACTG ATTATCTTGC TGCTTAAAGG CCTGCTCACC AATCTTTCTT    3282

TCACACCGTG TGGTCCGTGT TACTGGTATA CCCAGTATGT TCTCACTGAA GACATGGACT    3342

TTATATGTTC AAGTGCAGGA ATTGGAAAGT TGGACTTGTT TTCTATGATC CAAAACAGCC    3402

CTATAAGAAG GTTGGAAAAG GAGGAACTAT ATAGCAGCCT TGCTATTTT CTGCTACCAT     3462

TTCTTTTCCT CTGAAGCGGC CATGACATTC CCTTTGGCAA CTAACGTAGA AACTCAACAG    3522
```

FIG.24F

```
AACATTTTCC TTTCCTAGAG TCACCTTTTA GATGATAATG GACAACTATA GACTTGCTCA   3582

TTGTTCAGAC TGATTGCCCC TCACCTGAAT CCACTCTCTG TATTCATGCT CTTGGCAATT   3642

TCTTTGACTT TCTTTTAAGG GCAGAAGCAT TTTAGTTAAT TGTAGATAAA GAATAGTTTT   3702

CTTCCTCTTC TCCTTGGGCC AGTTAATAAT TGGTCCATGG CTACACTGCA ACTTCCGTCC   3762

AGTGCTGTGA TGCCCATGAC ACCTGCAAAA TAAGTTCTGC CTGGGCATTT TGTAGATATT   3822

AACAGGTGAA TTCCCGACTC TTTTGGTTTG AATGACAGTT CTCATTCCTT CTATGGCTGC   3882

AAGTATGCAT CAGTGCTTCC CACTTACCTG ATTTGTCTGT CGGTGGCCCC ATATGGAAAC   3942

CCTGCGTGTC TGTTGGCATA ATAGTTTACA AATGGTTTTT TCAGTCCTAT CCAAATTTAT   4002

TGAACCAACA AAAATAATTA CTTCTGCCCT GAGATAAGCA GATTAAGTTT GTTCATTCTC   4062

TGCTTTATTC TCTCCATGTG GCAACATTCT GTCAGCCTCT TTCATAGTGT GCAAACATTT   4122

TATCATTCTA AATGGTGACT CTCTGCCCTT GGACCCATTT ATTATTCACA GATGGGGAGA   4182

ACCTATCTGC ATGGACCCTC ACCATCCTCT GTGCAGCACA CACAGTGCAG GGAGCCAGTG   4242

GCGATGGCGA TGACTTTCTT CCCCTG                                        4268
```

FIG. 24G

```
hN5k          2218  ------------------------------------------------------ITSGGIDDASPNPML--ATAAPPAPVHAQHALSF
TAN-1         2209  ------------------------------------------------------LRSPR--QQSPSVPLNHLPGMPDTHLGIGHLNVA
rat NOTCH     2214  ------------------------------------------------------LRSPR--QQSPSMPLSHLPGMPDTHLGISHLNVA
XENOPUS NOTCH       ------------------------------------------------------MTSPR--QQSPSMPLNHLTSMPESQLGMNHINMA
DROSOPH NOTCH 2285  PVGVGMGGNLPSPYDTSSMYSNAMAAPLANGNPNTGAKQPRSYEDCIKNAQSMQSLQGNGLDMIKLDNYAYSMQSPR--QQELLNGQGLGMNGNGQRNGVGPGVLP
                                                                  CK-11                       CK-11 hN5k                SNLHEMQ-----------------------------------PLAHGASTVLPSVSQLLSHHHIVSPGS--GSAGSLSRLHPVPVPADW--MNRMEVNETQYNEMFGMVLAPAEG-THPGI
TAN-1         2250  A-KPEMAALGGGGRLAFETGPPRLSHLPVASGTSTVLGSSSGGALNFTVGGSTSLNGQCEWLSRLQSGMVPNQYNPLRGSVAPGPLSTQAPSLQHG-MVGPLHSSL
rat NOTCH     2242  A-KPEMAALAGGSRLAFEPPPRLSHLPVASSASTVLSTNGTGAMNFTVGAPASLNGQCEWLPRLQNGMVPSQYNPLRPGVTPGTLSTQAAGLQHGMM-SPIHSSL
XENOPUS NOTCH 2247  T-KQEMAA--GSNRMAFDAMVPRLTHL-NASSPNTIMS---NGSMHFTVGGAPTMNSQCDNLARLQNGMVQNQYDPIRNGIQQGN-AQQAQALQHGLMTS-LHNGL
DROSOPH NOTCH 2390  GGLCGMGGLSGAGNGNSHEQGLSPPYS-NQSPPHSVQSSLALSPHAYLGSPSPAKSRPSLPTSPTHIQAMRHATQQKQFGGSNLNSLLGGANGGGVVGGGGGGGV hN5k                APQSRPPEGK------HITTPREPLPP-IV-TFQLIPKGSIAQPAG------APQPQSTCPPAVAGPLPTMYQIP-----EMARL-P
TAN-1         2354  AASALSQMMS------YQGLPSTRLATQPHLVQTQQVQPQNLQMQQQNLQPANIQQQSLQPPPPPQPHLGVSSAASGHLGRSFLSGEPSQADVQPLGP
rat NOTCH     2344  STNTLSPII------YQGLPNTRLATQPHLVQTQQVQPQNLQIQPQN------LQPPS---QPHLSVSSAANGHLGRSFLSGEPSQADVQPLGP
XENOPUS NOTCH 2343  PATTLSQMMT------YQAMPNTRLANQPHLMQAQQMQQQQN------LQLHQSMQQQHHN-SSTTSTHINSPFCSSDISQTDLQQM--
DROSOPH NOTCH 2495  VGQGPQNSPVSLGIISPTGSDMGIMLAPPQSSKNSAIMQTISPQQQQQQQQQQQQHQQQQQQQQQQQLGGLEFGSAGLDLNG-FCGSPDSFHSGQMNPP hN5k          2448  SVAFPTAMMPQQDQQVAQTILPAYHPFPASVGKYHTPPSQHSYASSNAAERTPSHSGHLQGEHPYLTPSPESPDQWSSSSSPHSA-SDWSDVTSPTP
TAN-1         2423  SSLAVHTILPQ-ESPALPTSLPSSLVPPVTAAQFLTPPSQHSY-SS-PVENTPSHQLQVP-EHPFLTPSPESPDQWSSSSSPHSNVSDWSEGVSSPPT
rat NOTCH     2416  SSLPVHTILPQ-ESQALPTSLPSSMVPPMTTQFLTPPSQHSY-SSSPVINTPSHQLQVP-EHPFLTPSPESPDQWSSSSSRHSNISDWSEGISSPPT
XENOPUS NOTCH 2599  SSNNIHSVMPQ-DTQIFAASLPSNLTQSMTTAQFLTPPSQHSY-SS-PMDNTPSHQLQVP-DHPFLTPSPESPDQWSSSSPHSNMSDWSEGISSPPT
DROSOPH NOTCH       S---IQSSMSG-SSPSTNMLSPSSQHNQQAFYQYLTPSSQHS-----GGHTPQHLVQTIL-D-SYPTPSPESPGHWSSSSPRSN-SDWSEGVQSPAA
                                                                          PEST-CONTAINING REGION
```

FIG. 25C

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
        ( A ) LENGTH: 77 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:1:

```
Glu Asp Ile Asp Glu Cys Asp Gln Gly Ser Pro Cys Glu His Asn Gly
 1               5                  10                  15
Ile Cys Val Asn Thr Pro Gly Ser Tyr Arg Cys Asn Cys Ser Gln Gly
                20                  25                  30
Phe Thr Gly Pro Arg Cys Glu Thr Asn Ile Asn Glu Cys Glu Ser His
                35                  40                  45
Pro Cys Gln Asn Glu Gly Ser Cys Leu Asp Asp Pro Gly Thr Phe Arg
        50                  55                  60
Cys Val Cys Met Pro Gly Phe Thr Gly Thr Gln Cys Glu
 65                 70                  75
```

( 2 ) INFORMATION FOR SEQ ID NO:2:

( i ) SEQUENCE CHARACTERISTICS:
        ( A ) LENGTH: 78 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:2:

```
Asn Asp Val Asp Glu Cys Ser Leu Gly Ala Asn Pro Cys Glu His Gly
 1               5                  10                  15
Gly Arg Cys Thr Asn Thr Leu Gly Ser Phe Gln Cys Asn Cys Pro Gln
                20                  25                  30
Gly Tyr Ala Gly Pro Arg Cys Glu Ile Asp Val Asn Glu Cys Leu Ser
```

|   |   |   |   | 35 |   |   |   |   | 40 |   |   |   |   | 45 |   |
|---|---|---|---|----|---|---|---|---|----|---|---|---|---|----|---|
| Asn | Pro | Cys | Gln | Asn | Asp | Ser | Thr | Cys | Leu | Asp | Gln | Ile | Gly | Glu | Phe |
|   |   | 50 |   |   |   | 55 |   |   |   | 60 |   |   |   |   |   |
| Gln | Cys | Ile | Cys | Met | Pro | Gly | Tyr | Glu | Gly | Leu | Tyr | Cys | Glu |   |   |
| 65 |   |   |   |   | 70 |   |   |   |   | 75 |   |   |   |   |   |

(2) INFORMATION FOR SEQ ID NO:3:

(i) SEQUENCE CHARACTERISTICS:
        (A) LENGTH: 203 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:3:

| Gly | Ser | Phe | Glu | Leu | Arg | Leu | Lys | Tyr | Phe | Ser | Asn | Asp | His | Gly | Arg |
|-----|-----|-----|-----|-----|-----|-----|-----|-----|-----|-----|-----|-----|-----|-----|-----|
| 1 |   |   |   | 5 |   |   |   |   | 10 |   |   |   |   | 15 |   |
| Asp | Asn | Glu | Gly | Arg | Cys | Cys | Ser | Glu | Ser | Asp | Gly | Ala | Thr | Gly |   |
|   |   |   | 20 |   |   |   |   | 25 |   |   |   |   | 30 |   |   |
| Lys | Cys | Leu | Gly | Ser | Cys | Lys | Thr | Arg | Phe | Arg | Val | Cys | Leu | Lys | His |
|   |   |   | 35 |   |   |   |   | 40 |   |   |   |   | 45 |   |   |
| Tyr | Gln | Ala | Thr | Ile | Asp | Thr | Thr | Ser | Gln | Cys | Thr | Tyr | Gly | Asp | Val |
|   |   |   | 50 |   |   |   | 55 |   |   |   |   | 60 |   |   |   |
| Ile | Thr | Pro | Ile | Leu | Gly | Glu | Asn | Ser | Val | Asn | Leu | Thr | Asp | Ala | Gln |
| 65 |   |   |   |   | 70 |   |   |   |   | 75 |   |   |   |   | 80 |
| Arg | Phe | Gln | Asn | Lys | Gly | Phe | Thr | Asn | Pro | Ile | Gln | Phe | Pro | Phe | Ser |
|   |   |   |   | 85 |   |   |   |   | 90 |   |   |   |   | 95 |   |
| Phe | Ser | Trp | Pro | Gly | Thr | Phe | Ser | Leu | Ile | Val | Glu | Ala | Trp | His | Asp |
|   |   |   | 100 |   |   |   |   | 105 |   |   |   |   | 110 |   |   |
| Thr | Asn | Asn | Ser | Gly | Asn | Ala | Arg | Thr | Asn | Lys | Leu | Leu | Ile | Gln | Arg |
|   |   |   | 115 |   |   |   |   | 120 |   |   |   |   | 125 |   |   |
| Leu | Leu | Val | Gln | Gln | Val | Leu | Glu | Val | Ser | Ser | Glu | Trp | Lys | Thr | Asn |
|   |   | 130 |   |   |   |   | 135 |   |   |   |   | 140 |   |   |   |
| Lys | Ser | Glu | Ser | Gln | Tyr | Thr | Ser | Leu | Glu | Tyr | Asp | Phe | Arg | Val | Thr |
| 145 |   |   |   |   | 150 |   |   |   |   | 155 |   |   |   |   | 160 |
| Cys | Asp | Leu | Asn | Tyr | Tyr | Gly | Ser | Gly | Cys | Ala | Lys | Phe | Cys | Arg | Pro |
|   |   |   |   | 165 |   |   |   |   | 170 |   |   |   |   | 175 |   |
| Arg | Asp | Asp | Ser | Phe | Gly | His | Ser | Thr | Cys | Ser | Glu | Thr | Gly | Glu | Ile |
|   |   |   | 180 |   |   |   |   | 185 |   |   |   |   | 190 |   |   |
| Ile | Cys | Leu | Thr | Gly | Trp | Gln | Gly | Asp | Tyr | Cys |   |   |   |   |   |
|   |   |   | 195 |   |   |   |   | 200 |   |   |   |   |   |   |   |

(2) INFORMATION FOR SEQ ID NO:4:

(i) SEQUENCE CHARACTERISTICS:
        (A) LENGTH: 199 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:4:

| Gly | Asn | Phe | Glu | Leu | Glu | Ile | Leu | Glu | Ile | Ser | Asn | Thr | Asn | Ser | His |
|-----|-----|-----|-----|-----|-----|-----|-----|-----|-----|-----|-----|-----|-----|-----|-----|
| 1 |   |   |   | 5 |   |   |   |   | 10 |   |   |   |   | 15 |   |
| Leu | Leu | Asn | Gly | Tyr | Cys | Cys | Gly | Met | Pro | Ala | Glu | Leu | Arg | Ala | Thr |
|   |   |   | 20 |   |   |   |   | 25 |   |   |   |   | 30 |   |   |
| Lys | Thr | Ile | Gly | Cys | Ser | Pro | Cys | Thr | Thr | Ala | Phe | Arg | Leu | Cys | Leu |

3 5                              4 0                                    4 5

Lys  Glu  Tyr  Gln  Thr  Thr  Glu  Gln  Gly  Ala  Ser  Ile  Ser  Thr  Gly  Cys
                     50                       55                       60

Ser  Phe  Gly  Asn  Ala  Thr  Thr  Lys  Ile  Leu  Gly  Gly  Ser  Ser  Phe  Val
           65                       70                       75                            80

Leu  Ser  Asp  Pro  Gly  Val  Gly  Ala  Ile  Val  Leu  Pro  Phe  Thr  Phe  Arg
                               85                       90                            95

Trp  Thr  Lys  Ser  Phe  Thr  Leu  Ile  Leu  Gln  Ala  Leu  Asp  Met  Tyr  Asn
                          100                      105                      110

Thr  Ser  Tyr  Pro  Asp  Ala  Glu  Arg  Leu  Ile  Glu  Glu  Thr  Ser  Tyr  Ser
                          115                      120                      125

Gly  Val  Ile  Leu  Pro  Ser  Pro  Glu  Trp  Lys  Thr  Leu  Asp  His  Ile  Gly
                     130                      135                      140

Arg  Asn  Ala  Arg  Ile  Thr  Tyr  Arg  Val  Arg  Val  Gln  Cys  Ala  Val  Thr
           145                      150                      155                           160

Tyr  Tyr  Asn  Thr  Thr  Cys  Thr  Thr  Phe  Cys  Arg  Pro  Arg  Asp  Asp  Gln
                               165                      170                      175

Phe  Gly  His  Tyr  Ala  Cys  Gly  Ser  Glu  Gly  Gln  Lys  Leu  Cys  Leu  Asn
                          180                      185                      190

Gly  Trp  Gln  Gly  Val  Asn  Cys
                     195

( 2 ) INFORMATION FOR SEQ ID NO:5:

( i ) SEQUENCE CHARACTERISTICS:
           ( A ) LENGTH: 2892 base pairs
           ( B ) TYPE: nucleic acid
           ( C ) STRANDEDNESS: double
           ( D ) TOPOLOGY: unknown ( i i ) MOLECULE TYPE: cDNA ( i x ) FEATURE:
           ( A ) NAME/KEY: CDS
           ( B ) LOCATION: 142..2640

( x i ) SEQUENCE DESCRIPTION: SEQ ID NO:5:

GAATTCGGAG  GAATTATTCA  AAACATAAAC  ACAATAAACA  ATTTGAGTAG  TTGCCGCACA              60

CACACACACA  CACAGCCCGT  GGATTATTAC  ACTAAAAGCG  ACACTCAATC  CAAAAAATCA             120

GCAACAAAAA  CATCAATAAA  C ATG CAT TGG ATT AAA TGT TTA TTA ACA GCA                  171
                         Met His Trp Ile Lys Cys Leu Leu Thr Ala
                          1               5                  10

TTC ATT TGC TTC ACA GTC ATC GTG CAG GTT CAC AGT TCC GGC AGC TTT                    219
Phe Ile Cys Phe Thr Val Ile Val Gln Val His Ser Ser Gly Ser Phe
             15                  20                  25

GAG TTG CGC CTG AAG TAC TTC AGC AAC GAT CAC GGG CGG GAC AAC GAG                    267
Glu Leu Arg Leu Lys Tyr Phe Ser Asn Asp His Gly Arg Asp Asn Glu
             30                  35                  40

GGT CGC TGC TGC AGC GGG GAG TCG GAC GGA GCG ACG GGC AAG TGC CTG                    315
Gly Arg Cys Cys Ser Gly Glu Ser Asp Gly Ala Thr Gly Lys Cys Leu
             45                  50                  55

GGC AGC TGC AAG ACG CGG TTT CGC GTC TGC CTA AAG CAC TAC CAG GCC                    363
Gly Ser Cys Lys Thr Arg Phe Arg Val Cys Leu Lys His Tyr Gln Ala
         60                  65                  70

ACC ATC GAC ACC ACC TCC CAG TGC ACC TAC GGG GAC GTG ATC ACG CCC                    411
Thr Ile Asp Thr Thr Ser Gln Cys Thr Tyr Gly Asp Val Ile Thr Pro
75                   80                  85                  90

ATT CTC GGC GAG AAC TCG GTC AAT CTG ACC GAC GCC CAG CGC TTC CAG                    459
Ile Leu Gly Glu Asn Ser Val Asn Leu Thr Asp Ala Gln Arg Phe Gln
                 95                 100                 105

| | | | | | | | | | | | | | | | | |
|---|---|---|---|---|---|---|---|---|---|---|---|---|---|---|---|---|
| AAC | AAG | GGC | TTC | ACG | AAT | CCC | ATC | CAG | TTC | CCC | TTC | TCG | TTC | TCA | TGG | 507 |
| Asn | Lys | Gly | Phe | Thr | Asn | Pro | Ile | Gln | Phe | Pro | Phe | Ser | Phe | Ser | Trp | |
| | | | 110 | | | | | 115 | | | | | 120 | | | |
| CCG | GGT | ACC | TTC | TCG | CTG | ATC | GTC | GAG | GCC | TGG | CAT | GAT | ACG | AAC | AAT | 555 |
| Pro | Gly | Thr | Phe | Ser | Leu | Ile | Val | Glu | Ala | Trp | His | Asp | Thr | Asn | Asn | |
| | | 125 | | | | | 130 | | | | | 135 | | | | |
| AGC | GGC | AAT | GCG | CGA | ACC | AAC | AAG | CTC | CTC | ATC | CAG | CGA | CTC | TTG | GTG | 603 |
| Ser | Gly | Asn | Ala | Arg | Thr | Asn | Lys | Leu | Leu | Ile | Gln | Arg | Leu | Leu | Val | |
| | | 140 | | | | | 145 | | | | | 150 | | | | |
| CAG | CAG | GTA | CTG | GAG | GTG | TCC | TCC | GAA | TGG | AAG | ACG | AAC | AAG | TCG | GAA | 651 |
| Gln | Gln | Val | Leu | Glu | Val | Ser | Ser | Glu | Trp | Lys | Thr | Asn | Lys | Ser | Glu | |
| 155 | | | | | 160 | | | | | 165 | | | | | 170 | |
| TCG | CAG | TAC | ACG | TCG | CTG | GAG | TAC | GAT | TTC | CGT | GTC | ACC | TGC | GAT | CTC | 699 |
| Ser | Gln | Tyr | Thr | Ser | Leu | Glu | Tyr | Asp | Phe | Arg | Val | Thr | Cys | Asp | Leu | |
| | | | | 175 | | | | | 180 | | | | | 185 | | |
| AAC | TAC | TAC | GGA | TCC | GGC | TGT | GCC | AAG | TTC | TGC | CGG | CCC | CGC | GAC | GAT | 747 |
| Asn | Tyr | Tyr | Gly | Ser | Gly | Cys | Ala | Lys | Phe | Cys | Arg | Pro | Arg | Asp | Asp | |
| | | | 190 | | | | | 195 | | | | | 200 | | | |
| TCA | TTT | GGA | CAC | TCG | ACT | TGC | TCG | GAG | ACG | GGC | GAA | ATT | ATC | TGT | TTG | 795 |
| Ser | Phe | Gly | His | Ser | Thr | Cys | Ser | Glu | Thr | Gly | Glu | Ile | Ile | Cys | Leu | |
| | | | 205 | | | | | 210 | | | | | 215 | | | |
| ACC | GGA | TGG | CAG | GGC | GAT | TAC | TGT | CAC | ATA | CCC | AAA | TGC | GCC | AAA | GGC | 843 |
| Thr | Gly | Trp | Gln | Gly | Asp | Tyr | Cys | His | Ile | Pro | Lys | Cys | Ala | Lys | Gly | |
| | 220 | | | | | 225 | | | | | 230 | | | | | |
| TGT | GAA | CAT | GGA | CAT | TGC | GAC | AAA | CCC | AAT | CAA | TGC | GTT | TGC | CAA | CTG | 891 |
| Cys | Glu | His | Gly | His | Cys | Asp | Lys | Pro | Asn | Gln | Cys | Val | Cys | Gln | Leu | |
| 235 | | | | | 240 | | | | | 245 | | | | | 250 | |
| GGC | TGG | AAG | GGA | GCC | TTG | TGC | AAC | GAG | TGC | GTT | CTG | GAA | CCG | AAC | TGC | 939 |
| Gly | Trp | Lys | Gly | Ala | Leu | Cys | Asn | Glu | Cys | Val | Leu | Glu | Pro | Asn | Cys | |
| | | | | 255 | | | | | 260 | | | | | 265 | | |
| ATC | CAT | GGC | ACC | TGC | AAC | AAA | CCC | TGG | ACT | TGC | ATC | TGC | AAC | GAG | GGT | 987 |
| Ile | His | Gly | Thr | Cys | Asn | Lys | Pro | Trp | Thr | Cys | Ile | Cys | Asn | Glu | Gly | |
| | | | 270 | | | | | 275 | | | | | 280 | | | |
| TGG | GGA | GGC | TTG | TAC | TGC | AAC | CAG | GAT | CTG | AAC | TAC | TGC | ACC | AAC | CAC | 1035 |
| Trp | Gly | Gly | Leu | Tyr | Cys | Asn | Gln | Asp | Leu | Asn | Tyr | Cys | Thr | Asn | His | |
| | | 285 | | | | | 290 | | | | | 295 | | | | |
| AGA | CCC | TGC | AAG | AAT | GGC | GGA | ACC | TGC | TTC | AAC | ACC | GGC | GAG | GGA | TTG | 1083 |
| Arg | Pro | Cys | Lys | Asn | Gly | Gly | Thr | Cys | Phe | Asn | Thr | Gly | Glu | Gly | Leu | |
| | 300 | | | | | 305 | | | | | 310 | | | | | |
| TAC | ACA | TGC | AAA | TGC | GCT | CCA | GGA | TAC | AGT | GGT | GAT | GAT | TGC | GAA | AAT | 1131 |
| Tyr | Thr | Cys | Lys | Cys | Ala | Pro | Gly | Tyr | Ser | Gly | Asp | Asp | Cys | Glu | Asn | |
| 315 | | | | | 320 | | | | | 325 | | | | | 330 | |
| GAG | ATC | TAC | TCC | TGC | GAT | GCC | GAT | GTC | AAT | CCC | TGC | CAG | AAT | GGT | GGT | 1179 |
| Glu | Ile | Tyr | Ser | Cys | Asp | Ala | Asp | Val | Asn | Pro | Cys | Gln | Asn | Gly | Gly | |
| | | | | 335 | | | | | 340 | | | | | 345 | | |
| ACC | TGC | ATC | GAT | GAG | CCG | CAC | ACA | AAA | ACC | GGC | TAC | AAG | TGT | CAT | TGC | 1227 |
| Thr | Cys | Ile | Asp | Glu | Pro | His | Thr | Lys | Thr | Gly | Tyr | Lys | Cys | His | Cys | |
| | | | 350 | | | | | 355 | | | | | 360 | | | |
| GCC | AAC | GGC | TGG | AGC | GGA | AAG | ATG | TGC | GAG | GAG | AAA | GTG | CTC | ACG | TGT | 1275 |
| Ala | Asn | Gly | Trp | Ser | Gly | Lys | Met | Cys | Glu | Glu | Lys | Val | Leu | Thr | Cys | |
| | | 365 | | | | | 370 | | | | | 375 | | | | |
| TCG | GAC | AAA | CCC | TGT | CAT | CAG | GGA | ATC | TGC | CGC | AAC | GTT | CGT | CCT | GGC | 1323 |
| Ser | Asp | Lys | Pro | Cys | His | Gln | Gly | Ile | Cys | Arg | Asn | Val | Arg | Pro | Gly | |
| | 380 | | | | | 385 | | | | | 390 | | | | | |
| TTG | GGA | AGC | AAG | GGT | CAG | GGC | TAC | CAG | TGC | GAA | TGT | CCC | ATT | GGC | TAC | 1371 |
| Leu | Gly | Ser | Lys | Gly | Gln | Gly | Tyr | Gln | Cys | Glu | Cys | Pro | Ile | Gly | Tyr | |
| 395 | | | | | 400 | | | | | 405 | | | | | 410 | |
| AGC | GGA | CCC | AAC | TGC | GAT | CTC | CAG | CTG | GAC | AAC | TGC | AGT | CCG | AAT | CCA | 1419 |
| Ser | Gly | Pro | Asn | Cys | Asp | Leu | Gln | Leu | Asp | Asn | Cys | Ser | Pro | Asn | Pro | |
| | | | | 415 | | | | | 420 | | | | | 425 | | |

```
TGC ATA AAC GGT GGA AGC TGT CAG CCG AGC GGA AAG TGT ATT TGC CCA       1467
Cys Ile Asn Gly Gly Ser Cys Gln Pro Ser Gly Lys Cys Ile Cys Pro
        430                     435                     440

GCG GGA TTT TCG GGA ACG AGA TGC GAG ACC AAC ATT GAC GAT TGT CTT       1515
Ala Gly Phe Ser Gly Thr Arg Cys Glu Thr Asn Ile Asp Asp Cys Leu
            445                     450                     455

GGC CAC CAG TGC GAG AAC GGA GGC ACC TGC ATA GAT ATG GTC AAC CAA       1563
Gly His Gln Cys Glu Asn Gly Gly Thr Cys Ile Asp Met Val Asn Gln
    460                     465                     470

TAT CGC TGC CAA TGC GTT CCC GGT TTC CAT GGC ACC CAC TGT AGT AGC       1611
Tyr Arg Cys Gln Cys Val Pro Gly Phe His Gly Thr His Cys Ser Ser
475                     480                     485                 490

AAA GTT GAC TTG TGC CTC ATC AGA CCG TGT GCC AAT GGA GGA ACC TGC       1659
Lys Val Asp Leu Cys Leu Ile Arg Pro Cys Ala Asn Gly Gly Thr Cys
                495                     500                     505

TTG AAT CTC AAC AAC GAT TAC CAG TGC ACC TGT CGT GCG GGA TTT ACT       1707
Leu Asn Leu Asn Asn Asp Tyr Gln Cys Thr Cys Arg Ala Gly Phe Thr
            510                     515                     520

GGC AAG GAT TGC TCT GTG GAC ATC GAT GAG TGC AGC AGT GGA CCC TGT       1755
Gly Lys Asp Cys Ser Val Asp Ile Asp Glu Cys Ser Ser Gly Pro Cys
        525                     530                     535

CAT AAC GGC GGC ACT TGC ATG AAC CGC GTC AAT TCG TTC GAA TGC GTG       1803
His Asn Gly Gly Thr Cys Met Asn Arg Val Asn Ser Phe Glu Cys Val
    540                     545                     550

TGT GCC AAT GGT TTC AGG GGC AAG CAG TGC GAT GAG GAG TCC TAC GAT       1851
Cys Ala Asn Gly Phe Arg Gly Lys Gln Cys Asp Glu Glu Ser Tyr Asp
555                     560                     565                 570

TCG GTG ACC TTC GAT GCC CAC CAA TAT GGA GCG ACC ACA CAA GCG AGA       1899
Ser Val Thr Phe Asp Ala His Gln Tyr Gly Ala Thr Thr Gln Ala Arg
                575                     580                     585

GCC GAT GGT TTG ACC AAT GCC CAG GTA GTC CTA ATT GCT GTT TTC TCC       1947
Ala Asp Gly Leu Thr Asn Ala Gln Val Val Leu Ile Ala Val Phe Ser
            590                     595                     600

GTT GCG ATG CCT TTG GTG GCG GTT ATT GCG GCG TGC GTG GTC TTC TGC       1995
Val Ala Met Pro Leu Val Ala Val Ile Ala Ala Cys Val Phe Cys
        605                     610                     615

ATG AAG CGC AAG CGT AAG CGT GCT CAG GAA AAG GAC GAC GCG GAG GCC       2043
Met Lys Arg Lys Arg Lys Arg Ala Gln Glu Lys Asp Asp Ala Glu Ala
    620                     625                     630

AGG AAG CAG AAC GAA CAG AAT GCG GTG GCC ACA ATG CAT CAC AAT GGC       2091
Arg Lys Gln Asn Glu Gln Asn Ala Val Ala Thr Met His His Asn Gly
635                     640                     645                 650

AGT GGG GTG GGT GTA GCT TTG GCT TCA GCC TCT CTG GGC GGC AAA ACT       2139
Ser Gly Val Gly Val Ala Leu Ala Ser Ala Ser Leu Gly Gly Lys Thr
                655                     660                     665

GGC AGC AAC AGC GGT CTC ACC TTC GAT GGC GGC AAC CCG AAT ATC ATC       2187
Gly Ser Asn Ser Gly Leu Thr Phe Asp Gly Gly Asn Pro Asn Ile Ile
            670                     675                     680

AAA AAC ACC TGG GAC AAG TCG GTC AAC AAC ATT TGT GCC TCA GCA GCA       2235
Lys Asn Thr Trp Asp Lys Ser Val Asn Asn Ile Cys Ala Ser Ala Ala
        685                     690                     695

GCA GCG GCG GCG GCA GCA GCG GCG GAC GAG TGT CTC ATG TAC GGC           2283
Ala Ala Ala Ala Ala Ala Ala Ala Asp Glu Cys Leu Met Tyr Gly
    700                     705                     710

GGA TAT GTG GCC TCG GTG GCG GAT AAC AAC AAT GCC AAC TCA GAC TTT       2331
Gly Tyr Val Ala Ser Val Ala Asp Asn Asn Asn Ala Asn Ser Asp Phe
715                     720                     725                 730

TGT GTG GCT CCG CTA CAA AGA GCC AAG TCG CAA AAG CAA CTC AAC ACC       2379
Cys Val Ala Pro Leu Gln Arg Ala Lys Ser Gln Lys Gln Leu Asn Thr
                735                     740                     745
```

```
GAT  CCC  ACG  CTC  ATG  CAC  CGC  GGT  TCG  CCG  GCA  GGC  AGC  TCA  GCC  AAG      2427
Asp  Pro  Thr  Leu  Met  His  Arg  Gly  Ser  Pro  Ala  Gly  Ser  Ser  Ala  Lys
               750                           755                      760

GGA  GCG  TCT  GGC  GGA  GGA  CCG  GGA  GCG  GCG  GAG  GGC  AAG  AGG  ATC  TCT      2475
Gly  Ala  Ser  Gly  Gly  Gly  Pro  Gly  Ala  Ala  Glu  Gly  Lys  Arg  Ile  Ser
          765                           770                      775

GTT  TTA  GGC  GAG  GGT  TCC  TAC  TGT  AGC  CAG  CGT  TGG  CCC  TCG  TTG  GCG      2523
Val  Leu  Gly  Glu  Gly  Ser  Tyr  Cys  Ser  Gln  Arg  Trp  Pro  Ser  Leu  Ala
     780                      785                           790

GCG  GCG  GGA  GTG  GCC  GGA  GCC  TGT  TCA  TCC  CAG  CTA  ATG  GCT  GCA  GCT      2571
Ala  Ala  Gly  Val  Ala  Gly  Ala  Cys  Ser  Ser  Gln  Leu  Met  Ala  Ala  Ala
795                      800                      805                           810

TCG  GCA  GCG  GGC  AGC  GGA  GCG  GGG  ACG  GCG  CAA  CAG  CAG  CGA  TCC  GTG      2619
Ser  Ala  Ala  Gly  Ser  Gly  Ala  Gly  Thr  Ala  Gln  Gln  Gln  Arg  Ser  Val
                    815                      820                      825

GTC  TGC  GGC  ACT  CCG  CAT  ATG  TAACTCCAAA  AATCCGGAAG  GGCTCCTGGT              2670
Val  Cys  Gly  Thr  Pro  His  Met
               830

AAATCCGGAG  AAATCCGCAT  GGAGGAGCTG  ACAGCACATA  CACAAAGAAA  AGACTGGGTT              2730

GGGTTCAAAA  TGTGAGAGAG  ACGCCAAAAT  GTTGTTGTTG  ATTGAAGCAG  TTTAGTCGTC              2790

ACGAAAAATG  AAAAATCTGT  AACAGGCATA  ACTCGTAAAC  TCCCTAAAAA  ATTTGTATAG              2850

TAATTAGCAA  AGCTGTGACC  CAGCCGTTTC  GATCCCGAAT  TC                                  2892
```

( 2 ) INFORMATION FOR SEQ ID NO:6:

( i ) SEQUENCE CHARACTERISTICS:
        ( A ) LENGTH: 833 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:6:

```
Met  His  Trp  Ile  Lys  Cys  Leu  Leu  Thr  Ala  Phe  Ile  Cys  Phe  Thr  Val
 1              5                        10                       15

Ile  Val  Gln  Val  His  Ser  Ser  Gly  Ser  Phe  Glu  Leu  Arg  Leu  Lys  Tyr
               20                       25                       30

Phe  Ser  Asn  Asp  His  Gly  Arg  Asp  Asn  Glu  Gly  Arg  Cys  Cys  Ser  Gly
          35                       40                       45

Glu  Ser  Asp  Gly  Ala  Thr  Gly  Lys  Cys  Leu  Gly  Ser  Cys  Lys  Thr  Arg
     50                       55                       60

Phe  Arg  Val  Cys  Leu  Lys  His  Tyr  Gln  Ala  Thr  Ile  Asp  Thr  Thr  Ser
 65                      70                       75                       80

Gln  Cys  Thr  Tyr  Gly  Asp  Val  Ile  Thr  Pro  Ile  Leu  Gly  Glu  Asn  Ser
                    85                       90                       95

Val  Asn  Leu  Thr  Asp  Ala  Gln  Arg  Phe  Gln  Asn  Lys  Gly  Phe  Thr  Asn
               100                      105                      110

Pro  Ile  Gln  Phe  Pro  Phe  Ser  Phe  Ser  Trp  Pro  Gly  Thr  Phe  Ser  Leu
          115                      120                      125

Ile  Val  Glu  Ala  Trp  His  Asp  Thr  Asn  Asn  Ser  Gly  Asn  Ala  Arg  Thr
     130                      135                      140

Asn  Lys  Leu  Leu  Ile  Gln  Arg  Leu  Leu  Val  Gln  Val  Leu  Glu  Val
145                      150                      155                      160

Ser  Ser  Glu  Trp  Lys  Thr  Asn  Lys  Ser  Glu  Ser  Gln  Tyr  Thr  Ser  Leu
                    165                      170                      175

Glu  Tyr  Asp  Phe  Arg  Val  Thr  Cys  Asp  Leu  Asn  Tyr  Tyr  Gly  Ser  Gly
               180                      185                      190
```

```
Cys Ala Lys Phe Cys Arg Pro Arg Asp Asp Ser Phe Gly His Ser Thr
        195                 200                 205
Cys Ser Glu Thr Gly Glu Ile Ile Cys Leu Thr Gly Trp Gln Gly Asp
        210                 215                 220
Tyr Cys His Ile Pro Lys Cys Ala Lys Gly Cys Glu His Gly His Cys
225                 230                 235                 240
Asp Lys Pro Asn Gln Cys Val Cys Gln Leu Gly Trp Lys Gly Ala Leu
                245                 250                 255
Cys Asn Glu Cys Val Leu Glu Pro Asn Cys Ile His Gly Thr Cys Asn
            260                 265                 270
Lys Pro Trp Thr Cys Ile Cys Asn Glu Gly Trp Gly Gly Leu Tyr Cys
        275                 280                 285
Asn Gln Asp Leu Asn Tyr Cys Thr Asn His Arg Pro Cys Lys Asn Gly
    290                 295                 300
Gly Thr Cys Phe Asn Thr Gly Glu Gly Leu Tyr Thr Cys Lys Cys Ala
305                 310                 315                 320
Pro Gly Tyr Ser Gly Asp Asp Cys Glu Asn Glu Ile Tyr Ser Cys Asp
                325                 330                 335
Ala Asp Val Asn Pro Cys Gln Asn Gly Gly Thr Cys Ile Asp Glu Pro
            340                 345                 350
His Thr Lys Thr Gly Tyr Lys Cys His Cys Ala Asn Gly Trp Ser Gly
        355                 360                 365
Lys Met Cys Glu Glu Lys Val Leu Thr Cys Ser Asp Lys Pro Cys His
370                 375                 380
Gln Gly Ile Cys Arg Asn Val Arg Pro Gly Leu Gly Ser Lys Gly Gln
385                 390                 395                 400
Gly Tyr Gln Cys Glu Cys Pro Ile Gly Tyr Ser Gly Pro Asn Cys Asp
                405                 410                 415
Leu Gln Leu Asp Asn Cys Ser Pro Asn Pro Cys Ile Asn Gly Gly Ser
            420                 425                 430
Cys Gln Pro Ser Gly Lys Cys Ile Cys Pro Ala Gly Phe Ser Gly Thr
        435                 440                 445
Arg Cys Glu Thr Asn Ile Asp Asp Cys Leu Gly His Gln Cys Glu Asn
    450                 455                 460
Gly Gly Thr Cys Ile Asp Met Val Asn Gln Tyr Arg Cys Gln Cys Val
465                 470                 475                 480
Pro Gly Phe His Gly Thr His Cys Ser Ser Lys Val Asp Leu Cys Leu
                485                 490                 495
Ile Arg Pro Cys Ala Asn Gly Gly Thr Cys Leu Asn Leu Asn Asn Asp
            500                 505                 510
Tyr Gln Cys Thr Cys Arg Ala Gly Phe Thr Gly Lys Asp Cys Ser Val
        515                 520                 525
Asp Ile Asp Glu Cys Ser Ser Gly Pro Cys His Asn Gly Gly Thr Cys
    530                 535                 540
Met Asn Arg Val Asn Ser Phe Glu Cys Val Cys Ala Asn Gly Phe Arg
545                 550                 555                 560
Gly Lys Gln Cys Asp Glu Glu Ser Tyr Asp Ser Val Thr Phe Asp Ala
                565                 570                 575
His Gln Tyr Gly Ala Thr Thr Gln Ala Arg Ala Asp Gly Leu Thr Asn
            580                 585                 590
Ala Gln Val Val Leu Ile Ala Val Phe Ser Val Ala Met Pro Leu Val
        595                 600                 605
Ala Val Ile Ala Ala Cys Val Val Phe Cys Met Lys Arg Lys Arg Lys
```

|  |  |  | 610 |  |  |  | 615 |  |  |  | 620 |  |  |
|---|---|---|---|---|---|---|---|---|---|---|---|---|---|
| Arg<br>625 | Ala | Gln | Glu | Lys | Asp<br>630 | Asp | Ala | Glu | Ala | Arg<br>635 | Lys | Gln | Asn | Glu | Gln<br>640 |

Arg Ala Gln Glu Lys Asp Asp Ala Glu Ala Arg Lys Gln Asn Glu Gln
625                     630                     635                     640

Asn Ala Val Ala Thr Met His His Asn Gly Ser Gly Val Gly Val Ala
                    645                 650                     655

Leu Ala Ser Ala Ser Leu Gly Gly Lys Thr Gly Ser Asn Ser Gly Leu
                660                 665                 670

Thr Phe Asp Gly Gly Asn Pro Asn Ile Ile Lys Asn Thr Trp Asp Lys
            675             680                 685

Ser Val Asn Asn Ile Cys Ala Ser Ala Ala Ala Ala Ala Ala Ala Ala
        690             695                 700

Ala Ala Ala Asp Glu Cys Leu Met Tyr Gly Gly Tyr Val Ala Ser Val
705             710                 715                         720

Ala Asp Asn Asn Asn Ala Asn Ser Asp Phe Cys Val Ala Pro Leu Gln
                725             730                     735

Arg Ala Lys Ser Gln Lys Gln Leu Asn Thr Asp Pro Thr Leu Met His
            740             745                 750

Arg Gly Ser Pro Ala Gly Ser Ser Ala Lys Gly Ala Ser Gly Gly Gly
        755                 760                 765

Pro Gly Ala Ala Glu Gly Lys Arg Ile Ser Val Leu Gly Glu Gly Ser
770                 775                 780

Tyr Cys Ser Gln Arg Trp Pro Ser Leu Ala Ala Ala Gly Val Ala Gly
785             790                 795                         800

Ala Cys Ser Ser Gln Leu Met Ala Ala Ser Ala Ala Gly Ser Gly
                805             810                 815

Ala Gly Thr Ala Gln Gln Gln Arg Ser Val Val Cys Gly Thr Pro His
            820             825                 830

Met ( 2 ) INFORMATION FOR SEQ ID NO:7:

( i ) SEQUENCE CHARACTERISTICS:
        ( A ) LENGTH: 1067 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:7:

| GATCTACTAC | GAGGAGGTTA | AGGAGAGCTA | TGTGGGCGAG | CGACGCGAAT | ACGATCCCCA | 60 |
| CATCACCGAT | CCCAGGGTCA | CACGCATGAA | GATGGCCGGC | CTGAAGCCCA | ACTCCAAATA | 120 |
| CCGCATCTCC | ATCACTGCCA | CCACGAAAAT | GGGCGAGGGA | TCTGAACACT | ATATCGAAAA | 180 |
| GACCACGCTC | AAGGATGCCG | TCAATGTGGC | CCCTGCCACG | CCATCTTTCT | CCTGGGAGCA | 240 |
| ACTGCCATCC | GACAATGGAC | TAGCCAAGTT | CCGCATCAAC | TGGCTGCCAA | GTACCGAGGG | 300 |
| TCATCCAGGC | ACTCACTTCT | TTACGATGCA | CAGGATCAAG | GGCGAAACCC | AATGGATACG | 360 |
| CGAGAATGAG | GAAAAGAACT | CCGATTACCA | GGAGGTCGGT | GGCTTAGATC | CGGAGACCGC | 420 |
| CTACGAGTTC | CGCGTGGTGT | CCGTGGATGG | CCACTTTAAC | ACGGAGAGTG | CCACGCAGGA | 480 |
| GATCGACACG | AACACCGTTG | AGGGACCAAT | AATGGTGGCC | AACGAGACGG | TGGCCAATGC | 540 |
| CGGATGGTTC | ATTGGCATGA | TGCTGGCCCT | GGCCTTCATC | ATCATCCTCT | TCATCATCAT | 600 |
| CTGCATTATC | CGACGCAATC | GGGGCGGAAA | GTACGATGTC | CACGATCGGG | AGCTGGCCAA | 660 |
| CGGCCGGCGG | GATTATCCCG | AAGAGGGCGG | ATTCCACGAG | TACTCGCAAC | CGTTGGATAA | 720 |

-continued

```
CAAGAGCGCT GGTCGCCAAT CCGTGAGTTC AGCGAACAAA CCGGGCGTGG AAAGCGATAC      780

TGATTCGATG GCCGAATACG GTGATGGCGA TACAGGACAA TTTACCGAGG ATGGCTCCTT      840

CATTGGCCAA TATGTTCCTG GAAAGCTCCA ACCGCCGGTT AGCCCACAGC CACTGAACAA      900

TTCCGCTGCG GCGCATCAGG CGGCGCCAAC TGCCGGAGGA TCGGGAGCAG CCGGATCGGC      960

AGCAGCAGCC GGAGCATCGG GTGGAGCATC GTCCGCCGGA GGAGCAGCTG CCAGCAATGG     1020

AGGAGCTGCA GCCGGAGCCG TGGCCACCTA CGTCTAAGCT TGGTACC                   1067
```

( 2 ) INFORMATION FOR SEQ ID NO:8:

( i ) SEQUENCE CHARACTERISTICS:
        ( A ) LENGTH: 1320 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 442..1320

( x i ) SEQUENCE DESCRIPTION: SEQ ID NO:8:

```
CCGAGTCGAG CGCCGTGCTT CGAGCGGTGA TGAGCCCCTT TTCTGTCAAC GCTAAAGATC       60

TACAAAACAT CAGCGCCTAT CAAGTGGAAG TGTCAAGTGT GAACAAAACA AAAACGAGAG      120

AAGCACATAC TAAGGTCCAT ATAAATAATA AATAATAATT GTGTGTGATA ACAACATTAT      180

CCAAACAAAA CCAAACAAAA CGAAGGCAAA GTGGAGAAAA TGATACAGCA TCCAGAGTAC      240

GGCCGTTATT CAGCTATCCA GAGCAAGTGT AGTGTGGCAA AATAGAAACA AACAAAGGCA      300

CCAAAATCTG CATACATGGG CTAATTAAGG CTGCCCAGCG AATTTACATT TGTGTGGTGC      360

CAATCCAGAG TGAATCCGAA ACAAACTCCA TCTAGATCGC CAACCAGCAT CACGCTCGCA      420

AACGCCCCCA GAATGTACAA A ATG TTT AGG AAA CAT TTT CGG CGA AAA CCA       471
                         Met Phe Arg Lys His Phe Arg Arg Lys Pro
                          1               5                  10

GCT ACG TCG TCG TCG TTG GAG TCA ACA ATA GAA TCA GCA GAC AGC CTG       519
Ala Thr Ser Ser Ser Leu Glu Ser Thr Ile Glu Ser Ala Asp Ser Leu
                15                  20                  25

GGA ATG TCC AAG AAG ACG GCG ACA AAA AGG CAG CGT CCG AGG CAT CGG       567
Gly Met Ser Lys Lys Thr Ala Thr Lys Arg Gln Arg Pro Arg His Arg
         30                  35                  40

GTA CCC AAA ATC GCG ACC CTG CCA TCG ACG ATC CGC GAT TGT CGA TCA       615
Val Pro Lys Ile Ala Thr Leu Pro Ser Thr Ile Arg Asp Cys Arg Ser
     45                  50                  55

TTA AAG TCT GCC TGC AAC TTA ATT GCT TTA ATT TTA ATA CTG TTA GTC       663
Leu Lys Ser Ala Cys Asn Leu Ile Ala Leu Ile Leu Ile Leu Leu Val
 60                  65                  70

CAT AAG ATA TCC GCA GCT GGT AAC TTC GAG CTG GAA ATA TTA GAA ATC       711
His Lys Ile Ser Ala Ala Gly Asn Phe Glu Leu Glu Ile Leu Glu Ile
 75                  80                  85                  90

TCA AAT ACC AAC AGC CAT CTA CTC AAC GGC TAT TGC TGC GGC ATG CCA       759
Ser Asn Thr Asn Ser His Leu Leu Asn Gly Tyr Cys Cys Gly Met Pro
                 95                 100                 105

GCG GAA CTT AGG GCC ACC AAG ACG ATA GGC TGC TCG CCA TGC ACG ACG       807
Ala Glu Leu Arg Ala Thr Lys Thr Ile Gly Cys Ser Pro Cys Thr Thr
            110                 115                 120

GCA TTC CGG CTG TGC CTG AAG GAG TAC CAG ACC ACG GAG CAG GGT GCC       855
Ala Phe Arg Leu Cys Leu Lys Glu Tyr Gln Thr Thr Glu Gln Gly Ala
        125                 130                 135

AGC ATA TCC ACG GGC TGT TCG TTT GGC AAC GCC ACC ACC AAG ATA CTG       903
```

| | | | | | | | | | | | | | | | |
|---|---|---|---|---|---|---|---|---|---|---|---|---|---|---|---|
|Ser|Ile|Ser|Thr|Gly|Cys|Ser|Phe|Gly|Asn|Ala|Thr|Thr|Lys|Ile|Leu|
| |140| | | |145| | | |150| | | | | | |

```
GGT  GGC  TCC  AGC  TTT  GTG  CTC  AGC  GAT  CCG  GGT  GTG  GGA  GCC  ATT  GTG         951
Gly  Gly  Ser  Ser  Phe  Val  Leu  Ser  Asp  Pro  Gly  Val  Gly  Ala  Ile  Val
155                      160                      165                      170

CTG  CCC  TTT  ACG  TTT  CGT  TGG  ACG  AAG  TCG  TTT  ACG  CTG  ATA  CTG  CAG         999
Leu  Pro  Phe  Thr  Phe  Arg  Trp  Thr  Lys  Ser  Phe  Thr  Leu  Ile  Leu  Gln
                         175                      180                      185

GCG  TTG  GAT  ATG  TAC  AAC  ACA  TCC  TAT  CCA  GAT  GCG  GAG  AGG  TTA  ATT        1047
Ala  Leu  Asp  Met  Tyr  Asn  Thr  Ser  Tyr  Pro  Asp  Ala  Glu  Arg  Leu  Ile
               190                      195                      200

GAG  GAA  ACA  TCA  TAC  TCG  GGC  GTG  ATA  CTG  CCG  TCG  CCG  GAG  TGG  AAG        1095
Glu  Glu  Thr  Ser  Tyr  Ser  Gly  Val  Ile  Leu  Pro  Ser  Pro  Glu  Trp  Lys
          205                      210                      215

ACG  CTG  GAC  CAC  ATC  GGG  CGG  AAC  GCG  CGG  ATC  ACC  TAC  CGT  GTC  CGG        1143
Thr  Leu  Asp  His  Ile  Gly  Arg  Asn  Ala  Arg  Ile  Thr  Tyr  Arg  Val  Arg
     220                      225                      230

GTG  CAA  TGC  GCC  GTT  ACC  TAC  TAC  AAC  ACG  ACC  TGC  ACG  ACC  TTC  TGC        1191
Val  Gln  Cys  Ala  Val  Thr  Tyr  Tyr  Asn  Thr  Thr  Cys  Thr  Thr  Phe  Cys
235                      240                      245                      250

CGT  CCG  CGG  GAC  GAT  CAG  TTC  GGT  CAC  TAC  GCC  TGC  GGC  TCC  GAG  GGT        1239
Arg  Pro  Arg  Asp  Asp  Gln  Phe  Gly  His  Tyr  Ala  Cys  Gly  Ser  Glu  Gly
                         255                      260                      265

CAG  AAG  CTC  TGC  CTG  AAT  GGC  TGG  CAG  GGC  GTC  AAC  TGC  GAG  GAG  GCC        1287
Gln  Lys  Leu  Cys  Leu  Asn  Gly  Trp  Gln  Gly  Val  Asn  Cys  Glu  Glu  Ala
               270                      275                      280

ATA  TGC  AAG  GCG  GGC  TGC  GAC  CCC  GTC  CAC  GGC                                  1320
Ile  Cys  Lys  Ala  Gly  Cys  Asp  Pro  Val  His  Gly
          285                      290
```

( 2 ) INFORMATION FOR SEQ ID NO:9:

( i ) SEQUENCE CHARACTERISTICS:
        ( A ) LENGTH: 293 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:9:

```
Met  Phe  Arg  Lys  His  Phe  Arg  Arg  Lys  Pro  Ala  Thr  Ser  Ser  Ser  Leu
  1                 5                    10                            15

Glu  Ser  Thr  Ile  Glu  Ser  Ala  Asp  Ser  Leu  Gly  Met  Ser  Lys  Lys  Thr
                    20                    25                    30

Ala  Thr  Lys  Arg  Gln  Arg  Pro  Arg  His  Arg  Val  Pro  Lys  Ile  Ala  Thr
               35                    40                    45

Leu  Pro  Ser  Thr  Ile  Arg  Asp  Cys  Arg  Ser  Leu  Lys  Ser  Ala  Cys  Asn
          50                    55                    60

Leu  Ile  Ala  Leu  Ile  Leu  Ile  Leu  Leu  Val  His  Lys  Ile  Ser  Ala  Ala
 65                     70                    75                         80

Gly  Asn  Phe  Glu  Leu  Glu  Ile  Leu  Glu  Ile  Ser  Asn  Thr  Asn  Ser  His
                    85                    90                         95

Leu  Leu  Asn  Gly  Tyr  Cys  Cys  Gly  Met  Pro  Ala  Glu  Leu  Arg  Ala  Thr
               100                   105                   110

Lys  Thr  Ile  Gly  Cys  Ser  Pro  Cys  Thr  Thr  Ala  Phe  Arg  Leu  Cys  Leu
               115                   120                   125

Lys  Glu  Tyr  Gln  Thr  Thr  Glu  Gln  Gly  Ala  Ser  Ile  Ser  Thr  Gly  Cys
          130                   135                   140

Ser  Phe  Gly  Asn  Ala  Thr  Thr  Lys  Ile  Leu  Gly  Gly  Ser  Ser  Phe  Val
145                     150                   155                        160
```

| Leu | Ser | Asp | Pro | Gly | Val | Gly | Ala | Ile | Val | Leu | Pro | Phe | Thr | Phe | Arg |
|---|---|---|---|---|---|---|---|---|---|---|---|---|---|---|---|
| | | | | 165 | | | | | 170 | | | | | 175 | |

| Trp | Thr | Lys | Ser | Phe | Thr | Leu | Ile | Leu | Gln | Ala | Leu | Asp | Met | Tyr | Asn |
|---|---|---|---|---|---|---|---|---|---|---|---|---|---|---|---|
| | | | 180 | | | | | 185 | | | | | 190 | | |

| Thr | Ser | Tyr | Pro | Asp | Ala | Glu | Arg | Leu | Ile | Glu | Glu | Thr | Ser | Tyr | Ser |
|---|---|---|---|---|---|---|---|---|---|---|---|---|---|---|---|
| | | 195 | | | | | 200 | | | | | 205 | | | |

| Gly | Val | Ile | Leu | Pro | Ser | Pro | Glu | Trp | Lys | Thr | Leu | Asp | His | Ile | Gly |
|---|---|---|---|---|---|---|---|---|---|---|---|---|---|---|---|
| | 210 | | | | | 215 | | | | | 220 | | | | |

| Arg | Asn | Ala | Arg | Ile | Thr | Tyr | Arg | Val | Arg | Val | Gln | Cys | Ala | Val | Thr |
|---|---|---|---|---|---|---|---|---|---|---|---|---|---|---|---|
| 225 | | | | | 230 | | | | | 235 | | | | | 240 |

| Tyr | Tyr | Asn | Thr | Thr | Cys | Thr | Thr | Phe | Cys | Arg | Pro | Arg | Asp | Asp | Gln |
|---|---|---|---|---|---|---|---|---|---|---|---|---|---|---|---|
| | | | | 245 | | | | | 250 | | | | | 255 | |

| Phe | Gly | His | Tyr | Ala | Cys | Gly | Ser | Glu | Gly | Gln | Lys | Leu | Cys | Leu | Asn |
|---|---|---|---|---|---|---|---|---|---|---|---|---|---|---|---|
| | | | 260 | | | | | 265 | | | | | 270 | | |

| Gly | Trp | Gln | Gly | Val | Asn | Cys | Glu | Glu | Ala | Ile | Cys | Lys | Ala | Gly | Cys |
|---|---|---|---|---|---|---|---|---|---|---|---|---|---|---|---|
| | | 275 | | | | | 280 | | | | | 285 | | | |

| Asp | Pro | Val | His | Gly |
|---|---|---|---|---|
| | | 290 | | |

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: unknown (ii) MOLECULE TYPE: cDNA (ix) FEATURE:
        (A) NAME/KEY: modified_base
        (B) LOCATION: 6
        (D) OTHER INFORMATION: /mod_base= i
            / label= N (ix) FEATURE:
        (A) NAME/KEY: modified_base
        (B) LOCATION: 12
        (D) OTHER INFORMATION: /mod_base= i
            / label= N (xi) SEQUENCE DESCRIPTION: SEQ ID NO:10:

GAYGCNAAYG TNCARGAYAA YATGGG      26

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: single
        (D) TOPOLOGY: unknown (ii) MOLECULE TYPE: cDNA (ix) FEATURE:
        (A) NAME/KEY: modified_base
        (B) LOCATION: 3
        (D) OTHER INFORMATION: /mod_base= i
            / label= N (ix) FEATURE:
        (A) NAME/KEY: modified_base
        (B) LOCATION: 12
        (D) OTHER INFORMATION: /mod_base= i
            / label= N (ix) FEATURE:
        (A) NAME/KEY: modified_base ( B ) LOCATION: 18
( D ) OTHER INFORMATION: /mod_base= i
/ label= N ( x i ) SEQUENCE DESCRIPTION: SEQ ID NO:11:

ATNARRTCYT CNACCATNCC YTCDA 25

( 2 ) INFORMATION FOR SEQ ID NO:12:

( i ) SEQUENCE CHARACTERISTICS:
( A ) LENGTH: 26 base pairs
( B ) TYPE: nucleic acid
( C ) STRANDEDNESS: single
( D ) TOPOLOGY: unknown ( i i ) MOLECULE TYPE: cDNA ( i x ) FEATURE:
( A ) NAME/KEY: modified_base
( B ) LOCATION: 12
( D ) OTHER INFORMATION: /mod_base= i
/ label= N ( i x ) FEATURE:
( A ) NAME/KEY: modified_base
( B ) LOCATION: 18
( D ) OTHER INFORMATION: /mod_base= i
/ label= N ( i x ) FEATURE:
( A ) NAME/KEY: modified_base
( B ) LOCATION: 21
( D ) OTHER INFORMATION: /mod_base= i
/ label= N ( x i ) SEQUENCE DESCRIPTION: SEQ ID NO:12:

TCCATRTGRT CNGTDATNTC NCKRTT 26

( 2 ) INFORMATION FOR SEQ ID NO:13:

( i ) SEQUENCE CHARACTERISTICS:
( A ) LENGTH: 267 base pairs
( B ) TYPE: nucleic acid
( C ) STRANDEDNESS: double
( D ) TOPOLOGY: unknown ( i i ) MOLECULE TYPE: cDNA ( x i ) SEQUENCE DESCRIPTION: SEQ ID NO:13:

CGGTGGACTT CCTTCGTGTA TTGGTGGGAG CCCTCGGGAA CGGGGGGTAA CACTGAAAGG 60

TCGAGTACCC ATTTCCGTCA TAACGGGTTG GTCGCCCCCT AGGGGTCGGA GTCAGGTGGA 120

CGGGAGGTCG ACAACGCCCG GGGGACGGGT GGTACATGGT GTAAGGTCTT TACCGGACCG 180

GGCAAACGGG TCACACCGAA AGGGGTGAAC GGTAACTACG GGGTCGTCCT GCCCGTCCAT 240

CGAGTCTGGT AAGAGGGTCG CCTTAAG 267

( 2 ) INFORMATION FOR SEQ ID NO:14:

( i ) SEQUENCE CHARACTERISTICS:
( A ) LENGTH: 574 base pairs
( B ) TYPE: nucleic acid
( C ) STRANDEDNESS: double
( D ) TOPOLOGY: unknown ( i i ) MOLECULE TYPE: cDNA ( x i ) SEQUENCE DESCRIPTION: SEQ ID NO:14:

GAATTCCTTC CATTATACGT GACTTTTCTG AAACTGTAGC CACCCTAGTG TCTCTAACTC 60

CCTCTGGAGT TTGTCAGCTT TGGTCTTTTC AAAGAGCAGG CTCTCTTCAA GCTCCTTAAT 120

| | | | | | |
|---|---|---|---|---|---|
| GCGGGCATGC | TCCAGTTTGG | TCTGCGTCTC | AAGATCACCT | TTGGTAATTG | ATTCTTCTTC | 180 |
| AACCCGGAAC | TGAAGGCTGG | CTCTCACCCT | CTAGGCAGAG | CAGGAATTCC | GAGGTGGATG | 240 |
| TGTTAGATGT | GAATGTCCGT | GGCCCAGATG | GCTGCACCCC | ATTGATGTTG | GCTTCTCTCC | 300 |
| GAGGAGGCAG | CTCAGATTTG | AGTGATGAAG | ATGAAGATGC | AGAGGACTGT | TCTGCTAACA | 360 |
| TCATCACAGA | CTTGGTCTAC | CAGGGTGCCA | GCCTCCAGNC | CAGACAGACC | GGACTGGTGA | 420 |
| GATGGCCCTG | CACCTTGCAG | CCCGCTACTC | ACGGGCTGAT | GCTGCCAAGC | GTCTCCTGGA | 480 |
| TGCAGGTGCA | GATGCCAATG | CCCAGGACAA | CATGGGCCGC | TGTCCACTCC | ATGCTGCAGT | 540 |
| GGCACGTGAT | GCCAAGGTGT | ATTCAGATCT | GTTA | | | 574 |

( 2 ) INFORMATION FOR SEQ ID NO:15:

( i ) SEQUENCE CHARACTERISTICS:
        ( A ) LENGTH: 295 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:15:

| | | | | | |
|---|---|---|---|---|---|
| TCCAGATTCT | GATTCGCAAC | CGAGTAACTG | ATCTAGATGC | CAGGATGAAT | GATGGTACTA | 60 |
| CACCCCTGAT | CCTGGCTGCC | CGCCTGGCTG | TGGAGGGAAT | GGTGGCAGAA | CTGATCAACT | 120 |
| GCCAAGCGGA | TGTGAATGCA | GTGGATGACC | ATGGAAAATC | TGCTCTTCAC | TGGGCAGCTG | 180 |
| CTGTCAATAA | TGTGGAGGCA | ACTCTTTTGT | TGTTGAAAAA | TGGGGCCAAC | CGAGACATGC | 240 |
| AGGACAACAA | GGAAGAGACA | CCTCTGTTTC | TTGCTGCCCG | GGAGGAGCTA | TAAGC | 295 |

( 2 ) INFORMATION FOR SEQ ID NO:16:

( i ) SEQUENCE CHARACTERISTICS:
        ( A ) LENGTH: 333 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:16:

| | | | | | |
|---|---|---|---|---|---|
| GAGTCGTCGG | TCGCCGGTGG | ACCCGGCCTC | GAAGGACTCA | CCTCTCGGCT | CGGTCCGTCT | 60 |
| GCACGTCATG | ACCCGGGGTC | GTCGGACCGC | CACGTGTGAT | AAGACGGGGT | CCTCTCGGGG | 120 |
| CGGGACGGGT | GCAGCGACGG | TAGGAGCGAC | CAGGGTGGGC | ACTGGCGTCG | GGTCAAGGAC | 180 |
| TGCGGGGGGA | GCGTCGTGTC | GATGAGGAGC | GGACACCTGT | TGTGGGGGTC | GGTGGTCGAT | 240 |
| GTCCACGGAC | AAGGACATTA | CCATTACTAG | GCTAGAAGCC | TAGGAAGATT | TCCGAGTAGT | 300 |
| TAAAACTAGC | TTCGAGGGCT | GAGTACCCTT | AAG | | | 333 |

( 2 ) INFORMATION FOR SEQ ID NO:17:

( i ) SEQUENCE CHARACTERISTICS:
        ( A ) LENGTH: 582 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:17:

| | | | | | |
|---|---|---|---|---|---|
| GAATTCCTGC | CAGGAGGACG | CGGGCAACAA | GGTCTGCAGC | CTGCAGTGCA | ACAACCACGC | 60 |

-continued

| | | | | | |
|---|---|---|---|---|---|
| GTGCGGCTGG | GACGGCGGTG | ACTGCTCCCT | CAACTTCACA | ATGACCCCTG | GAAGAACTGC | 120
| ACGCAGTCTC | TGCAGTGCTG | GAAGTACTTC | AGTGACGGCC | ACTGTGACAG | CCAGTGCAAC | 180
| TCAGCCGGCT | GCCTCTTCGA | CGGCTTTGAC | TGCCAGCGGC | GGAAGGCCAG | TTGCAACCCC | 240
| CTGTACGACC | AGTACTGCAA | GGACCACTTC | AGCGACGGGC | ACTGCGACCA | GGGCTGCAAC | 300
| AGCGCGGAGT | NCAGNTGGGA | CGGGCTGGAC | TGTGCGGCAG | TGTACCCGAG | AGCTGGCGGC | 360
| GCACGCTGGT | GGTGGTGGTG | CTGATGCCGC | CGGAGCAGCT | GCGCAACAGC | TCCTTCCACT | 420
| TCCTGCGGGA | CGTCAGCCGC | GTGCTGCACA | CCAACGTGTC | TTCAAGCGTG | ACGCACACGG | 480
| CCAGCAGATG | ATGTTCCCCT | ACTACGGCCG | CGAGGAGGAG | CTGCGCAAGC | CCCATCAAGC | 540
| GTGCCGCCGA | GGGCTGGGCC | GCACCTGACG | CCTGCTGGGC | CA | | 582

( 2 ) INFORMATION FOR SEQ ID NO:18:

( i ) SEQUENCE CHARACTERISTICS:
        ( A ) LENGTH: 150 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:18:

| | | | | | |
|---|---|---|---|---|---|
| TCAGCCGAGT | GCTGCACACC | AACGTGTCTT | CAAGCGTGAC | GCACACGGCC | AGCAGATGAT | 60
| GTTCCCCTAC | TACGGCCGCG | AGGAGGAGCT | GCGCAAGCCC | CATCAAGCGT | GCCGCCGAGG | 120
| GCTGGGCCGC | ACCTGACGCC | TGCTGGGCCA | | | | 150

( 2 ) INFORMATION FOR SEQ ID NO:19:

( i ) SEQUENCE CHARACTERISTICS:
        ( A ) LENGTH: 247 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:19:

| | | | | | |
|---|---|---|---|---|---|
| TGGACCCGGC | CTCGAAGGAC | TCACCTCTCG | GCTCGGTCCG | TCTGCACGTC | GTGACCCGGG | 60
| GTCGTCGACC | GCCACGTGTG | ATAAGACGGG | GTCCTCTCGG | GGCGGGACGG | GTGCAGCGAC | 120
| GGTAGGAGCG | ACCAGGGTGG | GCACTGGCGT | CGGGTCAAGG | ACTGCGGGGG | GAGCGTCGTG | 180
| TCGATGAGGA | GCGGACACCT | GTTGTGGGGG | TCGGTGGTCG | ATGTCCACGG | ACAAGGACAT | 240
| TACCATT | | | | | | 247

( 2 ) INFORMATION FOR SEQ ID NO:20:

( i ) SEQUENCE CHARACTERISTICS:
        ( A ) LENGTH: 248 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:20:

| | | | | | |
|---|---|---|---|---|---|
| GAATTCCATT | CAGGAGGAAA | GGGTGGGGAG | AGAAGCAGGC | ACCCACTTTC | CCGTGGCTGG | 60
| ACTCGTTCCC | AGGTGGCTCC | ACCGGCAGCT | GTGACCGCCG | CAGGTGGGGG | CGGAGTGCCA | 120
| TTCAGAAAAT | TCCAGAAAAG | CCCTACCCCA | ACTCGGACGG | CAACGTCACA | CCCGTGGGTA | 180
| GCAACTGGCA | CACAAACAGC | CAGCGTGTCT | GGGGCACGGG | GGGATGGCAC | CCCCTGCAGG | 240

CAGAGCTG                                                                                                                          248

( 2 ) INFORMATION FOR SEQ ID NO:21:

( i ) SEQUENCE CHARACTERISTICS:
          ( A ) LENGTH: 323 base pairs
          ( B ) TYPE: nucleic acid
          ( C ) STRANDEDNESS: double
          ( D ) TOPOLOGY: unknown ( i i ) MOLECULE TYPE: cDNA ( x i ) SEQUENCE DESCRIPTION: SEQ ID NO:21:

TACGTATCTC    GAGCACAGAC    AGCTGACGTA    CACTTTTNNA    GTGCGAGGGA    CATTCGTCCG        60
ACCAGTACGA    ACATTTAGGC    TCAGTACGGT    AGGTCCATGG    CCAAGACTAG    GAGACGTAGG       120
GAGCTACAGG    TCCCGCTCGC    TAAACTCGGA    CCACTGAAAC    CTCCGGTCGA    CAGTCGGTAA       180
GCGAACAAGA    GGGCCAGATC    TTAGAGAAGG    TGTCGCGGCG    AGACTCGGGC    TCGGGTCAGG       240
CGGCCTTAAG    GACGTCGGGC    CCNNNAGGTG    ATCAAGATCT    CGNCNGGCG    GGCGCCACCT       300
CGAGGNCGAA    AACAAGGGAA    ATC                                                      323

( 2 ) INFORMATION FOR SEQ ID NO:22:

( i ) SEQUENCE CHARACTERISTICS:
          ( A ) LENGTH: 330 base pairs
          ( B ) TYPE: nucleic acid
          ( C ) STRANDEDNESS: double
          ( D ) TOPOLOGY: unknown ( i i ) MOLECULE TYPE: cDNA ( x i ) SEQUENCE DESCRIPTION: SEQ ID NO:22:

GAATTCCGAG    GTGGATGTGT    TAGATGTGAA    TGTCCGTGGC    CCAGATGGCT    GCACCCCATT        60
GATGTTGGCT    TCTCTCCGAG    GAGGCAGCTC    AGATTTGAGT    GATGAAGATG    AAGATGCAGA       120
GGACTCTTCT    GCTAACATCA    TCACAGACTT    GGTCTTACCA    GGGTGCCAGC    CTTCCAGGCC       180
CAAGAACAGA    CCGGACTTGG    TGAGATGGCC    CTGCACCTTG    CAGCCCGCTA    CTACGGGCTG       240
ATGCTGCCAA    GGTTCTGGAT    GCAGGTGCAG    ATGCCAATGC    CCAGGACAAC    ATGGGCCGCT       300
GTCCACTCCA    TGCTGCAGTG    GCACTGATGC                                               330

( 2 ) INFORMATION FOR SEQ ID NO:23:

( i ) SEQUENCE CHARACTERISTICS:
          ( A ) LENGTH: 167 base pairs
          ( B ) TYPE: nucleic acid
          ( C ) STRANDEDNESS: double
          ( D ) TOPOLOGY: unknown ( i i ) MOLECULE TYPE: cDNA ( x i ) SEQUENCE DESCRIPTION: SEQ ID NO:23:

TTCAAACAAG    TAAGAGACGA    AATAGAGAGG    TACACCGTTG    TAAGACAGTC    GGAGAAAGTA        60
TCACACGTTT    GTAAAATAGT    AAGATTTACC    ACTGAGAGAC    GGGAACGTGG    GTAAATAATA       120
AGTGTCCTAC    CCCTCTTGGA    TAGACGTACC    TGGGAGTGGT    AGGAGAC                       167

( 2 ) INFORMATION FOR SEQ ID NO:24:

( i ) SEQUENCE CHARACTERISTICS:
          ( A ) LENGTH: 225 base pairs
          ( B ) TYPE: nucleic acid
          ( C ) STRANDEDNESS: double
          ( D ) TOPOLOGY: unknown -continued (ii) MOLECULE TYPE: cDNA (xi) SEQUENCE DESCRIPTION: SEQ ID NO:24:

| AGGATGAATG | ATGGTACTAC | ACCCCTGATC | CTGGCTGCCC | GCCTGGCTGT | GGAGGGAATG | 60 |
| GTGGCAGAAC | TGATCAACTG | CCAAGCGGAT | GTGAATGCAG | TGGATGACCA | TGGAAAATCT | 120 |
| GCTCTTCACT | GGGCAGCTGC | TGTCAATAAT | GTGGAGGCAA | CTCTTTTGTT | GTTGAAAAAT | 180 |
| GGGGCCAACC | GAGACATGCA | GGACAACAAG | GAAGAGACAC | CTCTG | | 225 |

(2) INFORMATION FOR SEQ ID NO:25:

(i) SEQUENCE CHARACTERISTICS:
        (A) LENGTH: 121 base pairs
        (B) TYPE: nucleic acid
        (C) STRANDEDNESS: double
        (D) TOPOLOGY: unknown (ii) MOLECULE TYPE: cDNA (xi) SEQUENCE DESCRIPTION: SEQ ID NO:25:

| TTCAAACAAG | TAAGAGACGA | AATAGAGAGG | TACACCGTTG | TAAGACAGTC | GGAGAAAGTA | 60 |
| TCACACGTTT | GTAAAATAGT | AAGATTTACC | ACTGAGAGAC | GGGAACGTGG | GTAAATAATA | 120 |
| A | | | | | | 121 |

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:26:

ACTTCAGCAA CGATCACGGG     20

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:27:

TTGGGTATGT GACAGTAATC G     21

(2) INFORMATION FOR SEQ ID NO:28:

(i) SEQUENCE CHARACTERISTICS:
        (A) LENGTH: 14 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:28:

TTAAGTTAAC TTAA     14

(2) INFORMATION FOR SEQ ID NO:29:

( i ) SEQUENCE CHARACTERISTICS:
: ( A ) LENGTH: 12 base pairs
: ( B ) TYPE: nucleic acid
: ( C ) STRANDEDNESS: single
: ( D ) TOPOLOGY: unknown ( i i ) MOLECULE TYPE: cDNA ( x i ) SEQUENCE DESCRIPTION: SEQ ID NO:29:

GGAAGATCTT CC                                                                                                         1 2

( 2 ) INFORMATION FOR SEQ ID NO:30:

: ( i ) SEQUENCE CHARACTERISTICS:
: : ( A ) LENGTH: 4 amino acids
: : ( B ) TYPE: amino acid
: : ( C ) STRANDEDNESS: single
: : ( D ) TOPOLOGY: unknown : ( i i ) MOLECULE TYPE: peptide : ( x i ) SEQUENCE DESCRIPTION: SEQ ID NO:30:

Arg   Lys   Ile   Phe
 1

( 2 ) INFORMATION FOR SEQ ID NO:31:

: ( i ) SEQUENCE CHARACTERISTICS:
: : ( A ) LENGTH: 3234 base pairs
: : ( B ) TYPE: nucleic acid
: : ( C ) STRANDEDNESS: double
: : ( D ) TOPOLOGY: unknown : ( i i ) MOLECULE TYPE: cDNA : ( i x ) FEATURE:
: : ( A ) NAME/KEY: CDS
: : ( B ) LOCATION: 1..3234

: ( x i ) SEQUENCE DESCRIPTION: SEQ ID NO:31:

```
TGC   CAG   GAG   GAC   GCG   GGC   AAC   AAG   GTC   TGC   AGC   CTG   CAG   TGC   AAC   AAC        4 8
Cys   Gln   Glu   Asp   Ala   Gly   Asn   Lys   Val   Cys   Ser   Leu   Gln   Cys   Asn   Asn
 1                       5                        10                         15

CAC   GCG   TGC   GGC   TGG   GAC   GGC   GGT   GAC   TGC   TCC   CTC   AAC   TTC   AAT   GAC        9 6
His   Ala   Cys   Gly   Trp   Asp   Gly   Gly   Asp   Cys   Ser   Leu   Asn   Phe   Asn   Asp
                  20                            25                            30

CCC   TGG   AAG   AAC   TGC   ACG   CAG   TCT   CTG   CAG   TGC   TGG   AAG   TAC   TTC   AGT       1 4 4
Pro   Trp   Lys   Asn   Cys   Thr   Gln   Ser   Leu   Gln   Cys   Trp   Lys   Tyr   Phe   Ser
            35                            40                            45

GAC   GGC   CAC   TGT   GAC   AGC   CAG   TGC   AAC   TCA   GCC   GGC   TGC   CTC   TTC   GAC       1 9 2
Asp   Gly   His   Cys   Asp   Ser   Gln   Cys   Asn   Ser   Ala   Gly   Cys   Leu   Phe   Asp
      50                            55                            60

GGC   TTT   GAC   TGC   CAG   CGT   GCG   GAA   GGC   CAG   TGC   AAC   CCC   CTG   TAC   GAC       2 4 0
Gly   Phe   Asp   Cys   Gln   Arg   Ala   Glu   Gly   Gln   Cys   Asn   Pro   Leu   Tyr   Asp
65                      70                            75                            80

CAG   TAC   TGC   AAG   GAC   CAC   TTC   AGC   GAC   GGG   CAC   TGC   GAC   CAG   GGC   TGC       2 8 8
Gln   Tyr   Cys   Lys   Asp   His   Phe   Ser   Asp   Gly   His   Cys   Asp   Gln   Gly   Cys
                        85                            90                            95

AAC   AGC   GCG   GAG   TGC   GAG   TGG   GAC   GGG   CTG   GAC   TGT   GCG   GAG   CAT   GTA       3 3 6
Asn   Ser   Ala   Glu   Cys   Glu   Trp   Asp   Gly   Leu   Asp   Cys   Ala   Glu   His   Val
                  100                           105                           110

CCC   GAG   AGG   CTG   GCG   GCC   GGC   ACG   CTG   GTG   GTG   GTG   GTG   CTG   ATG   CCG       3 8 4
Pro   Glu   Arg   Leu   Ala   Ala   Gly   Thr   Leu   Val   Val   Val   Val   Leu   Met   Pro
            115                           120                           125

CCG   GAG   CAG   CTG   CGC   AAC   AGC   TCC   TTC   CAC   TTC   CTG   CGG   GAG   CTC   AGC       4 3 2
Pro   Glu   Gln   Leu   Arg   Asn   Ser   Ser   Phe   His   Phe   Leu   Arg   Glu   Leu   Ser
      130                           135                           140
```

| | | | | | | | | | | | | | | | | |
|---|---|---|---|---|---|---|---|---|---|---|---|---|---|---|---|---|
| CGC | GTG | CTG | CAC | ACC | AAC | GTG | GTC | TTC | AAG | CGT | GAC | GCA | CAC | GGC | CAG | 480 |
| Arg | Val | Leu | His | Thr | Asn | Val | Val | Phe | Lys | Arg | Asp | Ala | His | Gly | Gln | |
| 145 | | | | 150 | | | | | 155 | | | | | | 160 | |
| CAG | ATG | ATC | TTC | CCC | TAC | TAC | GGC | CGC | GAG | GAG | GAG | CTG | CGC | AAG | CAC | 528 |
| Gln | Met | Ile | Phe | Pro | Tyr | Tyr | Gly | Arg | Glu | Glu | Glu | Leu | Arg | Lys | His | |
| | | | | 165 | | | | | 170 | | | | | 175 | | |
| CCC | ATC | AAG | CGT | GCC | GCC | GAG | GGC | TGG | GCC | GCA | CCT | GAC | GCC | CTG | CTG | 576 |
| Pro | Ile | Lys | Arg | Ala | Ala | Glu | Gly | Trp | Ala | Ala | Pro | Asp | Ala | Leu | Leu | |
| | | | 180 | | | | | 185 | | | | | 190 | | | |
| GGC | CAG | GTG | AAG | GCC | TCG | CTC | CTC | CCT | GGT | GGC | AGC | GAG | GGT | GGG | CGG | 624 |
| Gly | Gln | Val | Lys | Ala | Ser | Leu | Leu | Pro | Gly | Gly | Ser | Glu | Gly | Gly | Arg | |
| | | 195 | | | | | 200 | | | | | 205 | | | | |
| CGG | CGG | AGG | GAG | CTG | GAC | CCC | ATG | GAC | GTC | CGC | GGC | TCC | ATC | GTC | TAC | 672 |
| Arg | Arg | Arg | Glu | Leu | Asp | Pro | Met | Asp | Val | Arg | Gly | Ser | Ile | Val | Tyr | |
| | 210 | | | | | 215 | | | | | 220 | | | | | |
| CTG | GAG | ATT | GAC | AAC | CGG | CAG | TGT | GTG | CAG | GCC | TCC | TCG | CAG | TGC | TTC | 720 |
| Leu | Glu | Ile | Asp | Asn | Arg | Gln | Cys | Val | Gln | Ala | Ser | Ser | Gln | Cys | Phe | |
| 225 | | | | | 230 | | | | | 235 | | | | | 240 | |
| CAG | AGT | GCC | ACC | GAC | GTG | GCC | GCA | TTC | CTG | GGA | GCG | CTC | GCC | TCG | CTG | 768 |
| Gln | Ser | Ala | Thr | Asp | Val | Ala | Ala | Phe | Leu | Gly | Ala | Leu | Ala | Ser | Leu | |
| | | | | 245 | | | | | 250 | | | | | 255 | | |
| GGC | AGC | CTC | AAC | ATC | CCC | TAC | AAG | ATC | GAG | GCC | GTG | CAG | AGT | GAG | ACC | 816 |
| Gly | Ser | Leu | Asn | Ile | Pro | Tyr | Lys | Ile | Glu | Ala | Val | Gln | Ser | Glu | Thr | |
| | | | 260 | | | | | 265 | | | | | 270 | | | |
| GTG | GAG | CCG | CCC | CCG | CCG | GCG | CAG | CTG | CAC | TTC | ATG | TAC | GTG | GCG | GCG | 864 |
| Val | Glu | Pro | Pro | Pro | Pro | Ala | Gln | Leu | His | Phe | Met | Tyr | Val | Ala | Ala | |
| | | 275 | | | | | 280 | | | | | 285 | | | | |
| GCC | GCC | TTT | GTG | CTT | CTG | TTC | TTC | GTG | GGC | TGC | GGG | GTG | CTG | CTG | TCC | 912 |
| Ala | Ala | Phe | Val | Leu | Leu | Phe | Phe | Val | Gly | Cys | Gly | Val | Leu | Leu | Ser | |
| | 290 | | | | | 295 | | | | | 300 | | | | | |
| CGC | AAG | CGC | CGG | CGG | CAG | CAT | GGC | CAG | CTC | TGG | TTC | CCT | GAG | GGC | TTC | 960 |
| Arg | Lys | Arg | Arg | Arg | Gln | His | Gly | Gln | Leu | Trp | Phe | Pro | Glu | Gly | Phe | |
| 305 | | | | | 310 | | | | | 315 | | | | | 320 | |
| AAA | GTG | TCT | GAG | GCC | AGC | AAG | AAG | AAG | CGG | CGG | GAG | CCC | CTC | GGC | GAG | 1008 |
| Lys | Val | Ser | Glu | Ala | Ser | Lys | Lys | Lys | Arg | Arg | Glu | Pro | Leu | Gly | Glu | |
| | | | | 325 | | | | | 330 | | | | | 335 | | |
| GAC | TCC | GTG | GGC | CTC | AAG | CCC | CTG | AAG | AAC | GCT | TCA | GAC | GGT | GCC | CTC | 1056 |
| Asp | Ser | Val | Gly | Leu | Lys | Pro | Leu | Lys | Asn | Ala | Ser | Asp | Gly | Ala | Leu | |
| | | | 340 | | | | | 345 | | | | | 350 | | | |
| ATG | GAC | GAC | AAC | CAG | AAT | GAG | TGG | GGG | GAC | GAG | GAC | CTG | GAG | ACC | AAG | 1104 |
| Met | Asp | Asp | Asn | Gln | Asn | Glu | Trp | Gly | Asp | Glu | Asp | Leu | Glu | Thr | Lys | |
| | | 355 | | | | | 360 | | | | | 365 | | | | |
| AAG | TTC | CGG | TTC | GAG | GAG | CCC | GTG | GTT | CTG | CCT | GAC | CTG | GAC | GAC | CAG | 1152 |
| Lys | Phe | Arg | Phe | Glu | Glu | Pro | Val | Val | Leu | Pro | Asp | Leu | Asp | Asp | Gln | |
| | 370 | | | | | 375 | | | | | 380 | | | | | |
| ACA | GAC | CAC | CGG | CAG | TGG | ACT | CAG | CAG | CAC | CTG | GAT | GCC | GCT | GAC | CTG | 1200 |
| Thr | Asp | His | Arg | Gln | Trp | Thr | Gln | Gln | His | Leu | Asp | Ala | Ala | Asp | Leu | |
| 385 | | | | | 390 | | | | | 395 | | | | | 400 | |
| CGC | ATG | TCT | GCC | ATG | GCC | CCC | ACA | CCG | CCC | CAG | GGT | GAG | GTT | GAC | GCC | 1248 |
| Arg | Met | Ser | Ala | Met | Ala | Pro | Thr | Pro | Pro | Gln | Gly | Glu | Val | Asp | Ala | |
| | | | | 405 | | | | | 410 | | | | | 415 | | |
| GAC | TGC | ATG | GAC | GTC | AAT | GTC | CGC | GGG | CCT | GAT | GGC | TTC | ACC | CCG | CTC | 1296 |
| Asp | Cys | Met | Asp | Val | Asn | Val | Arg | Gly | Pro | Asp | Gly | Phe | Thr | Pro | Leu | |
| | | | 420 | | | | | 425 | | | | | 430 | | | |
| ATG | ATC | GCC | TCC | TGC | AGC | GGG | GGC | GGC | CTG | GAG | ACG | GGC | AAC | AGC | GAG | 1344 |
| Met | Ile | Ala | Ser | Cys | Ser | Gly | Gly | Gly | Leu | Glu | Thr | Gly | Asn | Ser | Glu | |
| | | 435 | | | | | 440 | | | | | 445 | | | | |
| GAA | GAG | GAG | GAC | GCG | CCG | GCC | GTC | ATC | TCC | GAC | TTC | ATC | TAC | CAG | GGC | 1392 |
| Glu | Glu | Glu | Asp | Ala | Pro | Ala | Val | Ile | Ser | Asp | Phe | Ile | Tyr | Gln | Gly | |
| | 450 | | | | | 455 | | | | | 460 | | | | | |

```
GCC AGC CTG CAC AAC CAG ACA GAC CGC ACG GGC GAG ACC GCC TTG CAC    1440
Ala Ser Leu His Asn Gln Thr Asp Arg Thr Gly Glu Thr Ala Leu His
465             470                 475                 480

CTG GCC GCC CGC TAC TCA CGC TCT GAT GCC GCC AAG CGC CTG CTG GAG    1488
Leu Ala Ala Arg Tyr Ser Arg Ser Asp Ala Ala Lys Arg Leu Leu Glu
            485                 490                 495

GCC AGC GCA GAT GCC AAC ATC CAG GAC AAC ATG GGC CGC ACC CCG CTG    1536
Ala Ser Ala Asp Ala Asn Ile Gln Asp Asn Met Gly Arg Thr Pro Leu
        500                 505                 510

CAT GCG GCT GTG TCT GCC GAC GCA CAA GGT GTC TTC CAG ATC CTG ATC    1584
His Ala Ala Val Ser Ala Asp Ala Gln Gly Val Phe Gln Ile Leu Ile
            515                 520                 525

CGG AAC CGA GCC ACA GAC CTG GAT GCC CGC ATG CAT GAT GGC ACG ACG    1632
Arg Asn Arg Ala Thr Asp Leu Asp Ala Arg Met His Asp Gly Thr Thr
530                 535                 540

CCA CTG ATC CTG GCT GCC CGC CTG GCC GTG GAG GGC ATG CTG GAG GAC    1680
Pro Leu Ile Leu Ala Ala Arg Leu Ala Val Glu Gly Met Leu Glu Asp
545                 550                 555                 560

CTC ATC AAC TCA CAC GCC GAC GTC AAC GCC GTA GAT GAC CTG GGC AAG    1728
Leu Ile Asn Ser His Ala Asp Val Asn Ala Val Asp Asp Leu Gly Lys
            565                 570                 575

TCC GCC CTG CAC TGG GCC GCC GCC GTG AAC AAT GTG GAT GCC GCA GTT    1776
Ser Ala Leu His Trp Ala Ala Ala Val Asn Asn Val Asp Ala Ala Val
        580                 585                 590

GTG CTC CTG AAG AAC GGG GCT AAC AAA GAT ATG CAG AAC AAC AGG GAG    1824
Val Leu Leu Lys Asn Gly Ala Asn Lys Asp Met Gln Asn Asn Arg Glu
            595                 600                 605

GAG ACA CCC CTG TTT CTG GCC GCC CGG GAG GGC AGC TAC GAG ACC GCC    1872
Glu Thr Pro Leu Phe Leu Ala Ala Arg Glu Gly Ser Tyr Glu Thr Ala
    610                 615                 620

AAG GTG CTG CTG GAC CAC TTT GCC AAC CGG GAC ATC ACG GAT CAT ATG    1920
Lys Val Leu Leu Asp His Phe Ala Asn Arg Asp Ile Thr Asp His Met
625                 630                 635                 640

GAC CGC CTG CCG CGC GAC ATC GCA CAG GAG CGC ATG CAT CAC GAC ATC    1968
Asp Arg Leu Pro Arg Asp Ile Ala Gln Glu Arg Met His His Asp Ile
            645                 650                 655

GTG AGG CTG CTG GAC GAG TAC AAC CTG GTG CGC AGC CCG CAG CTG CAC    2016
Val Arg Leu Leu Asp Glu Tyr Asn Leu Val Arg Ser Pro Gln Leu His
        660                 665                 670

GGA GCC CCG CTG GGG GGC ACG CCC ACC CTG TCG CCC CCG CTC TGC TCG    2064
Gly Ala Pro Leu Gly Gly Thr Pro Thr Leu Ser Pro Pro Leu Cys Ser
            675                 680                 685

CCC AAC GGC TAC CTG GGC AGC CTC AAG CCC GGC GTG CAG GGC AAG AAG    2112
Pro Asn Gly Tyr Leu Gly Ser Leu Lys Pro Gly Val Gln Gly Lys Lys
    690                 695                 700

GTC CGC AAG CCC AGC AGC AAA GGC CTG GCC TGT GGA AGC AAG GAG GCC    2160
Val Arg Lys Pro Ser Ser Lys Gly Leu Ala Cys Gly Ser Lys Glu Ala
705                 710                 715                 720

AAG GAC CTC AAG GCA CGG AGG AAG AAG TCC CAG GAT GGC AAG GGC TGC    2208
Lys Asp Leu Lys Ala Arg Arg Lys Lys Ser Gln Asp Gly Lys Gly Cys
            725                 730                 735

CTG CTG GAC AGC TCC GGC ATG CTC TCG CCC GTG GAC TCC CTG GAG TCA    2256
Leu Leu Asp Ser Ser Gly Met Leu Ser Pro Val Asp Ser Leu Glu Ser
        740                 745                 750

CCC CAT GGC TAC CTG TCA GAC GTG GCC TCG CCG CCA CTG CTG CCC TCC    2304
Pro His Gly Tyr Leu Ser Asp Val Ala Ser Pro Pro Leu Leu Pro Ser
            755                 760                 765

CCG TTC CAG CAG TCT CCG TCC GTG CCC CTC AAC CAC CTG CCT GGG ATG    2352
Pro Phe Gln Gln Ser Pro Ser Val Pro Leu Asn His Leu Pro Gly Met
    770                 775                 780
```

```
CCC GAC ACC CAC CTG GGC ATC GGG CAC CTG AAC GTG GCG GCC AAG CCC      2400
Pro Asp Thr His Leu Gly Ile Gly His Leu Asn Val Ala Ala Lys Pro
785                 790                 795                 800

GAG ATG GCG GCG CTG GGT GGG GGC GGC CGG CTG GCC TTT GAG ACT GGC      2448
Glu Met Ala Ala Leu Gly Gly Gly Gly Arg Leu Ala Phe Glu Thr Gly
                805                 810                 815

CCA CCT CGT CTC TCC CAC CTG CCT GTG GCC TCT GGC ACC AGC ACC GTC      2496
Pro Pro Arg Leu Ser His Leu Pro Val Ala Ser Gly Thr Ser Thr Val
            820                 825                 830

CTG GGC TCC AGC AGC GGA GGG GCC CTG AAT TTC ACT GTG GGC GGG TCC      2544
Leu Gly Ser Ser Ser Gly Gly Ala Leu Asn Phe Thr Val Gly Gly Ser
                835                 840                 845

ACC AGT TTG AAT GGT CAA TGC GAG TGG CTG TCC CGG CTG CAG AGC GGC      2592
Thr Ser Leu Asn Gly Gln Cys Glu Trp Leu Ser Arg Leu Gln Ser Gly
850                 855                 860

ATG GTG CCG AAC CAA TAC AAC CCT CTG CGG GGT AGT GTG GCA CCA GGC      2640
Met Val Pro Asn Gln Tyr Asn Pro Leu Arg Gly Ser Val Ala Pro Gly
865                 870                 875                 880

CCC CTG AGC ACA CAG GCC CCC TCC CTG CAG CAT GGC ATG GTA GGC CCG      2688
Pro Leu Ser Thr Gln Ala Pro Ser Leu Gln His Gly Met Val Gly Pro
                885                 890                 895

CTG CAC AGT AGC CTT GCT GCC AGC GCC CTG TCC CAG ATG ATG AGC TAC      2736
Leu His Ser Ser Leu Ala Ala Ser Ala Leu Ser Gln Met Met Ser Tyr
                900                 905                 910

CAG GGC CTG CCC AGC ACC CGG CTG GCC ACC CAG CCT CAC CTG GTG CAG      2784
Gln Gly Leu Pro Ser Thr Arg Leu Ala Thr Gln Pro His Leu Val Gln
            915                 920                 925

ACC CAG CAG GTG CAG CCA CAA AAC TTA CAG ATG CAG CAG CAG AAC CTG      2832
Thr Gln Gln Val Gln Pro Gln Asn Leu Gln Met Gln Gln Gln Asn Leu
    930                 935                 940

CAG CCA GCA AAC ATC CAG CAG CAG CAA AGC CTG CAG CCG CCA CCA CCA      2880
Gln Pro Ala Asn Ile Gln Gln Gln Gln Ser Leu Gln Pro Pro Pro Pro
945                 950                 955                 960

CCA CCA CAG CCG CAC CTT GGC GTG AGC TCA GCA GCC AGC GGC CAC CTG      2928
Pro Pro Gln Pro His Leu Gly Val Ser Ser Ala Ala Ser Gly His Leu
                965                 970                 975

GGC CGG AGC TTC CTG AGT GGA GAG CCG AGC CAG GCA GAC GTG CAG CCA      2976
Gly Arg Ser Phe Leu Ser Gly Glu Pro Ser Gln Ala Asp Val Gln Pro
                980                 985                 990

CTG GGC CCC AGC AGC CTG GCG GTG CAC ACT ATT CTG CCC CAG GAG AGC      3024
Leu Gly Pro Ser Ser Leu Ala Val His Thr Ile Leu Pro Gln Glu Ser
            995                 1000                1005

CCC GCC CTG CCC ACG TCG CTG CCA TCC TCG CTG GTC CCA CCC GTG ACC      3072
Pro Ala Leu Pro Thr Ser Leu Pro Ser Ser Leu Val Pro Pro Val Thr
    1010                1015                1020

GCA GCC CAG TTC CTG ACG CCC CCC TCG CAG CAC AGC TAC TCC TCG CCT      3120
Ala Ala Gln Phe Leu Thr Pro Pro Ser Gln His Ser Tyr Ser Ser Pro
1025                1030                1035                1040

GTG GAC AAC ACC CCC AGC CAC CAG CTA CAG GTG CCT GTT CCT GTA ATG      3168
Val Asp Asn Thr Pro Ser His Gln Leu Gln Val Pro Val Pro Val Met
                1045                1050                1055

GTA ATG ATC CGA TCT TCG GAT CCT TCT AAA GGC TCA TCA ATT TTG ATC      3216
Val Met Ile Arg Ser Ser Asp Pro Ser Lys Gly Ser Ser Ile Leu Ile
                1060                1065                1070

GAA GCT CCC GAC TCA TGG                                              3234
Glu Ala Pro Asp Ser Trp
            1075
```

( 2 ) INFORMATION FOR SEQ ID NO:32:

(i) SEQUENCE CHARACTERISTICS:
    (A) LENGTH: 1078 amino acids
    (B) TYPE: amino acid
    (D) TOPOLOGY: unknown (ii) MOLECULE TYPE: protein (xi) SEQUENCE DESCRIPTION: SEQ ID NO:32:

```
Cys Gln Glu Asp Ala Gly Asn Lys Val Cys Ser Leu Gln Cys Asn Asn
 1               5                  10                  15

His Ala Cys Gly Trp Asp Gly Gly Asp Cys Ser Leu Asn Phe Asn Asp
            20                  25                  30

Pro Trp Lys Asn Cys Thr Gln Ser Leu Gln Cys Trp Lys Tyr Phe Ser
            35                  40                  45

Asp Gly His Cys Asp Ser Gln Cys Asn Ser Ala Gly Cys Leu Phe Asp
         50                  55                  60

Gly Phe Asp Cys Gln Arg Ala Glu Gly Gln Cys Asn Pro Leu Tyr Asp
 65                  70                  75                  80

Gln Tyr Cys Lys Asp His Phe Ser Asp Gly His Cys Asp Gln Gly Cys
             85                  90                  95

Asn Ser Ala Glu Cys Glu Trp Asp Gly Leu Asp Cys Ala Glu His Val
            100                 105                 110

Pro Glu Arg Leu Ala Ala Gly Thr Leu Val Val Val Val Leu Met Pro
            115                 120                 125

Pro Glu Gln Leu Arg Asn Ser Ser Phe His Phe Leu Arg Glu Leu Ser
            130                 135                 140

Arg Val Leu His Thr Asn Val Val Phe Lys Arg Asp Ala His Gly Gln
145                 150                 155                 160

Gln Met Ile Phe Pro Tyr Tyr Gly Arg Glu Glu Leu Arg Lys His
                165                 170                 175

Pro Ile Lys Arg Ala Ala Glu Gly Trp Ala Ala Pro Asp Ala Leu Leu
            180                 185                 190

Gly Gln Val Lys Ala Ser Leu Leu Pro Gly Gly Ser Glu Gly Gly Arg
            195                 200                 205

Arg Arg Arg Glu Leu Asp Pro Met Asp Val Arg Gly Ser Ile Val Tyr
210                 215                 220

Leu Glu Ile Asp Asn Arg Gln Cys Val Gln Ala Ser Ser Gln Cys Phe
225                 230                 235                 240

Gln Ser Ala Thr Asp Val Ala Ala Phe Leu Gly Ala Leu Ala Ser Leu
            245                 250                 255

Gly Ser Leu Asn Ile Pro Tyr Lys Ile Glu Ala Val Gln Ser Glu Thr
            260                 265                 270

Val Glu Pro Pro Pro Ala Gln Leu His Phe Met Tyr Val Ala Ala
            275                 280                 285

Ala Ala Phe Val Leu Leu Phe Phe Val Gly Cys Gly Val Leu Leu Ser
            290                 295                 300

Arg Lys Arg Arg Arg Gln His Gly Gln Leu Trp Phe Pro Glu Gly Phe
305                 310                 315                 320

Lys Val Ser Glu Ala Ser Lys Lys Lys Arg Arg Glu Pro Leu Gly Glu
            325                 330                 335

Asp Ser Val Gly Leu Lys Pro Leu Lys Asn Ala Ser Asp Gly Ala Leu
            340                 345                 350

Met Asp Asp Asn Gln Asn Glu Trp Gly Asp Glu Asp Leu Glu Thr Lys
            355                 360                 365

Lys Phe Arg Phe Glu Glu Pro Val Val Leu Pro Asp Leu Asp Asp Gln
            370                 375                 380
```

-continued

| | | | | | | | | | | | | | | |
|---|---|---|---|---|---|---|---|---|---|---|---|---|---|---|
| Thr | Asp | His | Arg | Gln | Trp | Thr | Gln | Gln | His | Leu | Asp | Ala | Ala | Asp | Leu |
| 385 | | | | | 390 | | | | 395 | | | | | | 400 |
| Arg | Met | Ser | Ala | Met | Ala | Pro | Thr | Pro | Pro | Gln | Gly | Glu | Val | Asp | Ala |
| | | | | 405 | | | | | 410 | | | | 415 | | |
| Asp | Cys | Met | Asp | Val | Asn | Val | Arg | Gly | Pro | Asp | Gly | Phe | Thr | Pro | Leu |
| | | | 420 | | | | 425 | | | | | | 430 | | |
| Met | Ile | Ala | Ser | Cys | Ser | Gly | Gly | Leu | Glu | Thr | Gly | Asn | Ser | Glu |
| | | 435 | | | | 440 | | | | | 445 | | | |
| Glu | Glu | Glu | Asp | Ala | Pro | Ala | Val | Ile | Ser | Asp | Phe | Ile | Tyr | Gln | Gly |
| | | 450 | | | | 455 | | | | | 460 | | | | |
| Ala | Ser | Leu | His | Asn | Gln | Thr | Asp | Arg | Thr | Gly | Glu | Thr | Ala | Leu | His |
| 465 | | | | 470 | | | | | 475 | | | | | | 480 |
| Leu | Ala | Ala | Arg | Tyr | Ser | Arg | Ser | Asp | Ala | Ala | Lys | Arg | Leu | Leu | Glu |
| | | | | 485 | | | | | 490 | | | | | 495 | |
| Ala | Ser | Ala | Asp | Ala | Asn | Ile | Gln | Asp | Asn | Met | Gly | Arg | Thr | Pro | Leu |
| | | | 500 | | | | | 505 | | | | | 510 | | |
| His | Ala | Ala | Val | Ser | Ala | Asp | Ala | Gln | Gly | Val | Phe | Gln | Ile | Leu | Ile |
| | | | 515 | | | | 520 | | | | | 525 | | | |
| Arg | Asn | Arg | Ala | Thr | Asp | Leu | Asp | Ala | Arg | Met | His | Asp | Gly | Thr | Thr |
| | 530 | | | | 535 | | | | | | 540 | | | | |
| Pro | Leu | Ile | Leu | Ala | Ala | Arg | Leu | Ala | Val | Glu | Gly | Met | Leu | Glu | Asp |
| 545 | | | | | 550 | | | | | 555 | | | | | 560 |
| Leu | Ile | Asn | Ser | His | Ala | Asp | Val | Asn | Ala | Val | Asp | Asp | Leu | Gly | Lys |
| | | | | 565 | | | | | 570 | | | | | 575 | |
| Ser | Ala | Leu | His | Trp | Ala | Ala | Ala | Val | Asn | Asn | Val | Asp | Ala | Ala | Val |
| | | | 580 | | | | | 585 | | | | | 590 | | |
| Val | Leu | Leu | Lys | Asn | Gly | Ala | Asn | Lys | Asp | Met | Gln | Asn | Asn | Arg | Glu |
| | | 595 | | | | 600 | | | | | 605 | | | | |
| Glu | Thr | Pro | Leu | Phe | Leu | Ala | Ala | Arg | Glu | Gly | Ser | Tyr | Glu | Thr | Ala |
| | 610 | | | | | 615 | | | | | 620 | | | | |
| Lys | Val | Leu | Leu | Asp | His | Phe | Ala | Asn | Arg | Asp | Ile | Thr | Asp | His | Met |
| 625 | | | | | 630 | | | | | 635 | | | | | 640 |
| Asp | Arg | Leu | Pro | Arg | Asp | Ile | Ala | Gln | Glu | Arg | Met | His | His | Asp | Ile |
| | | | | 645 | | | | | 650 | | | | | 655 | |
| Val | Arg | Leu | Leu | Asp | Glu | Tyr | Asn | Leu | Val | Arg | Ser | Pro | Gln | Leu | His |
| | | | 660 | | | | | 665 | | | | | 670 | | |
| Gly | Ala | Pro | Leu | Gly | Gly | Thr | Pro | Thr | Leu | Ser | Pro | Pro | Leu | Cys | Ser |
| | | 675 | | | | 680 | | | | | 685 | | | | |
| Pro | Asn | Gly | Tyr | Leu | Gly | Ser | Leu | Lys | Pro | Gly | Val | Gln | Gly | Lys | Lys |
| | 690 | | | | 695 | | | | | 700 | | | | | |
| Val | Arg | Lys | Pro | Ser | Ser | Lys | Gly | Leu | Ala | Cys | Gly | Ser | Lys | Glu | Ala |
| 705 | | | | 710 | | | | | 715 | | | | | | 720 |
| Lys | Asp | Leu | Lys | Ala | Arg | Arg | Lys | Lys | Ser | Gln | Asp | Gly | Lys | Gly | Cys |
| | | | | 725 | | | | | 730 | | | | | 735 | |
| Leu | Leu | Asp | Ser | Ser | Gly | Met | Leu | Ser | Pro | Val | Asp | Ser | Leu | Glu | Ser |
| | | | 740 | | | | | 745 | | | | | 750 | | |
| Pro | His | Gly | Tyr | Leu | Ser | Asp | Val | Ala | Ser | Pro | Pro | Leu | Leu | Pro | Ser |
| | | 755 | | | | | 760 | | | | | 765 | | | |
| Pro | Phe | Gln | Gln | Ser | Pro | Ser | Val | Pro | Leu | Asn | His | Leu | Pro | Gly | Met |
| | 770 | | | | | 775 | | | | | 780 | | | | |
| Pro | Asp | Thr | His | Leu | Gly | Ile | Gly | His | Leu | Asn | Val | Ala | Ala | Lys | Pro |
| 785 | | | | | 790 | | | | | 795 | | | | | 800 |
| Glu | Met | Ala | Ala | Leu | Gly | Gly | Gly | Gly | Arg | Leu | Ala | Phe | Glu | Thr | Gly |

|            |            |            | 805        |            |            |            |            | 810        |            |            |            |            | 815        |            |
|---|---|---|---|---|---|---|---|---|---|---|---|---|---|---|
| Pro | Pro | Arg | Leu | Ser | His | Leu | Pro | Val | Ala | Ser | Gly | Thr | Ser | Thr | Val |
|  |  |  | 820 |  |  |  | 825 |  |  |  | 830 |  |  |  |

Pro Pro Arg Leu Ser His Leu Pro Val Ala Ser Gly Thr Ser Thr Val
               820                825                830

Leu Gly Ser Ser Ser Gly Gly Ala Leu Asn Phe Thr Val Gly Gly Ser
           835                840                845

Thr Ser Leu Asn Gly Gln Cys Glu Trp Leu Ser Arg Leu Gln Ser Gly
       850                855                860

Met Val Pro Asn Gln Tyr Asn Pro Leu Arg Gly Ser Val Ala Pro Gly
865                870                875                880

Pro Leu Ser Thr Gln Ala Pro Ser Leu Gln His Gly Met Val Gly Pro
           885                890                895

Leu His Ser Ser Leu Ala Ala Ser Ala Leu Ser Gln Met Met Ser Tyr
           900                905                910

Gln Gly Leu Pro Ser Thr Arg Leu Ala Thr Gln Pro His Leu Val Gln
       915                920                925

Thr Gln Gln Val Gln Pro Gln Asn Leu Gln Met Gln Gln Asn Leu
930                935                940

Gln Pro Ala Asn Ile Gln Gln Gln Ser Leu Gln Pro Pro Pro Pro
945                950                955                960

Pro Pro Gln Pro His Leu Gly Val Ser Ser Ala Ala Ser Gly His Leu
           965                970                975

Gly Arg Ser Phe Leu Ser Gly Glu Pro Ser Gln Ala Asp Val Gln Pro
           980                985                990

Leu Gly Pro Ser Ser Leu Ala Val His Thr Ile Leu Pro Gln Glu Ser
           995                1000                1005

Pro Ala Leu Pro Thr Ser Leu Pro Ser Ser Leu Val Pro Pro Val Thr
1010                1015                1020

Ala Ala Gln Phe Leu Thr Pro Pro Ser Gln His Ser Tyr Ser Ser Pro
1025                1030                1035                1040

Val Asp Asn Thr Pro Ser His Gln Leu Gln Val Pro Val Pro Val Met
           1045                1050                1055

Val Met Ile Arg Ser Ser Asp Pro Ser Lys Gly Ser Ser Ile Leu Ile
           1060                1065                1070

Glu Ala Pro Asp Ser Trp
           1075

(2) INFORMATION FOR SEQ ID NO:33:

(i) SEQUENCE CHARACTERISTICS:
        (A) LENGTH: 4268 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 2..1972

(xi) SEQUENCE DESCRIPTION: SEQ ID NO:33:

```
G GAG GTG GAT GTG TTA GAT GTG AAT GTC CGT GGC CCA GAT GGC TGC       46
  Glu Val Asp Val Leu Asp Val Asn Val Arg Gly Pro Asp Gly Cys
   1               5                  10                 15

ACC CCA TTG ATG TTG GCT TCT CTC CGA GGA GGC AGC TCA GAT TTG AGT     94
Thr Pro Leu Met Leu Ala Ser Leu Arg Gly Gly Ser Ser Asp Leu Ser
             20                  25                  30

GAT GAA GAT GAA GAT GCA GAG GAC TCT TCT GCT AAC ATC ATC ACA GAC    142
Asp Glu Asp Glu Asp Ala Glu Asp Ser Ser Ala Asn Ile Ile Thr Asp
```

-continued

```
                       35                              40                              45
TTG  GTC  TAC  CAG  GGT  GCC  AGC  CTC  CAG  GCC  CAG  ACA  GAC  CGG  ACT  GGT         190
Leu  Val  Tyr  Gln  Gly  Ala  Ser  Leu  Gln  Ala  Gln  Thr  Asp  Arg  Thr  Gly
          50                       55                       60

GAG  ATG  GCC  CTG  CAC  CTT  GCA  GCC  CGC  TAC  TCA  CGG  GCT  GAT  GCT  GCC         238
Glu  Met  Ala  Leu  His  Leu  Ala  Ala  Arg  Tyr  Ser  Arg  Ala  Asp  Ala  Ala
     65                       70                       75

AAG  CGT  CTC  CTG  GAT  GCA  GGT  GCA  GAT  GCC  AAT  GCC  CAG  GAC  AAC  ATG         286
Lys  Arg  Leu  Leu  Asp  Ala  Gly  Ala  Asp  Ala  Asn  Ala  Gln  Asp  Asn  Met
80                            85                       90                       95

GGC  CGC  TGT  CCA  CTC  CAT  GCT  GCA  GTG  GCA  GCT  GAT  GCC  CAA  GGT  GTC         334
Gly  Arg  Cys  Pro  Leu  His  Ala  Ala  Val  Ala  Ala  Asp  Ala  Gln  Gly  Val
                         100                      105                      110

TTC  CAG  ATT  CTG  ATT  CGC  AAC  CGA  GTA  ACT  GAT  CTA  GAT  GCC  AGG  ATG         382
Phe  Gln  Ile  Leu  Ile  Arg  Asn  Arg  Val  Thr  Asp  Leu  Asp  Ala  Arg  Met
                    115                      120                      125

AAT  GAT  GGT  ACT  ACA  CCC  CTG  ATC  CTG  GCT  GCC  CGC  CTG  GCT  GTG  GAG         430
Asn  Asp  Gly  Thr  Thr  Pro  Leu  Ile  Leu  Ala  Ala  Arg  Leu  Ala  Val  Glu
               130                      135                      140

GGA  ATG  GTG  GCA  GAA  CTG  ATC  AAC  TGC  CAA  GCG  GAT  GTG  AAT  GCA  GTG         478
Gly  Met  Val  Ala  Glu  Leu  Ile  Asn  Cys  Gln  Ala  Asp  Val  Asn  Ala  Val
          145                      150                      155

GAT  GAC  CAT  GGA  AAA  TCT  GCT  CTT  CAC  TGG  GCA  GCT  GCT  GTC  AAT  AAT         526
Asp  Asp  His  Gly  Lys  Ser  Ala  Leu  His  Trp  Ala  Ala  Ala  Val  Asn  Asn
160                      165                      170                      175

GTG  GAG  GCA  ACT  CTT  TTG  TTG  TTG  AAA  AAT  GGG  GCC  AAC  CGA  GAC  ATG         574
Val  Glu  Ala  Thr  Leu  Leu  Leu  Leu  Lys  Asn  Gly  Ala  Asn  Arg  Asp  Met
                    180                      185                      190

CAG  GAC  AAC  AAG  GAA  GAG  ACA  CCT  CTG  TTT  CTT  GCT  GCC  CGG  GAG  GGG         622
Gln  Asp  Asn  Lys  Glu  Glu  Thr  Pro  Leu  Phe  Leu  Ala  Ala  Arg  Glu  Gly
               195                      200                      205

AGC  TAT  GAA  GCA  GCC  AAG  ATC  CTG  TTA  GAC  CAT  TTT  GCC  AAT  CGA  GAC         670
Ser  Tyr  Glu  Ala  Ala  Lys  Ile  Leu  Leu  Asp  His  Phe  Ala  Asn  Arg  Asp
          210                      215                      220

ATC  ACA  GAC  CAT  ATG  GAT  CGT  CTT  CCC  CGG  GAT  GTG  GCT  CGG  GAT  CGC         718
Ile  Thr  Asp  His  Met  Asp  Arg  Leu  Pro  Arg  Asp  Val  Ala  Arg  Asp  Arg
     225                      230                      235

ATG  CAC  CAT  GAC  ATT  GTG  CGC  CTT  CTG  GAT  GAA  TAC  AAT  GTG  ACC  CCA         766
Met  His  His  Asp  Ile  Val  Arg  Leu  Leu  Asp  Glu  Tyr  Asn  Val  Thr  Pro
240                      245                      250                      255

AGC  CCT  CCA  GGC  ACC  GTG  TTG  ACT  TCT  GCT  CTC  TCA  CCT  GTC  ATC  TGT         814
Ser  Pro  Pro  Gly  Thr  Val  Leu  Thr  Ser  Ala  Leu  Ser  Pro  Val  Ile  Cys
                    260                      265                      270

GGG  CCC  AAC  AGA  TCT  TTC  CTC  AGC  CTG  AAG  CAC  ACC  CCA  ATG  GGC  AAG         862
Gly  Pro  Asn  Arg  Ser  Phe  Leu  Ser  Leu  Lys  His  Thr  Pro  Met  Gly  Lys
               275                      280                      285

AAG  TCT  AGA  CGG  CCC  AGT  GCC  AAG  AGT  ACC  ATG  CCT  ACT  AGC  CTC  CCT         910
Lys  Ser  Arg  Arg  Pro  Ser  Ala  Lys  Ser  Thr  Met  Pro  Thr  Ser  Leu  Pro
          290                      295                      300

AAC  CTT  GCC  AAG  GAG  GCA  AAG  GAT  GCC  AAG  GGT  AGT  AGG  AGG  AAG  AAG         958
Asn  Leu  Ala  Lys  Glu  Ala  Lys  Asp  Ala  Lys  Gly  Ser  Arg  Arg  Lys  Lys
     305                      310                      315

TCT  CTG  AGT  GAG  AAG  GTC  CAA  CTG  TCT  GAG  AGT  TCA  GTA  ACT  TTA  TCC        1006
Ser  Leu  Ser  Glu  Lys  Val  Gln  Leu  Ser  Glu  Ser  Ser  Val  Thr  Leu  Ser
320                      325                      330                      335

CCT  GTT  GAT  TCC  CTA  GAA  TCT  CCT  CAC  ACG  TAT  GTT  TCC  GAC  ACC  ACA        1054
Pro  Val  Asp  Ser  Leu  Glu  Ser  Pro  His  Thr  Tyr  Val  Ser  Asp  Thr  Thr
                    340                      345                      350

TCC  TCT  CCA  ATG  ATT  ACA  TCC  CCT  GGG  ATC  TTA  CAG  GCC  TCA  CCC  AAC        1102
Ser  Ser  Pro  Met  Ile  Thr  Ser  Pro  Gly  Ile  Leu  Gln  Ala  Ser  Pro  Asn
```

```
                         355                          360                         365
CCT  ATG  TTG  GCC  ACT  GCC  GCC  CCT  CCT  GCC  CCA  GTC  CAT  GCC  CAG  CAT         1150
Pro  Met  Leu  Ala  Thr  Ala  Ala  Pro  Pro  Ala  Pro  Val  His  Ala  Gln  His
          370                 375                           380

GCA  CTA  TCT  TTT  TCT  AAC  CTT  CAT  GAA  ATG  CAG  CCT  TTG  GCA  CAT  GGG         1198
Ala  Leu  Ser  Phe  Ser  Asn  Leu  His  Glu  Met  Gln  Pro  Leu  Ala  His  Gly
     385                      390                           395

GCC  AGC  ACT  GTG  CTT  CCC  TCA  GTG  AGC  CAG  TTG  CTA  TCC  CAC  CAC  CAC         1246
Ala  Ser  Thr  Val  Leu  Pro  Ser  Val  Ser  Gln  Leu  Leu  Ser  His  His  His
400                           405                      410                      415

ATT  GTG  TCT  CCA  GGC  AGT  GGC  AGT  GCT  GGA  AGC  TTG  AGT  AGG  CTC  CAT         1294
Ile  Val  Ser  Pro  Gly  Ser  Gly  Ser  Ala  Gly  Ser  Leu  Ser  Arg  Leu  His
                    420                      425                           430

CCA  GTC  CCA  GTC  CCA  GCA  GAT  TGG  ATG  AAC  CGC  ATG  GAG  GTG  AAT  GAG         1342
Pro  Val  Pro  Val  Pro  Ala  Asp  Trp  Met  Asn  Arg  Met  Glu  Val  Asn  Glu
               435                      440                      445

ACC  CAG  TAC  AAT  GAG  ATG  TTT  GGT  ATG  GTC  CTG  GCT  CCA  GCT  GAG  GGC         1390
Thr  Gln  Tyr  Asn  Glu  Met  Phe  Gly  Met  Val  Leu  Ala  Pro  Ala  Glu  Gly
          450                      455                      460

ACC  CAT  CCT  GGC  ATA  GCT  CCC  CAG  AGC  AGG  CCA  CCT  GAA  GGG  AAG  CAC         1438
Thr  His  Pro  Gly  Ile  Ala  Pro  Gln  Ser  Arg  Pro  Pro  Glu  Gly  Lys  His
     465                      470                      475

ATA  ACC  ACC  CCT  CGG  GAG  CCC  TTG  CCC  CCC  ATT  GTG  ACT  TTC  CAG  CTC         1486
Ile  Thr  Thr  Pro  Arg  Glu  Pro  Leu  Pro  Pro  Ile  Val  Thr  Phe  Gln  Leu
480                           485                      490                      495

ATC  CCT  AAA  GGC  AGT  ATT  GCC  CAA  CCA  GCG  GGG  GCT  CCC  CAG  CCT  CAG         1534
Ile  Pro  Lys  Gly  Ser  Ile  Ala  Gln  Pro  Ala  Gly  Ala  Pro  Gln  Pro  Gln
                    500                      505                      510

TCC  ACC  TGC  CCT  CCA  GCT  GTT  GCG  GGC  CCC  CTG  CCC  ACC  ATG  TAC  CAG         1582
Ser  Thr  Cys  Pro  Pro  Ala  Val  Ala  Gly  Pro  Leu  Pro  Thr  Met  Tyr  Gln
               515                      520                      525

ATT  CCA  GAA  ATG  GCC  CGT  TTG  CCC  AGT  GTG  GCT  TTC  CCC  ACT  GCC  ATG         1630
Ile  Pro  Glu  Met  Ala  Arg  Leu  Pro  Ser  Val  Ala  Phe  Pro  Thr  Ala  Met
          530                      535                      540

ATG  CCC  CAG  CAG  GAC  GGG  CAG  GTA  GCT  CAG  ACC  ATT  CTC  CCA  GCC  TAT         1678
Met  Pro  Gln  Gln  Asp  Gly  Gln  Val  Ala  Gln  Thr  Ile  Leu  Pro  Ala  Tyr
     545                      550                      555

CAT  CCT  TTC  CCA  GCC  TCT  GTG  GGC  AAG  TAC  CCC  ACA  CCC  CCT  TCA  CAG         1726
His  Pro  Phe  Pro  Ala  Ser  Val  Gly  Lys  Tyr  Pro  Thr  Pro  Pro  Ser  Gln
560                           565                      570                      575

CAC  AGT  TAT  GCT  TCC  TCA  AAT  GCT  GCT  GAG  CGA  ACA  CCC  AGT  CAC  AGT         1774
His  Ser  Tyr  Ala  Ser  Ser  Asn  Ala  Ala  Glu  Arg  Thr  Pro  Ser  His  Ser
                    580                      585                      590

GGT  CAC  CTC  CAG  GGT  GAG  CAT  CCC  TAC  CTG  ACA  CCA  TCC  CCA  GAG  TCT         1822
Gly  His  Leu  Gln  Gly  Glu  His  Pro  Tyr  Leu  Thr  Pro  Ser  Pro  Glu  Ser
               595                      600                      605

CCT  GAC  CAG  TGG  TCA  AGT  TCA  TCA  CCC  CAC  TCT  GCT  TCT  GAC  TGG  TCA         1870
Pro  Asp  Gln  Trp  Ser  Ser  Ser  Ser  Pro  His  Ser  Ala  Ser  Asp  Trp  Ser
          610                      615                      620

GAT  GTG  ACC  ACC  AGC  CCT  ACC  CCT  GGG  GGT  GCT  GGA  GGA  GGT  CAG  CGG         1918
Asp  Val  Thr  Thr  Ser  Pro  Thr  Pro  Gly  Gly  Ala  Gly  Gly  Gly  Gln  Arg
     625                      630                      635

GGA  CCT  GGG  ACA  CAC  ATG  TCT  GAG  CCA  CCA  CAC  AAC  AAC  ATG  CAG  GTT         1966
Gly  Pro  Gly  Thr  His  Met  Ser  Glu  Pro  Pro  His  Asn  Asn  Met  Gln  Val
640                           645                      650                      655

TAT  GCG  TGAGAGAGTC  CACCTCCAGT  GTAGAGACAT  AACTGACTTT  TGTAAATGCT               2022
Tyr  Ala

GCTGAGGAAC  AAATGAAGGT  CATCCGGGAG  AGAAATGAAG  AAATCTCTGG  AGCCAGCTTC               2082

TAGAGGTAGG  AAAGAGAAGA  TGTTCTTATT  CAGATAATGC  AAGAGAAGCA  ATTCGTCAGT               2142
```

-continued

```
TTCACTGGGT ATCTGCAAGG CTTATTGATT ATTCTAATCT AATAAGACAA GTTTGTGGAA      2202
ATGCAAGATG AATACAAGCC TTGGGTCCAT GTTACTCTC TTCTATTTGG AGAATAAGAT       2262
GGATGCTTAT TGAAGCCCAG ACATTCTTGC AGCTTGGACT GCATTTAAG CCCTGCAGGC       2322
TTCTGCCATA TCCATGAGAA GATTCTACAC TAGCGTCCTG TTGGGAATTA TGCCCTGGAA      2382
TTCTGCCTGA ATTGACCTAC GCATCTCCTC CTCCTTGGAC ATTCTTTGT CTTCATTTGG       2442
TGCTTTTGGT TTTGCACCTC TCCGTGATTG TAGCCCTACC AGCATGTTAT AGGGCAAGAC      2502
CTTTGTGCTT TTGATCATTC TGGCCCATGA AAGCAACTTT GGTCTCCTTT CCCCTCCTGT      2562
CTTCCCGGTA TCCCTTGGAG TCTCACAAGG TTTACTTTGG TATGGTTCTC AGCACAAACC      2622
TTTCAAGTAT GTTGTTTCTT TGGAAAATGG ACATACTGTA TTGTGTTCTC CTGCATATAT     2682
CATTCCTGGA GAGAGAAGGG GAGAAGAATA CTTTTCTTCA ACAAATTTG GGGCAGGAG       2742
ATCCCTTCAA GAGGCTGCAC CTTAATTTTT CTTGTCTGTG TGCAGGTCTT CATATAAACT     2802
TTACCAGGAA GAAGGGTGTG AGTTTGTTGT TTTTCTGTGT ATGGGCCTGG TCAGTGTAAA    2862
GTTTTATCCT TGATAGTCTA GTTACTATGA CCCTCCCCAC TTTTTAAAA CCAGAAAAAG    2922
GTTTGGAATG TTGGAATGAC CAAGAGACAA GTTAACTCGT GCAAGAGCCA GTTACCCACC   2982
CACAGGTCCC CCTACTTCCT GCCAAGCATT CCATTGACTG CCTGTATGGA ACACATTTGT    3042
CCCAGATCTG AGCATTCTAG GCCTGTTTCA CTCACTCACC CAGCATATGA AACTAGTCTT    3102
AACTGTTGAG CCTTTCCTTT CATATCCACA GAAGACACTG TCTCAAATGT TGTACCCTTG    3162
CCATTTAGGA CTGAACTTTC CTTAGCCCAA GGGACCCAGT GACAGTTGTC TTCCGTTTGT    3222
CAGATGATCA GTCTCTACTG ATTATCTTGC TGCTTAAAGG CCTGCTCACC AATCTTTCTT    3282
TCACACCGTG TGGTCCGTGT TACTGGTATA CCCAGTATGT TCTCACTGAA GACATGGACT    3342
TTATATGTTC AAGTGCAGGA ATTGGAAAGT TGGACTTGTT TTCTATGATC CAAAACAGCC    3402
CTATAAGAAG GTTGGAAAAG GAGGAACTAT ATAGCAGCCT TTGCTATTTT CTGCTACCAT    3462
TTCTTTTCCT CTGAAGCGGC CATGACATTC CCTTTGGCAA CTAACGTAGA AACTCAACAG    3522
AACATTTTCC TTTCCTAGAG TCACCTTTTA GATGATAATG GACAACTATA GACTTGCTCA    3582
TTGTTCAGAC TGATTGCCCC TCACCTGAAT CCACTCTCTG TATTCATGCT CTTGGCAATT    3642
TCTTTGACTT TCTTTTAAGG GCAGAAGCAT TTTAGTTAAT TGTAGATAAA GAATAGTTTT    3702
CTTCCTCTTC TCCTTGGGCC AGTTAATAAT TGGTCCATGG CTACACTGCA ACTTCCGTCC    3762
AGTGCTGTGA TGCCCATGAC ACCTGCAAAA TAAGTTCTGC CTGGGCATTT TGTAGATATT    3822
AACAGGTGAA TTCCCGACTC TTTTGGTTTG AATGACAGTT CTCATTCCTT CTATGGCTGC    3882
AAGTATGCAT CAGTGCTTCC CACTTACCTG ATTTGTCTGT CGGTGGCCCC ATATGGAAAC    3942
CCTGCGTGTC TGTTGGCATA ATAGTTTACA AATGGTTTTT TCAGTCCTAT CCAAATTTAT    4002
TGAACCAACA AAATAATTA CTTCTGCCCT GAGATAAGCA GATTAAGTTT GTTCATTCTC    4062
TGCTTTATTC TCTCCATGTG GCAACATTCT GTCAGCCTCT TTCATAGTGT GCAAACATTT    4122
TATCATTCTA AATGGTGACT CTCTGCCCTT GGACCCATTT ATTATTCACA GATGGGGAGA    4182
ACCTATCTGC ATGGACCCTC ACCATCCTCT GTGCAGCACA CACAGTGCAG GGAGCCAGTG    4242
GCGATGGCGA TGACTTTCTT CCCCTG                                         4268
```

( 2 ) INFORMATION FOR SEQ ID NO:34:

( i ) SEQUENCE CHARACTERISTICS:
        ( A ) LENGTH: 657 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:34:

| Glu | Val | Asp | Val | Leu | Asp | Val | Asn | Val | Arg | Gly | Pro | Asp | Gly | Cys | Thr |
| 1 |   |   |   | 5 |   |   |   |   | 10 |   |   |   |   | 15 |   |

| Pro | Leu | Met | Leu | Ala | Ser | Leu | Arg | Gly | Ser | Ser | Asp | Leu | Ser | Asp |
|   |   |   | 20 |   |   |   | 25 |   |   |   |   | 30 |   |   |

| Glu | Asp | Glu | Asp | Ala | Glu | Asp | Ser | Ser | Ala | Asn | Ile | Ile | Thr | Asp | Leu |
|   |   | 35 |   |   |   | 40 |   |   |   |   | 45 |   |   |   |   |

| Val | Tyr | Gln | Gly | Ala | Ser | Leu | Gln | Ala | Gln | Thr | Asp | Arg | Thr | Gly | Glu |
|   | 50 |   |   |   | 55 |   |   |   |   | 60 |   |   |   |   |   |

| Met | Ala | Leu | His | Leu | Ala | Ala | Arg | Tyr | Ser | Arg | Ala | Asp | Ala | Ala | Lys |
| 65 |   |   |   | 70 |   |   |   |   | 75 |   |   |   |   | 80 |   |

| Arg | Leu | Leu | Asp | Ala | Gly | Ala | Asp | Ala | Asn | Ala | Gln | Asp | Asn | Met | Gly |
|   |   |   | 85 |   |   |   | 90 |   |   |   |   | 95 |   |   |   |

| Arg | Cys | Pro | Leu | His | Ala | Ala | Val | Ala | Ala | Asp | Ala | Gln | Gly | Val | Phe |
|   |   |   | 100 |   |   |   | 105 |   |   |   |   | 110 |   |   |   |

| Gln | Ile | Leu | Ile | Arg | Asn | Arg | Val | Thr | Asp | Leu | Asp | Ala | Arg | Met | Asn |
|   |   | 115 |   |   |   |   | 120 |   |   |   |   | 125 |   |   |   |

| Asp | Gly | Thr | Thr | Pro | Leu | Ile | Leu | Ala | Ala | Arg | Leu | Ala | Val | Glu | Gly |
|   | 130 |   |   |   | 135 |   |   |   |   | 140 |   |   |   |   |   |

| Met | Val | Ala | Glu | Leu | Ile | Asn | Cys | Gln | Ala | Asp | Val | Asn | Ala | Val | Asp |
| 145 |   |   |   | 150 |   |   |   | 155 |   |   |   |   | 160 |   |   |

| Asp | His | Gly | Lys | Ser | Ala | Leu | His | Trp | Ala | Ala | Ala | Val | Asn | Asn | Val |
|   |   |   |   | 165 |   |   |   | 170 |   |   |   |   | 175 |   |   |

| Glu | Ala | Thr | Leu | Leu | Leu | Leu | Lys | Asn | Gly | Ala | Asn | Arg | Asp | Met | Gln |
|   |   |   | 180 |   |   |   | 185 |   |   |   |   | 190 |   |   |   |

| Asp | Asn | Lys | Glu | Glu | Thr | Pro | Leu | Phe | Leu | Ala | Ala | Arg | Glu | Gly | Ser |
|   |   | 195 |   |   |   | 200 |   |   |   |   | 205 |   |   |   |   |

| Tyr | Glu | Ala | Ala | Lys | Ile | Leu | Leu | Asp | His | Phe | Ala | Asn | Arg | Asp | Ile |
|   | 210 |   |   |   | 215 |   |   |   |   | 220 |   |   |   |   |   |

| Thr | Asp | His | Met | Asp | Arg | Leu | Pro | Arg | Asp | Val | Ala | Arg | Asp | Arg | Met |
| 225 |   |   |   | 230 |   |   |   | 235 |   |   |   |   | 240 |   |   |

| His | His | Asp | Ile | Val | Arg | Leu | Leu | Asp | Glu | Tyr | Asn | Val | Thr | Pro | Ser |
|   |   |   |   | 245 |   |   |   | 250 |   |   |   |   | 255 |   |   |

| Pro | Pro | Gly | Thr | Val | Leu | Thr | Ser | Ala | Leu | Ser | Pro | Val | Ile | Cys | Gly |
|   |   |   | 260 |   |   |   | 265 |   |   |   |   | 270 |   |   |   |

| Pro | Asn | Arg | Ser | Phe | Leu | Ser | Leu | Lys | His | Thr | Pro | Met | Gly | Lys | Lys |
|   |   | 275 |   |   |   | 280 |   |   |   |   | 285 |   |   |   |   |

| Ser | Arg | Arg | Pro | Ser | Ala | Lys | Ser | Thr | Met | Pro | Thr | Ser | Leu | Pro | Asn |
|   | 290 |   |   |   | 295 |   |   |   |   | 300 |   |   |   |   |   |

| Leu | Ala | Lys | Glu | Ala | Lys | Asp | Ala | Lys | Gly | Ser | Arg | Arg | Lys | Lys | Ser |
| 305 |   |   |   | 310 |   |   |   | 315 |   |   |   |   | 320 |   |   |

| Leu | Ser | Glu | Lys | Val | Gln | Leu | Ser | Glu | Ser | Ser | Val | Thr | Leu | Ser | Pro |
|   |   |   |   | 325 |   |   |   | 330 |   |   |   |   | 335 |   |   |

| Val | Asp | Ser | Leu | Glu | Ser | Pro | His | Thr | Tyr | Val | Ser | Asp | Thr | Thr | Ser |
|   |   |   | 340 |   |   |   | 345 |   |   |   |   | 350 |   |   |   |

| Ser | Pro | Met | Ile | Thr | Ser | Pro | Gly | Ile | Leu | Gln | Ala | Ser | Pro | Asn | Pro |
|   |   | 355 |   |   |   | 360 |   |   |   |   | 365 |   |   |   |   |

| Met | Leu | Ala | Thr | Ala | Ala | Pro | Pro | Ala | Pro | Val | His | Ala | Gln | His | Ala |
| 370 |   |   |   | 375 |   |   |   |   | 380 |   |   |   |   |   |   |

| Leu | Ser | Phe | Ser | Asn | Leu | His | Glu | Met | Gln | Pro | Leu | Ala | His | Gly | Ala |
| 385 |   |   |   |   | 390 |   |   |   |   | 395 |   |   |   |   | 400 |

| | | | | | | | | | | | | | | |
|---|---|---|---|---|---|---|---|---|---|---|---|---|---|---|
|Ser|Thr|Val|Leu|Pro<br>405|Ser|Val|Ser|Gln|Leu<br>410|Leu|Ser|His|His<br>415|Ile|
|Val|Ser|Pro|Gly<br>420|Ser|Gly|Ser|Ala|Gly<br>425|Ser|Leu|Ser|Arg|Leu<br>430|His|Pro|
|Val|Pro|Val<br>435|Pro|Ala|Asp|Trp|Met<br>440|Asn|Arg|Met|Glu|Val<br>445|Asn|Glu|Thr|
|Gln|Tyr<br>450|Asn|Glu|Met|Phe|Gly<br>455|Met|Val|Leu|Ala|Pro<br>460|Ala|Glu|Gly|Thr|
|His<br>465|Pro|Gly|Ile|Ala|Pro<br>470|Gln|Ser|Arg|Pro|Pro<br>475|Glu|Gly|Lys|His|Ile<br>480|
|Thr|Thr|Pro|Arg|Glu<br>485|Pro|Leu|Pro|Pro|Ile<br>490|Val|Thr|Phe|Gln|Leu<br>495|Ile|
|Pro|Lys|Gly|Ser<br>500|Ile|Ala|Gln|Pro|Ala<br>505|Gly|Ala|Pro|Gln|Pro<br>510|Gln|Ser|
|Thr|Cys|Pro<br>515|Pro|Ala|Val|Ala|Gly<br>520|Pro|Leu|Pro|Thr|Met<br>525|Tyr|Gln|Ile|
|Pro|Glu<br>530|Met|Ala|Arg|Leu|Pro<br>535|Ser|Val|Ala|Phe|Pro<br>540|Thr|Ala|Met|Met|
|Pro<br>545|Gln|Gln|Asp|Gly|Gln<br>550|Val|Ala|Gln|Thr|Ile<br>555|Leu|Pro|Ala|Tyr|His<br>560|
|Pro|Phe|Pro|Ala|Ser<br>565|Val|Gly|Lys|Tyr|Pro<br>570|Thr|Pro|Pro|Ser|Gln<br>575|His|
|Ser|Tyr|Ala|Ser<br>580|Ser|Asn|Ala|Ala|Glu<br>585|Arg|Thr|Pro|Ser|His<br>590|Ser|Gly|
|His|Leu|Gln<br>595|Gly|Glu|His|Pro|Tyr<br>600|Leu|Thr|Pro|Ser|Pro<br>605|Glu|Ser|Pro|
|Asp|Gln<br>610|Trp|Ser|Ser|Ser|Ser<br>615|Pro|His|Ser|Ala|Ser<br>620|Asp|Trp|Ser|Asp|
|Val<br>625|Thr|Thr|Ser|Pro|Thr<br>630|Pro|Gly|Gly|Ala|Gly<br>635|Gly|Gly|Gln|Arg|Gly<br>640|
|Pro|Gly|Thr|His|Met<br>645|Ser|Glu|Pro|Pro|His<br>650|Asn|Asn|Met|Gln|Val<br>655|Tyr|
|Ala|

( 2 ) INFORMATION FOR SEQ ID NO:35:

( i ) SEQUENCE CHARACTERISTICS:
  ( A ) LENGTH: 654 amino acids
  ( B ) TYPE: amino acid
  ( C ) STRANDEDNESS: single
  ( D ) TOPOLOGY: unknown ( i i ) MOLECULE TYPE: peptide ( x i ) SEQUENCE DESCRIPTION: SEQ ID NO:35:

| | | | | | | | | | | | | | | |
|---|---|---|---|---|---|---|---|---|---|---|---|---|---|---|
|Thr<br>1|Pro|Pro|Gln|Gly<br>5|Glu|Ile|Glu|Ala|Asp<br>10|Cys|Met|Asp|Val|Asn<br>15|Val|
|Arg|Gly|Pro|Asp<br>20|Gly|Phe|Thr|Pro|Leu<br>25|Met|Ile|Ala|Ser|Cys<br>30|Ser|Gly|
|Gly|Gly|Leu|Glu|Thr<br>35|Gly|Asn|Ser|Glu|Glu<br>40|Glu|Glu|Asp|Ala<br>45|Ser|Ala|
|Asn|Met|Ile|Ser|Asp<br>50|Phe|Ile|Gly|Gln<br>55|Gly|Ala|Gln|Leu|His<br>60|Asn|Gln|
|Thr|Asp|Arg|Thr<br>65|Gly|Glu|Thr|Ala<br>70|Leu|His|Leu|Ala|Ala<br>75|Arg|Tyr|Ala<br>80|
|Arg|Ala|Asp|Ala|Ala<br>85|Lys|Arg|Leu|Leu|Glu<br>90|Ser|Ser|Ala|Asp|Ala<br>95|Asn|

-continued

```
Val Gln Asp Asn Met Gly Arg Thr Pro Leu His Ala Ala Val Ala Ala
            100                 105                 110
Asp Ala Gln Gly Val Phe Gln Ile Leu Ile Arg Asn Arg Ala Thr Asp
        115                 120                 125
Leu Asp Ala Arg Met Phe Asp Gly Thr Thr Pro Leu Ile Leu Ala Ala
    130                 135                 140
Arg Leu Ala Val Glu Gly Met Val Glu Glu Leu Ile Asn Ala His Ala
145                 150                 155                 160
Asp Val Asn Ala Val Asp Glu Phe Gly Lys Ser Ala Leu His Trp Ala
                165                 170                 175
Ala Ala Val Asn Asn Val Asp Ala Ala Val Leu Leu Lys Asn Ser
                180                 185                 190
Ala Asn Lys Asp Met Gln Asn Asn Lys Glu Glu Thr Ser Leu Phe Leu
        195                 200                 205
Ala Ala Arg Glu Gly Ser Tyr Glu Thr Ala Lys Val Leu Leu Asp His
    210                 215                 220
Tyr Ala Asn Arg Asp Ile Thr Asp His Met Asp Arg Leu Pro Arg Asp
225                 230                 235                 240
Ile Ala Gln Glu Arg Met His His Asp Ile Val His Leu Leu Asp Glu
                245                 250                 255
Tyr Asn Leu Val Lys Ser Pro Thr Leu His Asn Gly Pro Leu Gly Ala
            260                 265                 270
Thr Thr Leu Ser Pro Pro Ile Cys Ser Pro Asn Gly Tyr Met Gly Asn
        275                 280                 285
Met Lys Pro Ser Val Gln Ser Lys Lys Ala Arg Lys Pro Ser Ile Lys
    290                 295                 300
Gly Asn Gly Cys Lys Glu Ala Lys Glu Leu Lys Ala Arg Arg Lys Lys
305                 310                 315                 320
Ser Gln Asp Gly Lys Thr Thr Leu Leu Asp Ser Gly Ser Ser Gly Val
                325                 330                 335
Leu Ser Pro Val Asp Ser Leu Glu Ser Thr His Gly Tyr Leu Ser Asp
            340                 345                 350
Val Ser Ser Pro Pro Leu Met Thr Ser Pro Phe Gln Gln Ser Pro Ser
        355                 360                 365
Met Pro Leu Asn His Leu Thr Ser Met Pro Glu Ser Gln Leu Gly Met
    370                 375                 380
Asn His Ile Asn Met Ala Thr Lys Gln Glu Met Ala Ala Gly Ser Asn
385                 390                 395                 400
Arg Met Ala Phe Asp Ala Met Val Pro Arg Leu Thr His Leu Asn Ala
                405                 410                 415
Ser Ser Pro Asn Thr Ile Met Ser Asn Gly Ser Met His Phe Thr Val
            420                 425                 430
Gly Gly Ala Pro Thr Met Asn Ser Gln Cys Asp Trp Leu Ala Arg Leu
        435                 440                 445
Gln Asn Gly Met Val Gln Asn Gln Tyr Asp Pro Ile Arg Asn Gly Ile
    450                 455                 460
Gln Gln Gly Asn Ala Gln Gln Ala Gln Ala Leu Gln His Gly Leu Met
465                 470                 475                 480
Thr Ser Leu His Asn Gly Leu Pro Ala Thr Thr Leu Ser Gln Met Met
                485                 490                 495
Thr Tyr Gln Ala Met Pro Asn Thr Arg Leu Ala Asn Gln Pro His Leu
            500                 505                 510
Met Gln Ala Gln Gln Met Gln Gln Gln Gln Asn Leu Gln Leu His Gln
```

|   |   |   |   |   | 515 |   |   |   |   | 520 |   |   |   |   | 525 |   |   |
|---|---|---|---|---|---|---|---|---|---|---|---|---|---|---|---|---|---|
| Ser | Met 530 | Gln | Gln | Gln | His | His 535 | Asn | Ser | Ser | Thr | Thr 540 | Ser | Thr | His | Ile |
| Asn 545 | Ser | Pro | Phe | Cys | Ser 550 | Ser | Asp | Ile | Ser | Gln 555 | Thr | Asp | Leu | Gln | Gln 560 |
| Met | Ser | Ser | Asn | Asn 565 | Ile | His | Ser | Val | Met 570 | Pro | Gln | Asp | Thr | Gln 575 | Ile |
| Phe | Ala | Ala | Ser 580 | Leu | Pro | Ser | Asn | Leu 585 | Thr | Gln | Ser | Met | Thr 590 | Thr | Ala |
| Gln | Phe 595 | Leu | Thr | Pro | Pro | Ser | Gln 600 | His | Ser | Tyr | Ser | Ser 605 | Pro | Met | Asp |
| Asn | Thr 610 | Pro | Ser | His | Gln | Leu 615 | Gln | Val | Pro | Asp | His 620 | Pro | Phe | Leu | Thr |
| Pro 625 | Ser | Pro | Glu | Ser | Pro 630 | Asp | Gln | Trp | Ser | Ser 635 | Ser | Ser | Pro | His | Ser 640 |
| Asn | Met | Ser | Asp | Trp 645 | Ser | Glu | Gly | Ile | Ser 650 | Ser | Pro | Pro | Thr |   |   |

( 2 ) INFORMATION FOR SEQ ID NO:36:

( i ) SEQUENCE CHARACTERISTICS:
        ( A ) LENGTH: 666 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:36:

| Thr 1 | Pro | Pro | Gln | Gly 5 | Glu | Val | Asp | Ala | Cys 10 | Met | Asp | Val | Asn | Val 15 |
|---|---|---|---|---|---|---|---|---|---|---|---|---|---|---|
| Arg | Gly | Pro | Asp 20 | Gly | Phe | Thr | Pro | Leu 25 | Met | Ile | Ala | Ser | Cys 30 | Ser | Gly |
| Gly | Gly | Leu 35 | Glu | Thr | Gly | Asn | Ser 40 | Glu | Glu | Glu | Glu | Asp 45 | Ala | Pro | Ala |
| Val | Ile | Ser 50 | Asp | Phe | Ile | Tyr 55 | Gln | Gly | Ala | Ser | Leu 60 | His | Asn | Gln | Thr |
| Asp 65 | Arg | Thr | Gly | Glu | Thr 70 | Ala | Leu | His | Leu 75 | Ala | Ala | Arg | Tyr | Ser | Arg 80 |
| Ser | Asp | Ala | Ala | Lys 85 | Arg | Leu | Leu | Glu | Ala 90 | Ser | Ala | Asp | Ala | Asn 95 | Ile |
| Gln | Asp | Asn | Met 100 | Gly | Arg | Thr | Pro | Leu 105 | His | Ala | Ala | Val | Ser 110 | Ala | Asp |
| Ala | Gln | Gly 115 | Val | Phe | Gln | Ile | Leu 120 | Leu | Arg | Asn | Arg | Ala 125 | Thr | Asp | Leu |
| Asp | Ala | Arg 130 | Met | His | Asp | Gly | Thr 135 | Thr | Pro | Leu | Ile | Leu 140 | Ala | Ala | Arg |
| Leu 145 | Ala | Val | Glu | Gly | Met 150 | Leu | Glu | Asp | Leu 155 | Ile | Asn | Ser | His | Ala | Asp 160 |
| Val | Asn | Ala | Val | Asp 165 | Asp | Leu | Gly | Lys | Ser 170 | Ala | Leu | His | Trp | Ala | Ala 175 |
| Ala | Val | Asn | Asn 180 | Val | Asp | Ala | Ala | Val 185 | Val | Leu | Leu | Lys | Asn 190 | Gly | Ala |
| Asn | Lys | Asp 195 | Met | Gln | Asn | Asn | Lys 200 | Glu | Glu | Thr | Pro | Leu 205 | Phe | Leu | Ala |
| Ala | Arg 210 | Glu | Gly | Ser | Tyr | Glu 215 | Thr | Ala | Lys | Val | Leu 220 | Leu | Asp | His | Phe |

-continued

| | | | | | | | | | | | | | | |
|---|---|---|---|---|---|---|---|---|---|---|---|---|---|---|
| Ala 225 | Asn | Arg | Asp | Ile 230 | Thr | Asp | His | Met | Arg 235 | Leu | Pro | Arg | Asp | Ile 240 |
| Ala | Gln | Glu | Arg | Met 245 | His | His | Asp | Ile 250 | Val | Arg | Leu | Leu | Asp 255 | Tyr |
| Asn | Leu | Val | Arg 260 | Ser | Pro | Gln | Leu | His 265 | Gly | Thr | Ala | Leu 270 | Gly | Gly | Thr |
| Pro | Thr | Leu 275 | Ser | Pro | Thr | Leu | Cys 280 | Ser | Pro | Asn | Gly | Tyr 285 | Leu | Gly | Asn |
| Leu | Lys 290 | Ser | Ala | Thr | Gln 295 | Gly | Lys | Lys | Ala | Arg 300 | Lys | Pro | Ser | Thr | Lys |
| Gly 305 | Leu | Ala | Cys | Ser | Ser 310 | Lys | Glu | Ala | Lys | Asp 315 | Leu | Lys | Ala | Arg | Arg 320 |
| Lys | Lys | Ser | Gln | Asp 325 | Gly | Lys | Gly | Cys | Leu 330 | Leu | Asp | Ser | Ser | Ser 335 | Met |
| Leu | Ser | Pro | Val 340 | Asp | Ser | Leu | Glu | Ser 345 | Pro | His | Gly | Tyr | Leu 350 | Ser | Asp |
| Val | Ala | Ser 355 | Pro | Pro | Leu | Pro | Ser 360 | Pro | Phe | Gln | Gln | Ser 365 | Pro | Ser | Met |
| Pro | Leu 370 | Ser | His | Leu | Pro | Gly 375 | Met | Pro | Asp | Thr | His 380 | Leu | Gly | Ile | Ser |
| His 385 | Leu | Asn | Val | Ala | Ala 390 | Lys | Pro | Glu | Met | Ala 395 | Ala | Leu | Ala | Gly | Gly 400 |
| Ser | Arg | Leu | Ala | Phe 405 | Glu | Pro | Pro | Pro | Arg 410 | Leu | Ser | His | Leu 415 | Pro |
| Val | Ala | Ser | Ser 420 | Ala | Ser | Thr | Val | Leu 425 | Ser | Thr | Asn | Gly | Thr 430 | Gly | Ala |
| Met | Asn | Phe 435 | Thr | Val | Gly | Ala | Pro 440 | Ala | Ser | Leu | Asn | Gly 445 | Gln | Cys | Glu |
| Trp | Leu 450 | Pro | Arg | Leu | Gln | Asn 455 | Gly | Met | Val | Pro | Ser 460 | Gln | Tyr | Asn | Pro |
| Leu | Arg 465 | Pro | Gly | Val | Thr 470 | Pro | Gly | Thr | Leu | Ser 475 | Thr | Gln | Ala | Ala | Gly 480 |
| Leu | Gln | His | Gly | Met 485 | Met | Ser | Pro | Ile | His 490 | Ser | Ser | Leu | Ser | Thr 495 | Asn |
| Thr | Leu | Ser | Pro 500 | Ile | Ile | Tyr | Gln | Gly 505 | Leu | Pro | Asn | Thr | Arg 510 | Leu | Ala |
| Thr | Gln | Pro 515 | His | Leu | Val | Gln | Thr 520 | Gln | Gln | Val | Gln | Pro 525 | Gln | Asn | Leu |
| Gln | Ile 530 | Gln | Pro | Gln | Asn | Leu 535 | Gln | Pro | Pro | Ser | Gln 540 | Pro | His | Leu | Ser |
| Val 545 | Ser | Ser | Ala | Ala | Asn 550 | Gly | His | Leu | Gly | Arg 555 | Ser | Phe | Leu | Ser | Gly 560 |
| Glu | Pro | Ser | Gln | Ala 565 | Asp | Val | Gln | Pro | Leu 570 | Gly | Pro | Ser | Ser | Leu 575 | Pro |
| Val | His | Thr | Ile 580 | Leu | Pro | Gln | Glu | Ser 585 | Gln | Ala | Leu | Pro | Thr 590 | Ser | Leu |
| Pro | Ser | Ser 595 | Met | Val | Pro | Pro | Met 600 | Thr | Thr | Thr | Gln | Phe 605 | Leu | Thr | Pro |
| Pro | Ser | Gln 610 | His | Ser | Tyr | Ser 615 | Ser | Pro | Val | Asp 620 | Asn | Thr | Pro | Ser |
| His 625 | Gln | Leu | Gln | Val | Pro 630 | Glu | His | Pro | Phe | Leu 635 | Thr | Pro | Ser | Pro | Glu 640 |
| Ser | Pro | Asp | Gln | Trp | Ser | Ser | Ser | Ser | Arg | His | Ser | Asn | Ile | Ser | Asp |

645                              650                              655
         Trp  Ser  Glu  Gly  Ile  Ser  Ser  Pro  Pro  Thr
                        660                           665

( 2 ) INFORMATION FOR SEQ ID NO:37:

( i ) SEQUENCE CHARACTERISTICS:
            ( A ) LENGTH: 681 amino acids
            ( B ) TYPE: amino acid
            ( C ) STRANDEDNESS: single
            ( D ) TOPOLOGY: unknown ( i i ) MOLECULE TYPE: peptide ( x i ) SEQUENCE DESCRIPTION: SEQ ID NO:37:

Thr  Pro  Pro  Gln  Gly  Glu  Val  Asp  Ala  Asp  Cys  Met  Asp  Val  Asn  Val
         1                    5                        10                        15

Arg  Gly  Pro  Asp  Gly  Phe  Thr  Pro  Leu  Met  Ile  Ala  Ser  Cys  Ser  Gly
                        20                       25                        30

Gly  Gly  Leu  Glu  Thr  Gly  Asn  Ser  Glu  Glu  Glu  Asp  Ala  Pro  Ala
                   35                        40                        45

Val  Ile  Ser  Asp  Phe  Ile  Tyr  Gln  Gly  Ala  Ser  Leu  His  Asn  Gln  Thr
              50                        55                             60

Asp  Arg  Thr  Gly  Glu  Thr  Ala  Leu  His  Leu  Ala  Ala  Arg  Tyr  Ser  Arg
         65                        70                        75                        80

Ser  Asp  Ala  Ala  Lys  Arg  Leu  Leu  Glu  Ala  Ser  Ala  Asp  Ala  Asn  Ile
                             85                        90                        95

Gln  Asp  Asn  Met  Gly  Arg  Thr  Pro  Leu  His  Ala  Ala  Val  Ser  Ala  Asp
                        100                      105                       110

Ala  Gln  Gly  Val  Phe  Gln  Ile  Leu  Ile  Arg  Asn  Arg  Ala  Thr  Asp  Leu
                   115                      120                       125

Asp  Ala  Arg  Met  His  Asp  Gly  Thr  Thr  Pro  Leu  Ile  Leu  Ala  Ala  Arg
              130                      135                       140

Leu  Ala  Val  Glu  Gly  Met  Leu  Glu  Asp  Leu  Ile  Asn  Ser  His  Ala  Asp
        145                      150                       155                       160

Val  Asn  Ala  Val  Asp  Asp  Leu  Gly  Lys  Ser  Ala  Leu  His  Trp  Ala  Ala
                             165                      170                       175

Ala  Val  Asn  Asn  Val  Asp  Ala  Ala  Val  Val  Leu  Leu  Lys  Asn  Gly  Ala
                        180                           185                      190

Asn  Lys  Asp  Met  Gln  Asn  Asn  Arg  Glu  Glu  Thr  Pro  Leu  Phe  Leu  Ala
                   195                      200                       205

Ala  Arg  Glu  Gly  Ser  Tyr  Glu  Thr  Ala  Lys  Val  Leu  Leu  Asp  His  Phe
              210                      215                       220

Ala  Asn  Arg  Asp  Ile  Thr  Asp  His  Met  Asp  Arg  Leu  Pro  Arg  Asp  Ile
        225                      230                       235                       240

Ala  Gln  Glu  Arg  Met  His  His  Asp  Ile  Val  Arg  Leu  Leu  Asp  Glu  Tyr
                        245                           250                      255

Asn  Leu  Val  Arg  Ser  Pro  Gln  Leu  His  Gly  Ala  Pro  Leu  Gly  Gly  Thr
                        260                      265                       270

Pro  Thr  Leu  Ser  Pro  Pro  Leu  Cys  Ser  Pro  Asn  Gly  Tyr  Leu  Gly  Ser
                   275                      280                       285

Leu  Lys  Pro  Gly  Val  Gln  Gly  Lys  Lys  Val  Arg  Lys  Pro  Ser  Ser  Lys
              290                      295                       300

Gly  Leu  Ala  Cys  Gly  Ser  Lys  Glu  Ala  Lys  Asp  Leu  Lys  Ala  Arg  Arg
        305                      310                       315                       320

Lys  Lys  Ser  Gln  Asp  Gly  Lys  Gly  Cys  Leu  Leu  Asp  Ser  Ser  Gly  Met
                        325                           330                      335

```
Leu  Ser  Pro  Val  Asp  Ser  Leu  Glu  Ser  Pro  His  Gly  Tyr  Leu  Ser  Asp
               340                      345                     350

Val  Ala  Ser  Pro  Pro  Leu  Leu  Pro  Ser  Pro  Phe  Gln  Gln  Ser  Pro  Ser
          355                      360                    365

Val  Pro  Leu  Asn  His  Leu  Pro  Gly  Met  Pro  Asp  Thr  His  Leu  Gly  Ile
     370                      375                     380

Gly  His  Leu  Asn  Val  Ala  Ala  Lys  Pro  Glu  Met  Ala  Ala  Leu  Gly  Gly
385                           390                395                          400

Gly  Gly  Arg  Leu  Ala  Phe  Glu  Thr  Gly  Pro  Pro  Arg  Leu  Ser  His  Leu
                405                      410                          415

Pro  Val  Ala  Ser  Gly  Thr  Ser  Thr  Val  Leu  Gly  Ser  Ser  Ser  Gly  Gly
               420                      425                     430

Ala  Leu  Asn  Phe  Thr  Val  Gly  Gly  Ser  Thr  Ser  Leu  Asn  Gly  Gln  Cys
          435                      440                    445

Glu  Trp  Leu  Ser  Arg  Leu  Gln  Ser  Gly  Met  Val  Pro  Asn  Gln  Tyr  Asn
     450                      455                     460

Pro  Leu  Arg  Gly  Ser  Val  Ala  Pro  Gly  Pro  Leu  Ser  Thr  Gln  Ala  Pro
465                      470                     475                          480

Ser  Leu  Gln  His  Gly  Met  Val  Gly  Pro  Leu  His  Ser  Ser  Leu  Ala  Ala
               485                     490                          495

Ser  Ala  Leu  Ser  Gln  Met  Met  Ser  Tyr  Gln  Gly  Leu  Pro  Ser  Thr  Arg
               500                     505                     510

Leu  Ala  Thr  Gln  Pro  His  Leu  Val  Gln  Thr  Gln  Gln  Val  Gln  Pro  Gln
          515                      520                     525

Asn  Leu  Gln  Met  Gln  Gln  Asn  Leu  Gln  Pro  Ala  Asn  Ile  Gln  Gln
     530                      535                     540

Gln  Gln  Ser  Leu  Gln  Pro  Pro  Pro  Pro  Pro  Pro  Gln  Pro  His  Leu  Gly
545                      550                     555                          560

Val  Ser  Ser  Ala  Ala  Ser  Gly  His  Leu  Gly  Arg  Ser  Phe  Leu  Ser  Gly
               565                      570                          575

Glu  Pro  Ser  Gln  Ala  Asp  Val  Gln  Pro  Leu  Gly  Pro  Ser  Ser  Leu  Ala
               580                      585                     590

Val  His  Thr  Ile  Leu  Pro  Gln  Glu  Ser  Pro  Ala  Leu  Pro  Thr  Ser  Leu
          595                      600                     605

Pro  Ser  Ser  Leu  Val  Pro  Pro  Val  Thr  Ala  Ala  Gln  Phe  Leu  Thr  Pro
     610                      615                     620

Pro  Ser  Gln  His  Ser  Tyr  Ser  Ser  Pro  Val  Glu  Asn  Thr  Pro  Ser  His
625                      630                     635                          640

Gln  Leu  Gln  Val  Pro  Glu  His  Pro  Phe  Leu  Thr  Pro  Ser  Pro  Glu  Ser
               645                      650                     655

Pro  Asp  Gln  Trp  Ser  Ser  Ser  Ser  Pro  His  Ser  Asn  Val  Ser  Asp  Trp
               660                      665                     670

Ser  Glu  Gly  Val  Ser  Ser  Pro  Pro  Thr
          675                      680
```

SERRATE FRAGMENTS AND DERIVATIVES

This application is a continuation of application Ser. No. 07/879,038, filed Apr. 30, 1992, now abandoned, which is a continuation-in-part of application Ser. No. 07/791,923 filed Nov. 14, 1991, abandoned, which is a continuation-in-part of application Ser. No. 07/695,189, filed May 3, 1991, abandoned, each of which is incorporated by reference herein in its entirety.

This invention was made in part with government support under Grant numbers GM 29093 and NS 26084 awarded by the Department of Health and Human Services. The government has certain rights in the invention.

1. INTRODUCTION

The present invention relates to the human Notch and Delta genes and their encoded products. The invention also relates to sequences (termed herein "adhesive sequences") within the proteins encoded by toporythmic genes which mediate homotypic or heterotypic binding to sequences within proteins encoded by toporythmic genes. Such genes include but are not limited to Notch, Delta, and Serrate.

2. BACKGROUND OF THE INVENTION

Genetic analyses in Drosophila have been extremely useful in dissecting the complexity of developmental pathways and identifying interacting loci. However, understanding the precise nature of the processes that underlie genetic interactions requires a knowledge of the biochemical properties of the protein products of the genes in question.

Null mutations in any one of the zygotic neurogenic loci—Notch (N), Delta (Dl), mastermind (mam), Enhancer of Split (E(spl), neuralized (neu), and big brain (bib)—result in hypertrophy of the nervous system at the expense of ventral and lateral epidermal structures. This effect is due to the misrouting of epidermal precursor cells into a neuronal pathway, and implies that neurogenic gene function is necessary to divert cells within the neurogenic region from a neuronal fate to an epithelial fate. Studies that assessed the effects of laser ablation of specific embryonic neuroblasts in grasshoppers (Doe and Goodman 1985, Dev. Biol. 111, 206–219) have shown that cellular interactions between neuroblasts and the surrounding accessory cells serve to inhibit these accessory cells from adopting a neuroblast fate. Together, these genetic and developmental observations have led to the hypothesis that the protein products of the neurogenic loci function as components of a cellular interaction mechanism necessary for proper epidermal development (Artavanis-Tsakonas, 1988, Trends Genet. 4, 95–100).

Sequence analyses (Wharton et al., 1985, Cell 43, 567–581; Kidd et al., 1986, Mol. Cell. Biol. 6, 3094–3108; Vassin et al., 1987, EMBO J. 6, 3431–3440; Kopczynski et al., 1988, Genes Dev. 2, 1723–1735) have shown that two of the neurogenic loci, Notch and Delta, appear to encode transmembrane proteins that span the membrane a single time. The Notch gene encodes a ~300 kd protein (we use "Notch" to denote this protein) with a large N-terminal extracellular domain that includes 36 epidermal growth factor (EGF)—like tandem repeats followed by three other cysteine-rich repeats, designated Notch/lin-12 repeats (Wharton et al., 1985, Cell 43, 567–581; Kidd et al., 1986, Mol. Cell Biol. 6, 3094–3108; Yochem et al., 1988, Nature 335, 547–550). Delta encodes a ~100 kd protein (we use "Delta" to denote DLZM, the protein product of the predominant zygotic and maternal transcripts; Kopczynski et al., 1988, Genes Dev. 2, 1723–1735) that has nine EGF-like repeats within its extracellular domain (Vassin et al., 1987, EMBO J. 6, 3431–3440; Kopczynski et al., 1988, Genes Dev. 2, 1723–1735). Although little is known about the functional significance of these repeats, the EGF-like motif has been found in a variety of proteins, including those involved in the blood clotting cascade (Furie and Furie, 1988, Cell 53, 505–518). In particular, this motif has been found in extracellular proteins such as the blood clotting factors IX and X (Rees et al., 1988, EMBO J. 7, 2053–2061; Furie and Furie, 1988, Cell 53, 505–518), in other Drosophila genes (Knust et al., 1987, EMBO J. 761–766; Rothberg et al., 1988, Cell 55, 1047–1059), and in some cell-surface receptor proteins, such as thrombomodulin (Suzuki et al., 1987, EMBO J. 6, 1891–1897) and LDL receptor (Sudhof et al., 1985, Science 228, 815–822). A protein binding site has been mapped to the EGF repeat domain in thrombomodulin and urokinase (Kurosawa et al., 1988, J. Biol. Chem 263, 5993–5996; Appella et al., 1987, J. Biol. Chem. 262, 4437–4440).

An intriguing array of interactions between Notch and Delta mutations has been described (Vassin, et al., 1985, J. Neurogenet. 2, 291–308; Shepard et al., 1989, Genetics 122, 429–438; Xu et al., 1990, Genes Dev., 4, 464–475). A number of genetic studies (summarized in Alton et al., 1989, Dev. Genet. 10, 261–272) has indicated that the gene dosages of Notch and Delta in relation to one another are crucial for normal development. A 50% reduction in the dose of Delta in a wild-type Notch background causes a broadening of the wing veins creating a "delta" at the base (Lindsley and Grell, 1968, Publication Number 627, Washington, D.C., Carnegie Institute of Washington). A similar phenotype is caused by a 50% increase in the dose of Notch in a wild-type Delta background (a "Confluens" phenotype; Welshons, 1965, Science 150, 1122–1129). This Delta phenotype is partially suppressed by a reduction in the Notch dosage. Recent work in our laboratories has shown that lethal interactions between alleles that correlate with alterations in the EGF-like repeats in Notch can be rescued by reducing the dose of Delta (Xu et al., 1990, Genes Dev. 4, 464–475). Xu et al. (1990, Genes Dev. 4, 464–475) found that null mutations at either Delta or mam suppress lethal interactions between heterozygous combinations of certain Notch alleles, known as the Abruptex (Ax) mutations. Ax alleles are associated with missense mutations within the EGF-like repeats of the Notch extracellular domain (Kelley et al., 1987, Cell 51, 539–548; Hartley et al., 1987, EMBO J. 6, 3407–3417).

Notch is expressed on axonal processes during the outgrowth of embryonic neurons (Johansen et al., 1989, J. Cell Biol. 109, 2427–2440; Kidd et al., 1989, Genes Dev. 3, 1113–1129).

A study has shown that certain Ax alleles of Notch can severely alter axon pathfinding during sensory neural outgrowth in the imaginal discs, although it is not yet known whether aberrant Notch expression in the axon itself or the epithelium along which it grows is responsible for this defect (Palka et al., 1990, Development 109, 167–175).

3. SUMMARY OF THE INVENTION

The present invention relates to nucleotide sequences of the human Notch and Delta genes, and amino acid sequences of their encoded proteins, as well as fragments thereof containing an antigenic determinant or which are functionally active. The invention is also directed to fragments (termed herein "adhesive fragments"), and the sequences thereof, of the proteins ("toporythmic proteins") encoded by toporythmic genes which mediate homotypic or heterotypic binding to toporythmic proteins. Toporythmic genes, as used herein, refers to the genes Notch, Delta, and Serrate, as well as other members of the Delta/Serrate family which may be identified, e.g., by the methods described in Section 5.3, infra. Analogs and derivatives of the adhesive fragments which retain binding activity are also provided. Antibodies to human Notch and to adhesive fragments are additionally provided.

In specific embodiments, the adhesive fragment of Notch is that fragment comprising the Notch sequence most homologous to Drosophila Notch EGF-like repeats 11 and 12; the adhesive fragment of Delta mediating heterotypic binding is that fragment comprising the sequence most homologous to Drosophila Delta amino acids 1–230; the adhesive fragment of Delta mediating homotypic binding is that fragment comprising the sequence most homologous to Drosophila Delta amino acids 32–230; and the adhesive fragment of Serrate is that fragment comprising the sequence most homologous to Drosophila Serrate amino acids 85–283 or 79–282.

3.1. DEFINITIONS

As used herein, the following terms shall have the meanings indicated:

AA=amino acid
EGF=epidermal growth factor
ELR=EGF-like (homologous) repeat
IC=intracellular
PCR=polymerase chain reaction As used herein, underscoring the name of a gene shall indicate the gene, in contrast to its encoded protein product which is indicated by the name of the gene in the absence of any underscoring. For example, "Notch" shall mean the Notch gene, whereas "Notch" shall indicate the protein product of the Notch gene.

4. DESCRIPTION OF THE FIGURES

FIG. 1. Expression Constructs and Experimental Design for Examining Notch-Delta Interactions. S2 cells at log phase growth were transiently transfected with one of the three constructs shown. Notch encoded by the MGlla minigene (a cDNA/genomic chimeric construct: cDNA-derived sequences are represented by stippling, genomically derived sequences by diagonal-hatching (Ramos et al., 1989, Genetics 123, 337–348)) was expressed following insertion into the metallothionein promoter vector pRmHa-3 (Bunch et al., 1988, Nucl. Acids Res. 16, 1043–1061). Delta encoded by the Dl1 cDNA (Kopczynski et al., 1988, Genes Dev. 2, 1723–1735) was expressed after insertion into the same vector. The extracellular Notch (ECN1) variant was derived from a genomic cosmid containing the complete Notch locus (Ramos et al., 1989, Genetics 123, 337–348) by deleting the coding sequence for amino acids 1790–2625 from the intracellular domain (denoted by δ; Wharton et al., 1985, Cell 43, 567–581), leaving 25 membrane-proximal residues from the wild-type sequence fused to a novel 59 amino acid tail (see Experimental Procedures, Section 6.1, infra). This construct was expressed under control of the Notch promoter region. For constructs involving the metallothionein vector, expression was induced with $CuSO_4$ following transfection. Cells were then mixed, incubated under aggregation conditions, and scored for their ability to aggregate using specific antisera and immunofluorescence microscopy to visualize expressing cells. MT, metallothionein promoter; ATG, translation start site; TM, transmembrane domain; 3' N, Notch gene polyadenylation signal; 3' Adh, polyadenylation signal from Adh gene; 5' N, Notch gene promoter region.

Figure 2A:
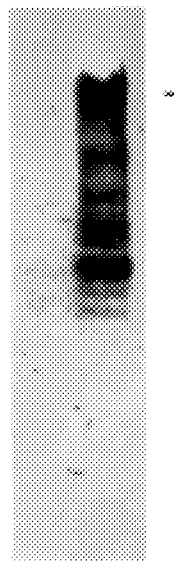
Figure 2B:
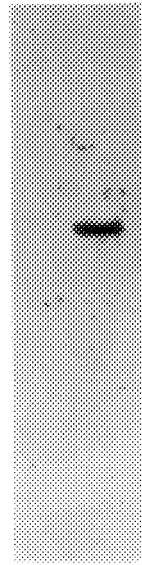

FIGS. 2A–2B. Expression of Notch and Delta in Cultured Cells. FIG. 2A: Lysates of nontransfected (S2) and Notch-transfected (N) cells induced with 0.7 mM $CuSO_4$ for 12–16 hr were prepared for sodium dodecyl sulfate polyacrylamide gel electrophoresis (SDS-PAGE), run on 3%–15% gradient gels, and blotted to nitrocellulose. Notch was visualized using a monoclonal antibody (MAb C17.9C6) against the intracellular domain of Notch. Multiple bands below the major band at 300 kd may represent degradation products of Notch. FIG. 2B: Lysates of nontransfected (S2) and Delta-transfected (Dl) cells visualized with a monoclonal antibody (MAb 201) against Delta. A single band of ~105 kd is detected. In both cases, there is no detectable endogenous Notch or Delta in the S2 cell line nor are there cross-reactive species. In each lane, 10 μl of sample (prepared as described in Experimental Procedures) was loaded.

FIGS. 3A–3I. S2 Cells That Express Notch and Delta Form Aggregates. In all panels, Notch is shown in green and Delta in red.

FIG. 3A: A single Notch$^+$ cell. Note the prominent intracellular stain, including vesicular structures as well as an obviously unstained nucleus.

FIG. 3A: Bright-field micrograph of same field, showing specificity of antibody staining.

FIG. 3B: A single Delta$^+$ cell. Staining is primarily at the cell surface.

FIG. 3B: Bright-field micrograph of same field.

FIG. 3C: Aggregate of Delta$^+$ cells from a 24 hr aggregation experiment. Note against that staining is primarily at the cell surface.

Figure 3D:
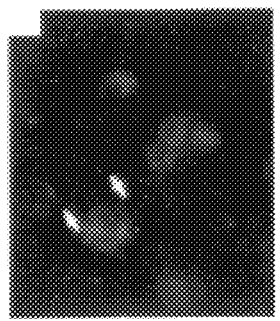
Figure 3E:
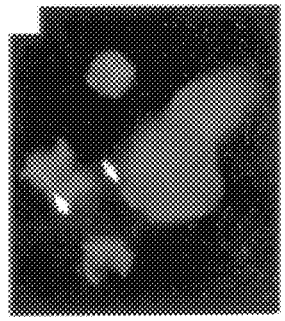
Figure 3F:
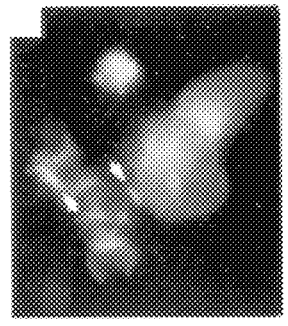

FIGS. 3D–3F: An aggregate of Notch$^+$ and Delta$^+$ cells formed from a 1:1 mixture of singly transfected cell populations that was allowed to aggregate overnight at room temperature. FIG. 3D: shows Notch$^+$ cells in this aggregate; FIG. 3E shows Delta$^+$ cells; and FIG. 3F is a double exposure showing both cell types. Bands of Notch and Delta are prominent at points of contact between Notch$^+$ and Delta$^+$ cells (arrows). In FIG. 3F, these bands appear yellow because of the coincidence of green and red at these points. The apparently doubly stained single cell (*) is actually two cells (one on top of the other), one expressing Notch and the other Delta.

Figure 3G:
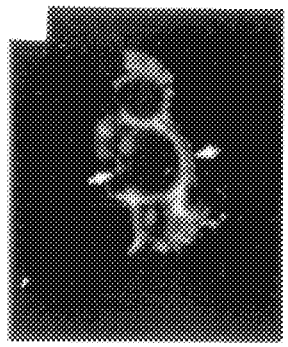
Figure 3H:
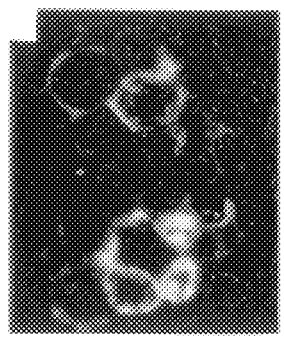

FIGS. 3G–3H: Pseudocolor confocal micrographs of Notch$^+$-Delta$^+$ cell aggregates. Note that in FIG. 3G extensions (arrows) formed by at least two Delta$^+$ cells completely encircle the Notch$^+$ cell in the center of the aggregate. FIG. 3H shows an aggregate formed from a 2 hr aggregation experiment performed at 4° C. Intense bands of Notch are apparent within regions of contact with Delta$^+$ cells.

Figure 3I:
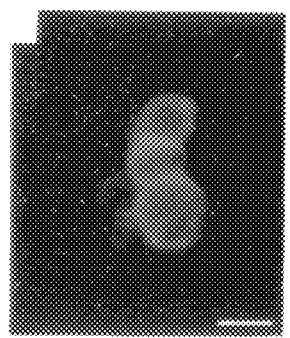

FIG. 3I: An aggregate composed of Delta$^+$ cells and cells that express only the extracellular domain of Notch (ECN1 construct). Scale bar=10 μm.

Figure 4A:
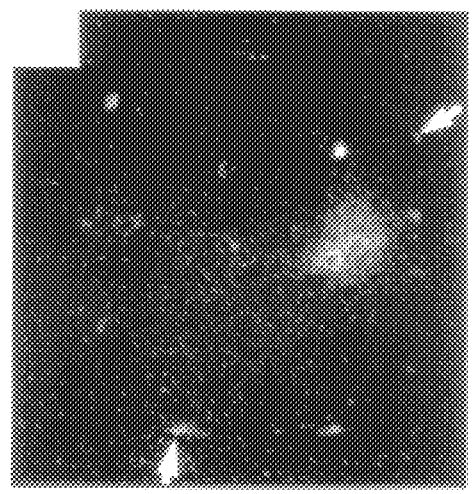
Figure 4B:
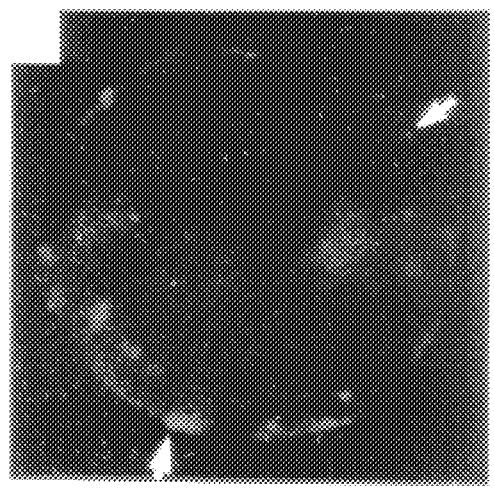
Figure 4C:
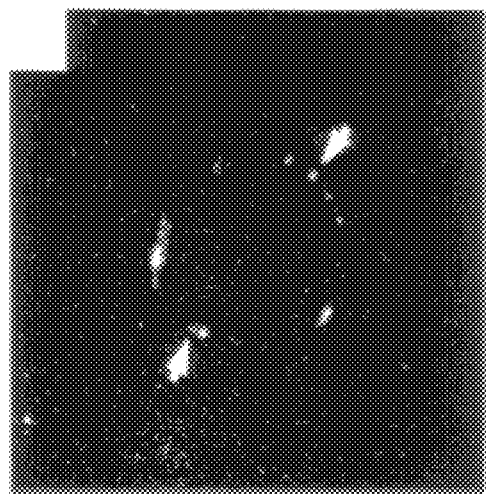
Figure 4D:
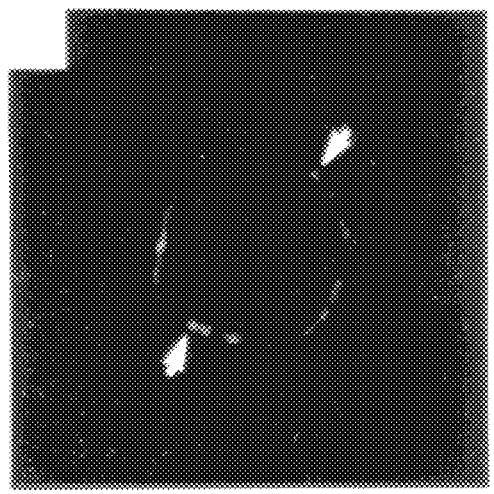
Figure 4E:
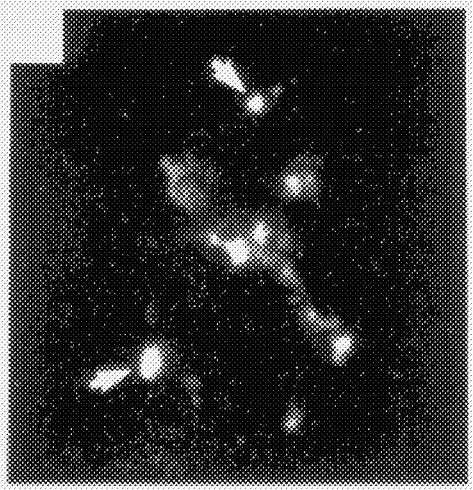
Figure 4F:
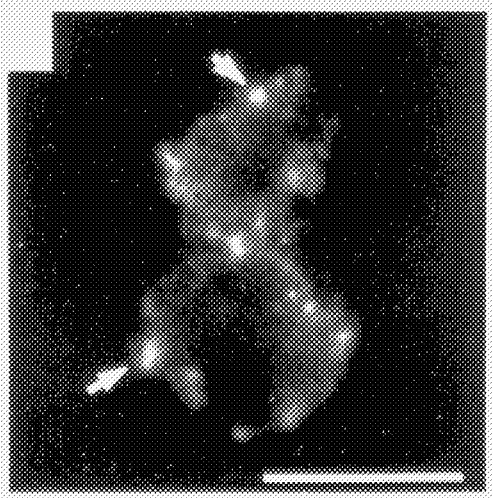

FIGS. 4A–4F. Notch and Delta are Associated in Cotransfected Cells. Staining for Notch is shown in the left column (FIGS. 4A, 4C, and 4E) and that for Delta is shown in the right column (FIGS. 4B, 4D, and 4F).

FIGS. 4A–4B: S2 cell cotransfected with both Notch and Delta constructs. In general, there was a good correlation between Notch and Delta localization at the cell surface (arrows).

FIGS. 4C–4D: Cotransfected cells were exposed to polyclonal anti-Notch antiserum (a 1:250 dilution of each anti-extracellular domain antiserum) for 1 hr at room temperature before fixation and staining with specific antisera. Note punctate staining of Notch and Delta and the correlation of their respective staining (arrows).

FIGS. 4E–4F: Cells cotransfected with the extracellular Notch (ECN1) and Delta constructs, induced, and then patched using anti-Notch polyclonal antisera. There was a close correlation between ECN1 and Delta staining at the surface as observed for full-length Notch. Scale bar=10 μm.

FIGS. 5A–5D. Coimmunoprecipitation Shows that Delta and Notch are Associated in Lysates from Transfected S2 and Drosophila Embryonic Cells. In all experiments, Delta was precipitated from NP-40/deoxycholate lysates using a polyclonal anti-Delta rat antiserum precipitated with fixed Staph A cells, and proteins in the precipitated fraction were visualized on Western blots (for details, see Experimental Procedures). Lanes 1, 2, 3, and 5: Notch visualized with MAb C17.9C6; Lanes 4 and 6: Delta visualized using MAb 201.

FIG. 5A, lanes 1 and 2 are controls for these experiments. Lane 1 shows a polyclonal anti-Delta immunoprecipitation from cells that express Notch alone visualized for Notch. No Notch was detectable in this sample, indicating that the polyclonal anti-Delta does not cross-react with Notch. Lane 2 shows Notch-Delta cotransfected cells immunoprecipitated with Staph A without initial treatment with anti-Delta antiserum and visualized for Notch, demonstrating that Notch is not precipitated nonspecifically by the Staph A or secondary antibody. Lane 3 shows protein precipitated with anti-Delta antiserum visualized for Delta (Dl), and lane 4 shows the same sample visualized for Notch (N). Lane 4 shows that Notch coprecipitates with immunoprecipitated Delta. Note that Notch appears as a doublet as is typical for Notch in immunoprecipitates.

FIG. 5B shows the same experiment using embryonic lysates rather than transfected cell lysates. Lane 5 shows protein precipitated with anti-Delta antiserum visualized for Delta (Dl), and lane 6 shows the same sample visualized for Notch (N). These lanes demonstrate that Notch and Delta are stably associated in embryo lysates. Bands (in all lanes) below the Delta band are from Staph A (SA) and the anti-Delta antiserum heavy (H) and light (L) chains.

Figure 6B:
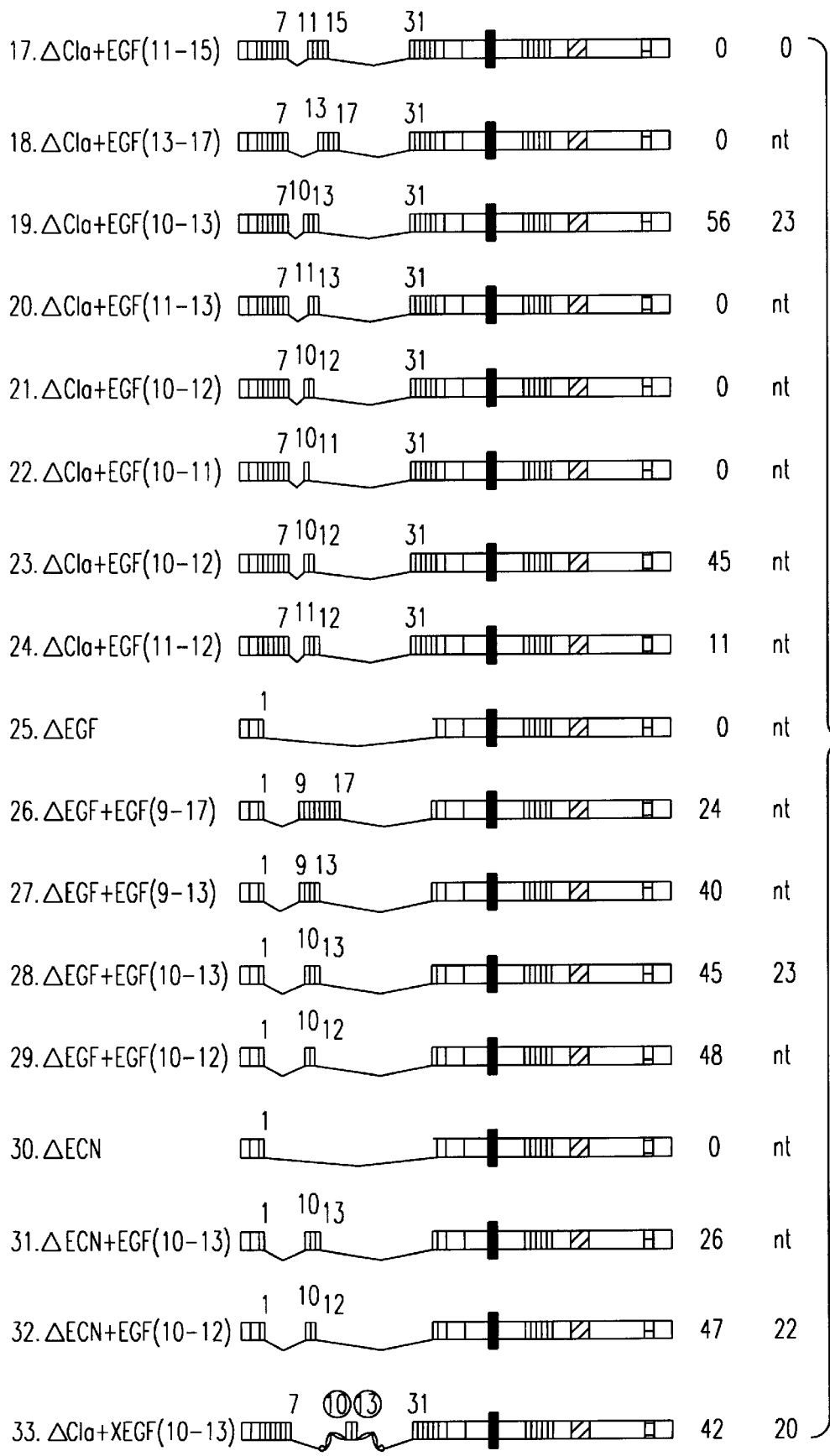

FIGS. 6A–6B. Notch Expression Constructs and the Deletion Mapping of the Delta/Serrate Binding Domain. S2 cells in log phase growth were transiently transfected with the series of expression constructs shown; the drawings represent the predicted protein products of the various Notch deletion mutants created. All expression constructs were derived from construct #1 pMtNMg. Transiently transfected cells were mixed with Delta expressing cells from the stably transformed line L49-6-7 or with transiently transfected Serrate expressing cells, induced with $CuSO_4$, incubated under aggregation conditions and then scored for their ability to aggregate using specific antisera and immunofluorescence microscopy. Aggregates were defined as clusters of four or more cells containing both Notch and Delta/Serrate expressing cells. The values given for % Aggregation refer to the percentage of all Notch expressing cells found in such clusters either with Delta (Dl) (left column) or with Serrate (Ser) (right column). The various Notch deletion constructs are represented diagrammatically with splice lines indicating the ligation junctions. Each EGF repeat is denoted as a stippled rectangular box and numbers of the EGF repeats on either side of a ligation junction are noted. At the ligation junctions, partial EGF repeats produced by the various deletions are denoted by open boxes and closed brackets (for example see #23 ΔCla+EGF(10–12)). Constructs #3–13 represent the ClaI deletion series. As diagrammed, four of the ClaI sites, in repeats 7, 9, 17 and 26, break the repeat in the middle, immediately after the third cysteine (denoted by open box repeats; see FIG. 7 for further clarification), while the fifth and most 3' site breaks neatly between EGF repeats 30 and 31 (denoted by closed box repeat 31; again see FIG. 7). In construct #15 split, EGF repeat 14 which carries the split point mutation, is drawn as a striped box. In construct #33 ΔCla+XEGF(10–13), the Xenopus Notch derived EGF repeats are distinguished from Drosophila repeats by a different pattern of shading. SP, signal peptide; EGF, epidermal growth factor repeat; N, Notch/lin-12 repeat; TM, transmembrane domain; cdc10, cdc10/ankyrin repeats; PA, putative nucleotide binding consensus sequence; opa, polyglutamine stretch termed opa; Dl, Delta; Ser, Serrate.

Figure 7:
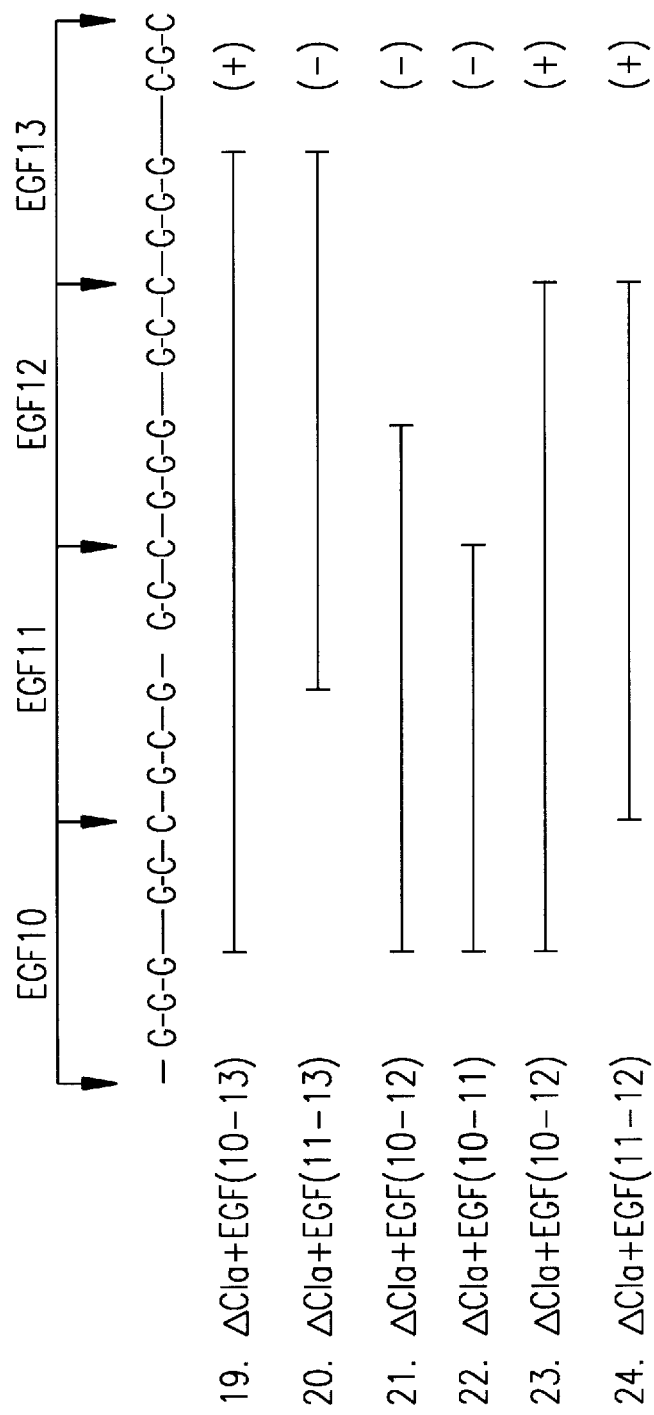

FIG. 7. Detailed Structure of Notch Deletion Constructs #19–24: Both EGF Repeats 11 and 12 are Required for Notch-Delta Aggregation. EGF repeats 10–13 are diagrammed at the top showing the regular spacing of the six cysteine residues (C). PCR products generated for these constructs (names and numbers as given in FIGS. 6A–6B) are represented by the heavy black lines and the exact endpoints are noted relative to the various EGF repeats. Ability to aggregate with Delta is recorded as (+) or (−) for each construct. The PCR fragments either break the EGF repeats in the middle, just after the third cysteine in the same place as four out of the five ClaI sites, or exactly in between two repeats in the same place as the most C-terminal ClaI site.

Figure 8:
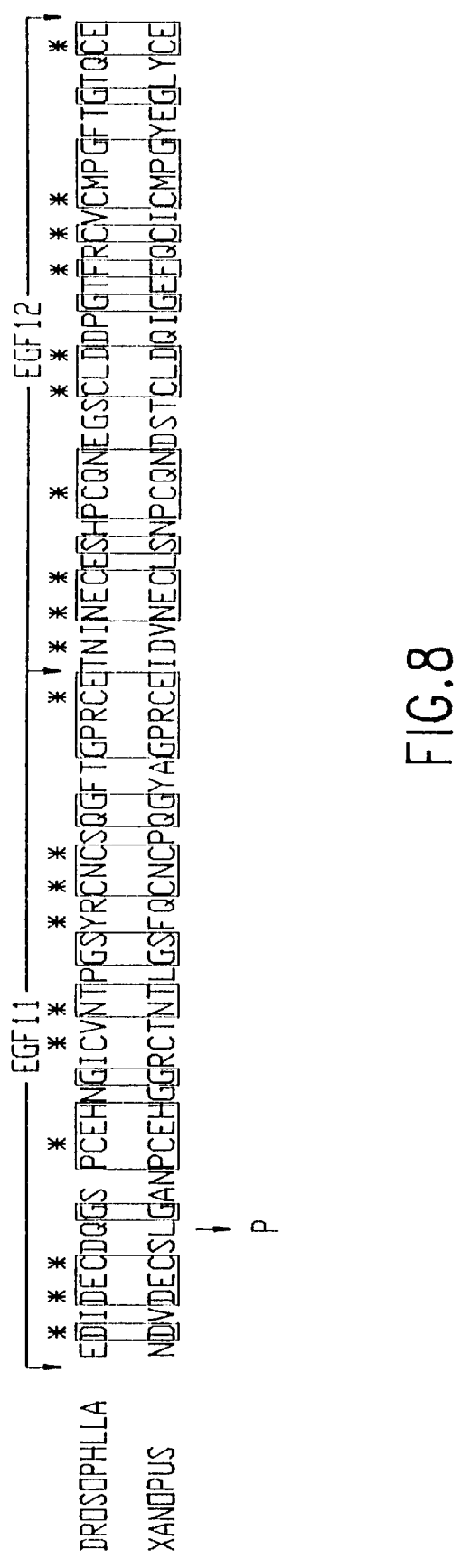

FIG. 8. Comparison of Amino Acid Sequence of EGF Repeats 11 and 12 from Drosophila and Xenopus Notch. The amino acid sequence of EGF repeats 11 and 12 of Drosophila Notch (Wharton et al., 1985, Cell 43:567–581; Kidd et al., 1986, Mol. Cell Biol. 6:3094–3108) is aligned with that of the same two EGF repeats from Xenopus Notch (Coffman et al., 1990, Science 249:1438–1441). Identical amino acids are boxed. The six conserved cysteine residues of each EGF repeat and the $Ca^{++}$ binding consensus residues (Rees et al., 1988, EMBO J. 7:2053–2061) are marked with an asterisk (*). The leucine to proline change found in the Xenopus PCR clone that failed to aggregate is noted underneath.

Figure 9A:
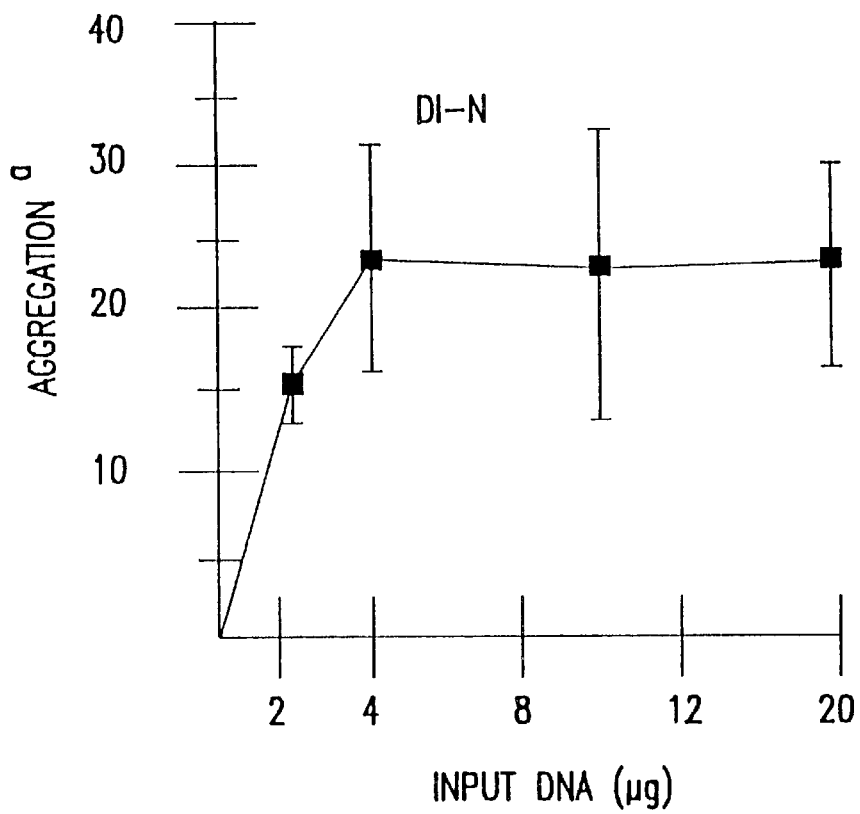
Figure 9B:
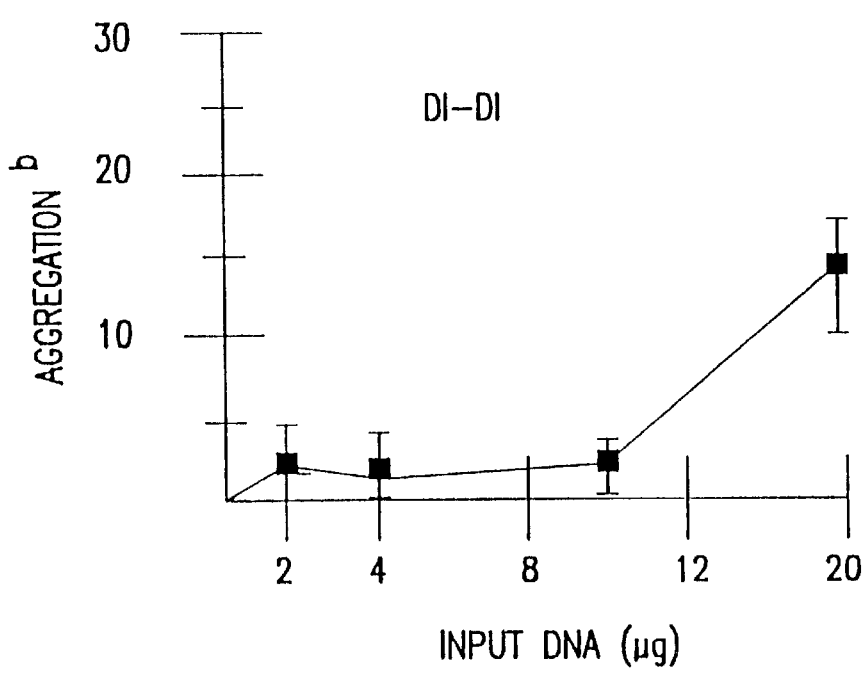
Figure 9C:
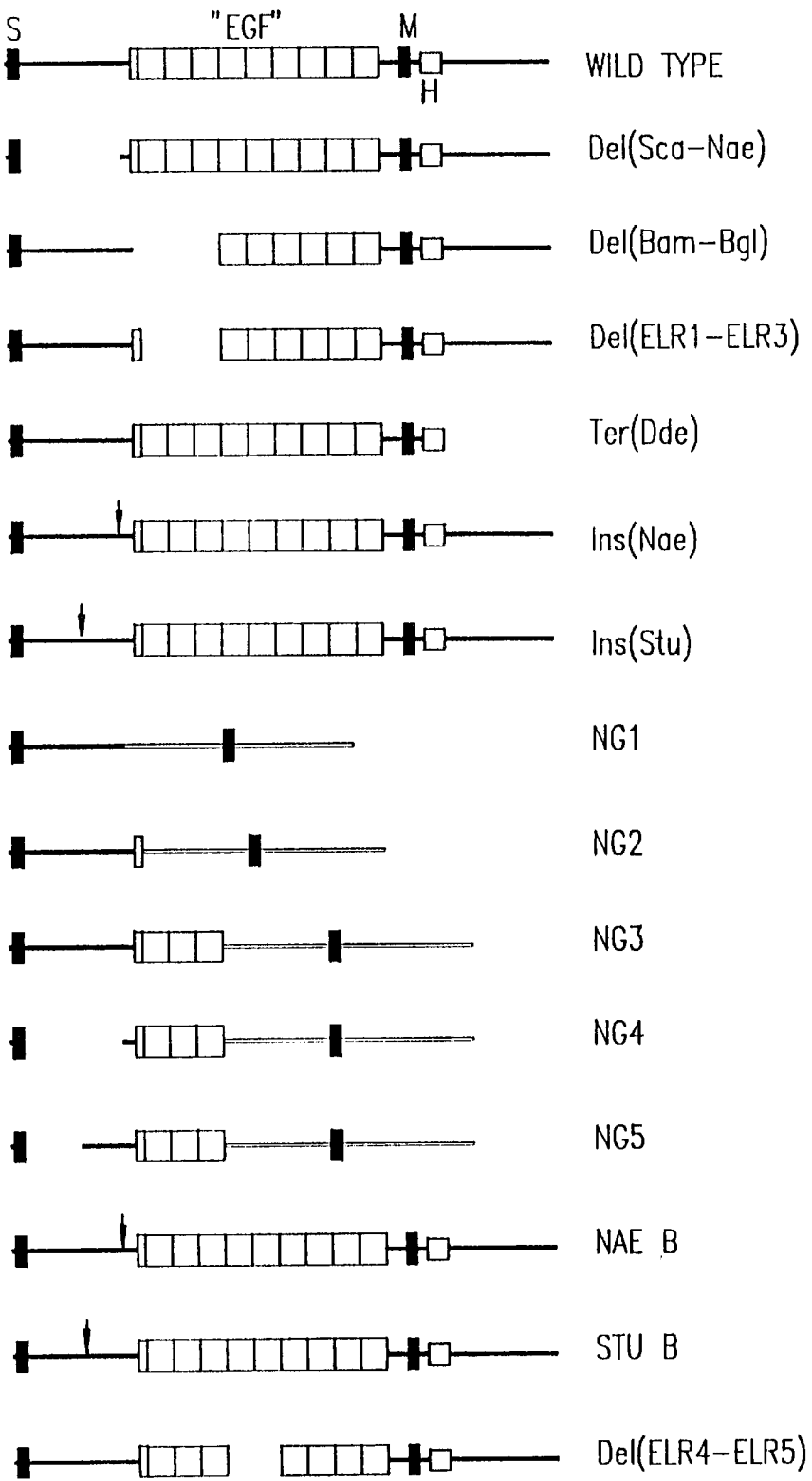

FIGS. 9A–9C. Constructs Employed in this Study. Schematic diagrams of the Delta variants defined in Table IV are shown. Extracellular, amino-proximal terminus is to the left in each case. S, signal peptide; "EGF", EGF-like motifs; M, membrane-spanning helix; H, stop-transfer sequence; solid lines, other Delta sequences; hatched lines, neuroglian sequences. Arrowheads indicate sites of translatable linker insertions. Sca, ScaI; Nae, NaeI; Bam, BamHI; Bgl, BglII; ELR, EGF-like repeat; Bst, BstEII; Dde, DdeI; Stu, StuI; NG1-NG5, Delta-neuroglian chimeras.

FIG. 9A. Dependence of Aggregation on Input DNA Amounts. Heterotypic aggregation observed using S2 cell populations transiently transfected, respectively, with varied amounts of pMTDl1 DNA (2, 4, 10 or 20 μg/plate) that were subsequently incubated under aggregation conditions with S2 cell populations transiently transfected with a constant amount of pMtNMg DNA (20 μg/plate). Data presented are mean fraction (%) of Delta cells in aggregates of four or more cells±standard error for each input DNA amount (N=3 replicates, except 2 μg and 10 μg inputs for which N=2). A minimum of 100 Delta-expressing cells were counted for each replicate. FIG. 9B, Homotypic aggregation observed using S2 cell populations transiently transfected, respectively, with varied amounts of pMTDl1 DNA (2, 4, 10 or 20 μg/plate) that were subsequently incubated under aggregation conditions. Data presented are mean fraction (%) of Delta cells in aggregates of four or more cells±standard error for each input DNA amount (N=3 replicates). A minimum of 500 Delta-expressing cells were counted for each replicate.

FIG. 10. Delta-Serrate Amino-Terminal Sequence Alignment. Residues are numbered on the basis of conceptual translation of Delta (Dl, upper sequence (SEQ ID NO:3); beginning at amino acid 24, ending at amino acid 226) and Serrate (Ser, lower sequence (SEQ ID NO:4); beginning at amino acid 85, ending at amino acid 283) coding sequences. Vertical lines between the two sequences indicates residues that are identical within the Delta and Serrate sequences, as aligned. Dots represent gaps in the alignment. Boxes enclose cysteine residues within the aligned regions. N1, amino-proximal domain 1; N2, amino-proximal domain 2; N3, amino-proximal domain 3. Translatable insertions associated with STU B [replacement of Delta amino acid 132 (A) with GKIFP] and NAE B [insertion of RKIF between Delta amino acid 197 and amino acid 198] constructs, respectively, are depicted above the wild type Delta sequence.

Figure 11A:
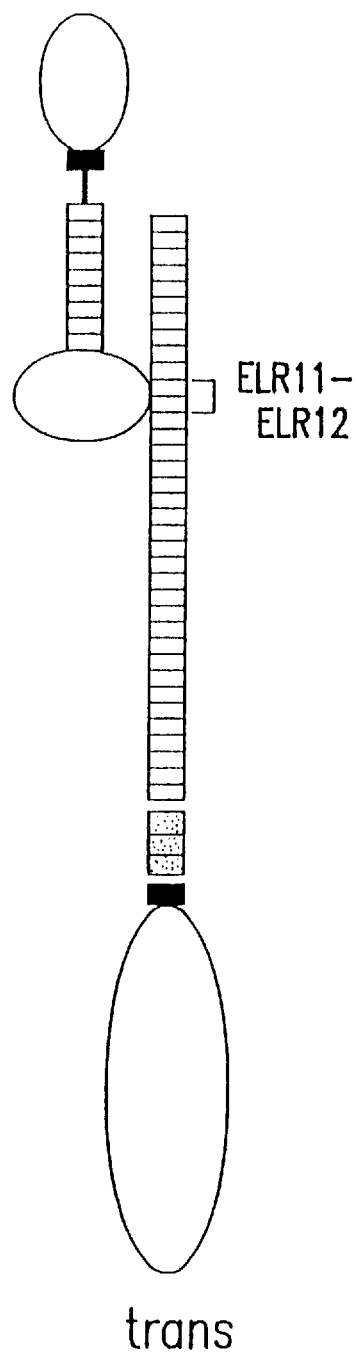
Figure 11B:
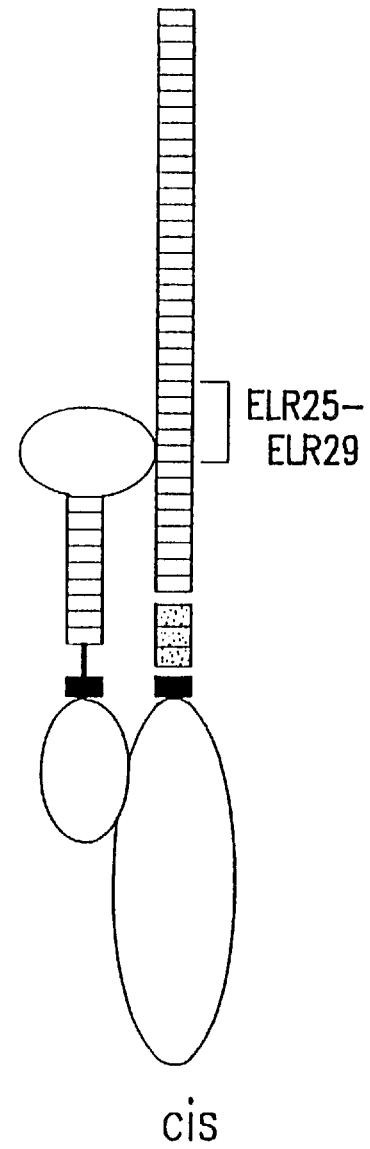

FIGS. 11A–11B. Potential Geometries of Delta-Notch Interactions. FIG. 11A, Potential register of Delta (left) and Notch (right) molecules interacting between opposing plasma membranes. FIG. 11B, Potential register of Delta (left) and Notch (right) molecules interacting within the same plasma membranes. ELR, EGF-like repeat; open boxes, EGF-like repeats; dotted boxes, LNR repeats; solid boxes, membrane-spanning helices. Delta amino-terminal domain and Delta and Notch intracellular domains represented by ovals.

FIGS. 12A–12C. Potential Geometries of Delta—Delta Interactions. FIGS. 12A–12B, Potential register of Delta molecules interacting between opposing plasma membranes. FIG. 12C, Potential register of Delta molecules interacting within the same plasma membranes. Open boxes, EGF-like repeats; solid boxes, membrane-spanning helices. Delta amino-terminal extracellular and intracellular domains represented by ovals.

FIGS. 13A–13F. Primary Nucleotide Sequence of the Delta cDNA Dl1 (SEQ ID NO:5) and Delta amino acid sequence (SEQ ID NO:6) The DNA sequence of the 5'–3' strand of the Dl1 cDNA is shown, which contains a number of corrections in comparison to that presented in Kopczynksi et al. (1988, Genes Dev. 2, 1723–1735).

FIG. 14. Primary Nucleotide Sequence of the Neuroglian cDNA 1B7A-250 (SEQ ID NO:7). This is the DNA sequence of a portion of the 5'–3' strand of the 1B7A-250 cDNA (A. J. Bieber, pers. comm.; Hortsch et al., 1990, Neuron 4, 697–709). Nucleotide 2890 corresponds to the first nucleotide of an isoleucine codon that encodes amino acid 952 of the conceptually translated neuroglian-long form protein.

FIGS. 15A–15B. Nucleic Acid Sequence Homologies Between Serrate and Delta. A portion of the Drosophila Serrate nucleotide sequence (SEQ ID NO:8), with the encoded Serrate protein sequence (SEQ ID NO:9) written below, (Fleming et al., 1990, Genes & Dev. 4, 2188–2201 at 2193-94) is shown. The four regions showing high sequence homology with the Drosophila Delta sequence are numbered above the line and indicated by brackets. The total region of homology spans nucleotide numbers 627 through 1290 of the Serrate nucleotide sequence (numbering as in FIG. 4 of Fleming et al., 1990, Genes & Dev. 4, 2188–2201).

FIGS. 16A–16C. Primers used for PCR in the Cloning of Human Notch. The sequence of three primers used for PCR to amplify DNA in a human fetal brain cDNA library are shown. The three primers, cdc1 (SEQ ID NO:10), cdc2 (SEQ ID NO:11), and cdc3 (SEQ ID NO:12), were designed to amplify either a 200 bp or a 400 bp fragment as primer pairs cdc1/cdc2 or cdc1/cdc3, respectively. I: inosine.

Figure 17:
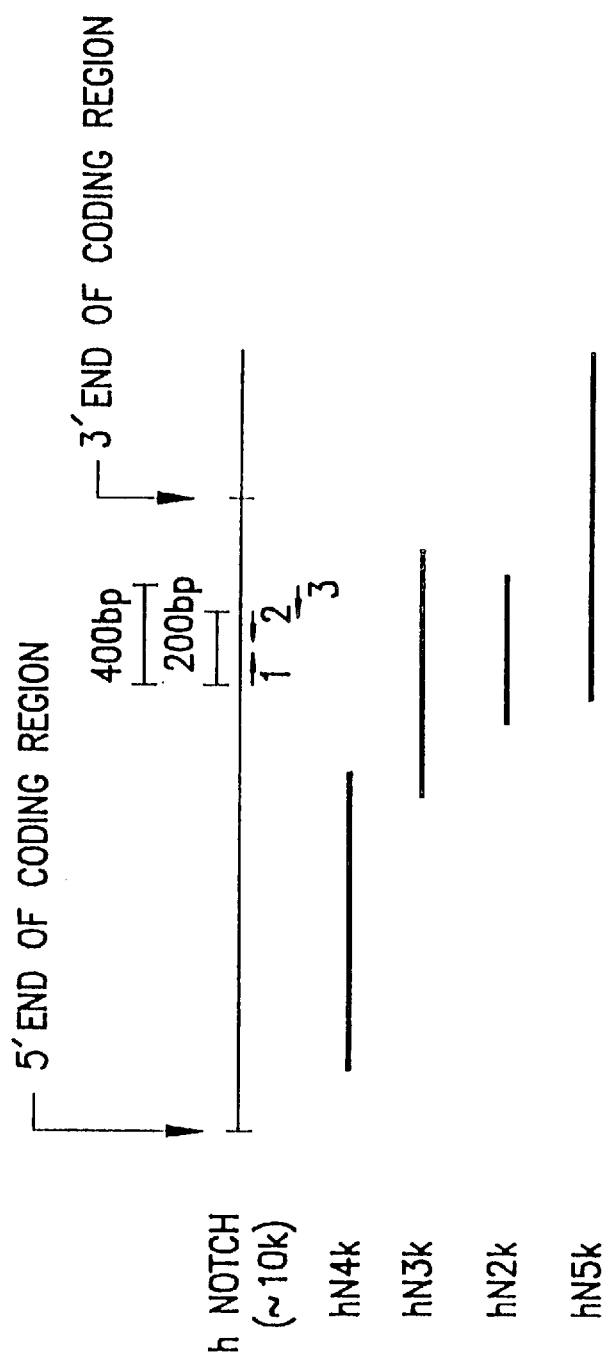

FIG. 17. Schematic Diagram of Human Notch Clones. A schematic diagram of human Notch is shown. Heavy bold-face lines below the diagram show that portion of the Notch sequence contained in each of the four cDNA clones. The location of the primers used in PCR, and their orientation, are indicated by arrows.

FIG. 18. Human Notch Sequences Aligned with Drosophila Notch Sequence. Numbered vertical lines correspond to Drosophila Notch coordinates. Horizontal lines below each map show where clones lie relative to stretches of sequence (thick horizontal lines).

FIGS. 19A–19C. Nucleotide Sequences of Human Notch Contained in Plasmid cDNA Clone hN2k. FIG. 19A: The DNA sequence (SEQ ID NO:13) of a portion of the human Notch insert is shown, starting at the EcoRI site at the 3' end, and proceeding in the 3' to 5' direction. FIG. 19B: The DNA sequence (SEQ ID NO:14) of a portion of the human Notch insert is shown, starting at the EcoRI site at the 5' end, and proceeding in the 5' to 3' direction. FIG. 19C: The DNA sequence (SEQ ID NO:15) of a portion of the human Notch insert is shown, starting 3' of the sequence shown in FIG. 19B, and proceeding in the 5' to 3' direction. The sequences shown are tentative, subject to confirmation by determination of overlapping sequences.

FIGS. 20A–20D. Nucleotide Sequences of Human Notch Contained in Plasmid cDNA clone hN3k. FIG. 20A: The DNA sequence (SEQ ID NO:16) of a portion of the human Notch insert is shown, starting at the EcoRI site at the 3' end, and proceeding in the 3' to 5' direction. FIG. 20B: The DNA sequence (SEQ ID NO:17) of a portion of the human Notch insert is shown, starting at the EcoRI site at the 5' end, and proceeding in the 5' to 3' direction. FIG. 20C: The DNA sequence (SEQ ID NO:18) of a portion of the human Notch insert is shown, starting 3' of the sequence shown in FIG. 20B, and proceeding in the 5' to 3' direction. FIG. 20D: The DNA sequence (SEQ ID NO:19) of a portion of the human Notch insert is shown, starting 5' of the sequence shown in FIG. 20A, and proceeding in the 3' to 5' direction. The sequences shown are tentative, subject to confirmation by determination of overlapping sequences.

FIGS. 21A–21B. Nucleotide Sequences of Human Notch Contained in Plasmid cDNA clone hN4k. FIG. 21A: The DNA sequence (SEQ ID NO:20) of a portion of the human Notch insert is shown, starting at the EcoRI site at the 5' end, and proceeding in the 5' to 3' direction. FIG. 21B: The DNA sequence (SEQ ID NO:21) of a portion of the human Notch insert is shown, starting near the 3' end, and proceeding in the 3' to 5' direction. The sequences shown are tentative, subject to confirmation by determination of overlapping sequences.

FIGS. 22A–22D. Nucleotide Sequences of Human Notch Contained in Plasmid cDNA Clone hN5k. FIG. 22A: The DNA sequence (SEQ ID NO:22) of a portion of the human Notch insert is shown, starting at the EcoRI site at the 5' end, and proceeding in the 5' to 3' direction. FIG. 22B: The DNA sequence (SEQ ID NO:23) of a portion of the human Notch insert is shown, starting near the 3' end, and proceeding in the 3' to 5' direction. FIG. 22C: The DNA sequence (SEQ ID NO:24) of a portion of the human Notch insert is shown, starting 3' of the sequence shown in FIG. 22A, and proceeding in the 5' to 3' direction. FIG. 22D: The DNA sequence (SEQ ID NO:25) of a portion of the human Notch insert is shown, starting 5' of the sequence shown in FIG. 22B, and proceeding in the 3' to 5' direction. The sequences shown are tentative, subject to confirmation by determination of overlapping sequences.

FIGS. 23A–23Q. DNA (SEQ ID NO:31) and Amino Acid (SEQ ID NO:34) Sequences of Human Notch Contained in Plasmid cDNA Clone hN3k.

FIGS. 24A–24G. DNA (SEQ ID NO:33) and Amino Acid (SEQ ID NO:34) Sequences of Human Notch Contained in Plasmid cDNA Clone hN5k.

Figure 25A:
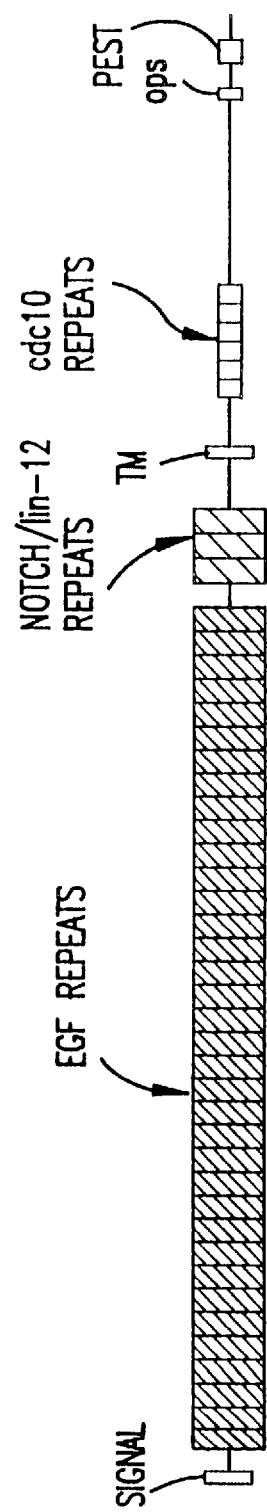
Figure 25B:
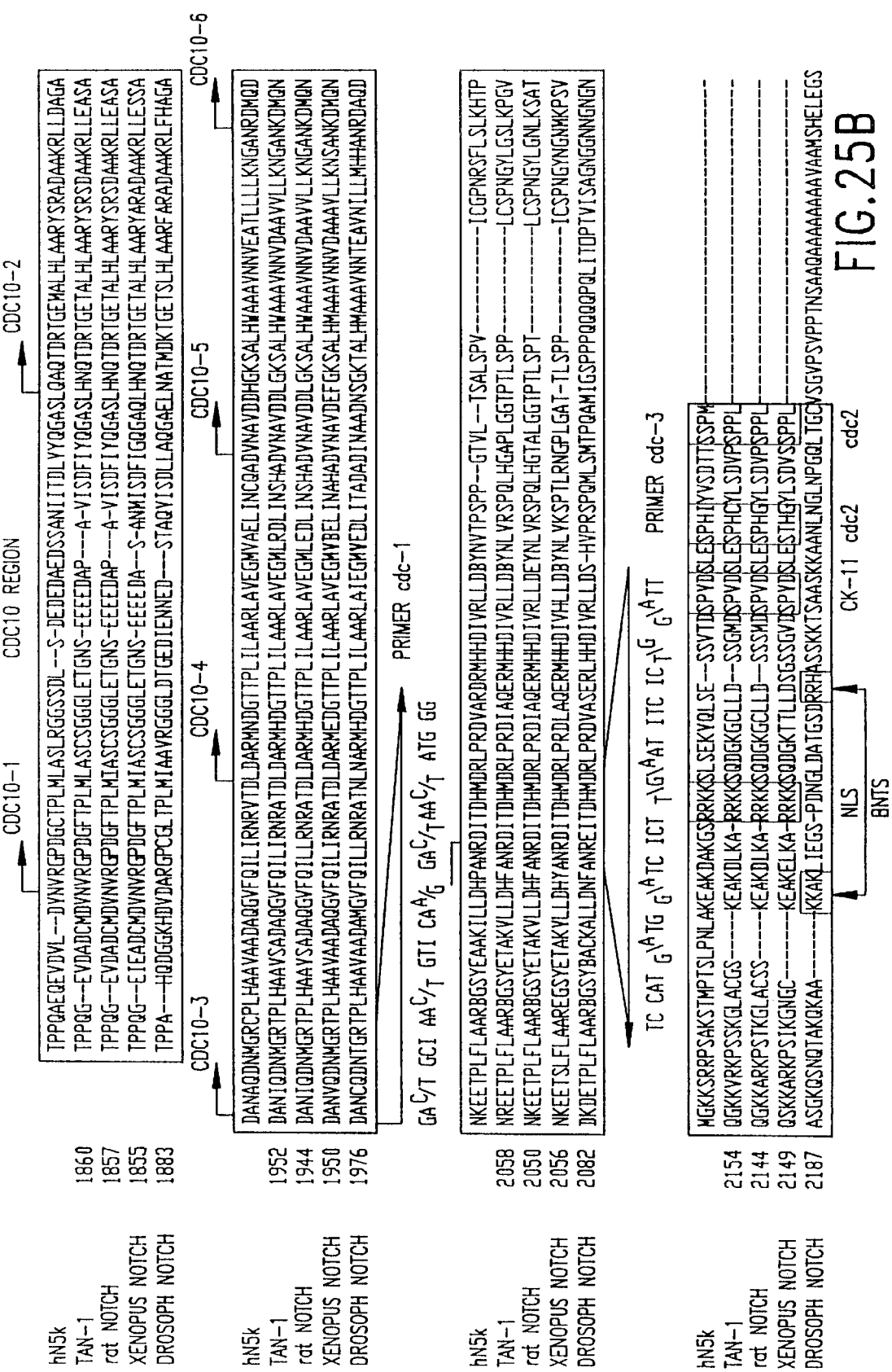

FIGS. 25A–25C. Comparison of hN5k With Other Notch Homologs. FIG. 25A. Schematic representation of Drosophila Notch. Indicated are the signal sequence (signal), the 36 EGF-like repeats, the three Notch/lin-12 repeats, the transmembrane domain (TM), the six CDC10 repeats, the OPA repeat, and the PEST (proline, glutamic acid, serine, threonine)-rich region. FIGS. 25B–25C. Alignment of the deduced amino acid sequence of hN5k with sequences of other Notch homologs. Amino acids are numbered on the left side. The cdc10 and PEST-rich regions are both boxed, and individual cdc10 repeats are marked. Amino acids which are identical in three or more sequences are highlighted. The primers used to clone hN5k are indicated below the sequences from which they were designed. The nuclear localization sequence (NLS), casein kinase II (CKII), and cdc2 kinase (cdc2) sites of the putative CcN motif of the vertebrate Notch homologs are boxed. The possible bipartite nuclear targeting sequence (BNTS) and proximal phosphorylation sites of Drosophila Notch are also boxed.

5. DETAILED DESCRIPTION OF THE INVENTION

The present invention relates to nucleotide sequences of the human Notch and Delta genes, and amino acid sequences of their encoded proteins. The invention further relates to fragments (termed herein "adhesive fragments") of the proteins encoded by toporythmic genes which mediate homotypic or heterotypic binding to toporythmic proteins or adhesive fragments thereof. Toporythmic genes, as used herein, shall mean the genes Notch, Delta, and Serrate, as well as other members of the Delta/Serrate family which may be identified, e.g. by the methods described in Section 5.3, infra.

The nucleic acid and amino acid sequences and antibodies thereto of the invention can be used for the detection and quantitation of mRNA for human Notch and Delta and adhesive molecules, to study expression thereof, to produce human Notch and Delta and adhesive sequences, in the study and manipulation of differentiation processes.

For clarity of disclosure, and not by way of limitation, the detailed description of the invention will be divided into the following sub-sections:

(i) Identification of and the sequences of toporythmic protein domains that mediate binding to toporythmic protein domains;
(ii) The cloning and sequencing of human Notch and Delta;
(iii) Identification of additional members of the Delta/Serrate family;
(iv) The expression of toporythmic genes;
(v) Identification and purification of the expressed gene product; and
(vi) Generation of antibodies to toporythmic proteins and adhesive sequences thereof.

5.1. IDENTIFICATION OF AND THE SEQUENCES OF TOPORYTHMIC PROTEIN DOMAINS THAT MEDIATE BINDING TO TOPORYTHMIC PROTEIN DOMAINS

The invention provides for toporythmic protein fragments, and analogs or derivatives thereof, which mediate homotypic or heterotypic binding (and thus are termed herein "adhesive"), and nucleic acid sequences relating to the foregoing.

In a specific embodiment, the adhesive fragment of Notch is that comprising the portion of Notch most homologous to ELR 11 and 12, i.e., amino acid numbers 447 through 527 (SEQ ID NO:1) of the Drosophila Notch sequence (see FIG. 8). In another specific embodiment, the adhesive fragment of Delta mediating homotypic binding is that comprising the portion of Delta most homologous to about amino acid numbers 32–230 of the Drosophila Delta sequence (SEQ ID NO:6). In yet another specific embodiment, the adhesive fragment of Delta mediating binding to Notch is that comprising the portion of Delta most homologous to about amino acid numbers 1–230 of the Drosophila Delta sequence (SEQ ID NO:6). In a specific embodiment relating to an adhesive fragment of Serrate, such fragment is that comprising the portion of Serrate most homologous to about amino acid numbers 85–283 or 79–282 of the Drosophila Serrate sequence (see FIG. 10 (SEQ ID NO:4), and FIGS. 15A–15B (SEQ ID NO:9)).

The nucleic acid sequences encoding toporythmic adhesive domains can be isolated from porcine, bovine, feline, avian, equine, or canine, as well as primate sources and any other species in which homologs of known toporythmic genes [including but not limited to the following genes (with the publication of sequences in parentheses): Notch (Wharton et al., 1985, Cell 43, 567–581), Delta (Vassin et al., 1987, EMBO J. 6, 3431–3440; Kopczynski et al., 1988, Genes Dev. 2, 1723–1735; note corrections to the Kopczynski et al. sequence found in FIGS. 13A–13F hereof (SEQ ID NO:5 and SEQ ID NO:6)) and Serrate (Fleming et al., 1990, Genes & Dev. 4, 2188–2201)] can be identified. Such sequences can be altered by substitutions, additions or deletions that provide for functionally equivalent (adhesive) molecules. Due to the degeneracy of nucleotide coding sequences, other DNA sequences which encode substantially the same amino acid sequence as the adhesive sequences may be used in the practice of the present invention. These include but are not limited to nucleotide sequences comprising all or portions of the Notch, Delta, or Serrate genes which are altered by the substitution of different codons that encode a functionally equivalent amino acid residue within the sequence, thus producing a silent change. Likewise, the adhesive protein fragments or derivatives thereof, of the invention include, but are not limited to, those containing, as a primary amino acid sequence, all or part of the amino acid sequence of the adhesive domains including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Adhesive fragments of toporythmic proteins and potential derivatives, analogs or peptides related to adhesive toporythmic protein sequences, can be tested for the desired binding activity e.g., by the in vitro aggregation assays described in the examples herein. Adhesive derivatives or adhesive analogs of adhesive fragments of toporythmic proteins include but are not limited to those peptides which are substantially homologous to the adhesive fragments, or whose encoding nucleic acid is capable of hybridizing to the nucleic acid sequence encoding the adhesive fragments, and which peptides and peptide analogs have positive binding activity e.g., as tested in vitro by an aggregation assay such as described in the examples sections infra. Such derivatives and analogs are envisioned and within the scope of the present invention.

The adhesive-protein related derivatives, analogs, and peptides of the invention can be produced by various methods known in the art. The manipulations which result in their production can occur at the gene or protein level. For example, the cloned adhesive protein-encoding gene sequence can be modified by any of numerous strategies known in the art (Maniatis, T., 1990, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of the gene encoding a derivative, analog, or peptide related to an adhesive domain, care should be taken to ensure that the modified gene remains within the same translational reading frame as the adhesive protein, uninterrupted by translational stop signals, in the gene region where the desired adhesive activity is encoded.

Additionally, the adhesive-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem 253, 6551), use of TAB® linkers (Pharmacia), etc.

Manipulations of the adhesive sequence may also be made at the protein level. Included within the scope of the invention are toporythmic protein fragments, analogs or derivatives which are differentially modified during or after translation, e.g., by glycosylation, acetylation, phosphorylation, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, NaBH$_4$; acetylation, formylation, oxidation, reduction; metabolic synthesis in the presence of tunicamycin; etc.

In addition, analogs and peptides related to adhesive fragments can be chemically synthesized. For example, a peptide corresponding to a portion of a toporythmic protein which mediates the desired aggregation activity in vitro can be synthesized by use of a peptide synthesizer.

Another specific embodiment of the invention relates to fragments or derivatives of a Delta protein which have the ability to bind to a second Delta protein or fragment or derivative thereof, but do not bind to Notch. Such binding or lack thereof can be assayed in vitro as described in Section 8. By way of example, but not limitation, such a Delta derivative is that containing an insertion of the tetrapeptide Arg-Lys-Ile-Phe (SEQ ID NO:30) between Delta residues 198 and 199 of the Drosophila protein.

5.2. THE CLONING AND SEQUENCING OF HUMAN NOTCH AND DELTA

The invention further relates to the amino acid sequences of human Notch and human Delta and fragments and derivatives thereof which comprise an antigenic determinant (i.e., can be recognized by an antibody) or which are functionally active, as well as nucleic acid sequences encoding the foregoing. "Functionally active" material as used herein refers to that material displaying one or more known functional activities associated with the full-length (wild-type) protein product, e.g., in the case of Notch, binding to Delta, binding to Serrate, antigenicity (binding to an anti-Notch antibody), etc.

In specific embodiments, the invention provides fragments of a human Notch protein consisting of at least 40 amino acids, or of at least 77 amino acids. In other embodiments, the proteins of the invention comprise or consist essentially of the intracellular domain, transmembrane region, extracellular domain, cdc10 region, Notch/lin-12 repeats, or the EGF-homologous repeats, or any combination of the foregoing, of a human Notch protein. Fragments, or proteins comprising fragments, lacking some or all of the EGF-homologous repeats of human Notch are also provided.

In other specific embodiments, the invention is further directed to the nucleotide sequences and subsequences of human Notch and human Delta consisting of at least 25 nucleotides, at least 50 nucleotides, or at least 121 nucleotides. Nucleic acids encoding the proteins and protein fragments described above are also provided, as well as nucleic acids complementary to and capable of hybridizing to such nucleic acids. In one embodiment, such a complementary sequence may be complementary to a human Notch cDNA sequence of at least 25 nucleotides, or of at least 121 nucleotides. In a preferred aspect, the invention relates to cDNA sequences encoding human Notch or a portion thereof. In a specific embodiment, the invention relates to the nucleotide sequence of the human Notch gene or cDNA, in particular, comprising those sequences depicted in FIGS. 19A–19C, 20A–20D, 21A–21B and/or 22A–22D (SEQ ID NO:13 through NO:25), or contained in plasmids hN3k, hN4k, or hN5k (see Section 9, infra), and the encoded Notch protein sequences. As is readily apparent, as used herein, a "nucleic acid encoding a fragment or portion of a Notch protein" shall be construed as referring to a nucleic acid encoding only the recited fragment or portion of the Notch protein and not other portions of the Notch protein.

In a preferred, but not limiting, aspect of the invention, a human Notch DNA sequence can be cloned and sequenced by the method described in Section 9, infra.

A preferred embodiment for the cloning of human Delta, presented as a particular example but not by way of limitation follows:

A human expression library is constructed by methods known in the art. For example, human mRNA is isolated, cDNA is made and ligated into an expression vector (e.g., a bacteriophage derivative) such that it is capable of being expressed by the host cell into which it is then introduced. Various screening assays can then be used to select for the expressed human Delta product. In one embodiment, selection can be carried out on the basis of positive binding to the adhesive domain of human Notch, (i.e., that portion of human Notch most homologous to Drosophila ELR 11 and 12 (SEQ ID NO:1)). In an alternative embodiment, anti-Delta antibodies can be used for selection.

In another preferred aspect, PCR is used to amplify the desired sequence in the library, prior to selection. For example, oligonucleotide primers representing part of the adhesive domains encoded by a homologue of the desired gene can be used as primers in PCR.

The above-methods are not meant to limit the following general description of methods by which clones of human Notch and Delta may be obtained.

Any human cell can potentially serve as the nucleic acid source for the molecular cloning of the Notch and Delta gene. The DNA may be obtained by standard procedures known in the art from cloned DNA (e.g., a DNA "library"), by chemical synthesis, by cDNA cloning, or by the cloning of genomic DNA, or fragments thereof, purified from the desired human cell. (See, for example Maniatis et al., 1982, Molecular Cloning, A Laboratory Manual, Cold Spring Harbor Laboratory, Cold Spring Harbor, N.Y.; Glover, D. M. (ed.), 1985, DNA Cloning: A Practical Approach, MRL Press, Ltd., Oxford, U.K. Vol. I, II.) Clones derived from genomic DNA may contain regulatory and intron DNA regions in addition to coding regions; clones derived from cDNA will contain only exon sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, if an amount of a portion of a Notch or Delta (of any species) gene or its specific RNA, or a fragment thereof e.g., the adhesive domain, is available and can be purified and labeled, the generated DNA fragments may be screened by nucleic acid hybridization to the labeled probe (Benton, W. and Davis, R., 1977, Science 196, 180; Grunstein, M. And Hogness, D., 1975, Proc. Natl. Acad. Sci. U.S.A. 72, 3961). Those DNA fragments with substantial homology to the probe will hybridize. It is also possible to identify the appropriate fragment by restriction enzyme digestion(s) and comparison of fragment sizes with those expected according to a known restriction map if such is available. Further selection can be carried out on the basis of the properties of the gene. Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, in vitro aggregation activity ("adhesiveness") or antigenic properties as known for Notch or Delta. If an antibody to Notch or Delta is available, the Notch or Delta protein may be identified by binding of labeled antibody to the putatively Notch or Delta synthesizing clones, in an ELISA (enzyme-linked immunosorbent assay)-type procedure.

The Notch or Delta gene can also be identified by mRNA selection by nucleic acid hybridization followed by in vitro translation. In this procedure, fragments are used to isolate complementary mRNAs by hybridization. Such DNA fragments may represent available, purified Notch or Delta DNA of another species (e.g., Drosophila). Immunoprecipitation analysis or functional assays (e.g., aggregation ability in vitro; see examples infra) of the in vitro translation products of the isolated products of the isolated mRNAs identifies the mRNA and, therefore, the complementary DNA fragments that contain the desired sequences. In addition, specific mRNAs may be selected by adsorption of polysomes isolated from cells to immobilized antibodies specifically directed against Notch or Delta protein. A radiolabelled Notch or Delta cDNA can be synthesized using the selected mRNA (from the adsorbed polysomes) as a template. The radiolabelled mRNA or cDNA may then be used as a probe to identify the Notch or Delta DNA fragments from among other genomic DNA fragments.

Alternatives to isolating the Notch or Delta genomic DNA include, but are not limited to, chemically synthesizing the gene sequence itself from a known sequence or making cDNA to the mRNA which encodes the Notch or Delta gene. For example, RNA for cDNA cloning of the Notch or Delta gene can be isolated from cells which express Notch or Delta. Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid derivatives. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and Notch or Delta gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionization, can be done before insertion into the cloning vector.

In specific embodiments, transformation of host cells with recombinant DNA molecules that incorporate the isolated Notch or Delta gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The human Notch and Delta sequences provided by the instant invention include those nucleotide sequences encoding substantially the same amino acid sequences as found in human Notch and in human Delta, and those encoded amino acid sequences with functionally equivalent amino acids, all as described supra in Section 5.1 for adhesive portions of toporythmic proteins.

5.3. IDENTIFICATION OF ADDITIONAL MEMBERS OF THE DELTA/SERRATE FAMILY

A rational search for additional members of the Delta/Serrate gene family may be carried out using an approach that takes advantage of the existence of the conserved segments of strong homology between Serrate and Delta (see FIG. 10, SEQ ID NO:3 and NO:4). For example, additional members of this gene family may be identified by selecting, from among a diversity of nucleic acid sequences, those sequences that are homologous to both Serrate and Delta (see FIGS. 13A–13F (SEQ ID NO:5), and FIGS. 15A–15B (SEQ ID NO:8)), and further identifying, from among the selected sequences, those that also contain nucleic acid sequences which are non-homologous to Serrate and Delta. The term "non-homologous" may be construed to mean a region which contains at least about 6 contiguous nucleotides in which at least about two nucleotides differ from Serrate and Delta sequence.

For example, a preferred specific embodiment of the invention provides the following method. Corresponding to two conserved segments between Delta and Serrate, Delta AA 63–73 and Delta AA 195–206 (see FIGS. 13A–13F, SEQ ID NO:6), sets of degenerate oligonucleotide probes of about 10–20 nucleotides may be synthesized, representing all of the possible coding sequences for the amino acids found in either Delta and Serrate for about three to seven contiguous codons. In another embodiment, oligonucleotides may be obtained corresponding to parts of the four highly conserved regions between Delta and Serrate shown in FIGS. 15A–15B (SEQ ID NO:8 and NO:9), i.e., that represented by Serrate AA 124–134, 149–158, 214–219, and 250–259. The synthetic oligonucleotides may be utilized as primers to amplify by PCR sequences from a source (RNA or DNA) of potential interest. (PCR can be carried out, e.g., by use of a Perkin-Elmer Cetus thermal cycler and Taq polymerase (Gene Amp™)). This might include mRNA or cDNA or genomic DNA from any eukaryotic species that could express a polypeptide closely related to Serrate and Delta. By carrying out the PCR reactions, it may be possible to detect a gene or gene product sharing the above-noted segments of conserved sequence between Serrate and Delta. If one chooses to synthesize several different degenerate primers, it may still be possible to carry out a complete search with a reasonably small number of PCR reactions. It is also possible to vary the stringency of hybridization conditions used in priming the PCR reactions, to allow for greater or lesser degrees of nucleotide sequence similarity between the unknown gene and Serrate or Delta. If a segment of a previously unknown member of the Serrate/Delta gene family is amplified successfully, that segment may be molecularly cloned and sequenced, and utilized as a probe to isolate a complete cDNA or genomic clone. This, in turn, will permit the determination of the unknown gene's complete nucleotide sequence, the analysis of its expression, and the production of its protein product for functional analysis. In this fashion, additional genes encoding "adhesive" proteins may be identified.

In addition, the present invention provides for the use of the Serrate/Delta sequence homologies in the design of novel recombinant molecules which are members of the Serrate/Delta gene family but which may not occur in nature. For example, and not by way of limitation, a recombinant molecule can be constructed according to the invention, comprising portions of both Serrate and Delta genes. Such a molecule could exhibit properties associated with both Serrate and Delta and portray a novel profile of biological activities, including agonists as well as antagonists. The primary sequence of Serrate and Delta may also be used to predict tertiary structure of the molecules using computer simulation (Hopp and Woods, 1981, Proc. Natl. Acad. Sci. U.S.A. 78, 3824–3828); Serrate/Delta chimeric recombinant genes could be designed in light of correlations between tertiary structure and biological function. Likewise, chimeric genes comprising portions of any one or more members of the toporythmic gene family (e.g., Notch) may be constructed.

5.4. THE EXPRESSION OF TOPORYTHMIC GENES

The nucleotide sequence coding for an adhesive fragment of a toporythmic protein (preferably, Notch, Serrate, or Delta), or an adhesive analog or derivative thereof, or human Notch or Delta or a functionally active fragment or derivative thereof, can be inserted into an appropriate expression vector, i.e., a vector which contains the necessary elements for the transcription and translation of the inserted protein-coding sequence. The necessary transcriptional and translational signals can also be supplied by the native toporythmic gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. In a specific embodiment, the adhesive portion of the Notch gene, e.g., that encoding EGF-like repeats 11 and 12, is expressed. In another embodiment, the adhesive portion of the Delta gene, e.g., that encoding amino acids 1–230, is expressed. In other specific embodiments, the human Notch or human Delta gene is expressed, or a sequence encoding a functionally active portion of human Notch or Delta. In yet another embodiment, the adhesive portion of the Serrate gene is expressed.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of nucleic acid sequence encoding a toporythmic protein or peptide fragment may be regulated by a second nucleic acid sequence so that the toporythmic protein or peptide is expressed in a host transformed with the recombinant DNA molecule. For example, expression of a toporythmic protein may be controlled by any promoter/enhancer element known in the art. Promoters which may be used to control toporythmic gene expression include, but are not limited to, the SV40 early promoter region (Bernoist and Chambon, 1981, Nature 290, 304–310), the promoter contained in the 3' long terminal repeat of Rous sarcoma virus (Yamamoto, et al., 1980, Cell 22, 787–797), the herpes thymidine kinase promoter (Wagner et al., 1981, Proc. Natl. Acad. Sci. U.S.A. 78, 1441–1445), the regulatory sequences of the metallothionein gene (Brinster et al., 1982, Nature 296, 39–42); prokaryotic expression vectors such as the β-lactamase promoter (Villa-Kamaroff, et al., 1978, Proc. Natl. Acad. Sci. U.S.A. 75, 3727–3731), or the tac promoter (DeBoer, et al., 1983, Proc. Natl. Acad. Sci. U.S.A. 80, 21–25); see also "Useful proteins from recombinant bacteria" in Scientific American, 1980, 242, 74–94; plant expression vectors comprising the nopaline synthetase promoter region (Herrera-Estrella et al., Nature 303, 209–213) or the cauliflower mosaic virus 35S RNA promoter (Gardner, et al., 1981, Nucl. Acids Res. 9, 2871), and the promoter of the photosynthetic enzyme ribulose biphosphate carboxylase (Herrera-Estrella et al., 1984, Nature 310, 115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38, 639–646; Ornitz et al., 1986, Cold Spring Harbor Symp. Quant. Biol. 50, 399–409; MacDonald, 1987, Hepatology 7, 425–515); insulin gene control region which is active in pancreatic beta cells (Hanahan, 1985, Nature 315, 115–122), immunoglobulin gene control region which is active in lymphoid cells (Grosschedl et al., 1984, Cell 38, 647–658; Adames et al., 1985, Nature 318, 533–538; Alexander et al., 1987, Mol. Cell. Biol. 7, 1436–1444), mouse mammary tumor virus control region which is active in testicular, breast, lymphoid and mast cells (Leder et al., 1986, Cell 45, 485–495), albumin gene control region which is active in liver (Pinkert et al., 1987, Genes and Devel. 1, 268–276), alpha-fetoprotein gene control region which is active in liver (Krumlauf et al., 1985, Mol. Cell. Biol. 5, 1639–1648; Hammer et al., 1987, Science 235, 53–58; alpha 1-antitrypsin gene control region which is active in the liver (Kelsey et al., 1987, Genes and Devel. 1, 161–171), beta-globin gene control region which is active in myeloid cells (Mogram et al., 1985, Nature 315, 338–340; Kollias et al., 1986, Cell 46, 89–94; myelin basic protein gene control region which is active in oligodendrocyte cells in the brain (Readhead et al., 1987, Cell 48, 703–712); myosin light chain-2 gene control region which is active in skeletal muscle (Sani, 1985, Nature 314, 283–286), and gonadotropic releasing hormone gene control region which is active in the hypothalamus (Mason et al., 1986, Science 234, 1372–1378).

Expression vectors containing toporythmic gene inserts can be identified by three general approaches: (a) nucleic acid hybridization, (b) presence or absence of "marker" gene functions, and (c) expression of inserted sequences. In the first approach, the presence of a foreign gene inserted in an expression vector can be detected by nucleic acid hybridization using probes comprising sequences that are homologous to an inserted toporythmic gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the toporythmic gene is inserted within the marker gene sequence of the vector, recombinants containing the toporythmic insert can be identified by the absence of the marker gene function. In the third approach, recombinant expression vectors can be identified by assaying the foreign gene product expressed by the recombinant. Such assays can be based, for example, on the physical or functional properties of the toporythmic gene product in vitro assay systems, e.g., aggregation (adhesive) ability (see Sections 6–8, infra).

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered toporythmic protein may be controlled. Furthermore, different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous mammalian toporythmic protein. Furthermore, different vector/host expression systems may effect processing reactions such as proteolytic cleavages to different extents.

In other specific embodiments, the adhesive toporythmic protein, fragment, analog, or derivative may be expressed as a fusion, or chimeric protein product (comprising the protein, fragment, analog, or derivative joined to a heterologous protein sequence). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

Both cDNA and genomic sequences can be cloned and expressed.

In other embodiments, a human Notch cDNA sequence may be chromosomally integrated and expressed. Homologous recombination procedures known in the art may be used.

5.4.1. IDENTIFICATION AND PURIFICATION OF THE EXPRESSED GENE PRODUCT

Once a recombinant which expresses the toporythmic gene sequence is identified, the gene product may be analyzed. This can be achieved by assays based on the physical or functional properties of the product, including radioactive labelling of the product followed by analysis by gel electrophoresis.

Once the toporythmic protein is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any suitable assay, including, but not limited to, aggregation assays (see Sections 6–8).

5.5. GENERATION OF ANTIBODIES TO TOPORYTHMIC PROTEINS AND ADHESIVE SEQUENCES THEREOF

According to the invention, toporythmic protein fragments or analogs or derivatives thereof which mediate homotypic or heterotypic binding, or human Notch or human Delta proteins or fragments thereof, may be used as an immunogen to generate anti-toporythmic protein antibodies. Such antibodies can be polyclonal or monoclonal. In a specific embodiment, antibodies specific to EGF-like repeats 11 and 12 of Notch may be prepared. In other embodiments, antibodies reactive with the "adhesive portion" of Delta can be generated. One example of such antibodies may prevent aggregation in an in vitro assay. In another embodiment, antibodies specific to human Notch are produced.

Various procedures known in the art may be used for the production of polyclonal antibodies to a toporythmic protein or peptide. In a particular embodiment, rabbit polyclonal antibodies to an epitope of the human Notch protein encoded by a sequence depicted in FIGS. 19A–19C, 20A–20D, 21A–21B or 22A–22D (SEQ ID NO:13 through NO:25), or a subsequence thereof, can be obtained. For the production of antibody, various host animals can be immunized by injection with the native toporythmic protein, or a synthetic version, or fragment thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhold limpet hemocyanins, dinitrophenol, and potentially useful human adjuvants such as BCG (bacille Calmette-Guerin) and corynebacterium parvum.

For preparation of monoclonal antibodies directed toward a toporythmic protein sequence, any technique which provides for the production of antibody molecules by continuous cell lines in culture may be used. For example, the hybridoma technique originally developed by Kohler and Milstein (1975, Nature 256, 495–497), as well as the trioma technique, the human B-cell hybridoma technique (Kozbor et al., 1983, Immunology Today 4, 72), and the EBV-hybridoma technique to produce human monoclonal antibodies (Cole et al., 1985, in Monoclonal Antibodies and Cancer Therapy, Alan R. Liss, Inc., pp. 77–96).

Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g. ELISA (enzyme-linked immunosorbent assay). For example, to select antibodies which recognize the adhesive domain of a toporythmic protein, one may assay generated hybridomas for a product which binds to a protein fragment containing such domain. For selection of an antibody specific to human Notch, one can select on the basis of positive binding to human Notch and a lack of binding to Drosophila Notch.

The foregoing antibodies can be used in methods known in the art relating to the localization and activity of the protein sequences of the invention. For example, various immunoassays known in the art can be used, including but not limited to competitive and non-competitive assay systems using techniques such as radioimmiunoassays, ELISA (enzyme linked immunosorbent assay), "sandwich" immunoassays, precipitin reactions, gel diffusion precipitin reactions, immunodiffusion assays, agglutination assays, fluorescent immunoassays, protein A immunoassays, and immunoelectrophoresis assays, to name but a few.

5.6. DELIVERY OF AGENTS INTO NOTCH-EXPRESSING CELLS

The invention also provides methods for delivery of agents into Notch-expressing cells. As discussed in Section 8 infra, upon binding to a Notch protein on the surface of a Notch-expressing cell, Delta protein appears to be taken up into the Notch-expressing cell. The invention thus provides for delivery of agents into a Notch-expressing cell by conjugation of an agent to a Delta protein or an adhesive fragment or derivative thereof capable of binding to Notch, and exposing a Notch-expressing cell to the conjugate, such that the conjugate is taken up by the cell. The conjugated agent can be, but is not limited to, a label or a biologically active agent. The biologically active agent can be a therapeutic agent, a toxin, a chemotherapeutic, a growth factor, an enzyme, a hormone, a drug, a nucleic acid, (e.g., antisense DNA or RNA), etc. In one embodiment, the label can be an imaging agent, including but not limited to heavy metal contrast agents for x-ray imaging, magnetic resonance imaging agents, and radioactive nuclides (i.e., isotopes) for radio-imaging. In a preferred aspect, the agent is conjugated to a site in the amino terminal half of the Delta molecule.

The Delta-agent conjugate can be delivered to the Notch-expressing cell by exposing the Notch-expressing cell to cells expressing the Delta-agent conjugate or exposing the Notch-expressing cell to the Delta-agent conjugate in a solution, suspension, or other carrier. Where delivery is in vivo, the Delta-agent conjugate can be formulated in a pharmaceutically acceptable carrier or excipient, to comprise a pharmaceutical composition. The pharmaceutically acceptable carrier can comprise saline, phosphate buffered saline, etc. The Delta-agent conjugate can be formulated as a liquid, tablet, pill, powder, in a slow-release form, in a liposome, etc., and can be administered orally, intravenously, intramuscularly, subcutaneously, intraperitoneally, to name but a few routes, with the preferred choice readily made based on the knowledge of one skilled in the art.

6. MOLECULAR INTERACTIONS BETWEEN THE PROTEIN PRODUCTS OF THE NEUROGENIC LOCI NOTCH AND DELTA, TWO EGF-HOMOLOGOUS GENES IN DROSOPHILA

To examine the possibility of intermolecular association between the products of the Notch and Delta genes, we studied the effects of their expression on aggregation in Drosophila Schneider's 2 (S2) cells (Fehon et al., 1990, Cell 61, 523–534). We present herein direct evidence of intermolecular interactions between Notch and Delta, and describe an assay system that will be used in dissecting the components of this interaction. We show that normally nonadhesive Drosophila S2 cultured cells that express Notch bind specifically to cells that express Delta, and that this aggregation is calcium dependent. Furthermore, while cells that express Notch do not bind to one another, cells that express Delta do bind to one another, suggesting that Notch and Delta can compete for binding to Delta at the cell surface. We also present evidence indicating that Notch and Delta form detergent-soluble complexes both in cultured cells and embryonic cells, suggesting that Notch and Delta interact directly at the molecular level in vitro and in vivo. Our analyses suggest that Notch and Delta proteins interact at the cell surface via their extracellular domains.

6.1. EXPERIMENTAL PROCEDURES
6.1.1. EXPRESSION CONSTRUCTS

For the Notch expression construct, the 6 kb HpaI fragment from the 5' end of the Notch coding sequence in MgIIa (Ramos et al., 1989, Genetics 123, 337–348) was blunt-end ligated into the metallothionein promoter vector pRmHa-3 (Bunch, et al., 1988, Nucl. Acids Res. 16, 1043–1061) after the vector had been cut with EcoRI and the ends were filled with the Klenow fragment of DNA polymerase I (Maniatis et al., 1982, Molecular Cloning: A Laboratory Manual (Cold Spring Harbor, N.Y.: Cold Spring Harbor Laboratory)). A single transformant, incorrectly oriented, was isolated. DNA from this transformant was then digested with SacI, and a resulting 3 kb fragment was isolated that contained the 5' end of the Notch coding sequence fused to the polylinker from pRmHa-3. This fragment was then ligated into the SacI site of pRmHa-3 in the correct orientation. DNA from this construct was digested with KpnI and XbaI to remove must of the Notch sequence and all of the Adh polyadenylation signal in pRmHa-3 and ligated to an 11 kb KpnI-XbaI fragment from MgIIa containing the rest of the Notch coding sequence and 3' sequences necessary for polyadenylation. In the resulting construct, designated pMtNMg, the metallothionein promoter in pRmHa-3 is fused to Notch sequences starting 20 nucleotides upstream of the translation start site.

For the extracellular Notch construct (ECN1), the CosP479BE Notch cosmid (Ramos et al., 1989, Genetics 123, 337–348), which contains all Notch genomic sequences necessary for normal Notch function in vivo, was partially digested with AatII. Fragment ends were made blunt using the exonuclease activity of T4 DNA polymerase (Maniatis et al., 1982, Molecular Cloning: A Laboratory Manual (Cold Spring Harbor, N.Y.: Cold Spring Harbor Laboratory)), and the fragments were then redigested completely with StuI. The resulting fragments were separated in a low melting temperature agarose gel (SeaPlaque, FMC BioProducts), and the largest fragment was excised. This fragment was then blunt-end ligated to itself. This resulted in an internal deletion of the Notch coding sequences from amino acid 1790 to 2625 inclusive (Wharton et al., 1985, Cell 43, 567–581), and a predicted frameshift that produces a novel 59 amino acid carboxyl terminus. (The ligated junction of this construct has not been checked by sequencing.) For the Delta expression construct, the Dl1 cDNA (Kopczynski et al., 1988, Genes Dev. 2, 1723–1735), which includes the complete coding capacity for Delta, was inserted into the EcoRI site of pRmHa-3. This construct was called pMTDl1.

6.1.2. ANTIBODY PREPARATION

Hybridoma cell line C17.9C6 was obtained from a mouse immunized with a fusion protein based on a 2.1 kb SalI-HindIII fragment that includes coding sequences for most of the intracellular domain of Notch (amino acids 1791–2504; Wharton et al., 1985, Cell 43, 567–581). The fragment was subcloned into pUR289 (Ruther and Muller-Hill, 1983, EMBO J. 2, 1791–1794), and then transferred into the pATH 1 expression vector (Dieckmann and Tzagoloff, 1985, J. Biol. Chem. 260, 1513–1520) as a BglII-HindIII fragment. Soluble fusion protein was expressed, precipitated by 25% $(NH_4)_2SO_4$, resuspended in 6M urea, and purified by preparative isoelectric focusing using a Rotofor (Bio-Rad) (for details, see Fehon, 1989, Rotofor Review No. 7, Bulletin 1518, Richmond, Calif.: Bio-Rad Laboratories).

Mouse polyclonal antisera were raised against the extracellular domain of Notch using four BstYl fragments of 0.8 kb (amino acids 237–501: Wharton et al., 1985, Cell 43, 567–581), 1.1 kb (amino acids 501–868), 0.99 kb (amino acids 868–1200), and 1.4 kb (amino acids 1465–1935) length, which spanned from the fifth EGF-like repeat across the transmembrane domain, singly inserted in-frame into the appropriate pGEX expression vector (Smith and Johnson, 1988, Gene 67, 31–40). Fusion proteins were purified on glutathione-agarose beads (SIGMA). Mouse and rat antisera were precipitated with 50% $(NH_4)_2SO_4$ and resuspended in PBS (150 mM NaCl, 14 mM $Na_2HPO_4$, 6 mM $NaH_2PO_4$) with 0.02% $NaN_3$.

Hybridoma cell line 201 was obtained from a mouse immunized with a fusion protein based on a 0.54 kb ClaI fragment that includes coding sequences from the extracellular domain of Delta (Kopczynski et al., 1988, Genes Dev. 2, 1723–1735) subcloned into the ClaI site within the lacZ gene of pUR 288 (Ruther and Muller-Hill, 1983, EMBO J. 2, 1791–1794). This fragment includes sequences extending from the fourth through the ninth EGF-like repeats in Delta (amino acids 350–529). Fusion protein was prepared by isolation of inclusion bodies (Gilmer et al., 1982, Proc. Natl. Acad. Sci. USA 79, 2152–2156); inclusion bodies were solubilized in urea (Carroll and Laughon, 1987, in DNA Cloning, Volume III, D. M. Glover, ed. (Oxford: IRL Press), pp. 89–111) before use in immunization.

Rat polyclonal antisera were obtained following immunization with antigen derived from the same fusion protein construct. In this case, fusion protein was prepared by lysis of IPTG-induced cells in SDS-Laemmli buffer (Carroll and Laughon, 1987, in DNA Cloning, Volume III, D. M. Glover, ed. (Oxford: IRL Press), pp. 89–111), separation of proteins by SDS-PAGE, excision of the appropriate band from the gel, and electroelution of antigen from the gel slice for use in immunization (Harlow and Lane, 1988, Antibodies: A Laboratory Manual (Cold Spring Harbor, N.Y.: Cold Spring Harbor Laboratory)).

6.1.3. CELL CULTURE AND TRANSFECTION

The S2 cell line (Schneider, 1972, J. Embryol. Exp. Morph. 27, 353–365) was grown in M3 medium (prepared by Hazleton Co.) supplemented with 2.5 mg/ml Bacto-Peptone (Difco), 1 mg/ml TC Yeastolate (Difco), 11% heat-inactivated fetal calf serum (FCS) (Hyclone), and 100 U/ml penicillin-100 μg/ml streptomycin-0.25 μg/ml fungizone (Hazleton). Cells growing in log phase at $\sim 2 \times 10^6$ cells/ml were transfected with 20 μg of DNA-calcium phosphate coprecipitate in 1 ml per 5 ml of culture as previously described (Wigler et al., 1979, Proc. Natl. Acad. Sci. USA 78, 1373–1376), with the exception that BES buffer (SIGMA) was used in place of HEPES buffer (Chen and Okayama, 1987, Mol. Cell. Biol. 7, 2745–2752). After 16–18 hr, cells were transferred to conical centrifuge tubes, pelleted in a clinical centrifuge at full speed for 30 seconds, rinsed once with ¼ volume of fresh complete medium, resuspended in their original volume of complete medium, and returned to the original flask. Transfected cells were then allowed to recover for 24 hr before induction.

6.1.4. AGGREGATION ASSAYS

Expression of the Notch and Delta metallothionein constructs was induced by the addition of $CuSO_4$ to 0.7 mM. Cells transfected with the ECN1 construct were treated similarly. Two types of aggregation assays were used. In the first assay, a total of 3 ml of cells ($5-10 \times 10^6$ cells/ml) was placed in a 25 ml Erlenmeyer flask and rotated at 40–50 rpm on a rotary shaker for 24–48 hr at room temperature. For these experiments, cells were mixed 1–4 hr after induction began and induction was continued throughout the aggregation period. In the second assay, ~0.6 ml of cells were placed in a 0.6 ml Eppendorf tube (leaving a small bubble) after an overnight induction (12–16 hr) at room temperature and rocked gently for 1–2 hr at 4° C. The antibody inhibition and $Ca^{2+}$ dependence experiments were performed using the latter assay. For $Ca^{2+}$ dependence experiments, cells were first collected and rinsed in balanced saline solution (BSS) with 11% FCS (BSS-FCS; FCS was dialyzed against 0.9% NaCl, 5 mM Tris [pH 7.5]) or in $Ca^{2+}$ free BSS-FCS containing 10 mM EGTA (Snow et al., 1989, Cell 59, 313–323) and then resuspended in the same medium at the original volume. For the antibody inhibition experiments, Notch-transfected cells were collected and rinsed in M3 medium and then treated before aggregation in M3 medium for 1 hr at 4° C. with a 1:250 dilution of immune or preimmune sera from each of the four mice immunized with fusion proteins containing segments from the extracellular domain of Notch (see Antibody Preparation above).

6.1.5. IMMUNOFLUORESCENCE

Cells were collected by centrifugation (3000 rpm for 20 seconds in an Eppendorf microcentrifuge) and fixed in 0.6 ml Eppendorf tubes with 0.5 ml of freshly made 2% paraformaldehyde in PBS for 10 min at room temperature. After fixing, cells were collected by centrifugation, rinsed twice in PBS, and stained for 1 hr in primary antibody in PBS with 0.1% saponin (SIGMA) and 1% normal goat serum (Pocono Rabbit Farm, Canadensis, Pa.). Monoclonal antibody supernatants were diluted 1:10 and mouse or rat sera were diluted 1:1000 for this step. Cells were then rinsed once in PBS and stained for 1 hr in specific secondary antibodies (double-labeling grade goat anti-mouse and goat anti-rat, Jackson Immunoresearch) in PBS-saponin-normal goat serum. After this incubation, cells were rinsed twice in PBS and mounted on slides in 90% glycerol, 10% 1M Tris (pH 8.0), and 0.5% n-propyl gallate. Cells were viewed under epifluorescence on a Leitz Orthoplan 2 microscope.

Confocal micrographs were taken using the Bio-Rad MRC 500 system connected to a Zeiss Axiovert compound microscope. Images were collected using the BHS and GHS filter sets, aligned using the ALIGN program, and merged using MERGE. Fluorescent bleed-through from the green into the red channel was reduced using the BLEED program (all software provided by Bio-Rad). Photographs were obtained directly from the computer monitor using Kodak Ektar 125 film.

6.1.6. CELL LYSATES, IMMUNOPRECIPITATIONS, AND WESTERN BLOTS

Nondenaturing detergent lysates of tissue culture and wild-type Canton-S embryos were prepared on ice in ~10 cell vol of lysis buffer (300 mM NaCl, 50 mM Tris [pH 8.0], 0.5% NP-40, 0.5% deoxycholate, 1 mM $CaCl_2$, 1 mM $MgCl_2$) with 1 mM phenylmethysulfonyl fluoride (PMSF) and diisopropyl fluorophosphate diluted 1:2500 as protease inhibitors. Lysates were sequentially triturated using 18G, 21G, and 25G needles attached to 1 cc tuberculin syringes and then centrifuged at full speed in a microfuge 10 min at 4° C. to remove insoluble material. Immunoprecipitation was performed by adding ~1 μg of antibody (1–2 μl of polyclonal antiserum) to 250–500 μl of cell lysate and incubating for 1 hr at 4° C. with agitation. To this mixture, 15 μg of goat anti-mouse antibodies (Jackson Immunoresearch; these antibodies recognize both mouse and rat IgG) were added and allowed to incubate for 1 hr at 4° C. with agitation. This was followed by the addition of 100 μl of fixed Staphylococcus aureus (Staph A) bacteria (Zysorbin, Zymed; resuspended according to manufacturer's instructions), which had been collected, washed five times in lysis buffer, and incubated for another hour. Staph A-antibody complexes were then pelleted by centrifugation and washed three times in lysis buffer followed by two 15 min washes in lysis buffer. After being transferred to a new tube, precipitated material was suspended in 50 μl of SDS-PAGE sample buffer, boiled immediately for 10 min, run on 3%–15% gradient gels, blotted to nitrocellulose, and detected using monoclonal antibodies and HRP-conjugated goat anti-mouse secondary antibodies as previously described (Johansen et al., 1989, J. Cell Biol. 109, 2427–2440). For total cellular protein samples used on Western blots (FIGS. 2A–2B), cells were collected by centrifugation, lysed in 10 cell vol of sample buffer that contained 1 mM PMSF, and boiled immediately.

6.2. RESULTS 6.2.1. THE EXPRESSION OF NOTCH AND DELTA IN CULTURED CELLS

To detect interactions between Notch and Delta, we examined the behavior of cells expressing these proteins on their surfaces using an aggregation assay. We chose the S2 cell line (Schneider, 1972, J. Embryol. Exp. Morph. 27, 353–365) for these studies for several reasons. First, these cells are relatively nonadhesive, grow in suspension, and have been used previously in a similar assay to study fasciclin III function (Snow et al., 1989, Cell 59, 313–323). Second, they are readily transfectable, and an inducible metallothionein promoter vector that has been designed for expression of exogenous genes in Drosophila cultured cells is available (Bunch et al., 1988, Nucl. Acids Res. 16, 1043–1061). Third, S2 cells express an aberrant Notch message and no detectable Notch due to a rearrangement of the 5' end of the Notch coding sequence (see below). These cells also express no detectable Delta (see below).

Schematic drawings of the constructs used are shown in FIG. 1 (see Experimental Procedures, Section 6.1, for details). To express Notch in cultured cells, the Notch minigene MGlla, described in Ramos et al. (1989, Genetics 123, 337–348) was inserted into the metallothionein promoter vector pRmHa-3 (Bunch et al., 1988, Nucl. Acids Res. 16, 1043–1061). The Delta expression construct was made by inserting Dl1 cDNA, which contains the entire coding sequence for Delta from the major embryonic Delta transcript (5.4Z; Kopczynski et al., 1988, Genes Dev. 2, 1723–1735), into the same vector. A third construct, designated ECN1 for "extracellular Notch 1", contains the 5' Notch promoter region and 3' Notch polyadenylation signal together with coding capacity for the extracellular and transmembrane regions of the Notch gene from genomic sequences, but lacks coding sequences for 835 amino acids of the ~1000 amino acid intracellular domain. In addition, due to a predicted frameshift, the remaining 78 carboxy-terminal amino acid residues are replaced by a novel 59 amino acid carboxyterminal tail (see Experimental Procedures).

For all of the experiments described in this paper, expression constructs were transfected into S2 cells and expressed transiently rather than in stable transformants. Expressing cells typically composed 1%–5% of the total cell population, as judged by immunofluorescent staining (data not shown). A Western blot of proteins expressed after transfection is shown in FIGS. 2A–2B. Nontransfected cells do not express detectable levels of Notch or Delta. However, after transfection, proteins of the predicted apparent molecular weights are readily detectable using monoclonal antibodies specific for each of these proteins, respectively. In the case of Notch, multiple bands were apparent in transfected cells below the ~300 kd full-length product. We do not yet know whether these bands represent degradation of Notch during sample preparation or perhaps synthesis or processing intermediates of Notch that are present within cells, but we consistently detect them in samples from transfected cells and from embryos. In addition, we performed immunofluorescent staining of live transfected cells with antibodies specific for the extracellular domains of each protein to test for cell surface expression of these proteins. In each case we found surface staining as expected for a surface antigen. Taken together, these results clearly show that the Notch and Delta constructs support expression of proteins of the expected sizes and subcellular localization.

FIGS. 3A—3I shows representative photomicrographs from aggregation experiments, and Table I presents the results in numerical form. As is apparent from FIG. 3C and Table I, while Notch-expressing (Notch+) cells alone do not form aggregates in our assay, Delta-expressing (Delta+) cells do.

TABLE I

PERCENTAGES OF NOTCH+ AND DELTA+ CELLS IN AGGREGATES[a]

|  | Notch+ | | Delta+ | | Notch+–Delta | | |
|---|---|---|---|---|---|---|---|
|  | Control | Aggregated | Control | Aggregated | | | |
|  | Cells[b] | Cells[c] | Cells[b] | Cells[c] | Overall[d] | N Cells[e] | D1 Cells[f] |
| Experiment 1 | 0 | 0 | 19 | 37 | 32 | 26 | 42 |
| Experiment 2 | — | 1 | — | 40 | 54 | 47 | 79 |
| Experiment 3 | 0 | — | 12 | — | 43 | 42 | 44 |
| Experiment 4 | 5 | 5 | 20 | — | 47 | 41 | 59 |
| Experiment 5[gh] | — | 2 | — | 48 | 71 | 66 | 82 |
| Experiment 6[h] | 0 | 0 | 13 | 61 | 63 | 60 | 73 |

[a]Aggregates defined as clusters of four or more expressing cells. For all values, at least 100 expressing cell units (single cells or cell clusters) were scored. Notch+, Notch-expressing; Delta+, Delta expressing.
[b]Control cells taken directly from transfection flasks without incubation in the aggregation assay.
[c]Control cells after incubation in the aggregation assay.
[d]Combined aggregation data for both Notch+ and Delta+ cells in Notch+–Delta+ aggregates.
[e]Aggregation data for Notch+ cells in Notch+–Delta+ aggregates.
[f]Aggregation data for Delta+ cells in Notch+–Delta+ aggregates.
[g]Cells from this experiment from same transfection as Experiment 4.
[h]Data from 48 hr aggregation experiments. All other data are from 24 hr aggregation experiments.

6.2.2. CELLS THAT EXPRESS NOTCH AND DELTA AGGREGATE

To test the prediction that Notch and Delta interact, we designed a simple aggregation assay to detect these interactions between proteins expressed on the surface of S2 cells. We reasoned that if Notch and Delta are able to form stable heterotypic complexes at the cell surface, then cells that express these proteins might bind to one another and form aggregates under appropriate conditions. A similar assay system has recently been described for the fasciclin III protein (Snow et al., 1989, Cell 59, 313–323).

S2 cells in log phase growth were separately transfected with either the Notch or Delta metallothionein promoter construct. After induction with CuSO$_4$, transfected cells were mixed in equal numbers and allowed to aggregate overnight at room temperature (for details, see Experimental Procedures, Section 6.1). Alternatively, in some experiments intended to reduce metabolic activity, cells were mixed gently at 4° C. for 1–2 hr. To determine whether aggregates had formed, cells were processed for immunofluorescence microscopy using antibodies specific for each gene product and differently labeled fluorescent secondary antibodies. As previously mentioned, expressing cells usually constituted less than 5% of the total cell population because we used transient rather than stable transformants. The remaining cells either did not express a given protein or expressed at levels too low for detection by immunofluorescence microscopy. As controls, we performed aggregations with only a single type of transfected cell.

The tendency for Delta+ cells to aggregate was apparent even in nonaggregated control samples (Table I), where cell clusters of 4–8 cells that probably arose from adherence between mitotic sister cells commonly occurred. However, clusters were more common after incubation under aggregation conditions (e.g., 19% of Delta+ cells in aggregates before incubation vs. 37% of Delta+ cells in aggregates after incubation; Experiment 1 in Table I), indicating that Delta+ cells are able to form stable contacts with one another in this assay. It is important to note that while nonstaining cells constituted over 90% of the cells in our transient transfections, we never found them within aggregates. On rare occasions, nonstaining cells were found at the edge of an aggregate. Due to the common occurrence of weakly staining cells at the edges of aggregates, it is likely that these apparently nonexpressing cells were transfected but expressed levels of Delta insufficient to be detected by immunofluorescence.

In remarkable contrast to control experiments with Notch+ cells alone, aggregation of mixtures of Notch+ and Delta+ cells resulted in the formation of clusters of up to 20 or more cells (FIGS. 3D–3H, Table I). As Table I shows, the fraction of expressing cells found in clusters of four or more stained cells after 24 hr of aggregation ranged from 32%–54% in mixtures of Notch+ and Delta+ cells. This range was similar to that seen for Delta+ cells alone (37%–40%) but very different from that for Notch+ cells alone (only 0%–5%). Although a few clusters that consisted only of Delta+ cells were found, Notch+ cells were never found in clusters of greater than four to five cells unless Delta+ cells were also present. Again, all cells within these clusters expressed either Notch or Delta, even though transfected cells composed only a small fraction of the total cell population. At 48 hr (Table I, experiments 5 and 6), the degree of aggregation appeared higher (63%–71%), suggesting that aggregation had not yet reached a maximum after 24 hr under these conditions. Also, cells cotransfected with Notch and Delta constructs (so that all transfected cells express both proteins) aggregated in a similar fashion under the same experimental conditions.

These results indicate that the aggregation observed in these experiments requires the expression of Notch and Delta and is not due to the fortuitous expression of another interacting protein in nontransfected S2 cells. We further tested the specificity of this interaction by diluting Notch$^+$ and Delta$^+$ cells 10-fold with nontransfected S2 cells and allowing them to aggregate for 24 hr at room temperature. In this experiment, 39% of the expressing cells were found in aggregates with other expressing cells, although they composed less than 0.1% of the total cell population. Not surprisingly, however, these aggregates were smaller on average than those found in standard aggregation experiments. In addition, to control for the possibility that Notch$^+$ cells are nonspecifically recruited into the Delta$^+$ aggregates because they overexpress a single type of protein on the cell surface, we mixed Delta$^+$ cells with cells that expressed neuroglian, a transmembrane cell-surface protein (Bieber et al., 1989, Cell 59, 447–460), under the control of the metallothionein promoter (this metallothionein-neuroglian construct was kindly provided by A. Bieber and C. Goodman). We observed no tendency for neuroglian$^+$ cells to adhere to Delta$^+$ aggregates, indicating that Notch-Delta aggregation is not merely the result of high levels of protein expression on the cell surface.

We also tested directly for Notch involvement in the aggregation process by examining the effect of a mixture of polyclonal antisera directed against fusion proteins that spanned almost the entire extracellular domain of Notch on aggregation (see Experimental Procedures, Section 6.1). To minimize artifacts that might arise due to a metabolic response to patching of surface antigens, antibody treatment and the aggregation assay were performed at 4° C. in these experiments. Notch$^+$ cells were incubated with either pre-immune or immune mouse sera for 1 hr, Delta$^+$ cells were added, and aggregation was performed for 1–2 hr. While Notch$^+$ cells pretreated with preimmune sera aggregated with Delta$^+$ cells (in one of three experiments, 23% of the Notch$^+$ cells were in Notch$^+$-Delta$^+$ cell aggregates), those treated with immune sera did not (only 2% of Notch$^+$ cells were in aggregates). This result suggests that the extracellular domain of Notch is required for Notch$^+$-Delta$^+$ cell aggregation, although we cannot rule out the possibility that the reduced aggregation was due to inhibitory steric or membrane structure effects resulting from exposure of Notch$^+$ cells to the antiserum.

Three other observations worth noting are apparent in FIGS. 3A—3I. First, while Delta was almost always apparent only at the cell surface (FIGS. 3B and 3C), Notch staining was always apparent both at the cell surface and intracellularly, frequently associated with vesicular structures (FIG. 3A). Second, we consistently noted a morphological difference between Delta$^+$ and Notch$^+$ cells in mixed aggregates that were incubated overnight. Delta$^+$ cells often had long extensions that completely surrounded adjacent Notch$^+$ cells, while Notch$^+$ cells were almost always rounded in appearance without noticeable cytoplasmic extensions (FIG. 3G). Third, Notch and Delta often appeared to gather within regions of contact between Notch$^+$ and Delta$^+$ cells, producing a sharp band of immunofluorescent staining (FIGS. 3D–3F). These bands were readily visible in optical sections viewed on the confocal microscope (FIG. 3H), indicating that they were not merely due to a whole-mount artifact. We also observed that these bands formed rapidly (within 2 hr of mixing cells) and at 4° C., indicating that their formation probably did not depend upon cellular metabolism. These observations would be expected if, within regions of cell contact, Notch and Delta bind to one another and therefore become immobilized. This pattern of expression is also consistent with that observed for other proteins that mediate cell aggregation (Takeichi, 1988, Development 102, 639–655; Snow et al., 1989, Cell 59, 313–323).

6.2.3. NOTCH-DELTA-MEDIATED AGGREGATION IS CALCIUM DEPENDENT

Previous studies have suggested that EGF-like repeats that contain a particular consensus sequence may serve as calcium ($Ca^{2+}$) binding domains (Morita et al., 1984, J. Biol. Chem. 259, 5698–5704; Sugo et al., 1984, J. Biol. Chem. 259, 5705–5710; Rees et al., 1988, EMBO J. 7, 2053–2061; Handford et al., 1990, EMBO J. 9, 475–480). For at least two of these proteins, C and C1, $Ca^{2+}$ binding has further been shown to be a necessary component of their interactions with other proteins (Villiers et al., 1980, FEBS Lett. 117, 289–294; Esmon et al., 1983, J. Biol. Chem. 258, 5548–5553; Johnson, et al., 1983, J. Biol. Chem. 258, 5554–5560). Many of the EGF-homologous repeats within Notch and most of those within Delta contain the necessary consensus sequence for $Ca^{2+}$ binding (Rees et al., 1988, EMBO J. 7, 2053–2061; Stenflo et al., 1987, Proc. Natl. Acad. Sci. USA 84, 368–372; Kopczynski et al., 1988, Genes Dev. 2, 1723–1735; Handford et al., 1990, EMBO J. 9, 475–480), although it has not yet been determined whether or not these proteins do bind calcium. We therefore tested the ability of expressing cells to aggregate in the presence or absence of $Ca^{2+}$ ions to determine whether there is a $Ca^{2+}$ ion requirement for Notch-Delta aggregation. To minimize possible nonspecific effects due to metabolic responses to the removal of $Ca^{2+}$, these experiments were performed at 4° C. Control mixtures of Notch$^+$ and Delta$^+$ cells incubated under aggregation conditions in $Ca^{2+}$-containing medium at 4° C. readily formed aggregates (an average of 34%±13%, mean±SD, n=3; Table II). In contrast, cells mixed in medium that lacked $Ca^{2+}$ ions and contained EGTA formed few aggregates (5%±5%). These results clearly demonstrate a dependence of Notch-Delta-mediated aggregation on exogenous $Ca^{2+}$ and are in marked contrast to those recently published for the Drosophila fasciclin III and fasciclin I proteins in S2 cells (Snow et al., 1989, Cell 59, 313–323; Elkins et al., 1990, J. Cell Biol. 110, 1825–1832), which detected no effect of $Ca^{2+}$ ion removal on aggregation mediated by either protein.

TABLE II

EFFECT OF EXOGENOUS $Ca^{2+}$ ON NOTCH$^+$–DELTA$^+$ AGGREGATION[a]

| | Without Ca2+ Ions | | | With $Ca^{2+}$ Ions | | |
|---|---|---|---|---|---|---|
| | Over-all[b] | N Cells[c] | D1 Cells[d] | Over-all[b] | N Cells[c] | D1 Cells[d] |
| Experiment 1 | 4 | 2 | 5 | 28 | 28 | 27 |
| Experiment 2 | 12 | 0 | 13 | 53 | 63 | 50 |
| Experiment 3 | 0 | 0 | 0 | 22 | 28 | 17 |

[a]Data presented as percentage of expressing cells found in aggregates (as in Table I).
[b]Combined aggregation data for both Notch$^+$ and Delta$^+$ cells.
[c]Aggregation data for Notch$^+$ cells in Notch$^+$–Delta$^+$ aggregates.
[d]Aggregation data for Delta$^+$ cells in Notch$^+$–Delta$^+$ aggregates.

6.2.4. NOTCH AND DELTA INTERACT WITHIN A SINGLE CELL

We asked whether Notch and Delta are associated within the membrane of one cell that expresses both proteins by examining the distributions of Notch and Delta in cotransfected cells. As shown in FIGS. 4A and 4B, these two proteins often show very similar distributions at the surface of cotransfected cells. To test whether the observed colocalization was coincidental or represented a stable interaction between Notch and Delta, we treated live cells with an excess of polyclonal anti-Notch antiserum. This treatment resulted in "patching" of Notch on the surface of expressing cells into discrete patches as detected by immunofluorescence. There was a distinct correlation between the distributions of Notch and Delta on the surfaces of these cells after this treatment (FIGS. 4C and 4D), indicating that these proteins are associated within the membrane. It is important to note that these experiments do not address the question of whether this association is direct or mediated by other components, such as the cytoskeleton. To control for the possibility that Delta is nonspecifically patched in this experiment, we cotransfected cells with Notch and with the previously mentioned neuroglian construct (A. Bieber and C. Goodman, unpublished data) and patched with anti-Notch antisera. In this case there was no apparent correlation between Notch and neuroglian.

6.2.5. INTERACTIONS WITH DELTA DO NOT REQUIRE THE INTRACELLULAR DOMAIN OF NOTCH

In addition to a large extracellular domain that contains EGF-like repeats, Notch has a sizeable intracellular (IC) domain of ~940 amino acids. The IC domain includes a phosphorylation site (Kidd et al., 1989, Genes Dev. 3, 1113–1129), a putative nucleotide binding domain, a polyglutamine stretch (Wharton et al., 1985, Cell 43, 567–581; Kidd, et al., 1986, Mol. Cell. Biol. 6, 3094–3108), and sequences homologous to the yeast cdc10 gene, which is involved in cell cycle control in yeast (Breeden and Nasmyth, 1987, Nature 329, 651–654). Given the size and structural complexity of this domain, we wondered whether it is required for Notch-Delta interactions. We therefore used a variant Notch construct from which coding sequences for ⁻835 amino acids of the IC domain, including all of the structural features noted above, had been deleted (leaving 25 membrane-proximal amino acids and a novel 59 amino acid carboxyl terminus; see Experimental Procedures and FIG. 1 for details). This construct, designated ECN1, was expressed constitutively under control of the normal Notch promoter in transfected cells at a level lower than that observed for the metallothionein promoter constructs, but still readily detectable by immunofluorescence.

In aggregation assays, cells that expressed the ECN1 construct consistently formed aggregates with Delta⁺ cells (31% of ECN1-expressing cells were in aggregates in one of three experiments; see also FIG. 3I), but not with themselves (only 4% in aggregates), just as we observed for cells that expressed intact Notch. We also observed sharp bands of ECN1 staining within regions of contact with Delta⁺ cells, again indicating a localization of ECN1 within regions of contact between cells. To test for interactions within the membrane, we repeated the surface antigen co-patching experiments using cells cotransfected with the ECN1 and Delta constructs. As observed for intact Notch, we found that when ECN1 was patched using polyclonal antisera against the extracellular domain of Notch, ECN1 and Delta colocalized at the cell surface (FIGS. 4E and 4F). These results demonstrate that the observed interactions between Notch and Delta within the membrane do not require the deleted portion of the IC domain of Notch and are therefore probably mediated by the extracellular domain. However, it is possible that the remaining transmembrane or IC domain sequences in ECN1 are sufficient to mediate interactions within a single cell.

6.2.6. NOTCH AND DELTA FORM DETERGENT-SOLUBLE INTERMOLECULAR COMPLEXES

Together, we take the preceding results to indicate molecular interactions between Notch and Delta present within the same membrane and between these proteins expressed on different cells. As a further test for such interactions, we asked whether these proteins would coprecipitate from nondenaturing detergent extracts of cells that express Notch and Delta. If Notch and Delta form a stable intermolecular complex either between or within cells, then it should be possible to precipitate both proteins from cell extracts using specific antisera directed against one of these proteins. We performed this analysis by immunoprecipitating Delta with polyclonal antisera from NP-40/deoxycholate lysates (see Experimental Procedures) of cells cotransfected with the Notch and Delta constructs that had been allowed to aggregate overnight or of 0–24 hr wild-type embryos. We were unable to perform the converse immunoprecipitates because it was not possible to discern unambiguously a faint Delta band among background Staph A bands. It is important to note that we tested this polyclonal anti-Delta antiserum for cross-reactivity against Notch in cell lysates (FIG. 5A, lane 1) and by immunofluorescence (e.g., compare FIGS. 3D and 3E) and found none. After repeated washing to remove nonspecifically adhering proteins, we assayed for coprecipitation of Notch using a monoclonal antibody (MAb C17.9C6) against Notch on Western blots.

As FIGS. 5A–5B shows, we did detect coprecipitation of Notch in Delta immunoprecipitates from cotransfected cells and embryos. However, coprecipitating Notch appeared to be present in much smaller quantities than Delta and was therefore difficult to detect. This disparity is most likely due to the disruption of Notch-Delta complexes during the lysis and washing steps of the procedure. However, it is also possible that this disparity reflects a nonequimolar interaction between Notch and Delta or greatly different affinities of the antisera used to detect these proteins. The fact that immunoprecipitation of Delta results in the coprecipitation of Notch constitutes direct evidence that these two proteins form stable intermolecular complexes in transfected S2 cells and in embryonic cells.

6.3. DISCUSSION

We have studied interactions between the protein products of two of the neurogenic loci, Notch and Delta, in order to understand their cellular functions better. Using an in vitro aggregation assay that employs normally nonadhesive S2 cells, we showed that cells that express Notch and Delta adhere specifically to one another. The specificity of this interaction is apparent from the observation that Notch⁺-Delta⁺ cell aggregates rarely contained nonexpressing cells, even though nonexpressing cells composed the vast majority of the total cell population in these experiments. We propose that this aggregation is mediated by heterotypic binding between the extracellular domains of Notch and Delta present on the surfaces of expressing cells. Consistent with this proposal, we find that antisera directed against the extracellular domain of Notch inhibit Notch-Delta-mediated aggregation, and that the ECN1 Notch variant, which lacks almost all of the Notch intracellular domain, can mediate aggregation with cells that express Delta. We also found that cells that express only Delta aggregate with one another, while those that express only Notch do not. These findings suggest that Delta can participate in a homotypic interaction when present on apposed cell surfaces but that Notch cannot under our assay conditions.

The proposal that Notch and Delta interact at the cell surface is further supported by three lines of evidence. First, we find an intense localization of both proteins within regions of contact which Notch⁺ and Delta⁺ cells, implying that Notch and Delta interact directly, even when expressed in different cells. Second, Notch and Delta colocalize on the surface of cells that express both proteins, suggesting that these proteins can interact within the cell membrane. Third, Notch and Delta can be coprecipitated from nondenaturing detergent extracts of cultured cells that express both proteins as well as from extracts of embryonic cells. Together, these results strongly support the hypothesis that Notch and Delta can interact heterotypically when expressed on the surfaces of either the same or different cells.

The underlying basis for the observed genetic interactions between Notch and Delta and between Notch and mam (Xu et al., 1990, Genes Dev. 4, 464–475) may be a dose-sensitive interaction between the proteins encoded by these genes.

Two lines of evidence suggest that the Notch and Delta proteins function similarly in vitro and in vivo. First, the genetic analyses have indicated that the stoichiometry of Notch and Delta is crucial for their function in development. Our observations that both Notch-Delta and Delta—Delta associations may occur in vitro imply that Notch and Delta may compete for binding to Delta. Thus, dose-sensitive genetic interactions between Notch and Delta may be the result of competitive binding interactions between their protein products. Second, we were able to detect Notch-Delta association in lysates of cultured cells and in lysates of Drosophila embryos using immunoprecipitation. Taken together, these genetic and biochemical analyses suggest that Notch and Delta do associate in vivo in a manner similar to that which we propose on the basis of our aggregation assays.

Genetic and molecular analyses of Notch have also raised the possibility that there may be interactions between individual Notch proteins (Portin, 1975, Genetics 81, 121–133; Kelley et al., 1987, Cell 51, 539–548; Artavanis-Tsakonas, 1988, Trends Genet. 4, 95–100). Indeed, Kidd et al. (1989, Genes Dev. 3, 1113–1129) have proposed that this protein forms disulfide cross-linked dimers, although this point has not yet been rigorously proven. With or without the formation of covalent cross-links, such interactions could presumably occur either within a single cell or between cells. However, our find that Notch⁺ cells do not aggregate homotypically suggests that Notch—Notch associations are likely to occur within a single cell and not between cells. Alternatively, it is possible that homotypic Notch interactions require gene products that are not expressed in S2 cells.

The Notch-Delta interactions indicated by our analysis are probably mediated by the extracellular domains of these proteins. Aggregation experiments using the ECN1 construct, from which almost the entire intracellular domain of Notch has been removed or altered by in vitro mutagenesis, confirmed this conclusion. Further experiments that demonstrate ECN1-Delta associations within the membrane on the basis of their ability to co-patch indicated that these interactions are also likely to be mediated by the extracellular domains of Notch and Delta, although in this case we cannot exclude possible involvement of the transmembrane domain or the remaining portion of the Notch intracellular domain. These results are especially interesting in light of the fact that both Notch and Delta have EGF-like repeats within their extracellular domains (Wharton et al., 1985, Cell 43, 567–581; Kidd et al., 1986, Mol. Cell Biol. 6, 3094–3108; Vassin et al., 1987, EMBO J. 6, 3431–3440; Kopczynski et al., 1988, Genes Dev. 2, 1723–1735).

A second issue of interest regarding EGF domains is the proposal that they can serve as $Ca^{2+}$ binding domains when they contain a consensus sequence consisting of Asp, Asp/Asn, Asp/Asn, and Tyr/Phe residues at conserved positions within EGF-like repeats (Rees et al., 1988, EMBO J. 7, 2053–2061; Handford et al., 1990, EMBO J. 9, 475–480). Comparisons with a proposed consensus sequence for $Ca^{2+}$ binding have revealed that similar sequences are found within many of the EGF-like repeats of Notch (Rees et al., 1988, EMBO J. 7, 2053–2061) and within most of the EGF-like repeats of Delta (Kopczynski et al., 1988, Genes Dev. 2, 1723–1735). Furthermore, sequence analyses of Notch mutations have shown that certain Ax alleles are associated with changes in amino acids within this putative $Ca^{2+}$ binding domain (Kelley et al., 1987, Cell 51, 539–548; Hartley et al., 1987, EMBO J. 6, 3407–3417; Rees et al., 1988, EMBO J. 7, 2053–2061). For example, the $AxE^2$ mutation, which correlates with a His to Tyr change in the 29th EGF-like repeat, appears to change this repeat toward the consensus for $Ca^{2+}$ binding. Conversely, the $Ax^{9B2}$ mutation appears to change the 24th EGF-like repeat away from this consensus as a result of an Asp to Val change. Thus, the genetic interactions between Ax alleles and Delta mutations (Xu et al., 1990, Genes Dev., 4, 464–475) raise the possibility that $Ca^{2+}$ ions play a role in Notch-Delta interactions. Our finding that exogenous $Ca^{2+}$ is necessary for Notch-Delta-mediated aggregation of transfected S2 cells supports this contention.

As we have argued (Johansen et al., 1989, J. Cell Biol. 109, 2427–2440; Alton et al., 1989, Dev. Genet. 10, 261–272), on the basis of previous molecular and genetic analyses one could not predict with any certainty the cellular function of either Notch or Delta beyond their involvement in cell—cell interactions. However, given the results presented here, it now seems reasonable to suggest that Notch and Delta may function in vivo to mediate adhesive interactions between cells. At the same time, it is quite possible that the observed Notch-Delta interactions may not reflect a solely adhesive function and may in addition reflect receptor-ligand binding interactions that occur in vivo. Indeed, the presence of a structurally complex 1000 amino acid intracellular domain within Notch may be more consistent with a role in signal transduction than with purely adhesive interactions. Given that Notch may have an adhesive function in concert with Delta, axonal expression of Notch may play some role in axon guidance.

7. EGF REPEATS 11 AND 12 OF NOTCH ARE REQUIRED AND SUFFICIENT FOR NOTCH-DELTA-MEDIATED AGGREGATION

In this study, we use the same aggregation assay as described in Section 6, together with deletion mutants of Notch to identify regions within the extracellular domain of Notch necessary for interactions with Delta. We present evidence that the EGF repeats of Notch are directly involved in this interaction and that only two of the 36 EGF repeats appear necessary. We demonstrate that these two EGF repeats are sufficient for binding to Delta and that the calcium dependence of Notch-Delta mediated aggregation also associates with these two repeats. Finally, the two corresponding EGF repeats from the Xenopus homolog of Notch also mediate aggregation with Delta, implying that not only has the structure of Notch been evolutionarily conserved, but also its function. These results suggest that the extracellular domain of Notch is surprisingly modular, and could potentially bind a variety of proteins in addition to Delta.

7.1. EXPERIMENTAL PROCEDURES
7.1.1. EXPRESSION CONSTRUCTS

The constructs described are all derivatives of the full length Notch expression construct #1 pMtNMg (see Section 6, supra). All ligations were performed using DNA fragments cut from low melting temperature agarose gels (Sea Plaque, FMC BioProducts). The 6 kb EcoRI-XhoI fragment from pMtNMg containing the entire extracellular domain of Notch was ligated into the EcoRI-XhoI sites of the Bluescript vector (Stratagene), and named RI/XBS. All subsequent deletions and insertions of EGF repeats were performed in this subclone. The Notch sequence containing the EcoRI-XhoI fragment of these RI/XBS derivatives was then mixed with the 5.5 kb XhoI-XbaI fragment from pMtNMg containing the intracellular domain and 3' sequences needed for polyadenylation, and then inserted into the EcoRI-XbaI site of pRMHa-3 (Bunch et al., 1988, Nucl. Acids Res. 16, 1043–1061) in a three piece ligation. All subsequent numbers refer to nucleotide coordinates of the Notch sequence according to Wharton et al. (1985, Cell 43, 567–581).

For construct #2 DSph, RI/XBS was digested to completion with SphI and then recircularized, resulting in a 3.5 kb in-frame deletion from SphI(996) to SphI(4545).

For construct #3 ΔCla, RI/XBS was digested to completion with ClaI and then religated, producing a 2.7 kb in-frame deletion from ClaI(1668) to ClaI(4407). The ligation junction was checked by double strand sequencing (as described by Xu et al., 1990, Genes Dev. 4, 464–475) using the Sequenase Kit (U.S. Biochemical Corp., Cleveland). We found that although the ClaI site at position 4566 exists according to the sequence, it was not recognized under our conditions by the ClaI restriction enzyme.

For constructs #4–12, RI/XBS was partially digested with ClaI and then religated to produce all possible combinations of in-frame deletions: construct #4 ΔEGF7–17 removed the sequence between ClaI(1668) and ClaI(2820); Construct #5 ΔEGF9–26 removed the sequence between ClaI(1905) and ClaI(3855); construct #6 ΔEGF17–31 removed the sequence between ClaI(2820) and ClaI(4407); construct #7 ΔEGF7–9 removed the sequence between ClaI(1668) and ClaI(1905); construct #8 ΔEGF9–17 removed the sequence between ClaI(1905) and ClaI(2820); construct #9 ΔEGF17–26 removed the sequence between ClaI(2820) and ClaI(3855); construct #10 ΔEGF 26–30 removed the sequence between ClaI(3855) and ClaI(4407); construct #11 ΔEGF9–30 removed the sequence between ClaI(1905) and ClaI(4407); construct #12 ΔEGF 7–26 removed the sequence between ClaI(1668) and ClaI(3855).

For constructs #13 ΔCla+EGF9–17 and #14 ΔCla+EGF17–26, the ~0.9 kb fragment between ClaI(1905) and ClaI(2820), and the ~1.0 kb fragment between ClaI(2820) and ClaI(3855), respectively, were inserted into the unique ClaI site of construct #3 ΔCla.

For construct #16 split, the 11 kb KpnI/XbaI fragment of pMtNMg was replaced with the corresponding KpnI/XbaI fragment from a Notch minigene construct containing the split mutation in EGF repeat 14.

For constructs #17–25, synthetic primers for polymerase chain reaction (PCR) were designed to amplify stretches of EGF repeats while breaking the EGF repeats at the ends of the amplified piece in the same place as the common ClaI sites just after the third cysteine of the repeat (see FIG. 7). The PCR products were gel purified as usual and ligated into the ClaI site of construct #3 ΔCla which was made blunt by filling with the Klenow fragment of DNA Polymerase I (Maniatis et al., 1990, Molecular Cloning, A Laboratory Manual, Cold Spring Harbor Laboratory, Cold Spring Harbor, N.Y.). The correct orientation of the inserts was determined by PCR using a sense strand primer within the insert together with an antisense strand primer in EGF repeat 35. All primers were 20-mers, and were named with the number of the nucleotide at their 5' end, according to the nucleotide coordinates of the Notch sequence in Wharton et al. (1985, Cell 43, 567–581), and S refers to a sense strand primer while A refers to an antisense strand primer. Construct #16 ΔCla+EGF(9–13) used primers S1917 and A2367. Construct #17 ΔCla+EGF(11–15) used primers S2141 and A2591. Construct #18 ΔCla+EGF(13–17) used primers S2375 and A2819. Construct #19 ΔCla+EGF (10–13) used primers S2018 and A2367. Construct #20 ΔCla+EGF(11–13) used primers S2141 and A2367. Construct #21 ΔCla+EGF (10–12) used primers S2018 and A2015. Construct #22 ΔCla+EGF(10–11) used primers S2018 and A2322. Construct #23 ΔCla+EGF(10–12) used primers S2018 and A2322. Construct #24 ΔCla+EGF (11–12) used primers S2081 and A2322.

For construct #25 ΔEGF, construct R1/XBS was digested to completion with SphI(996) and partially digested with BamHI(5135). The resulting incompatible ends were joined using a synthetic linker designed to create a unique ClaI site. This produced an in frame deletion which removed all 36 EGF repeats with the exception of the first half of repeat 1. For constructs #26–29, the EGF fragments were inserted into this ClaI site as previously described for the corresponding constructs #13, 16, 19, and 23.

For construct #30 ΔECN, construct R1/XBS was digested to completion with BglI, EcoRI and XhoI. The ~0.2 kb EcoRI-BglI fragment (722–948) and the ~0.7 kb BglI-XhoI (5873–6627) fragments were ligated with EcoRI-XhoI cut Bluescript vector and a synthetic linker designed to create a unique ClaI site, resulting in an in-frame deletion from BglI(941) to BglI(5873) that removed all 36 EGF repeats except for the first third of repeat 1 as well as the 3 Notch/lin-12 repeats. For constructs #31 and 32, the EGF fragments were inserted into the unique ClaI site as previously described for constructs #19 and 23.

For constructs #33 and 34, PCR primers S1508 and A1859 based on the Xenopus Notch sequence (Coffman et al., 1990, Science 249, 1438–1441; numbers refer to nucleotide coordinates used in this paper), were used to amplify EGF repeats 11 and 12 out of a Xenopus stage 17 cDNA library (library was made by D. Melton and kindly provided by M. Danilchek). The fragment was ligated into construct #3 DCla and sequenced.

7.1.2. CELL CULTURE AND TRANSFECTION

The Drosphila S2 cell line was grown and transfected as described in Section 6, supra. The Delta-expressing stably transformed S2 cell line L-49-6-7 (kindly established by L. Cherbas) was grown in M3 medium (prepared by Hazleton Co.) supplemented with 11% heat inactivated fetal calf serum (FCS) (Hyclone), 100 U/ml penicillin-100 µg/ml streptomycin-0.25 µg/ml fungizone (Hazleton), $2\times10^{-7}$M methotrexate, 0.1 mM hypoxanthine, and 0.016 mM thymidine.

7.1.3. AGGREGATION ASSAYS AND IMMUNOFLUORESCENCE

Aggregation assays and $Ca^{++}$ dependence experiments were as described supra, Section 6. Cells were stained with the anti-Notch monoclonal antibody 9C6.C17 and anti-Delta rat polyclonal antisera (details described in Section 6, supra). Surface expression of Notch constructs in unpermeabilized cells was assayed using rat polyclonal antisera raised against the 0.8 kb (amino acids 237–501; Wharton et al., 1985, Cell 43, 567–581) BstYI fragment from the extracellular domain of Notch. Cells were viewed under epifluorescence on a Leitz Orthoplan 2 microscope.

7.2. RESULTS
7.2.1. EGF REPEATS 11 AND 12 OF NOTCH ARE REQUIRED FOR NOTCH-DELTA MEDIATED AGGREGATION

We have undertaken an extensive deletion analysis of the extracellular domain of the Notch protein, which we have shown (supra, Section 6) to be involved in Notch-Delta interactions, to identify the precise domain of Notch mediating these interactions. We tested the ability of cells transfected with the various deletion constructs to interact with Delta using the aggregation assay described in Section 6. Briefly, Notch deletion constructs were transiently transfected into Drosophila S2 cells, induced with $CuSO_4$, and then aggregated overnight at room temperature with a small amount of cells from the stably transformed Delta expressing cell line L49-6-7(Cherbas), yielding a population typically composed of ~1% Notch expressing cells and ~5% Delta expressing cells, with the remaining cells expressing neither protein. To assay the degree of aggregation, cells were stained with antisera specific to each gene product and examined with immunofluorescent microscopy (see experimental procedures for details). Aggregates were defined as clusters of four or more cells containing both Notch and Delta expressing cells, and the values shown in FIGS. 6A–6B represent the percentage of all Notch expressing cells found in such clusters. All numbers reflect the average result from at least two separate transfection experiments in which at least 100 Notch expressing cell units (either single cells or clusters) were scored.

Schematic drawings of the constructs tested and results of the aggregation experiments are shown in FIGS. 6A–6B (see Experimental Procedures for details). All expression constructs were derivatives of the full length Notch expression construct #1 pMtNMg (described in Section 6, supra).

The initial constructs (#2 DSph and #3 ΔCla) deleted large portions of the EGF repeats. Their inability to promote Notch-Delta aggregation suggested that the EGF repeats of Notch were involved in the interaction with Delta. We took advantage of a series of six in-frame ClaI restriction sites to further dissect the region between EGF repeats 7 and 30. Due to sequence homology between repeats, five of the ClaI sites occur in the same relative place within the EGF repeat, just after the third cysteine, while the sixth site occurs just before the first cysteine of EGF repeat 31 (FIG. 7). Thus, by performing a partial ClaI digestion and then religating, we obtained deletions that not only preserved the open reading frame of the Notch protein but in addition frequently maintained the structural integrity and conserved spacing, at least theoretically, of the three disulfide bonds in the chimeric EGF repeats produced by the religation (FIGS. 6A–6B, constructs #4–14). Unfortunately, the most 3' ClaI site was resistant to digestion while the next most 3' ClaI site broke between EGF repeats 30 and 31. Therefore, when various ClaI digestion fragments were reinserted into the framework of the complete ClaI digest (construct #3 ΔCla), the overall structure of the EGF repeats was apparently interrupted at the 3' junction.

Several points about this series of constructs are worth noting. First, removal of the ClaI restriction fragment breaking in EGF repeats 9 and 17 (construct #8 ΔEGF9–17) abolished aggregation with Delta, while reinsertion of this piece into construct #3 ΔCla, which lacks EGF repeats 7–30, restored aggregation to roughly wild type levels (construct #13 ΔCla+EGF9–17), suggesting that EGF repeats 9 through 17 contain sequences important for binding to Delta. Second, all constructs in this series (#4–14) were consistent with the binding site mapping to EGF repeats 9 through 17. Expression constructs containing these repeats (#6, 7, 9, 10, 13) promoted Notch-Delta interactions while constructs lacking these repeats (#4, 5, 8, 11, 12, 14) did not. To confirm that inability to aggregate with Delta cells was not simply due to failure of the mutagenized Notch protein to reach the cell surface, but actually reflected the deletion of the necessary binding site, we tested for cell surface expression of all constructs by immunofluorescently staining live transfected cells with antibodies specific to the extracellular domain of Notch. All constructs failing to mediate Notch-Delta interactions produced a protein that appeared to be expressed normally at the cell surface. Third, although the aggregation assay is not quantitative, two constructs which contained EGF repeats 9–17, #9 ΔEGF17–26 or most noticeably #10 ΔEGF26–30, aggregated at a seemingly lower level. Cells transfected with constructs #9 ΔEGF17–26 and 10 ΔEGF26–30 showed considerably less surface staining than normal, although fixed and permeabilized cells reacted with the same antibody stained normally, indicating we had not simply deleted the epitopes recognized by the antisera. By comparing the percentage of transfected cells in either permeabilized or live cell populations, we found that roughly 50% of transfected cells for construct #9 ΔEGF17–26 and 10% for construct #10 ΔEGF26–30 produced detectable protein at the cell surface. Thus these two constructs produced proteins which often failed to reach the cell surface, perhaps because of misfolding, thereby reducing, but not abolishing, the ability of transfected cells to aggregate with Delta-expressing cells.

Having mapped the binding site to EGF repeats 9 through 17, we checked whether any Notch mutations whose molecular lesion has been determined mapped to this region. The only such mutation was split, a semidominant Notch allele that correlates with a point mutation in EGF repeat 14 (Hartley et al., 1987, EMBO J. 6, 3407–3417; Kelley et al., 1987, Mol. Cell. Biol. 6, 3094–3108). In fact, a genetic screen for second site modifiers of split revealed several alleles of Delta, suggesting a special relationship between the split allele of Notch, and Delta (Brand and Campus-Ortega, 1990, Roux's Arch. Dev. Biol. 198(5), 275–285). To test for possible effects of the split mutation on Notch-Delta mediated aggregation, an 11 kb fragment containing the missense mutation associated with split was cloned into the Notch expression construct (#15 split). However, aggregation with Delta-expressing cells was unaffected in this construct suggesting, as was confirmed by subsequent constructs, that EGF repeat 14 of Notch was not involved in the interactions with Delta modelled by our tissue culture assay.

Thus, to further map the Delta binding domain within EGF repeats 9–17, we used specific oligonucleotide primers and the PCR technique to generate several subfragments of this region. To be consistent with constructs #4–14 which produced proteins that were able to interact with Delta, we designed the primers to splice the EGF repeats just after the third cysteine, in the same place as the common ClaI site (FIG. 7). The resulting PCR products were ligated into the ClaI site of construct #3 ΔCla. Three overlapping constructs, #16, 17 and 18 were produced, only one of which, #16 ΔCla+EGF9–13, when transfected into S2 cells, allowed aggregation with Delta cells. Construct #19 ΔCla+EGF (10–13), which lacks EGF repeat 9, further defined EGF repeats 10–13 as the region necessary for Notch-Delta interactions.

Constructs #20–24 represented attempts to break this domain down even further using the same PCR strategy (see FIG. 7). We asked first whether both EGF repeats 11 and 12 were necessary, and second, whether the flanking sequences from EGF repeats 10 and 13 were directly involved in binding to Delta. Constructs #20 ΔCla+EGF(11–13), in which EGF repeat 12 is the only entire repeat added, and #21 ΔCla+EGF(10–12), in which EGF repeat 11 is the only entire repeat added, failed to mediate aggregation, suggesting that the presence of either EGF repeat 11 or 12 alone was not sufficient for Notch-Delta interactions. However, since the 3' ligation juncture of these constructs interrupted the overall structure of the EGF repeats, it was possible that a short "buffer" zone was needed to allow the crucial repeat to function normally. Thus for example in construct #19 ΔCla+EGF(10–13), EGF repeat 12 might not be directly involved in binding to Delta but instead might contribute the minimum amount of buffer sequence needed to protect the structure of EGF repeat 11, thereby allowing interactions with Delta. Constructs #22–24 addressed this issue. We designed PCR primers that broke at the end of the EGF repeat and therefore were less likely to disrupt the EGF disulfide formation at the 3' ligation juncture. Constructs #22 ΔCla+EGF(10–11), which did not mediate aggregation, and #23 ΔCla+EGF(10–12), which did, again suggested that both repeats 11 and 12 are required while the flanking sequence from repeat 13 clearly is not. Finally, construct #24 ΔCla+EGF(11–12), although now potentially structurally disrupted at the 5' junction, convincingly demonstrated that the sequences from EGF repeat 10 are not crucial. Thus based on entirely consistent data from 24 constructs, we propose that EGF repeats 11 and 12 of Notch together define the smallest functional unit obtainable from this analysis that contains the necessary sites for binding to Delta in transfected S2 cells.

7.2.2. EGF REPEATS 11 AND 12 OF NOTCH ARE SUFFICIENT FOR NOTCH-DELTA MEDIATED AGGREGATION

The large ClaI deletion into which PCR fragments were inserted (#3 ΔCla) retains roughly ⅓ of the original 36 EGF repeats as well as the three Notch/lin-12 repeats. While these are clearly not sufficient to promote aggregation, it is possible that they form a necessary framework within which specific EGF repeats can interact with Delta. To test whether only a few EGF repeats were in fact sufficient to promote aggregation, we designed two constructs, #25 ΔEGF which deleted all 36 EGF repeats except for the first two-thirds of repeat 1, and #30 ΔECN which deleted the entire extracellular portion of Notch except for the first third of EGF repeat 1 and ⁻35 amino acids just before the transmembrane domain. Fragments which had mediated Notch-Delta aggregation in the background of construct #3 ΔCla, when inserted into construct #25 ΔEGF, were again able to promote interactions with Delta (constructs #26–30). Analogous constructs (#31,32) in which the Notch/lin-12 repeats were also absent, again successfully mediated Notch-Delta aggregation. Thus EGF repeats 11 and 12 appear to function as independent modular units which are sufficient to mediate Notch-Delta interactions in S2 cells, even in the absence of most of the extracellular domain of Notch.

7.2.3. EGF REPEATS 11 AND 12 OF NOTCH MAINTAIN THE CALCIUM DEPENDENCE OF NOTCH-DELTA MEDIATED AGGREGATION

As described in Section 6, supra (Fehon et al., 1990, Cell 61, 523–534), we showed that Notch-Delta-mediated S2 cell aggregation is calcium dependent. We therefore examined the ability of cells expressing certain deletion constructs to aggregate with Delta expressing cells in the presence or absence of $Ca^{++}$ ions. We tested constructs #1 pMtNMg as a control, and #13, 16, 19, 23, 24, 26, 27 and 28, and found that cells mixed in $Ca^{++}$ containing medium at 4° C. readily formed aggregates while cells mixed in $Ca^{++}$ free medium containing EGTA failed to aggregate (Table III).

TABLE III

EFFECT OF EXOGENOUS $Ca^{++}$ ON NOTCH - DELTA AGGREGATION[a]

| | Without $Ca^{++}$ Ions | With $Ca^{++}$ Ions |
|---|---|---|
| 1. pMtNMg | 0 | 37 |
| 13. ΔCla + EGF(9–17) | 0 | 31 |
| 16. ΔCla + EGF(9–13) | 0 | 38 |
| 19. ΔCla + EGF(10–13) | 0 | 42 |
| 23. ΔCla + EGF(10–12) | 0 | 48 |
| 29. ΔEGF + EGF(10–12) | 0 | 44 |
| 32. ΔECN + EGF(10–12) | 0 | 39 |
| 33. ΔCla + XEGF(10–13 | 0 | 34 |

[a]Data presented as percentage of Notch-expressing cells found in aggregates (as in FIGS. 6A–6B).

Clearly, the calcium dependence of the interaction has been preserved in even the smallest construct, consistent with the notion that the minimal constructs containing EGF repeats 11 and 12 bind to Delta in a manner similar to that of full length Notch. This result is also interesting in light of recent studies suggesting EGF-like repeats with a particular consensus sequence may act as $Ca^{++}$ binding domains (Morita et al., 1984, J. Biol. Chem. 259, 5698–5704; Sugo et al., 1984, J. Biol. Chem. 259, 5705–5710; Rees et al., 1988, EMBO J. 7, 2053–2061; Handford et al., 1990, EMBO J. 9, 475–480). Over half of the EGF repeats in Notch, including repeats 11 and 12, conform to this consensus, further strengthening the argument that EGF repeats 11 and 12 are responsible for promoting Notch-Delta interactions.

7.2.4. THE DELTA BINDING FUNCTION OF EGF REPEATS 11 AND 12 OF NOTCH IS CONSERVED IN THE XENOPUS HOMOLOG OF NOTCH

Having mapped the Delta binding site to EGF repeats 11 and 12 of Notch, we were interested in asking whether this function was conserved in the Notch homolog that has been identified in Xenopus (Coffman et al., 1990, Science 249, 1438–1441). This protein shows a striking similarity to Drosophila Notch in overall structure and organization. For example, within the EGF repeat region both the number and linear organization of the repeats has been preserved, suggesting a possible functional conservation as well. To test this, we made PCR primers based on the Xenopus Notch sequence (Coffman et al., 1990, Science 249, 1438–1441) and used these to obtain an ~350 bp fragment from a Xenopus Stage 17 cDNA library that includes EGF repeats 11 and 12 flanked by half of repeats 10 and 13 on either side. This fragment was cloned into construct #3 ΔCla, and three independent clones were tested for ability to interact with Delta in the cell culture aggregation assay. Two of the clones, #33a&bΔCla+XEGF(10–13), when transfected into S2 cells were able to mediate Notch-Delta interactions at a level roughly equivalent to the analogous Drosophila Notch construct #19ΔCla+EGF(10–13), and again in a calcium dependent manner (Table III). However, the third clone #33cΔCla+XEGF(10–13) failed to mediate Notch-Delta interactions although the protein was expressed normally at the cell surface as judged by staining live unpermeabilized cells. Sequence comparison of the Xenopus PCR product in constructs #33a and 33c revealed a missense mutation resulting in a leucine to proline change (amino acid #453, Coffman, et al., 1990, Science 249, 1438–1441) in EGF repeat 11 of construct #33c. Although this residue is not conserved between Drosophila and Xenopus Notch (FIG. 8), the introduction of a proline residue might easily disrupt the structure of the EGF repeat, and thus prevent it from interacting properly with Delta.

Comparison of the amino acid sequence of EGF repeats 11 and 12 of Drosophila and Xenopus Notch reveals a high degree of amino acid identity, including the calcium binding consensus sequence (FIG. 8, SEQ ID NO:1 and NO:2). However the level of homology is not strikingly different from that shared between most of the other EGF repeats, which overall exhibit about 50% identity at the amino acid level. This one to one correspondence between individual EGF repeats suggests that perhaps they too may comprise conserved functional units.

7.3. DISCUSSION

We have continued our study of interactions between the protein products of the genes Notch and Delta, using the in vitro S2 cell aggregation assay described in Section 6, supra. Based on an extensive deletion analysis of the extracellular domain of Notch, we show that the regions of Notch containing EGF-homologous repeats 11 and 12 are both necessary and sufficient for Notch-Delta-mediated aggregation, and that this Delta binding capability has been conserved in the same two EGF repeats of Xenopus Notch. Our finding that the aggregation mapped to EGF repeats 11 and 12 of Notch demonstrates that the EGF repeats of Notch also function as specific protein binding domains.

Recent studies have demonstrated that EGF domains containing a specific consensus sequence can bind $Ca^{++}$ ions (Morita et al., 1984, J. Biol. Chem. 259, 5698–5704; Sugo et al., 1984, J. Biol. Chem. 259, 5705–5710; Rees et al., 1988, EMBO J. 7, 2053–2061; Handford et al., 1990, EMBO J. 9, 475–480). In fact, about one half of the EGF repeats in Notch, including. repeats 11 and 12, conform to this consensus. We have shown that exogenous $Ca^{++}$ was necessary for Notch-Delta mediated aggregation of transfected S2 cells (see Section 6; Fehon et al., 1990, Cell 61, 523–534). We tested a subset of our deletion constructs and found that EGF repeats 11 and 12 alone (#32ΔECN+EGF (11–12)) were sufficient to maintain the $Ca^{++}$ dependence of Notch-Delta interactions.

A number of studies have suggested that the genetic interactions between Notch and Delta may reflect a dose sensitive interaction between their protein products. Genetic studies have indicated that the relative gene dosages of Notch and Delta are crucial for normal development. For example, Xu et al. (1990, Genes Dev. 4, 464–475) found that null mutations at Delta could suppress lethal interactions between heterozygous combinations of Abruptex (Ax) alleles, a class of Notch mutations that correlate with missense mutations within the EGF repeats (Hartley et al., 1987, EMBO J. 6, 3407–3417; Kelley et al., 1987, Mol. Cell Biol. 6, 3094–3108). The in vitro interactions we have described in which we observe both Notch-Delta and Delta—Delta associations (see Section 6) imply that a competitive interaction between Notch and Delta for binding to Delta may reflect the underlying basis for the observed genetic interactions. Furthermore, we were able to coimmunoprecipate Notch and Delta from both tissue culture and embryonic cell extracts (see Section 6), indicating a possible in vivo association of the two proteins. In addition, mRNA in situ analyses of Notch and Delta expression patterns in the embryo suggest that expression of the two is overlapping but not identical (Kopczynski and Muskavitch, 1989, Development 107, 623–636; Hartley et al., 1987, EMBO J. 6, 3407–3417). Detailed antibody analysis of Notch protein expression during development have recently revealed Notch expression to be more restricted at the tissue and subcellular levels than previous studies had indicated (Johansen et al., 1989, J. Cell Biol. 109, 2427–2440; Kidd et al., 1989, Genes Dev. 3, 1113–1129).

Our finding that the same two EGF repeats from the Xenopus Notch homolog are also able to mediate interactions with Delta in tissue culture cells argues strongly that a similar function will have been conserved in vivo. Although these two EGF repeats are sufficient in vitro, it is of course possible that in vivo more of the Notch molecule may be necessary to facilitate Notch-Delta interactions. In fact, we were somewhat surprised for two reasons to find that the Delta binding site did not map to EGF repeats where several of the Ax mutations have been shown to fall, first, because of the genetic screen (Xu et al., 1990, Genes Dev. 4, 464–475) demonstrating interactions between Ax alleles and Delta mutations, and second, because of sequence analyses that have shown certain Ax alleles are associated with single amino acid changes within the putative $Ca^{++}$ binding consensus of the EGF repeats. For example, the $AX^{E2}$ mutation changes EGF repeat 29 toward the $Ca^{++}$ binding consensus sequence while the $AX^{9B2}$ mutation moves EGF repeat 24 away from the consensus. It is possible that in vivo these regions of the Notch protein may be involved in interactions, either with Delta and/or other proteins, that may not be accurately modelled by our cell culture assay.

Our in vitro mapping of the Delta binding domain to EGF repeats 11 and 12 of Notch represents the first assignment of function to a structural domain of Notch. In fact, the various deletion constructs suggest that these two EGF repeats function as a modular unit, independent of the immediate context into which they are placed. Thus, neither the remaining 34 EGF repeats nor the three Notch/lin-12 repeats appear necessary to establish a structural framework required for EGF repeats 11 and 12 to function. Interestingly, almost the opposite effect was observed: although our aggregation assay does not measure the strength of the interaction, as we narrowed down the binding site to smaller and smaller fragments, we observed an increase in the ability of the transfected cells to aggregate with Delta expressing cells, suggesting that the normal flanking EGF sequences actually impede association between the proteins. For two separate series of constructs, either in the background of construct #3 ΔCla (compare #9, 16, 19, 23) or in the background of construct #25 ΔEGF (compare #26, 27, 28), we observed an increase in ability to aggregate such that the smallest constructs (#19, 23, 28, 29) consistently aggregated above wild type levels (#1 pMtNMg). These results imply that the surrounding EGF repeats may serve to limit the ability of EGF repeats 11 and 12 to access Delta, thereby perhaps modulating Notch-Delta interactions in vivo.

Notch encodes a structurally complex transmembrane protein that has been proposed to play a pleotropic role throughout Drosophila development. The fact that EGF repeats 11 and 12 appear to function as an independent modular unit that is sufficient, at least in cell culture, for interactions with Delta, immediately presents the question of the role of the hypothesis is that these may also form modular binding domains for other proteins interacting with Notch at various times during development.

In addition to Xenopus Notch, lin-12 and qlp-1, two genes thought to function in cell-cell interactions involved in the specification of certain cell fates during *C. elegans* development, encode EGF homologous transmembrane proteins which are structurally quite similar to Drosophila and Xenopus Notch. All four proteins contain EGF homologous repeats followed by three other cysteine rich repeats (Notch/lin-12 repeats) in the extracellular domain, a single transmembrane domain, and six cdc10/ankyrin repeats in the intracellular region. Unlike Xenopus Notch, which, based on both sequence comparison as well as the results of our Delta binding assay, seems likely to encode the direct functional counterpart of Drosophila Notch, lin-12 and glp-1 probably encode distinct members of the same gene family. Comparison of the predicted protein products of lin-12 and glp-1 with Notch reveal specific differences despite an overall similar organization of structural motifs. The most obvious difference is that lin-12 and glp-1 proteins contain only 13 and 10 EGF repeats, respectively, as compared to the 36 for both Xenopus and Drosophila Notch. In addition, in the nematode genes the array of EGF repeats is interrupted after the first EGF repeat by a distinct stretch of sequence absent from Notch. Furthermore, with respect to the Delta binding domain we have defined as EGF repeats 11 and 12 of Notch, there are no two contiguous EGF repeats in the lin-12 or glp-1 proteins exhibiting the $Ca^{++}$ binding consensus sequence, nor any two contiguous repeats exhibiting striking similarity to EGF repeats 11 and 12 of Notch, again suggesting that the lin-12 and glp-1 gene products are probably functionally distinct from Notch.

Our finding that EGF repeats 11 and 12 of Notch form a discrete Delta binding unit represents the first concrete evidence supporting the idea that each EGF repeat or small subset of repeats may play a unique role during development, possibly through direct interactions with other proteins. The homologies seen between the adhesive domain of Delta and Serrate (see Section 8.3.4, infra) suggest that the homologous portion of Serrate is "adhesive" in that it mediates binding to other toporythmic proteins. In addition, the gene scabrous, which encodes a secreted protein with similarity to fibrinogen, may interact with Notch.

In addition to the EGF repeat, multiple copies of other structural motifs commonly occur in a variety of proteins. One relevant example is the cdc10/ankyrin motif, six copies of which are found in the intracellular domain of Notch. Ankyrin contains 22 of these repeats. Perhaps repeated arrays of structural motifs may in general represent a linear assembly of a series of modular protein binding units. Given these results together with the known structural, genetic and developmental complexity of Notch, Notch may interact with a number of different ligands in a precisely regulated temporal and spacial pattern throughout development. Such context specific interactions with extracellular proteins could be mediated by the EGF and Notch/lin-12 repeats, while interactions with cytoskeletal and cytoplasmic proteins could be mediated by the intracellular cdc10/ankyrin motifs.

8. THE AMINO-TERMINUS OF DELTA IS AN EGF-BINDING DOMAIN THAT INTERACTS WITH NOTCH AND DELTA

Aggregation of cultured cells programmed to express wild type and variant Delta proteins has been employed to delineate Delta sequences required for heterotypic interaction with Notch and homotypic Delta interaction. We have found that the amino terminus of the Delta extracellular domain is necessary and sufficient for the participation of Delta in heterotypic (Delta-Notch) and homotypic (Delta—Delta) interactions. We infer that the amino terminus of Delta is an EGF motif-binding domain (EBD), given that Notch EGF-like sequences are sufficient to mediate hetero-typic interaction with Delta. The Delta EBD apparently possesses two activities: the ability to bind EGF-related sequences and the ability to self-associate. We also find that Delta is taken up by cultured cells that express Notch, which may be a reflection of a mechanism by which these proteins interact in vivo.

8.1. MATERIALS AND METHODS
8.1.1. CELL LINES

The S2 Drosophila cell line (Schneider, 1972, J. Embryol. Exp. Morph. 27, 353–365)) used in these experiments was grown as described in Section 6.

8.1.2. IMMUNOLOGICAL PROBES

Immunohistochemistry was performed as described in Section 6, supra, or sometimes with minor modifications of this procedure. Antisera and antibodies employed included mouse polyclonal anti-Delta sera raised against a Delta ELR array segment that extends from the fourth through ninth ELRs (see Section 6); rat polyclonal anti-Delta sera raised against the same Delta segment (see Section 6); rat polyclonal anti-Notch sera raised against a Notch ELR array segment that extends from the fifth through thirteenth ELRs; mouse monoclonal antibody C17.9C6 (see Section 6), which recognizes the Notch intracellular domain; and mouse monoclonal antibody BP-104 (Hortsch et al., 1990, Neuron 4, 697–709), which recognizes the long form of Drosophila neuroglian.

8.1.3. EXPRESSION VECTOR CONSTRUCTS

Constructs employed to program expression of wild type Delta (pMTDl1) and wild type Notch (pMTNMg) are described in Section 6, supra. Constructs that direct expression of variant Delta proteins were generated using pMTDl1, the Dl1 cDNA cloned into Bhluescript+ (pBSDll; Kopczynski et al., 1988, Genes Dev. 2, 1723–1735), and pRmHa3–104 (A. J. Bieber, pers. comm.), which consists of the insertion of the 1B7A-250 cDNA into the metallothionein promoter vector pRmHa-3 (Bunch et al., 1988, Nucl. Acids Res. 16, 1043–1061) and supports inducible expression of the long form of Drosophila neuroglian (Hortsch et al., 1990, Neuron 4, 697–709).

Briefly, constructs were made as follows:

Del(Sca-Nae)—Cut pBSDl1 with SalI (complete digest) and ScaI (partial), isolate vector-containing fragment. Cut pBSDl1 with NaeI (partial) and SalI (complete), isolate Delta carboxyl-terminal coding fragment. Ligate fragments, transform, and isolate clones. Transfer EcoRI insert into pRmHa-3.

Del(Bam-Bgl)—Cut pBSDl1 with BglII (complete) and BamHI (partial), fill ends with Klenow DNA polymerase, ligate, transform, and isolate clones. Transfer EcoRI insert into pRmHa-3.

Del(ELR1-ELR3)—PCR-amplify basepairs 236–830 of the Dl1 CDNA using 5-ACTTCAGCAACGATCACGGG-3' (SEQ ID NO:26) and 5'-TTGGGTATGTGACAGTAATCG-3' (SEQ ID NO:27), treat with T4 DNA polymerase, ligate into pBSDl1 cut with ScaI (partial) and BglII (complete) and end-filled with Klenow DNA polymerase, transform, and isolate clones. Transfer BamHI-SalI Delta carboxyl-terminal coding fragment into pRmHa-3.

Del(ELR4-ELR5)—pBSDl1 was digested to completion with BglII and partially with PstI. The 5.6 kb vector-containing fragment was isolated, circularized using T4 DNA ligase in the presence of a 100× molar excess of the oligonucleotide 5'-GATCTGCA-3', and transformed and clones were isolated. The resulting EcoRI insert was then transferred into pRmHa-3.

Ter(Dde)—Cut pBSDl1 with DdeI (partial), end-fill with Klenow DNA polymerase, ligate with 100× molar excess of 5'-TTAAGTTAACTTAA-3' (SEQ ID NO:28), transform, and isolate clones. Transfer EcoRI insert into pRmHa-3.

Ins(Nae)A—Cut pMTDl1 with NaeI (partial), isolate vector-containing fragment, ligate with 100× molar excess of 5'-GGAAGATCTTCC-3' (SEQ ID NO:29), transform, and isolate clones.

NAE B—pMTDl1 was digested partially with NaeI, and the population of tentatively linearized circles approximately 5.8 kb in length was isolated. The fragments were recircularized using T4 DNA ligase in the presence of a 100× molar excess of the oligonucleotide 5'-GGAAGATCTTCC-3' (SEQ ID NO:29) and transformed, and a clone (NAE A) that contained multiple inserts of the linker was isolated. NAE A was digested to completion with BglII, and the resulting 0.4 kb and 5.4 kb fragments were isolated, ligated and transformed, and clones were isolated.

Ins(Stu)—Cut pMTDl1 with StuI (complete), isolate vector-containing fragment, ligate with 100× molar excess of 5'-GGAAGATCTTCC-3'(SEQ ID NO:29), transform and isolate clones.

STU B—pMTDl1 was digested completely with StuI, and the resulting 5.8 kb fragment was isolated. The fragment was recircularized using T4 DNA ligase in the presence of a 100× molar excess of the oligonucleotide 5'-GGAAGATCTTCC-3' (SEQ ID NO:29) and transformed, and a clone (STU A) that contained multiple inserts of the linker was isolated. STU B was digested to completion with BglII, and the resulting 0.6 kb and 5.2 kb fragments were isolated, ligated and transformed, and clones were isolated.

NG1—Cut pRmHa3–104 with BglII (complete) and EcoRI (complete), isolate vector-containing fragment. Cut Ins(Nae)A with EcoRI (complete) and BglII (complete), isolate Delta amino-terminal coding fragment. Ligate fragments, transform and isolate clones.

NG2—Cut pRmHa3–104 with BglII (complete) and EcoRI (complete), isolate vector-containing fragment. Cut Del(ELR1-ELR3) with EcoRI (complete) and BglII (complete), isolate Delta amino-terminal coding fragment. Ligate fragments, transform and isolate clones.

NG3—Cut pRmHa3–104 with BglII (complete) and EcoRI (complete), isolate vector-containing fragment. Cut pMTDl1 with EcoRI (complete) and BglII (complete), isolate Delta amino-terminal coding fragment. Ligate fragments, transform and isolate clones.

NG4—Cut pRmHa3–104 with BglII (complete) and EcoRI (complete), isolate vector containing fragment. Cut Del(Sca-Nae) with EcoRI (complete) and BglII (complete), isolate Delta amino-terminal coding fragment. Ligate fragments, transform and isolate clones.

NG5—Generate Del(Sca-Stu) as follows: cut pMTDl1 with ScaI (complete) and StuI (complete), isolate ScaI-ScaI amino-terminal coding fragment and StuI-ScaI carboxyl-terminal coding fragment, ligate, transform and isolate clones. Cut Del(Sca-Stu) with EcoRI (complete) and BglII (complete), isolate Delta amino terminal coding fragment. Cut pRmHa3–104 with BglII (complete) and EcoRI (complete), isolate vector-containing fragment. Ligate fragments, transform and isolate clones.

The sequence contents of the various Delta variants are shown in Table IV. Schematic diagrams of the Delta variants defined in Table IV are shown in FIG. 9C.

TABLE IV

SEQUENCE CONTENTS OF DELTA VARIANTS EMPLOYED IN THIS STUDY

|  | Nucleotides | Amino Acids |
|---|---|---|
| Wild type | 1-2892[A] | 1-833 |
| Del(Sca-Nae) | 1-235/734-2892 | 1-31/W/199-833 |
| Del(Bam-Bgl) | 1-713/1134-2892 | 1-191/332-833 |
| Del(ELR1-ELR3) | 1-830/1134-2892 | 1-230/332-833 |
| Del(ELR4-ELR5) | 1-1137/1405-2892 | 1-332/422-833 |
| Ter(Dde) | 1-2021/TTAAGTTAACTTAA[E]/2227-2892 | 1-626/H |
| Ins(Nae)A | 1-733/(GGAAGATCTTCC)$_n$[F]/734-2892[B] | 1-197/(RKIF)$_n$ 198-833 |
| NAE B | 1-733/GGAAGATCTTCC[F]/734-2892 | 1-197/RKIF 198-833 |
| Ins(Stu) | 1-535/(GGAAGATCTTCC)$_n$[F]/536-2892[B] | 1-131/G(KIFR)$_{n-1}$ KIFP/133-833 |
| STU B | 1-535/GGAAGATCTTCC[F]/536-2892 | 1-131/GKIFP 133-833 |
| NG1 | 1-733/GGAA/2889-3955(NG)[c] | 1-198/K/952-1302[D] |
| NG2 | 1-830/2889-3955(NG) | 1-230/952-1302 |
| NG3 | 1-1133/2889-3955(NG) | 1-331/952-1302 |
| NG4 | 1-235/734-1133/2889-3955(NG) | 1-31/199-331/952-1302 |
| NG5 | 1-235/536-1133/2889-3955(NG) | 1-31/S/133-952-1302 |

[A]Coordinates for Delta sequences correspond to the sequence of the Dl1 cDNA (FIGS. 12A–12C).
[B]The exact number of linkers inserted has not been determined for this construct.
[c]Coordinates for neuroglian (Bieber et al., 1989, Cell 59, 447–460; Hortsch et al., 1990, Neuron 4, 697–709) nucleotide sequences present in Delta-neuroglian chimeras correspond to the sequence of the 1B7A-250 cDNA (FIGS. 13A–13F, SEQ ID NO:5) and are indicated in bold face type.
[D]Neuroglian amino acid sequences are derived from conceptual translation of the 1B7A-250 cDNA nucleotide sequence (FIGS. 13A–13F, SEQ ID NO:5) and are indicated in bold face type.
[E]SEQ ID NO:28
[F]SEQ ID NO:29

8.1.4. AGGREGATION PROTOCOLS

Cell transfection and aggregation were performed as described in Section 6, supra, or with minor modifications thereof.

8.2. RESULTS 8.2.1. AMINO-TERMINAL SEQUENCES WITHIN THE DELTA EXTRACELLULAR DOMAIN ARE NECESSARY AND SUFFICIENT FOR THE HETEROTYPIC INTERACTION WITH NOTCH

Because we anticipated that some Delta variants might not be efficiently localized on the cell surface, we investigated the relationship between the level of expression of wild type Delta and the extent of aggregation with Notch-expressing cells by varying the input amount of Delta expression construct in different transfections. We found that the heterotypic Delta-Notch interaction exhibits only slight dependence on the Delta input level over a 10-fold range in this assay (FIGS. 9A–9B). Given the robustness of the heterotypic interaction over the range tested and our observations that each of the Delta variants we employed exhibited substantial surface accumulation in transfected cells, we infer that the inability of a given Delta variant to support heterotypic aggregation most probably reflects a functional deficit exhibited by that variant, as opposed to the impact of reduced levels of surface expression on heterotypic aggregation.

The results of the heterotypic aggregation experiments mediated by Delta variants and wild-type Notch are shown in Table V.

TABLE V

HETEROTYPIC AGGREGATION MEDIATED BY DELTA VARIANTS AND WILD TYPE NOTCH

| Construct | Aggregated Total[A] | Unaggregated Total | Expt. # | Aggregated Notch+ | Aggregated Delta+ | Unaggregated Notch+[B] | Unaggregated Delta+ |
|---|---|---|---|---|---|---|---|
| Wild type | 33 (H)[C] | 179 | 1 | 15 | 18 | 67 | 112 |
|  | 58 (H) | 247 | 2 | 37 | 21 | 218 | 29 |
|  | 38 (H) | 209 | 3 | 21 | 17 | 148 | 61 |
|  | 29 (H) | 174 | 4 | 18 | 11 | 95 | 79 |
|  | 175 (B) | 68 | 5 | 84 | 91 | 37 | 31 |
| Del (Sca—Nae) | 0 (H) | 207 | 1 | 0 | 0 | 125 | 82 |
|  | 0 (H) | 226 | 2 | 0 | 0 | 215 | 11 |
|  | 0 (H) | 287 | 3 | 0 | 0 | 215 | 72 |
|  | 0 (H) | 200 | 4 | ND[D] | ND | ND | ND |
| Del (Bam—Bgl) | 4 (H) | 245 | 1 | 3 | 1 | 171 | 74 |
|  | 0 (H) | 200 | 2 | 0 | 0 | 110 | 90 |
|  | 0 (H) | 200 | 3 | ND | ND | ND | ND |
| Del (ELR1–ELR3) | 28 (B) | 296 | 1 | 11 | 17 | 139 | 157 |
|  | 20 (B) | 90 | 2 | 9 | 11 | 53 | 37 |
|  | 22 (B) | 227 | 3 | 19 | 13 | 114 | 113 |
|  | 127 (B) | 97 | 4 | 19 | 78 | 66 | 61 |
| Del (ELR4–ELR5) | 38 (H) | 188 | 1 | 26 | 12 | 141 | 47 |
|  | 36 (H) | 204 | 2 | 20 | 16 | 90 | 114 |
| Ter (Dde) | 53 (H) | 236 | 1 | 24 | 29 | 144 | 92 |
|  | 51 (H) | 214 | 2 | 30 | 21 | 126 | 88 |
|  | 52 (H) | 190 | 3 | 30 | 22 | 110 | 80 |
| Ins (Nae) A | 0 (B) | 205 | 1 | 0 | 0 | 111 | 94 |
|  | 0 (B) | 254 | 2 | 0 | 0 | 161 | 93 |
|  | 0 (B) | 201 | 3 | 0 | 0 | 121 | 80 |
| NG1 | 0 (B) | 208 | 1 | 0 | 0 | 140 | 68 |
|  | 0 (B) | 114 | 2 | 0 | 0 | 38 | 76 |
|  | 0 (B) | 218 | 3 | 0 | 0 | 76 | 142 |
| NG2 | 14 (B) | 106 | 1 | 7 | 7 | 54 | 52 |
|  | 50 (B) | 216 | 2 | 35 | 15 | 94 | 122 |
|  | 36 (B) | 168 | 3 | 12 | 24 | 29 | 139 |
| NG3 | 71 (B) | 175 | 1 | 43 | 28 | 84 | 91 |
| NG4 | 0 (B) | 254 | 1 | 0 | 0 | 150 | 104 |
|  | 0 (B) | 215 | 2 | 0 | 0 | 35 | 180 |
|  | 0 (B) | 200 | 3 | 0 | 0 | 93 | 107 |

[A]Total number of expressing cells in aggregates that contain four or more cells.
[B]Cells that express neuroglian-based constructs (NGn) were detected using a monoclonal antibody that recognizes the intracellular domain of neuroglian (see Materials and Methods).
[C](H) indicates that cells were aggregated in a 25 ml Erlenmeyer flask, (B) indicates that cells were aggregated in a 12-well microtiter plate (see Materials and Methods).
[D]Data for individual cell types (i.e., Delta+ and Notch+) in aggregates and unaggregated were not recorded.

Delta amino acids (AA) 1–230 is the current minimum sequence interval defined as being sufficient for interaction with Notch. This is based on the success of NG2-Notch aggregation. Within this interval, Delta AA198–230 are critical because their deletion in the NG1 construct inactivated the Notch-binding activity observed for the NG2 construct. Also within this interval, Delta AA32–198 are critical because their deletion in the NG4 construct also inactivated the Notch-binding activity observed for the NG3 construct. The importance of Delta AA192–230 is also supported by the observation that the Del(ELR1-ELR3) variant, which contains all Delta amino acids except AA231–331, possessed Notch-binding activity, while the Del(Bam-Bgl) variant, which contains all Delta amino acids except AA192–331, was apparently inactivated for Notch-binding activity.

Conformation and/or primary sequence in the vicinity of Delta AA197/198 is apparently critical because a multimeric insertion of the tetrapeptide -Arg-Lys-Ile-Phe [in one letter code (see e.g. Lehninger et al., 1975, Biochemistry, 2d ed., p. 72), RKIF] (SEQ ID NO:30)—between these two residues, as in the Ins(Nae)A construct, inactivated the Notch-binding activity observed with wild type Delta.

In addition, the observation that the Del(ELR1-ELR3) construct supported aggregation implies that ELR1-ELR3 are not required for Delta-Notch interaction; the observation that the Del(ELR4-ELR5) construct supported aggregation implies that ELR4 and ELR5 are not required for Delta-Notch interaction, and the observation that the Ter(Dde) construct supported aggregation implies that the Delta intracellular domain is not required for Delta-Notch interaction.

8.2.2. AMINO-TERMINAL SEQUENCES WITHIN THE DELTA EXTRACELLULAR DOMAIN ARE NECESSARY AND SUFFICIENT FOR HOMOTYPIC INTERACTION

The results of the homotypic aggregation experiments mediated by Delta variants is shown in Table VI.

TABLE VI

HOMOTYPIC AGGREGATION MEDIATED BY DELTA VARIANTS

| Construct | Aggregated | Unaggregated | Expt. # |
|---|---|---|---|
| Wild type | 38 (H)[A] | 175 | 1 |
|  | 48 (H) | 171 | 2 |
|  | 13 (H) | 95 | 3 |
|  | 33 (H) | 173 | 4 |
|  | 134 (B) | 72 | 5 |
| Del(Sca-Nae) | 0 (H) | 200 | 1 |

TABLE VI-continued

HOMOTYPIC AGGREGATION MEDIATED BY DELTA VARIANTS

| Construct | Aggregated | Unaggregated | Expt. # |
|---|---|---|---|
| | 0 (H) | 200 | 2 |
| | 0 (H) | 200 | 3 |
| Del(Bam-Bgl) | 0 (H) | 200 | 1 |
| | 0 (H) | 200 | 2 |
| | 0 (H) | 200 | 3 |
| Del(ELR1-ELR3) | 160 (B) | 62 | 1 |
| | 55 (B) | 80 | 2 |
| | 0 (B) | 200 | 3 |
| | 4 (B) | 203 | 4 |
| | 41 (B) | 234 | 5 |
| | 4 (B) | 366 | 6[B] |
| | 23 (B) | 325 (1:20) | |
| | 0 (B) | 400 | 7[B] |
| | 5 (B) | 347 (1:5) | |
| | 10 (B) | 228 (1:20) | |
| | 0 (B) | 400 | 8[B] |
| | 16 (B) | 346 (1:5) | |
| | 4 (B) | 268 (1:20) | |
| | 4 (B) | 500 | 9[C] |
| | 18 (B) | 500 (1:5) | |
| | 12 (B) | 271 (1:20) | |
| | 7 (B) | 128 (1:50) | |
| | 0 (B) | 500 | 10[C] |
| | 0 (B) | 500 (1:5) | |
| | 0 (B) | 500 (1:20) | |
| | 21 (B) | 246 (1:50) | |
| | 0 (B) | 500 | 11[C] |
| | 5 (B) | 500 (1:5) | |
| | 8 (B) | 177 (1:20) | |
| | 4 (B) | 69 (1:50) | |
| Del(ELR4-ELR5) | 21 (H) | 175 | 1 |
| | 29 (H) | 243 | 2 |
| | 35 (H) | 179 | 3 |
| Ter(Dde) | 53 (H) | 164 | 1 |
| | 33 (H) | 178 | 2 |
| | 36 (H) | 203 | 3 |
| Ins(Nae)A | 0 (B) | 200 | 1 |
| | 0 (B) | 200 | 2 |
| | 0 (B) | 200 | 3 |

[A](H) indicates that cells were aggregated in a 25 ml Erlenmeyer flask; (B) indicates that cells were aggregated in a 12-well microtiter plate (see Materials and Methods).
[B]Transfected cells were incubated under aggregation conditions overnight, then diluted into the appropriate volume of log-phase S2 cells in the presence of inducer and incubated under aggregation conditions for an additional four to six hours.
[C]Transfected cells to which inducer had been added were diluted into the appropriate volume of log-phase S2 cells to which inducer had been added, and the cell mixture was incubated under aggregation conditions overnight.

Deletion of Delta AA32–198 [Del(Sca-Nae)] or Delta AA192–331 [Del(Bam-Bgl)] from the full-length Delta protein eliminated the Delta—Delta interaction. Deletion of Delta AA231–331 [Del(ELR1–ELR3)] did not eliminate the Delta—Delta interaction. Therefore, sequences within the Delta AA32–230 are required for the Delta—Delta interaction.

Conformation and/or primary sequence in the vicinity of Delta AA197/198 is apparently critical for the Delta—Delta interaction because a multimeric insertion of the tetrapeptide -Arg-Lys-Ile-Phe- (SEQ ID NO:30) between these two residues, as in the Ins(Nae)A construct, inactivated Delta—Delta interaction.

In addition, the observation that the Del(ELR1–ELR3) construct could support aggregation implies that ELR1–ELR3 are not required for Delta—Delta interaction; the observation that the Del(ELR–ELR5) construct supported aggregation implies that ELR4 and ELR5 are not required for Delta—Delta interaction, and the observation that the Ter(Dde) construct supported aggregation implies that the Delta intracellular domain is not required for Delta—Delta interaction.

A summary of the results of assays for heterotypic and homotypic aggregation with various constructs are shown in Table VI A.

TABLE VI A

AGGREGATION MEDIATED BY WILD TYPE AND VARIANT DELTA PROTEINS

| | HETEROTYPIC AGGREGATION[a] | | HOMOTYPIC AGGREGATION[b] |
|---|---|---|---|
| CONSTRUCT | DELTA | NOTCH | DELTA |
| Wild Type | 33 ± 12[c] | 26 ± 11[c] | 27 ± 10[c] |
| Del(Sca-Nae) | 0 | 0 | 0 |
| Del(Bam-Bgl) | 0.4 ± 0.4 | 0.6 ± 0.6 | 0 |
| Del(ELR1-ELR3) | 25 ± 11[d] | 15 ± 3[d] | 32 + 15[d] |
| Del(ELR4-ELR5) | 17 ± 2 | 18 ± 2 | 13 ± 2 |
| Ter(Dde) | 22 ± 1 | 18 ± 2 | 18 ± 3 |
| NAE B | 25 ± 5 | 0 | 27 ± 7 |
| STU B | 0 | 0 | 0 |
| NG1 | 0 | 0 | 0 |
| NG2 | 13 ± 1 | 23 ± 6 | 4 ± 1[d] |
| NG3 | 16 ± 1 | 13 ± 1 | 27 ± 17 |
| NG4 | 0 | 0 | 0.5 ± 0.3 |

[a]Mean fraction (%) of Delta or Notch cells in aggregates of four or more cells (± standard error). N = 3 replicates, unless otherwise noted.
[b]Mean fraction (%) of Delta cells in aggregates of four or more cells (± standard error). N = 3 replicates, unless otherwise noted.
[c]N = 5 replicates.
[d]N = 4 replicates.

8.2.3. DELTA SEQUENCES INVOLVED IN HETEROTYPIC AND HOMOTYPIC INTERACTIONS ARE QUALITATIVELY DISTINCT

The respective characteristics of Delta sequences repaired for heterotypic and homotypic interaction were further defined using Delta variants in which short, in-frame, translatable linker insertions were introduced into the Delta amino terminus (i.e., NAE B and STU B; FIG. 9C, Table VI A). Replacement of Delta residue 132 (A) with the pentapeptide GKIFP (STU B variant) leads to the inactivation of heterotypic and homotypic interaction activities of the Delta amino terminus. This suggests that some Delta sequences required for these two distinct interactions are coincident and reside in proximity to residue 132. On the other hand, insertion of the tetrapeptide RKIF between Delta residues 198 and 199 (NAE B variant) eliminates the ability of the Delta amino terminus to mediate heterotypic interaction with Notch, but has no apparent effect on the ability of the altered amino terminus to mediate homotypic interaction. The finding that the NAE B insertion affects only one of the two activities of the Delta amino terminus implies that the Delta sequences that mediate heterotypic and homotypic interactions, while coincident, are qualitatively distinct.

8.2.4. DELTA IS TAKEN UP BY CELLS THAT EXPRESS NOTCH

During the course of many heterotypic aggregation experiments, we have noted that Delta protein can sometimes be found within cells that have been programmed to express Notch, but not Delta. We conduct heterotypic aggregation assays by mixing initially separate populations of S2 cells that have been independently transfected with expression constructs that program expression of either Delta or Notch. Yet, we often detect punctate staining of Delta within Notch-expressing cells found in heterotypic aggregates using Delta-specific antisera. Our observations are consistent with Delta binding directly to Notch at the cell surface and subsequent clearance of this Delta-Notch complex from the cell surface via endocytosis.

8.3. DISCUSSION
8.3.1. AMINO-TERMINAL SEQUENCES UNRELATED TO EGF ARE INVOLVED IN THE INTERACTION BETWEEN DELTA AND NOTCH

We have employed cell aggregation assays to define a region within the amino-proximal region of the Delta extracellular domain that is necessary and sufficient to mediate the Delta-Notch interaction. Functional analyses of a combination of deletion and sufficiency constructs revealed that this region extends, maximally, from AA1 through AA230. It is striking that this region does not include any of the EGF-like sequences that reside within the Delta extracellular domain. It is probable that the particular Delta sequences within the sufficient interval required for interaction with Notch include AA198–230 because deletion of these residues eliminates Notch-binding activity. The fact that deletion of AA32–198 also inactivates Notch-binding activity suggests that sequences amino-proximal to AA198 are also required, although the deleterious impact of this deletion could result from the removal of additional amino acids in the immediate vicinity of AA198.

Sequences within Delta sufficient for interaction with Notch can be grouped into three subdomains—N1, N2, and N3—that differ in their respective contents of cysteine residues (FIG. 10, SEQ ID NO:3). The N1 and N3 domains each contain six cysteine residues, while the N2 domain contains none. The even number of cysteines present in N1 and N3, respectively, allows for the possibility that the respective structures of these subdomains are dictated, in part, by the formation of particular disulfide bonds. The broad organizational pattern of the Delta amino-terminus is also generally analogous to that of the extracellular domain of the vertebrate EGF receptor (Lax et al., 1988, Mol. Cell. Biol. 8, 1970–1978), in which sequences believed to interact with EGF are bounded by two cysteine-rich subdomains.

8.3.2. DELTA SEQUENCES REQUIRED FOR HOMOTYPIC AND FOR HOMOTYPIC HETEROTYPIC INTERACTIONS APPEAR TO BE COINCIDENT

Our results also indicate that sequences essential for homotypic Delta interaction reside within the interval AA32–230. Deletion of sequences or insertion of additional amino acids within this amino-proximal domain eliminate the ability of such Delta variants to singly promote cell aggregation. Thus, sequences required for Dleta—Delta interaction map within the same domain of the protein as those required for Delta-Notch interaction.

8.3.3. THE DELTA AMINO TERMINUS CONSTITUTES AN EGF-BINDING MOTIF

The work described in examples supra has revealed that Notch sequences required for Delta-Notch interaction in the cell aggregation assay map within the EGF-like repeat array of the Notch extracellular domain. This finding implies that Delta and Notch interact by virtue of the binding of the Delta amino-terminus to EGF-like sequences within Notch and, therefore, that the amino-terminus of the Delta extracellular domain constitutes an EGF-binding domain (FIGS. 11A–11B).

These results also raise the possibility that homotypic Delta interaction involves the binding of the Delta amino-terminus to EGF-like sequences within the Delta extracellular domain (FIGS. 12A–12C). However, none of the EGF-like repeats within the Delta extracellular domain are identical to any of the EGF-like repeats within the Notch extracellular domain (FIGS. 13A–13F, SEQ ID NO:6; Wharton et al., 1985, Cell 43, 567–581). Given this fact, if Delta homotypic interactions are indeed mediated by interaction between the Delta amino-terminus and Delta EGF-like repeats, then the Delta EGF-binding domain has the capacity to interact with at least two distinct EGF-like sequences.

8.3.4. DELTA SEQUENCES INVOLVED IN THE DELTA-NOTCH INTERACTION ARE CONSERVED IN THE SERRATE PROTEIN

Alignment of amino acid sequences from the amino termini of the Delta (FIGS. 13A–13F, SEQ ID NO:6, and FIGS. 15A–15B, SEQ ID NO:9) and Serrate (Fleming et al., 1990, Genes & Dev. 4, 2188–2201; Thomas et al., 1991, Devel. 111, 749–761) reveals a striking conservation of structural character and sequence composition. The general N1-N2-N3 subdomain structure of the Delta amino terminus is also observed within the Serrate amino terminus, as is the specific occurrence of six cysteine residues within the Delta N1- and Delta N3-homologous domains of the Serrate protein. Two notable blocks of conservation correspond to Delta AA63–73 (8/11 residues identical) and Delta AA195–206 (10/11 residues identical). The latter block is of particular interest because insertion of additional amino acids in this interval can eliminate the ability of Delta to bind to Notch or Delta.

8.3.5. CIS AND TRANS INTERACTIONS BETWEEN DELTA AND NOTCH MAY INVOLVE DIFFERENT SEQUENCES WITHIN NOTCH

Inspection of the overall structures of Delta and Notch suggests that Delta-Notch interaction could involve contacts between the Delta EGF-binding domain with either of two regions within Notch, depending on whether the interaction were between molecules that reside on opposing membranes or within the same membrane (FIGS. 11A–11B). The cell aggregation assays, which presumably detect the interaction of molecules in opposing membranes, imply that the Delta EGF-binding domain interacts with Notch EGF-like repeats 11 and 12 (see examples supra). If tandem arrays of EGF-like motifs do form rod-like structures (Engel, 1989, FEBS Lett. 251, 1–7) within the Delta and Notch proteins, then the estimated displacement of the Delta EGF-binding domain from the cell surface would presumably be sufficient to accommodate the rigid array of Notch EGF-like repeats 1–10. It is also intriguing to note that the displacement of the Delta EGF-binding domain from the cell surface could place this domain in the vicinity of the Notch EGF-like repeats (25–29) that are affected by Abruptex mutations (Hartley et al., 1987, EMBO J. 6, 3407–3417; Kelley et al., 1987, Mol. Cell. Biol. 6, 3094–3108) and could allow for interaction of Delta and Notch proteins present within the same membrane.

8.3.6. INTERACTIONS ANALOGOUS TO THE DELTA-NOTCH INTERACTION IN VERTEBRATES

Given the interaction between Delta and Notch in Drosophila, it is quite probable that a Delta homologue (Helta?) exists in vertebrates and that the qualitative and molecular aspects of the Delta-Notch and Delta—Delta interactions that we have defined in Drosophila will be highly conserved in vertebrates, including humans. Such homologs can be cloned and sequenced as described supra, Section 5.2.

9. SEQUENCES WHICH MEDIATE NOTCH-SERRATE INTERACTIONS

We report a novel molecular interaction between Notch and Serrate, and show that the two EGF repeats of Notch which mediate interactions with Delta, namely EGF repeats 11 and 12, also constitute a Serrate binding domain.

To test whether Notch and Serrate directly interact, S2 cells were transfected with a Serrate expression construct and mixed with Notch expressing cells in our aggregation assay. For the Serrate expression construct, a synthetic primer containing an artificial BamHI site immediately 5' to the initiator AUG at position 442 (all sequence numbers are according to Fleming et al., 1990, Genes & Dev. 4:2188–2201) and homologous through position 464, was used in conjunction with a second primer from position 681–698 to generate a DNA fragment of ~260 base pairs. This fragment was cut with BamHI and KpnI (position 571) and ligated into Bluescript KS+ (Stratagene). This construct, BTSer5'PCR, was checked by sequencing, then cut with KpnI. The Serrate KpnI fragment (571–2981) was inserted and the proper orientation selected, to generate BTSer5'PCR-Kpn. The 5' SacII fragment of BTSer5'PCR-Kpn (SacII sites in Bluescript polylinker and in Serrate (1199)) was isolated and used to replace the 5' SacII fragment of cDNA C1 (Fleming et al., 1990, Genes & Dev. 4:2188–2201), thus regenerating the full length Serrate cDNA minus the 5' untranslated regions. This insert was isolated by a SalI and partial BamHI digestion and shuttled into the BamHI and SalI sites of pRmHa-3 to generate the final expression construct, Ser-mtn.

We found that Serrate expressing cells adhere to Notch expressing cells in a calcium dependent manner (FIGS. 6A–6B and Table VII). However, unlike Delta, under the experimental conditions tested, Serrate does not appear to interact homotypically. In addition, we detect no interactions between Serrate and Delta.

TABLE VII

Effect of Exogenous Ca++ on Notch - Serrate Aggregation<sup>a</sup>

| | Notch-Serrate | |
|---|---|---|
| | Without Ca++ | With Ca++ |
| 1. pMtNMg | 0 | 15 |
| 32. ΔECN + EGF(10–12) | 0 | 13 |
| 33. ΔCla + XEGF(10–13) | 0 | 15 |

<sup>a</sup>Data presented as percentage of Notch expressing cells found in aggregates (as in FIGS. 6A–6B). All numbers are from single transfection experiments (rather than an average of values from several separate experiments as in FIGS. 6A–6B).

We have tested a subset of our Notch deletion constructs to map the Serrate-binding domain and have found that EGF repeats 11 and 12, in addition to binding to Delta, also mediate interactions with Serrate (FIGS. 6A–6B; Constructs #1, 7–10, 13, 16, 17, 19, 28, and 32). In addition, the Serrate-binding function of these repeats also appears to have been conserved in the corresponding two EGF repeats of Xenopus Notch (#33ΔCla+XEGF(10–13)). These results unambiguously show that Notch interacts with both Delta and Serrate, and that the same two EGF repeats of Notch mediate both interactions. We were also able to define the Serrate region which is essential for the Notch/Serrate aggregation. Deleting nucleotides 676–1287 (i.e. amino acids 79–282) (See FIGS. 15A–15B) eliminates the ability of the Serrate protein to aggregate with Notch.

Notch and Serrate appear to aggregate less efficiently than Notch and Delta, perhaps because the Notch-Serrate interaction is weaker. For example, when scoring Notch-Delta aggregates, we detect ~40% of all Notch expressing cells in clusters with Delta expressing cells (FIGS. 6A–6B, #1 pMtNMg) and ~40% of all Delta expressing cells in contact with Notch expressing cells. For Notch-Serrate, we find only ~20% of all Notch expressing cells (FIGS. 6A–6B; pMtNMg) and ~15% of all Serrate expressing cells in aggregates. For the various Notch deletion constructs tested, we consistently detect a reduction in the amount of aggregation between Notch and Serrate as compared to the corresponding Notch-Delta levels (FIGS. 6A–6B), with the possible exception of constructs #9 and 10 which exhibit severely reduced levels of aggregation even with Delta. One trivial explanation for this reduced amount of aggregation could be that our Serrate construct simply does not express as much protein at the cell surface as the Delta construct, thereby diminishing the strength of the interaction. Alternatively, the difference in strength of interaction may indicate a fundamental functional difference between Notch-Delta and Notch-Serrate interactions that may be significant in vivo.

10. THE CLONING, SEQUENCING, AND EXPRESSION OF HUMAN NOTCH 10.1. ISOLATION AND SEQUENCING OF HUMAN NOTCH

Clones for the human Notch sequence were originally obtained using the polymerase chain reaction (PCR) to amplify DNA from a 17–18 week human fetal brain cDNA library in the Lambda Zap II vector (Stratagene). Degenerate primers to be used in this reaction were designed by comparing the amino acid sequences of the Xenopus homolog of Notch with Drosophila Notch. Three primers (cdc1 (SEQ ID NO:10), cdc2 (SEQ ID NO:11), and cdc3 (SEQ ID NO:12); FIGS. 16A–16C) were designed to amplify either a 200 bp or a 400 bp fragment as primer pairs cdc1/cdc2 or cdc1/cdc3, respectively.

The 400 bp fragment obtained in this manner was then used as a probe with which to screen the same library for human Notch clones. The original screen yielded three unique clones, hN3k, hN2K, and hN5k, all of which were shown by subsequent sequence analysis to fall in the 3' end of human Notch (FIG. 17). A second screen using the 5' end of hN3k as probe was undertaken to search for clones encompassing the 5' end of human Notch. One unique clone, hN4k, was obtained from this screen, and preliminary sequencing data indicate that it contains most of the 5' end of the gene (FIG. 17). Together, clones hN4k, hN3k and hN5k encompass about 10 kb of the human Notch homolog, beginning early in the EGF-repeats and extending into the 3' untranslated region of the gene. All three clones are cDNA inserts in the EcoRI site of pBluescript SK<sup>−</sup> (Stratagene). The host E. coli strain is XL1-Blue (see Maniatis, T., 1990, Molecular Cloning, A Laboratory Manual, 2d ed., Cold Spring Harbor Laboratory, Cold Spring Harbor, N.Y., p. A12).

The sequence of various portions of Notch contained in the cDNA clones was determined (by use of Sequenase®, U.S. Biochemical Corp.) and is shown in FIGS. 19A–22D (SEQ ID NO:13 through NO:25).

The complete nucleotide sequences of the human Notch cDNA contained in hN3k and hN5k was determined by the dideoxy chain termination method using the Sequenase® kit (U.S. Biochemical Corp.). Those nucleotide sequences encoding human Notch, in the appropriate reading frame, were readily identified since translation in only one out of the three possible reading frames yields a sequence which, upon comparison with the published Drosophila Notch deduced amino acid sequence, yields a sequence with a substantial degree of homology to the Drosophila Notch sequence. Since there are no introns, translation of all three possible reading frames and comparison with Drosophila Notch was easily accomplished, leading to the ready identification of the coding region. The DNA and deduced protein sequences of the human Notch cDNA in hN3k and hN5k are presented in FIGS. 23A–23Q and and 24A–24G, respectively. Clone hN3k encodes a portion of a Notch polypeptide starting at approximately the third Notch/lin-12 repeat to several amino acids short of the carboxy-terminal amino acid. Clone hN5k encodes a portion of a Notch polypeptide starting approximately before the cdc10 region through the end of the polypeptide, and also contains a 3' untranslated region.

Comparing the DNA and protein sequences presented in FIGS. 23A–23Q (SEQ ID NO:31 and NO:32) with those in FIGS. 24A–24G (SEQ ID NO:33 and NO:34) reveals significant differences between the sequences, suggesting that hN3k and hN5k represent part of two distinct Notch-homologous genes. Our data thus suggest that the human genome harbors more than one Notch-homologous gene. This is unlike Drosophila, where Notch appears to be a single-copy gene.

Comparison of the DNA and amino acid sequences of the human Notch homologs contained in hN3k and hN5k with the corresponding Drosophila Notch sequences (as published in Wharton et al., 1985, Cell 43:567–581) and with the corresponding Xenopus Notch sequences (as published in Coffman et al., 1990, Science 249:1438–1441 or available from Genbank® (accession number M33874)) also revealed differences.

The amino acid sequence shown in FIGS. 23A–23Q (hN3k) was compared with the predicted sequence of the TAN-1 polypeptide shown in FIG. 2 of Ellisen et al., August 1991, Cell 66:649–661. Some differences were found between the deduced amino acid sequences; however, overall the hN3k Notch polypeptide sequence is 99% identical to the corresponding TAN-1 region (TAN-1 amino acids 1455 to 2506). Four differences were noted: in the region between the third Notch/lin-12 repeat and the first cdc10 motif, there is an arginine (hN3k) instead of an X (TAN-1 amino acid 1763); (2) there is a proline (hN3k) instead of an X (TAN-1, amino acid 1787); (3) there is a conservative change of an aspartic acid residue (hN3k) instead of a glutamic acid residue (TAN-1, amino acid 2495); and (4) the carboxyl-terminal region differs substantially between TAN-1 amino acids 2507 and 2535.

The amino acid sequence shown in FIGS. 24A–24G (hN5k) was compared with the predicted sequence of the TAN-1 polypeptide shown in FIG. 2 of Ellisen et al., August 1991, Cell 66:649–661. Differences were found between the deduced amino acid sequences. The deduced Notch polypeptide of hN5k is 79% identical to the TAN-1 polypeptide (64% identical to Drosophila Notch) in the cdc10 region that encompasses both the cc10 motif (TAN-1 amino acids 1860 to 2217) and the well-conserved flanking regions (FIG. 25). The cdc10 region covers amino acids 1860 through 2217 of the TAN-1 sequence. In addition, the hN5k encoded polypeptide is 65% identical to the TAN-1 polypeptide (44% identical to Drosophila Notch) at the carboxy-terminal end of the molecule containing a PEST (proline, glutamic acid, serine, threonine)-rich region (TAN-1 amino acids 2482 to 2551) (FIG. 25B). The stretch of 215 amino acids lying between the aforementioned regions is not well conserved among any of the Notch-homologous clones represented by hN3k, hN5k, and TAN-1. Neither the hN5k polypeptide nor Drosophila Notch shows significant levels of amino acid identity to the other proteins in this region (e.g., hN5k/TAN-1=24% identity; hN5k/Drosophila Notch=11% identity; TAN-1/Drosophila Notch=17% identity). In contrast, Xenopus Notch (Xotch) (SEQ ID NO:35), rat Notch (SEQ ID NO:36), and TAN-1 (SEQ ID NO:37) continue to share significant levels of sequence identity with one another (e.g., TAN-1/rat Notch=75% identity, TAN-1/Xenopus Notch=45% identity, rat Notch/Xenopus Notch=50% identity).

Finally, examination of the sequence of the intracellular domains of the vertebrate Notch homologs shown in FIGS. 25B–25C revealed an unexpected finding: all of these proteins, including hN5k, contain a putative CcN motif, associated with nuclear targeting function, in the conserved region following the last of the six cdc10 repeats (FIGS. 25B–25C). Although Drosophila Notch lacks such a defined motif, closer inspection of its sequence revealed the presence of a possible bipartite nuclear localization sequence (Robbins et al., 1991, Cell 64:615–623), as well as of possible CK II and cdc2 phosphorylation sites, all in relative proximity to one another, thus possibly defining an alternative type of CcN motif (FIGS. 25B–25C).

10.2. EXPRESSION OF HUMAN NOTCH

Expression constructs were made using the human Notch cDNA clones discussed in Section 10.1 above. In the cases of hN3k and hN2k, the entire clone was excised from its vector as an EcoRI restriction fragment and subcloned into the EcoRI restriction site of each of the three pGEX vectors (Glutathione S-Transferase expression vectors; Smith and Johnson, 1988, Gene 7, 31–40). This allows for the expression of the Notch protein product from the subclone in the correct reading frame. In the case of hN5k, the clone contains two internal EcoRI restriction sites, producing 2.6, 1.5 and 0.6 kb fragments. Both the 2.6 and the 1.5 kb fragments have also been subcloned into each of the pGEX vectors.

The pGEX vector system was used to obtain expression of human Notch fusion (chimeric) proteins from the constructs described below. The cloned Notch DNA in each case was inserted, in phase, into the appropriate pGEX vector. Each construct was then electroporated into bacteria (*E. coli*), and was expressed as a fusion protein containing the Notch protein sequences fused to the carboxyl terminus of glutathione S-transferase protein. Expression of the fusion proteins was confirmed by analysis of bacterial protein extracts by polyacrylamide gel electrophoresis, comparing protein extracts obtained from bacteria containing the pGEX plasmids with and without the inserted Notch DNA. The fusion proteins were soluble in aqueous solution, and were purified from bacterial lysates by affinity chromatography using glutathione-coated agarose (since the carboxyl terminus of glutathione S-transferase binds to glutathionine). The expressed fusion proteins were bound by an antibody to Drosophila Notch, as assayed by Western blotting.

The constructs used to make human Notch-glutathione S-transferase fusion proteins were as follows:

hNFP#2—PCR was used to obtain a fragment starting just before the cdc10 repeats at nucleotide 192 of the hN5k insert to just before the PEST-rich region at nucleotide 1694. The DNA was then digested with BamHI and SmaI and the resulting fragment was ligated into pGEX-3. After expression, the fusion protein was purified by binding to glutathione agarose. The purified polypeptide was quantitated on a 4–15% gradient polyacrylamide gel. The resulting fusion protein had an approximate molecular weight of 83 kD.

hN3FP#1—The entire hN3k DNA insert (nucleotide 1 to 3235) was excised from the Bluescript (SK) vector by digesting with EcoRI. The DNA was ligated into pGEX-3.

hN3FP#2—A 3' segment of hN3k DNA (nucleotide 1847 to 3235) plus some of the polylinker was cut out of the Bluescript (SK) vector by digesting with XmaI. The fragment was ligated into pGEX-1.

Following purification, these fusion proteins are used to make either polyclonal and/or monoclonal antibodies to human Notch.

| Bacteria | carrying | Plasmid | ATCC Accession No. |
|---|---|---|---|
| E. coli XL1-Blue | | hN4k | 68610 |
| E. coli XL1-Blue | | hN3k | 68609 |
| E. coli XL1-Blue | | hN5k | 68611 |

11. DEPOSIT OF MICROORGANISMS

The following recombinant bacteria, each carrying a plasmid encoding a portion of human Notch, were deposited on May 2, 1991 with the American Type Culture Collection, 1201 Parklawn Drive, Rockville, Md. 20852, under the provisions of the Budapest Treaty on the International Recognition of the Deposit of Microorganisms for the Purposes of Patent Procedures.

The present invention is not to be limited in scope by the microorganisms deposited or the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A substantially purified fragment of a Serrate protein, which fragment is characterized by the ability in vitro, when expressed on the surface of a first cell, to bind to a Notch protein expressed on the surface of a second cell, which fragment lacks one or more amino acids of the extracellular domain of the Serrate protein.

2. A substantially purified fragment of a Serrate protein which is the portion of the Serrate protein with the greatest homology over a sequence of 199 amino acids to the amino acid sequence as depicted in FIGS. 15A–15B (SEQ ID NO:9) from about amino acid numbers 85–283, which fragment lacks one or more amino acids of the extracellular domain of the Serrate protein.

3. A chimeric protein comprising the fragment of claim 2 joined to a protein sequence of a second protein, in which said second protein is not said Serrate protein, and in which the fragment does not contain a complete EGF-homologous repeat of the Serrate protein.

4. A substantially purified fragment of a Serrate protein which is the portion of the Serrate protein with the greatest homology over a sequence of 204 amino acids, to the amino acid sequence as depicted in FIGS. 15A–15B (SEQ ID NO:9) from about amino acid numbers 79–282, which fragment lacks one or more amino acids of the extracellular domain of the Serrate protein.

5. The fragment of claim 1 which consists of at least a portion of a Serrate protein with the greatest homology over a sequence of 199 amino acids, to the amino acid depicted in FIGS. 15A–15B (SEQ ID NO:9) from about amino acid members 85–283.

6. The fragment of claim 1, which consists of at least a portion of a Serrate protein with the greatest homology over a sequence of 204 amino acids, to the amino acid sequence as depicted in FIGS. 15A–15B (SEQ ID NO:9) from about amino acid numbers 79–282.

7. A chimeric protein comprising the fragment of claim 5 joined to a protein sequence of a second protein, in which said second protein is not said Serrate protein, and in which the fragment does not contain a complete EFG-homologous repeat of the Serrate protein.

8. A chimeric protein comprising the fragment of claim 6 joined to a protein sequence of a second protein, in which said second protein is not said Serrate protein, and in which the fragment does not contain a complete EFG-homologous repeat of the Serrate protein.

9. The fragment of claim 1 which consists of at least the amino acid sequence as depicted in FIGS. 15A–15B (SEQ ID NO:9) from about amino acid numbers 85–283.

10. The fragment of claim 1 which consists of at least the amino acid sequence as depicted in FIGS. 15A–15B (SEQ ID NO:9) from about amino acid numbers 79–282.

11. A derivative of the fragment of claim 1, which derivative is characterized by the ability in vitro, when expressed on the surface of a first cell, to bind to a Notch protein expressed on the surface of a second cell, the derivative having an insertion, substitution or deletion of one or more amino acids relative to the fragment, said derivative lacking one or more amino acids of the extracellular domain of the Serrate protein.

12. The fragment of claims 1, 2, 4, 5, 6, 9 or 10, which does not contain a complete EGF-homologous repeat of the Serrate protein.

13. The derivative of claim 11 which does not contain a complete EGF-homologous repeat of the Serrate protien.

14. A substantially pure derivative of a Serrate protein, which derivative is characterized by the ability in vitro, when expressed on the surface of a first cell, to bind to a Notch protein expressed on the surface of a second cell, the derivative having an insertion, substitution, or deletion of one or more amino acids in at least the extracellular domain of the Serrate protein.

15. The derivative of claim 14 in which the insertion, substitution, or deletion is in at least a portion of an EFG-homologous repeat.

16. A chimeric protein comprising the derivative of claims 11, 13, 14 or 15 joined to a protein sequence of a second protein, in which said second protein is not said Serrate protein.

17. A chimeric protein comprising the fragment of claim 1 joined to a protein sequence of a second protien, in which said second protein is not said Serrate protein.

18. A substantially purified fragment of a Serrate protein consisting essentially of amino acid numbers 79–282 of the amino acid sequence as depicted in FIGS. 15A–15B (SEQ ID NO:9), which fragment is characterized by the ability in vitro, when expressed on the surface of a first cell, to bind to a Notch protein expressed on the surface of a second cell.

19. A substantially purified fragment of a Serrate protein consisting essentially of amino acid numbers 85–283 of the amino acid sequence as depicted in FIGS. 15A–15B (SEQ ID NO:9), which fragment is characterized by the ability in vitro, when expressed on the surface of a first cell, to bind to a Notch protein expressed on the surface of a second cell.

* * * * *